US010174046B2

(12) United States Patent
Mackenzie et al.

(10) Patent No.: US 10,174,046 B2
(45) Date of Patent: Jan. 8, 2019

(54) SHIP1 MODULATORS AND METHODS RELATED THERETO

(71) Applicant: Aquinox Pharmaceuticals (Canada) Inc., Vancouver (CA)

(72) Inventors: Lloyd F. Mackenzie, North Vancouver (CA); Thomas B. MacRury, Point Roberts, WA (US); Curtis Harwig, Vancouver (CA); David Bogucki, Surrey (CA); Jeffery R. Raymond, Vancouver (CA); Jeremy D. Pettigrew, Burnaby (CA)

(73) Assignee: Aquinox Pharmaceuticals (Canada) Inc., Vancouver, BC (CA)

( * ) Notice: Subject to any disclaimer, the term of this patent is extended or adjusted under 35 U.S.C. 154(b) by 0 days.

(21) Appl. No.: 15/676,726

(22) Filed: Aug. 14, 2017

(65) Prior Publication Data

US 2017/0362250 A1  Dec. 21, 2017
US 2018/0155359 A9  Jun. 7, 2018

Related U.S. Application Data

(62) Division of application No. 14/772,731, filed as application No. PCT/US2014/019126 on Feb. 27, 2014, now Pat. No. 9,765,085.

(Continued)

(51) Int. Cl.
*C07D 493/10* (2006.01)
*A61K 31/416* (2006.01)
(Continued)

(52) U.S. Cl.
CPC .......... *C07D 493/10* (2013.01); *A61K 31/416* (2013.01); *C07C 35/21* (2013.01); *C07C 35/23* (2013.01); *C07C 215/26* (2013.01); *C07C 215/38* (2013.01); *C07C 233/23* (2013.01); *C07C 255/30* (2013.01); *C07C 275/22* (2013.01); *C07C 335/10* (2013.01); *C07D 211/58* (2013.01); *C07D 213/30* (2013.01); *C07D 213/38* (2013.01); *C07D 213/75* (2013.01); *C07D 213/82* (2013.01); *C07D 215/227* (2013.01); *C07D 221/16* (2013.01); *C07D 221/18* (2013.01); *C07D 231/54* (2013.01); *C07D 231/56* (2013.01); *C07D 261/20* (2013.01); *C07D 277/24* (2013.01); *C07D 277/28* (2013.01);
(Continued)

(58) Field of Classification Search
CPC .. C07D 493/10; C07D 211/58; C07D 213/30; C07D 213/38; C07D 213/75; C07D 213/82; C07D 215/227; C07D 221/16; C07D 221/18; C07D 231/54; C07D 231/56; C07D 261/20; C07D 277/24; C07D 277/28; C07D 277/64; C07D 307/42; C07D 307/52; C07D 333/16; C07D 333/20; A61K 31/416; C07C 35/21; C07C 35/23; C07C 215/26; C07C 215/38; C07C 233/23; C07C 255/30; C07C 275/22; C07C 335/10; C07C 2601/14; C07C 2602/24

See application file for complete search history.

(56) References Cited

U.S. PATENT DOCUMENTS 3,682,983 A  8/1972  Prezewowsky et al.
3,869,467 A  3/1975  Guthrie et al.
(Continued)

FOREIGN PATENT DOCUMENTS

DE  1 084 718  7/1960
GB  1291644  10/1972
(Continued)

OTHER PUBLICATIONS

Ahmad and Khan, "The Baeyer-Villiger Oxidation of 5α-Cholestane-3,6-Dione," *Acta Chim. Acad. Sci. Hung.* 106(2): 111-113, 1981.
(Continued)

*Primary Examiner* — Robert H Havlin
(74) *Attorney, Agent, or Firm* — Seed IP Law Group LLP

(57) ABSTRACT

Compounds of formula (II):

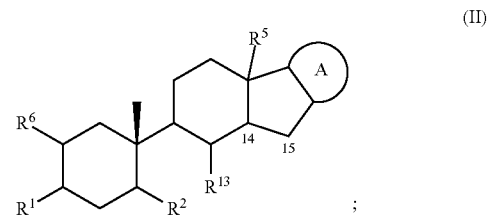

(II)

wherein

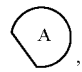

$R^1$, $R^2$, $R^5$ and $R^{13}$ are described herein, or a stereoisomer, enantiomer or tautomer thereof or mixtures thereof, or a pharmaceutically acceptable salt or solvate thereof, are described herein, as well as other compounds. These compounds have activity as SHIP1 modulators, and thus may be useful in treating a variety of diseases, disorders or conditions that would benefit from SHIP1 modulation. Compositions comprising a compound of the invention are also disclosed, as are methods of SHIP1 modulation by administration of such compounds to an animal in need thereof.

11 Claims, No Drawings

Related U.S. Application Data

(60) Provisional application No. 61/786,020, filed on Mar. 14, 2013.

(51) Int. Cl.

| | | |
|---|---|---|
| C07D 213/75 | (2006.01) |
| C07D 213/82 | (2006.01) |
| C07D 215/227 | (2006.01) |
| C07C 275/22 | (2006.01) |
| C07D 221/18 | (2006.01) |
| C07D 231/54 | (2006.01) |
| C07C 215/26 | (2006.01) |
| C07C 215/38 | (2006.01) |
| C07C 335/10 | (2006.01) |
| C07C 233/23 | (2006.01) |
| C07D 261/20 | (2006.01) |
| C07D 277/24 | (2006.01) |
| C07D 277/28 | (2006.01) |
| C07C 255/30 | (2006.01) |
| C07D 211/58 | (2006.01) |
| C07D 213/30 | (2006.01) |
| C07D 307/42 | (2006.01) |
| C07D 333/16 | (2006.01) |
| C07D 231/56 | (2006.01) |
| C07D 277/64 | (2006.01) |
| C07C 35/21 | (2006.01) |
| C07C 35/23 | (2006.01) |
| C07D 213/38 | (2006.01) |
| C07D 221/16 | (2006.01) |
| C07D 307/52 | (2006.01) |
| C07D 333/20 | (2006.01) |

(52) U.S. Cl.
CPC ......... *C07D 277/64* (2013.01); *C07D 307/42* (2013.01); *C07D 307/52* (2013.01); *C07D 333/16* (2013.01); *C07D 333/20* (2013.01); C07C 2601/14 (2017.05); C07C 2602/24 (2017.05)

(56) References Cited

U.S. PATENT DOCUMENTS

| | | | |
|---|---|---|---|
| 3,962,275 | A | 6/1976 | Guthrie et al. |
| 5,686,621 | A | 11/1997 | Clark et al. |
| 6,046,185 | A | 4/2000 | Burgoyne et al. |
| 6,635,629 | B2 | 10/2003 | Raymond et al. |
| 6,696,580 | B2 | 2/2004 | Burgoyne et al. |
| 6,982,329 | B2 | 1/2006 | Burgoyne et al. |
| 7,601,874 | B2 | 10/2009 | Raymond et al. |
| 7,999,010 | B2 | 8/2011 | Raymond et al. |
| 8,084,503 | B2 | 12/2011 | Raymond et al. |
| 8,673,975 | B2 | 3/2014 | Raymond et al. |
| 9,000,050 | B2 | 4/2015 | Wang et al. |
| 9,765,085 | B2 | 9/2017 | Mackenzie et al. |
| 2001/0010293 | A1 | 8/2001 | Ishida et al. |
| 2010/0323990 | A1 | 12/2010 | Andersen et al. |
| 2011/0263539 | A1 | 10/2011 | Andersen et al. |
| 2014/0371252 | A1 | 12/2014 | Raymond et al. |
| 2016/0031899 | A1 | 2/2016 | Mackenzie et al. |
| 2016/0083387 | A1 | 3/2016 | Mackenzie et al. |
| 2016/0376222 | A1 | 12/2016 | Mackenzie et al. |
| 2017/0204048 | A1 | 7/2017 | Harwig et al. |
| 2017/0362250 | A1 | 12/2017 | Mackenzie et al. |
| 2018/0085460 | A1 | 3/2018 | Mackenzie et al. |
| 2018/0155273 | A1 | 6/2018 | Mackenzie et al. |

FOREIGN PATENT DOCUMENTS

| | | | |
|---|---|---|---|
| JP | | 1-290624 A | 11/1989 |
| JP | | 5-221901 A | 8/1993 |
| JP | | 5-221924 A | 8/1993 |
| WO | WO 93/13124 A1 | | 7/1993 |
| WO | WO 94/14833 A2 | | 7/1994 |
| WO | WO 95/01960 A1 | | 1/1995 |
| WO | WO 96/11939 A1 | | 4/1996 |
| WO | WO 03/033517 A1 | | 4/2003 |
| WO | WO 2004/035601 A1 | | 4/2004 |
| WO | WO 2004/092100 A1 | | 10/2004 |
| WO | WO 2007/147251 A1 | | 12/2007 |
| WO | WO 2007/147252 A1 | | 12/2007 |
| WO | WO 2011/069118 A1 | | 6/2011 |
| WO | WO 2014/143561 A1 | | 9/2014 |
| WO | WO 2014/158654 A1 | | 10/2014 |
| WO | WO 2016/210146 A1 | | 12/2016 |
| WO | WO 2017/127753 A1 | | 7/2017 |
| WO | WO 2018/058144 A1 | | 3/2018 |

OTHER PUBLICATIONS

Altomare et al., "SIR97: a new tool for crystal structure determination and refinement," *J. Appl. Cryst.* 32: 115-119, 1999.

Barber et al., "PI3Kγ inhibition blocks glomerulonephritis and extends lifespan in a mouse model of systemic lupus," *Nature Medicine* 11(9): 933-935, Sep. 2005.

Buckingham et al., "6-Phenylazocholestane derivatives: Reassignment of the Structures of Products from Phenylhydrazine and Ozonised Cholesterol Derivatives," *J. Chem. Soc.*(C) 18: 1703-1706, 1967.

Camps et al., "Blockade of PI3Kγ suppresses joint inflammation and damage in mouse models of rheumatoid arthritis," *Nature Medicine* 11(9): 936-943, Sep. 2005.

Clinton et al., "Steroidal[3,2-c]pyrazoles. II. Androstanes, 19-Norandrostanes and their Unsaturated Analogs," *Journal of the American Chemical Society* 83: 1478-1491, Mar. 20, 1961.

Coggeshall et al., "How do inhibitory phosphatases work?," *Molecular Immunology* 39: 521-529, 2002.

Cookson et al., "Photochemical Rearrangement of α-Hydroxyketones to Lactones,"*J. Chem. Soc.* (C): 2494-2500, 1968.

Damen et al., "The 145-kDa protein induced to associate with Shc by multiple cytokines is an inositol tetraphosphate and phosphatidylinositol 3,4,5-trisphosphate 5-phosphatase," *Proc. Natl. Acad. Sci. USA* 93: 1689-1693, Feb. 1996.

Dauben et al., "Stereocontrolled Synthesis of Steroidal Side Chains," *J. Am. Chem. Soc.* 103: 237-238, 1981.

Deane et al., "Phosphoinositide 3-Kinase: Diverse Roles in Immune Cell Activation," *Annu. Rev. Immunol.* 22: 563-598, 2004.

Fan et al., "A dual PI3 kinase/mTOR inhibitor reveals emergent efficacy in glioma," *Cancer Cell* 9: 341-349, May 2006.

Feuer et al., "The Reduction of Oximes, Oxime Ethers, and Oxime Esters with Diborane. A Novel Synthesis of Amines," *The Journal of Organic Chemistry* 34(6): 1817-1821, Jun. 1969.

Fukuda et al., "Alteration of phosphatidylinositol 3-kinase cascade in the multilobulated nuclear formation of adult T cell leukemia/lymphoma (ATLL)," *PNAS* 102(42): 15213-15218, Oct. 18, 2005.

Gallou et al., "Practical Synthesis of Unsymmetrical Ureas from Isopropenyl Carbamates," *J. Org. Chem* 70: 6960-6963, 2005.

Goclik et al., "Pelorol from the Tropical Marine Sponge *Dactylospongia elegans,*" *J. Nat. Prod.* 63: 1150-1152, 2000.

Gumulka et al, "Oxidative Cleavage of the Double Bond of 7-Dehydrocholesterol Acetate Peroxide," *Polish Journal of Chemistry* 57(4/5/6): 403-411, 1983.

Habermacher et al., "Prostatitis/Chronic Pelvic Pain Syndrome," *Annu. Rev. Med.* 57: 195-206, 2006.

Halpern et al., "On the Nature of the Chemical Mediators Involved in Anaphylactic Reactions in Mice," *Brit. J. Pharmacol.* 20: 389-398, 1963.

Hara, "Azasteroid. IV. Synthesis of B-Azacholane Derivative," Chemical Abstracts Online, Accession No. 1959:17427, 1959. See also *Yakugaku Zasshi* 78(9): 1030-1033, Sep. 1958.

Hazen et al., "SHIP is required for a functional hematopoietic stem cell niche," *Blood* 113(13): 2924-2933, Mar. 26, 2009.

Helgason et al., "A Dual Role for Src Homology 2 Domain-containing Inositol-5-Phosphatase (SHIP) in Immunity: Aberrant

(56) References Cited

OTHER PUBLICATIONS

Development and Enhanced Function of B Lymphocytes in SHIP$^{-/-}$ Mice," *J. Exp. Med.* 191(5): 781-794, Mar. 6, 2000.
Helgason et al., "Targeted disruption of SHIP leads to hemopoietic perturbations, lung pathology, and a shortened life span," *Genes & Development* 12: 1610-1620, 1998.
Hennessy et al., "Exploiting the PI3K/AKT Pathway for Cancer Drug Discovery," *Nature Reviews|Drug Discovery* 4: 988-1004, Dec. 2005.
Ibers et al., "Dispersion corrections and crystal structure refinements," *Acta Cryst.* 17: 781-782, 1964.
Kalesnikoff et al., "The role of SHIP in cytokine-induced signaling," *Rev. Physiol. Biochem. Pharmacol.* 149: 87-103, 2003.
Kaspar et al., "Steroid Binding to the Cytosolic Estrogen Receptor From Rat Uterus. Influence of the Orientation of Substituents in the 17-Position of the 8β- and 8α-Series," *J. steroid Biochem.* 23(3): 259-265, 1985.
Kubinyi, (3D QSAR in Drug Design: Ligand-Protein Interactions and Molecular Similarity, vol. 2-3, Springer, 1998, 800 pages), pp. 243-244 provided.
Knight et al., "A Pharmacological Map of the PI3-K Family Defines a Role for p110α in Insulin Signaling," *Cell* 125: 733-747, May 19, 2006.
Krieger et al., "NIH Consensus Definition and Classification of Prostatitis," *JAMA* 281(3): 236-237, Jul. 21, 1999.
Kwak et al., "Sesquiterpene Quinols/Quinones from the Micronesian Sponge *Petrosaspongia metachromia*," *J. Nat. Prod.* 63: 1153-1156, 2000.
Leaker et al., "The effects of the novel SHIP1 activator AQX-1125 on allergen-induced responses in mild-to-moderate asthma," *Clinical & Experimental Allergy* 44: 1146-1153, 2014.
Lettré and Werner, "Polyols from steroids and steroid derivatives. IV. 7,8-Seco-derivatives of cholestanols," Chemical Abstracts Online, Accession No. 1967:46521, 1967. See Also *Justus Liebigs Annalen Der Chemie* 697: 217-221, 1966.
Lettré and Werner, "Mehrwertige Alkohole aus Sterinen and Sterinderivaten. IV. 7.8-seco-Derivate des Cholestanols," *Justus Liebigs Annalen Der Chemie* 697: 217-221, 1966.
Ley et al., "Microencapsulation of Osmium Tetroxide in Polyurea," *Organic Letters* 5(2): 185-187, 2003.
Liang et al., "Quantification of change in phosphorylation of BCR-ABL kinase and its substrates in response to Imatinib treatment in human chronic myelogenous leukemia cells," *Proteomics* 6: 4554-4564, 2006.
Luo et al., "Mutation Analysis of SHIP Gene in Acute Leukemia," *Journal of Experimental Hematology* 12(4): 420-426, 2004.
Macrae et al., "Mercury CSD 2.0—new features for the visualization and investigation of crystal structures," *J. Appl. Cryst.* 41: 466-470, 2008.
Madaio et al., "Minor 5,6-Secosterols From the Marine Sponge *Hippospongia Communis*. Isolation and Synthesis of (7Z,22E,24R)-24-Methyl-5,6-Secocholesta-7,22-Diene-3β,5β,6-Triol," *Journal of Natural Products* 53(3): 565-572, May-Jun. 1990.
Manson et al., "Steroidal Heterocycles. VII. Androstano[2,3-d]isoxazoles and Related Compounds," *J. Med. Chem.* 6(1): 1-9, Jan. 18, 1963.
Mincione and Bovicelli, Synthesis via Organoiron Complexes of 9-(4-Keto-1-Methylcyclohex-2-enyl)-8-Keto-des-AB-Ergost-22,23-ene; A Useful Chiral Intermediate in Steroid Synthesis, *Heterocycles* 23(7): 1607-1610, 1985.
Mirjafary et al., "Oxime ethers as versatile precursors in organic synthesis: a review," *RSC Adv.* 5: 79361-79384, 2015.
Nickel et al., "Category III Chronic Prostatitis/Chronic Pelvic Pain Syndrome: Insights from the National Institutes of Health Chronic Prostatitis Collaborative Research Network Studies," *Curr. Urol. Rep.* 9(4): 320-327, 2008.
Nickel et al., "A Phase II Study of the Efficacy and Safety of the Novel Oral SHIP1 Activator AQX-1125 in Subjects with Moderate to Severe Interstitial Cystitis/Bladder Pain Syndrome," *The Journal of Urology* 196: 747-754, Sep. 2016.

Nicolaou et al., "An Expedient Procedure for the Oxidative Cleavage of Olefinic Bonds with PhI(OAc)$_2$, NMO, and Catalytic OsO$_4$," *Org. Lett.* 12(7): 1552-1555, Apr. 2, 2010.
Ong et al., "Small-molecule agonists of SHIP1 inhibit the phosphoinositide 3-kinase pathway in hematopoietic cells," *Blood* 110(6): 1942-1949, Sep. 15, 2007.
Ovary et al., "Passive Cutaneous Anaphylaxis in the Mouse," *J. Immunol.* 81: 355-357, 1958.
Radhakrishnan et al., "Development and characterization of a novel animal model of prostate inflammation-induced chronic pelvic pain," *Inflammopharmacology* 17: 23-28, 2009.
Reichstein and Meystre, "Über Bestandteile der Nebennierenrinde und verwandte Stoffe—Allo-pregnan-diol-(3, 17)-Derivate der 17(β)-Reihe. Weiterer Beweis für die Zugehörigkeit der Substanzen P und K zur 17(β)-Reihe," *Helv. Chim. Acta* 22(III): 728-741, 1939.
Rodewald et al., "Secosteroids. I. Synthesis of vic-Diols in B-Secocholestane Group," *Journal Prakt. Chem.* 330(5): 775-881, 1988.
Rodewald et al., "Selective Esterification of Hydroxyl Groups in Methyl Ester of 3β,8α-Dihydroxy-7,8-Secocholestan-7-oic Acid," *Roczniki Chemii Ann. Soc. Chim. Polonorum* 51(4): 809-814, 1977.
Rohrschneider et al., "Structure, function, and biology of SHIP proteins," *Genes & Development* 14: 505-520, 2000.
Savitzky et al., "Smoothing and Differentiation of Data by Simplified Least Squares Procedures," *Analytical Chemistry* 36(8): 1627-1639, Jul. 1964.
Seto et al., "Epimerization at C-5 of brassinolide with sodium methoxide and the biological activity of 5-epi-brassinolide in the rice lamina inclination test," *J. Chem. Soc., Perkin Trans.* 1: 3355-3358, 1998.
Simon, "Using Isoform-Specific Inhibitors to Target Lipid Kinases," *Cell* 125: 647-649, May 19, 2006.
Sly et al., "SHIP, SHIP2, and PTEN activities are regulated in vivo by modulation of their protein levels: SHIP is up-regulated in macrophages and mast cells by lipopolysaccharide," *Experimental Hematology* 31: 1170-1181, 2003.
Sly et al., "LPS-Induced Upregulation of SHIP is Essential for Endotoxin Tolerance," *Immunity* 21: 227-239, Aug. 2004.
Speckamp et al., "6-Thiasteroids a Novel Stereoselective Preparation of 6-Heterosteroids," *Tetrahedron Letters* 38: 3405-3408, 1974.
Stenton et al., "Characterization of AQX-1125, a small-molecule SHIP1 activator Part 1. Effects on inflammatory cell activation and chemotaxis in vitro and pharmacokinetic characterization in vivo," *British Journal of Pharmacology* 168: 1506-1518, 2013.
Suginome and Yamada, "Photoinduced Transformations. 77. A Four-Step Substitution of a Carbonyl Group of Steroidal Ketones by an Oxygen Atom. A New Method for the Synthesis of Cyclic Ethers," *Journal of Organic Chemistry* 50(14): 2489-2494, 1985.
Tu et al., "Painful urological syndromes: Overview of the diagnosis and treatment of painful bladder syndrome/interstitial cystitis and chronic non-bacterial prostatitis/chronic pelvic pain syndrome (CPPS)," *Doul. et Analq.* 20: 154-166, 2007.
Vanderwinden et al., "Differences in signaling pathways and expression level of the phosphoinositide phosphatase SHIP1 between two oncogenic mutants of the receptor tyrosine kinase KIT," *Cellular Signalling* 18: 661-669, 2006.
Vivanco et al., "The Phosphatidylinositol 3-Kinase-AKT Pathway in Human Cancer," *Nature Reviews: Cancer* 2: 489-501, Jul. 2002.
Vonakis et al., "Src homology 2 domain-containing inositol 5' phosphatase is negatively associated with histamine release to human recombinant histamine-releasing factor in human basophils," *J. Allergy Clin. Immunol.* 108: 822-831, 2001.
Vykhovanets et al., "Experimental rodent models of prostatitis: limitations and potential," *Prostate Cancr and Prostatic Diseases* 10: 15-29, 2007.
Wermuth, The Practice of Medicinal Chemistry, 2nd ed. (2003), 768 pages, Chapters 9-10 provided.
Westmijze et al., "Ag(I)-Assisted Hydrolysis of Mestranol Methanesulfonate Into Epimestranol," *Tetrahedron Letters* 21: 2665-2666, Apr. 15, 1980.
Winter et al., "Carrageenin-Induced Edema in Hind Paw of the Rat as an Assay for Antiinflammatory Drugs," *Proc. Soc. Exp. Biol. Med.* 111: 544-547, 1962.

(56) References Cited

OTHER PUBLICATIONS

Workman et al., "Drugging the PI3 kinome," *Nature Biotechnology* 24(7): 794-796, Jul. 2006.
Xing et al., "Gold(I)-Catalyzed Oxidative Cleavage of a C-C Double Bond in Water," *Organic Letters* 8(4): 693-696, 2006.
Yang et al., "Ruthenium-Catalyzed Oxidative Cleavage of Olefins to Aldehydes," *J. Org. Chem.* 66: 4814-4818, 2001.
Yang et al., "Synthesis of Pelorol and Analogues: Activators of the Inositol 5-Phosphatase SHIP," *Organic Letters* 7(6): 1073-1076, 2005.
Yong et al., "Synthesis of CD-ring modified 1 α,25-dihydroxy vitamin D analogues: Five-membered D-ring analogues," *Bioorganic & Medicinal Chemistry Letters* 7(7): 923-928, 1997.
Beilstein Database, Beilstein Registry No. 3061562, 1968.
Beilstein Database, Beilstein Registry No. 3102039, 1967.
Chemical Abstracts Database, Accession No. 82:73301, 1974.
Chemical Abstracts Database, Accession No. 101:192278, 1983.
Chemical Abstracts Database, Accession No. 112:211000, Nov. 1989.
Chemical Abstracts Database, Accession No. 120:77523, Aug. 1993.
Chemical Abstracts Online, Accession No. 1959:17427, 1959, 2 pages.
Chemical Abstracts Online, Accession No. 1967:46521, 1966, 2 pages.
Chemical Abstracts Online, Accession No. 2013:381943, 2013, 2 pages.
International Preliminary Report on Patentability, dated Oct. 21, 2005, for International Application No. PCT/CA2004/000566, 8 pages.
International Preliminary Report on Patentability, dated Sep. 15, 2015, for International Application No. PCT/US2014/019125, 8 pages.
International Preliminary Report on Patentability, dated Sep. 15, 2015, for International Application No. PCT/US2014/019126, 11 pages.
International Search Report, dated Sep. 6, 2016, for PCTAN PCT/US2016/039040, 6 pages.
Written Opinion of the International Searching Authority, dated Sep. 6, 2016, for PCTAN PCT/US2016/039040, 9 pages.
International Search Report, dated Mar. 13, 2017, for PCTAN PCT/US2017/014446, 5 pages.
Written Opinion of the International Searching Authority, dated Mar. 13, 2017, for PCTAN PCT/US2017/014446, 7 pages.
International Search Report and Written Opinion, dated Dec. 11, 2017, for PCTAN PCT/US2017/053554, 14 pages.
Cross et al., "AQX-1125, small molecule SHIP1 activator inhibits bleomycin-induced pulmonary fibrosis," *British Journal of Pharmacology* 174: 3045-3057, 2017.
Florence, "Polymorph screening in pharmaceutical development," *European Pharmaceutical Review*, Aug. 19, 2010, retrieved from the Internet: URL:https://www.europeanpharmaceuticalreview.com/article/3659/polymorph-screening-in-pharmaceutical-development/ [retrieved on Mar. 7, 2018], 14 pages.
Lee, "A practical guide to pharmaceutical polymorph screening & selection," *Asian Journal of Pharmaceutical Sciences* 9: 163-175, 2014.
International Search Report and Written Opinion, dated Mar. 19, 2018, for PCTAN PCT/US2017/0687644, 14 pages.

SHIP1 MODULATORS AND METHODS RELATED THERETO

FIELD OF THE INVENTION

The present invention is generally directed to SHIP1 modulators, as well as to compositions and methods related to the same.

BACKGROUND OF THE INVENTION

In response to extracellular signals, phosphoinositide 3-kinase (PI3K) becomes activated and phosphorylates phosphatidylinositol-4,5-bisphosphate (PI-4,5-$P_2$) within the plasma membrane to generate phosphatidylinositol-3,4,5-trisphosphate ($PIP_3$). $PIP_3$ then initiates a cascade of downstream signaling pathways by interacting with pleckstrin homology (PH) domain-containing proteins, such as protein kinase B (PKB, also known as Akt), that regulate cellular activation, function, proliferation and/or survival, depending on the cell type and stimulus (Deane et al., *Annu Rev Immunol* 22, 563-598, 2004). Cellular levels of $PIP_3$ are normally tightly regulated by PI3K, the 5' inositol phosphatases SHIP1 (SH2 domain-containing inositol phosphatase), SHIP2, and by the 3' inositol phosphatase PTEN. SHIP1 and SHIP2 dephosphorylate $PIP_3$ to phosphatidylinositol-3,4-bisphosphate (PI-3,4-$P_2$), whereas PTEN dephosphorylates $PIP_3$ to PI-4,5-$P_2$ (Sly et al., *Exp Hematol* 31, 1170-1181, 2003; Vivanco et al., *Nat Rev Cancer* 2, 489-501, 2002). Of these three, SHIP1 is unique in that its expression is restricted primarily to immune and hematopoietic cells (Sly et al., *Exp Hematol* 31, 1170-1181, 2003; Damen et al., *Proc Natl Acad Sci USA* 93, 1689-1693, 1996).

SHIP1's role in immune cell homeostasis is shown both by the myeloproliferative syndrome observed in SHIP1$^{-/-}$ mice, as well as the hypersensitivity of SHIP1$^{-/-}$ mice and cells to immune stimulation (Helgason et al., *Genes Dev* 12, 1610-1620, 1998; Sly et al., *Immunity* 21, 227-239, 2004). SHIP1 has been shown to mediate signaling from the inhibitory FcγRIIB receptor (Coggeshall et al., *Mol Immunol* 39, 521-529, 2002), and is important in terminating signal transduction from activating immune/hematopoietic cell receptor systems (Kalesnikoff et al., *Rev Physiol Biochem Pharmacol* 149, 87-103, 2003).

Diminished SHIP1 activity or expression has been observed in human inflammatory diseases (Vonakis et al., *J Allergy Clin Immunol* 108, 822-831, 2001) and hematopoietic malignancies (Liang et al., *Proteomics* 6, 4554-4564, 2006; Fukuda et al., *Proc Natl Acad Sci USA* 102, 15213-15218, 2005; Luo et al., *Zhongguo Shi Yan Xue Ye Xue Za Zhi* 12, 420-426, 2004; Vanderwinden et al., *Cell Signal* 18, 661-669, 2006; Ong, C. J. et al., *Blood* (2007), Vol. 110, No. 6, pp. 1942-1949).

Because dysregulated activation of the PI3K pathway contributes to inflammatory/immune disorders and cancer, intense efforts have been invested into the development of inhibitors of PI3K itself, as well as downstream protein kinases (Workman et al., *Nat Biotechnol* 24, 794-796, 2006; Simon, *Cell* 125, 647-649, 2006; Hennessy et al., *Nat Rev Drug Discov* 4, 988-1004, 2005; Knight et al., *Cell* 125, 733-747, 2006; Ong, C. J. et al., *Blood* (2007), Vol. 110, No. 6, pp. 1942-1949). The precedent for discovery and biologic efficacy of kinase inhibitors is well established, and a number of promising new PI3K isoform-specific inhibitors have recently been developed and used in mouse models of inflammatory disease (Camps et al., *Nat Med* 11, 936-943, 2005; Barber et al., *Nat Med* 11, 933-935, 2005) and glioma (Fan et al., *Cancer Cell* 9, 341-349, 2006) with minimal toxicities. However, because of the dynamic interplay between phosphatases and kinases in regulating biologic processes, inositol phosphatase activators represent a complementary, alternative approach to reduce cellular $PIP_3$ levels. Of the phosphoinositol phosphatases that degrade $PIP_3$, SHIP1 is a particularly ideal target for development of therapeutics for treating immune and hemopoietic disorders because its hematopoietic-restricted expression (Hazen A L, et al. 113, 2924-33, 2009; Rohrschneider L R, Fuller J F, Wolf I, Liu Y, Lucas D M. Structure, function, and biology of SHIP proteins. Genes Dev. 14:505-20, 2000) would limit the effects of a specific SHIP1 agonist to target cells.

To date, a number of small molecule SHIP1 modulators have been disclosed, including sesquiterpene compounds such as pelorol. Pelorol is a natural product isolated from the topical marine sponge *Dactylospongia elegans* (Kwak et al., *J Nat Prod* 63, 1153-1156, 2000; Goclik et al., *J Nat Prod* 63, 1150-1152, 2000). Other reported SHIP1 modulators include the compounds set forth in PCT Published Patent Application Nos. WO 2003/033517, WO 2004/035601, WO 2004/092100 (or U.S. Pat. No. 7,601,874), WO 2007/147251, WO 2007/147252 and WO 2011/069118.

While significant strides have been made in this field, there remains a need for effective small molecule SHIP1 modulators. There is also a need for pharmaceutical compositions containing such compounds, as well as for methods relating to the use thereof to treat disorders or conditions that would benefit from SHIP1 modulation. The present invention fulfills these needs, and provides other related advantages.

SUMMARY OF THE INVENTION

The present invention is generally directed to compounds which are SHIP1 modulators and pharmaceutical compositions comprising the compounds and methods of using the compounds and the pharmaceutical compositions of the invention for the treatment of diseases, disorders or conditions that would benefit from SHIP1 modulation. As used herein, a SHIP1 modulator can serve as either an agonist or antagonist to SHIP1.

Accordingly, in one aspect, this invention is directed to compounds of formula (I):

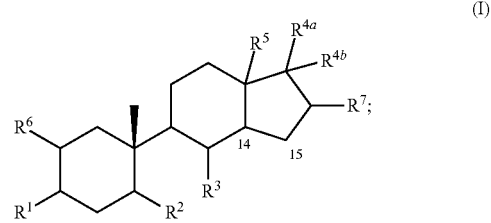

wherein:
$R^1$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—C(O)$OR^9$, —$R^8$—C(O)$N(R^9)_2$ or —$N(R^9)$C(O)$OR^9$;
$R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—$N(R^9)$S(O)$_tR^9$ (where t is 1 or 2), —$R^8$—$N(R^9)$C(=$NR^9$)$N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl;

$R^3$ is $-R^8-N(R^9)C(O)R^{11}$, $-R^8-N(R^9)-R^{12}$, $-R^8-N(R^9)C(=NCN)N(R^{9a})_2$, $-R^8-N(R^9)C(O)N(R^{9a})_2$ or $-R^8-N(R^9)C(S)N(R^{9a})_2$;

$R^{4a}$ and $R^{4b}$ are each independently hydrogen, alkyl, alkenyl or alkynyl;

or $R^{4a}$ is hydrogen, alkyl, alkenyl or alkynyl and $R^{4b}$ is a direct bond to the carbon to which $R^7$ is attached;

or $R^{4a}$ and $R^{4b}$ together form alkylidene or haloalkylidene;

$R^5$ is alkyl or $R^5$ is a direct bond to the carbon at C14;

$R^6$ is hydrogen, $-R^8-OR^9$ or $-R^8-N(R^9)_2$;

$R^7$ is hydrogen, $-R^8-OR^9$, $-R^8-N(R^9)_2$, or a direct bond to C15, provided that when $R^7$ is a direct bond to C15, $R^{4b}$ is not a direct bond to the carbon to which $R^7$ is attached;

each $R^8$ is independently a direct bond, a straight or branched alkylene chain, a straight or branched alkenylene chain or a straight or branched alkynylene chain;

each $R^9$ is hydrogen, alkyl, optionally substituted aryl and optionally substituted aralkyl;

each $R^{9a}$ is hydrogen, alkyl, optionally substituted aryl, optionally substituted aralkyl; optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

each $R^{10}$ is independently a straight or branched alkylene chain, a straight or branched alkenylene chain or a straight or branched alkynylene chain;

$R^{11}$ is optionally substituted heteroaryl; and $R^{12}$ is optionally substituted heterocyclyl;

or a stereoisomer, enantiomer or tautomer thereof or mixtures thereof, or a pharmaceutically acceptable salt or solvate thereof;

or a compound of formula (II):

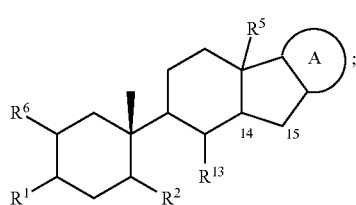

(II)

wherein:

is an optionally substituted fused heterocyclyl or an optionally substituted fused heteroaryl;

$R^1$, $R^2$, $R^5$ and $R^6$ are each as described above for compounds of formula (I);

$R^{13}$ is $-R^8-OR^9$, $-R^8-N(R^9)_2$, $-R^8-O-R^{10}-OR^9$, $-R^8-O-R^{10}-N(R^9)_2$, $-R^8-N(R^9)-R^{10}-OR^9$, $-R^8-N(R^9)-R^{10}-N(R^9)_2$, $-R^8-OC(O)R^9$, $-R^8-C(O)OR^9$, $-R^8-C(O)N(R^9)_2$, $-N(R^9)C(O)OR^9$, $-R^8-N(R^9)S(O)_tR^9$ (where t is 1 or 2), $-R^8-N(R^9)C(=NR^9)N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; and each $R^8$, $R^9$ and $R^{10}$ are as described above for compounds of formula (I);

or a stereoisomer, enantiomer or tautomer thereof or mixtures thereof, or a pharmaceutically acceptable salt or solvate thereof;

or a compound of formula (III):

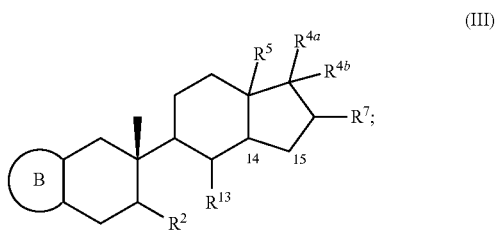

(III)

wherein:

is an optionally substituted fused heterocyclyl or an optionally substituted fused heteroaryl;

$R^2$, $R^5$, $R^{4a}$, $R^{4b}$ and $R^7$ are each as described above for compounds of formula (I); and $R^{13}$ is as described above for compounds of formula (II);

or a stereoisomer thereof or a pharmaceutically acceptable salt thereof;

or a compound of formula (IV):

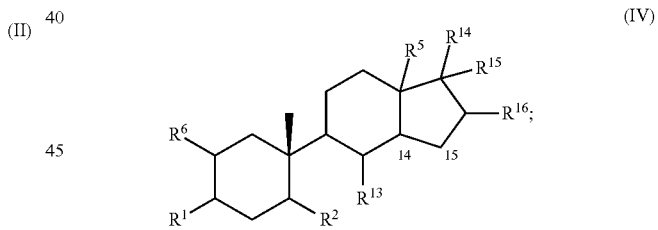

(IV)

wherein:

$R^1$, $R^2$, $R^5$ and $R^6$ are described above for the compounds of formula (I);

$R^{13}$ is as described for the compounds of formula (II);

$R^{14}$ is alkyl, alkenyl, alkynyl, optionally substituted aryl or optionally substituted heteroaryl;

$R^{15}$ is alkyl, $-R^8-OR^9$ or a direct bond to the carbon to which $R^{16}$ is attached, provided that $R^{15}$ is not alkyl when $R^{14}$ is alkyl, alkenyl or alkynyl;

$R^{16}$ is hydrogen, $-R^8-OR^9$, $-R^8-N(R^9)_2$, or a direct bond to C15, provided that when $R^{16}$ is a direct bond to C15, $R^{15}$ is not a direct bond to the carbon to which $R^{16}$ is attached; and each $R^8$ and $R^9$ is as described above for the compounds of formula (I);

or a stereoisomer, enantiomer or tautomer thereof or mixtures thereof, or a pharmaceutically acceptable salt or solvate thereof;

or a compound of formula (V):

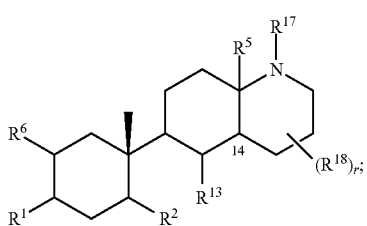

wherein:
r is 0, 1, 2 or 3;
$R^1$, $R^2$, $R^5$ and $R^6$ are as described above for the compounds of formula (I);
$R^{13}$ is as described for the compounds of formula (II);
$R^{17}$ is hydrogen, alkyl, haloalkyl, optionally substituted aryl, optionally substituted aralkyl or —C(O)OR$^9$;
$R^{18}$ is hydrogen, halo, haloalkyl, alkyl, optionally substituted aryl, optionally substituted aralkyl, oxo or —OR$^9$; and
$R^9$ is as described for the compounds of formula (I);
or a stereoisomer, enantiomer or tautomer thereof or mixtures thereof, or a pharmaceutically acceptable salt or solvate thereof;
or a compound of formula (VI):

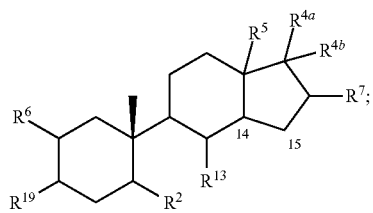

wherein:
$R^2$, $R^{4a}$, $R^{4b}$, $R^5$, $R^6$ and $R^7$ are as described above for the compounds of formula (I);
$R^{13}$ is as described above for the compounds of formula (II);
$R^{19}$ is —R$^8$—N(R$^9$)C(O)R$^9$;
$R^8$ and each $R^9$ are as described above for the compounds of formula (I);
or a stereoisomer, enantiomer or tautomer thereof or mixtures thereof, or a pharmaceutically acceptable salt or solvate thereof.

In another aspect, this invention is directed to compositions comprising a pharmaceutically acceptable excipient, carrier and/or diluent and a compound of formula (I), or a stereoisomer, enantiomer or tautomer thereof or mixtures thereof; or a pharmaceutically acceptable salt or solvate thereof.

In another aspect, this invention is directed to a method for modulating SHIP1 activity in a mammal comprising administering an effective amount of a compound of formula (I), or a stereoisomer, enantiomer or tautomer thereof or mixtures thereof; or a pharmaceutically acceptable salt or solvate thereof, or a composition comprising a compound of formula (I), or a stereoisomer, enantiomer or tautomer thereof or mixtures thereof; or a pharmaceutically acceptable salt or solvate thereof, to the mammal in need thereof.

In another aspect, this invention is directed to methods for treating a disease, disorder or condition in a mammal comprising administering an effective amount of a compound of formula (I), or a stereoisomer, enantiomer or tautomer thereof or mixtures thereof; or a pharmaceutically acceptable salt or solvate thereof, as set forth above, to the mammal in need thereof, where the disease, disorder or condition is an autoimmune disease, disorder or condition, an inflammatory disease, disorder or condition, or a neoplastic or cell proliferative disease, disorder or condition.

In another aspect, this invention is directed to methods of treating a disease, disorder or condition in a mammal comprising administering an effective amount of a compound of formula (I), or a stereoisomer, enantiomer or tautomer thereof or mixtures thereof; or a pharmaceutically acceptable salt or solvate thereof, typically in the form of a composition, to the mammal in need thereof. Methods of this invention include administering an effective amount of a compound of formula (I), or a stereoisomer, enantiomer or tautomer thereof or mixtures thereof; or a pharmaceutically acceptable salt or solvate thereof, to the mammal in need thereof (such as a human).

In another aspect, this invention is directed to methods of preparing compounds of formula (I), or stereoisomers, enantiomers or tautomers thereof or mixtures thereof; or pharmaceutically acceptable salts or solvates thereof.

These aspects and embodiments thereof are described in more detail below. To this end, various references are set forth herein which describe in more detail certain background information, procedures, compounds and/or compositions, and are each hereby incorporated by reference in their entirety.

DETAILED DESCRIPTION OF THE INVENTION

Definitions

As used in the specification and appended claims, unless specified to the contrary, the following terms have the meaning indicated:

"Oxo" refers to =O.
"Cyano" refers to —CN.
"Nitro" refers to —NO$_2$.
"Hydroxy" refers to —OH.
"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, halo, haloalkyl, cyano, nitro, aryl, cycloalkyl, heterocyclyl, heteroaryl, oxo, trimethylsilanyl, —OR$^{20}$, —OC(O)—R$^{20}$, —N(R$^{20})_2$, —C(O)R$^{20}$, —C(O)OR$^{20}$, —C(O)N(R$^{20})_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20})_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)R^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms, preferably one to eight carbon atoms and which is attached to the rest of the molecule by a single bond, e.g., prop-2-ynyl, but-2-ynyl, pent-3-ynyl and the like. When specifically stated in the specification, an alkynyl group may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)R^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkoxy" refers to a radical of the formula —$OR_a$ where $R_a$ is an alkyl radical as defined above containing one to twelve carbon atoms. The alkyl part of the alkoxy radical may be optionally substituted as defined above for an alkyl radical "Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., —$CH_2$—, —$CH_2$—$CH_2$—, —$CH_2$—$CH_2$—$CH_2$—, and the like. The alkylene chain is attached to the rest of the molecule through a single bond and to the radical group through a single bond. When specifically stated in the specification, an alkylene chain may be optionally substituted by one of the following groups: alkyl, alkenyl, halo, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)R^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following groups: alkyl, alkenyl, halo, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)R^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following groups: alkyl, alkenyl, halo, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)R^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylidene" refers to a straight or branched hydrocarbon radical group consisting solely of carbon and hydrogen, containing at least one double bond, having from one to seven carbon atoms, and that is attached to the rest of the molecule through a double bond, e.g., methylene, ethylidene, propylidene, and the like. When specifically stated in the specification, an alkylidene radical may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)R^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})$ $C(O)OR^{22}$, —$R^{21}$—$N(R^{20})C(O)R^{22}$, —$R^{21}$—$N(R^{20})S(O)$ $R^{22}$ (where p is 1 to 2), —$R^{21}$—$N=C(OR^{20})R^{20}$, —$R^{21}$—$S(O)_pOR^{22}$ (where p is 1 to 2), —$R^{21}$—$S(O)_tR^{22}$ (where t is 0 to 2), and —$R^{21}$—$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Aralkenyl" refers to a radical of the formula —$R_d R_c$ where $R_d$ is an alkenylene chain as defined above and $R_c$ is one or more aryl radicals as defined above, which may be optionally substituted as described above.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptly, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, halo, haloalkyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})$ $C(O)OR^{22}$, —$R^{21}$—$N(R^{20})C(O)R^{22}$, —$R^{21}$—$N(R^{20})S(O)$ $R^{22}$ (where p is 1 to 2), —$R^{21}$—$N=C(OR^{20})R^{20}$, —$R^{21}$—$S(O)_pOR^{22}$ (where p is 1 to 2), —$R^{21}$—$S(O)_tR^{22}$ (where t is 0 to 2), and —$R^{21}$—$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_b R_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkylidene" refers an alkylidene radical, as defined above, that is substituted by one or more halo radicals, as defined above. When specifically stated in the specification, an alkylidene radical may be optionally substituted by one of the following groups: alkyl, haloalkyl, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)$ $R^{22}$, —$N(R^{20})S(O)R^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, cyano, oxo, thioxo, nitro, aryl, aralkyl, cycloalkyl, cycloalkylalkyl, optionally substituted heterocyclyl, optionally substituted heterocyclylalkyl, optionally substituted heteroaryl, optionally substituted heteroarylalkyl, —$R^{21}$—$OR^{20}$, —$R^{21}$—OC(O)—$R^{20}$, —$R^{21}$—$N(R^{20})_2$, —$R^{21}$—$C(O)R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$R^{22}$ (where p is 1 to 2), —$R^{21}$—N=C($OR^{20}$)$R^{20}$, —$R^{21}$—S(O)$_p$$OR^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and where the optional substituents on the heterocyclyl, heterocyclylalkyl, heteroaryl and heteroarylalkyl substituents are selected from alkyl, halo or haloalkyl.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl. When specifically stated in the specification, an N-heterocyclyl radical may be optionally substituted as described above for an optionally substituted heterocyclyl radical.

"Heterocyclylalkyl" refers to a radical of the formula —$R_b R_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkylene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzo[d]imidazolyl, benzthiazolyl, benzindolyl, benzodioxolyl, benzofuranyl, benzooxazolyl, benzothiazolyl, benzo[d]isoxazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazo[1,2-a]pyridinyl, imidazo[1,2-a]pyrimidinyl, imidazo[1,2-a]pyrazinyl, imidazo[1,5-a]pyrazinyl, imidazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrido[2,3-d]pyrimidinonyl, pyrazolo[1,5-a]pyrimidinyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—$N(R^{20})_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$R^{22}$ (where p is 1 to 2), —$R^{21}$—N=C($OR^{20}$)$R^{20}$, —$R^{21}$—S(O)$_p$$OR^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —$R_b R_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Heteroarylalkenyl" refers to a radical of the formula —$R_d R_i$ where $R_d$ is an alkenylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkenylene chain part of the heteroarylalkyl radical may be optionally substituted as defined above for an optionally substituted alkenylene chain.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable.

A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like. Further, in the case of a carboxylic acid (—C(O)OH), esters may be employed, such as methyl esters, ethyl esters, and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent. Furthermore, some of the crystalline forms of the compounds of the invention may exist as polymorphs, which are included in the present invention.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition alleviated by the modulation of SHIP1 in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, i.e., relieving inflammation without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts or solvates thereof, may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. Compounds of the invention may also possess axial chirality which may result in atropisomers. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable.

The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure*, 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. For example, the following substituent group:

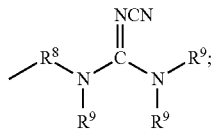

is represented herein as —$R^8$—N($R^9$)C(=NCN)N($R^{9a}$)$_2$.

The chemical naming protocol and structure diagrams used herein are a modified form of the I.U.P.A.C. nomenclature system, using ChemBioDraw Ultra Version 12.0 software program, wherein the compounds of the invention are named herein as derivatives of a central core structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Certain carbons are identified by numerals in formula (I), (II), (III), (IV), (V) and (VI) of the compounds of the invention. For purposes herein, the carbon at numeral 14 in formula (I) is indicated herein as C14 and the carbon at numeral 15 is indicated herein as C15, and so forth. These numerals may or may not be the same as the locants in the compound names given herein.

Thus, for example, a compound of formula (IV) wherein $R^1$ is —OH, $R^2$ is —$CH_2$—OH, $R^5$ is methyl, $R^6$ is hydrogen, $R^{13}$ is —$CH_2$—$NH_2$, $R^{14}$ is furanyl, $R^{15}$ is —OH and $R^{16}$ is hydrogen, i.e., a compound of the following structure:

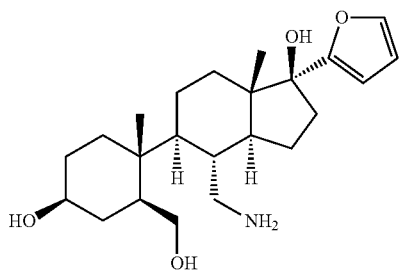 [SMILES: C[C@]1([C@H]2CC[C@@]3(C)[C@@H](CC[C@@]3(O)c3ccco3)[C@@H]2CN)CC[C@H](O)C[C@@H]1CO]

is named herein as (1S,3aS,4R,5S,7aS)-4-(aminomethyl)-1-(furan-2-yl)-5-((1R,2S,4S)-4-hydroxy-2-(hydroxymethyl)-1-methylcyclohexyl)-7a-methyloctahydro-1H-inden-1-ol.

Embodiments of the Invention

Of the various aspects of the invention set forth above in the Summary of the Invention, certain embodiments are preferred.

One embodiment of the invention is a compound of formula (I):

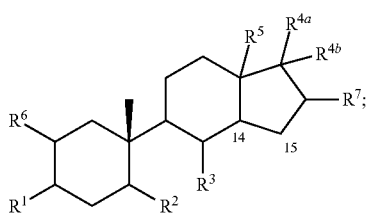

wherein $R^1$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R(R^9)$—$R^{10}$—$OR^9$, —$R^8$—$N(R^9)$—$R^{10}$—$N(R^9)_2$, —$R^8$—C(O)$OR^9$, —$R^8$—C(O)$N(R^9)_2$ or —$N(R^9)$C(O)$OR^9$; $R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—$N(R^9)S(O)_tR^9$ (where t is 1 or 2), —$R^8$—$N(R^9)C(=NR^9)N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^3$ is —$R^8$—$N(R^9)C(O)R^{11}$, —$R^8$—$N(R^9)$—$R^{12}$, —$R^8$—$N(R^9)C(=NCN)N(R^{9a})_2$, —$R^8$—$N(R^9)C(O)N(R^{9a})_2$ or —$R^8$—$N(R^9)C(S)N(R^{9a})_2$; $R^{4a}$ and $R^{4b}$ are each independently hydrogen, alkyl, alkenyl or alkynyl; or $R^{4a}$ is hydrogen, alkyl, alkenyl or alkynyl and $R^{4b}$ is a direct bond to the carbon to which $R^7$ is attached; or $R^{4a}$ and $R^{4b}$ together form alkylidene or haloalkylidene; $R^5$ is alkyl or $R^5$ is a direct bond to the carbon at C14; $R^6$ is hydrogen, —$R^8$—$OR^9$ or —$R^8$—$N(R^9)_2$; $R^7$ is hydrogen, —$R^8$—$OR^9$, —$R^8$—$N(R^9)_2$, or a direct bond to C15, provided that when $R^7$ is a direct bond to C15, $R^{4b}$ is not a direct bond to the carbon to which $R^7$ is attached; each $R^8$ is independently a direct bond, a straight or branched alkylene chain, a straight or branched alkenylene chain or a straight or branched alkynylene chain; each $R^9$ is hydrogen, alkyl, optionally substituted aryl and optionally substituted aralkyl; each $R^{9a}$ is hydrogen, alkyl, optionally substituted aryl, optionally substituted aralkyl; optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; each $R^{10}$ is independently a straight or branched alkylene chain, a straight or branched alkenylene chain or a straight or branched alkynylene chain; $R^{11}$ is optionally substituted heteroaryl; and $R^{12}$ is optionally substituted heterocyclyl; or a stereoisomer, enantiomer or tautomer thereof or mixtures thereof, or a pharmaceutically acceptable salt or solvate thereof.

Of the embodiment of a compound of formula (I), one embodiment is a compound of formula (I) wherein $R^1$ is —$R^8$—$OR^9$; $R^2$ is —$R^8$—$OR^9$; $R^3$ is —$R^8$—$N(R^9)C(O)R^{11}$, —$R^8$—$N(R^9)$—$R^{12}$, —$R^8$—$N(R^9)C(=NCN)N(R^{9a})_2$, —$R^8$—$N(R^9)C(O)N(R^{9a})_2$ or —$R^8$—$N(R^9)C(S)N(R^{9a})_2$; $R^{4a}$ and $R^{4b}$ are each independently hydrogen, alkyl, alkenyl or alkynyl; or $R^{4a}$ is hydrogen, alkyl, alkenyl or alkynyl and $R^{4b}$ is a direct bond to the carbon to which $R^7$ is attached; or $R^{4a}$ and $R^{4b}$ together form alkylidene or haloalkylidene; $R^5$ is alkyl or $R^5$ is a direct bond to the carbon at C14; $R^6$ is hydrogen, —$R^8$—$OR^9$ or —$R^8$—$N(R^9)_2$; $R^7$ is hydrogen, —$R^8$—$OR^9$, —$R^8$—$N(R^9)_2$, or a direct bond to C15, provided that when $R^7$ is a direct bond to C15, $R^{4b}$ is not a direct bond to the carbon to which $R^7$ is attached; each $R^8$ is independently a direct bond or a straight or branched alkylene chain; each $R^9$ is hydrogen, alkyl, optionally substituted aryl and optionally substituted aralkyl; each $R^{9a}$ is hydrogen, alkyl, optionally substituted aryl, optionally substituted aralkyl; optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; $R^{11}$ is optionally substituted heteroaryl; and $R^{12}$ is optionally substituted heterocyclyl.

Of the embodiment of a compound of formula (I), another embodiment is a compound of formula (I) wherein $R^1$ is —$R^8$—$OR^9$; $R^2$ is —$R^8$—$OR^9$; $R^3$ is —$R^8$—$N(R^9)C(O)R^{11}$, —$R^8$—$N(R^9)$—$R^{12}$, —$R^8$—$N(R^9)C(=NCN)N(R^{9a})_2$, —$R^8$—$N(R^9)C(O)N(R^{9a})_2$ or —$R^8$—$N(R^9)C(S)N(R^{9a})_2$; $R^{4a}$ and $R^{4b}$ are each alkyl; $R^5$ is a direct bond to the carbon at C14; $R^6$ is hydrogen; $R^7$ is hydrogen; each $R^8$ is independently a direct bond or a straight or branched alkylene chain; each $R^9$ is hydrogen or alkyl; each $R^{9a}$ is hydrogen, alkyl or optionally substituted heteroaryl; $R^{11}$ is optionally substituted heteroaryl; and $R^{12}$ is optionally substituted heterocyclyl.

Of the embodiment of a compound of formula (I), another embodiment is a compound of formula (I) wherein $R^1$ is —OH; $R^2$ is —$CH_2$—OH; $R^3$ is —$R^8$—$N(R^9)C(O)R^{11}$, —$R^8$—$N(R^9)$—$R^{12}$, —$R^8$—$N(R^9)C(=NCN)N(R^{9a})_2$, —$R^8$—$N(R^9)C(O)N(R^{9a})_2$ or —$R^8$—$N(R^9)C(S)N(R^{9a})_2$; $R^{4a}$ and $R^{4b}$ are each methyl; $R^5$ is a direct bond to the carbon at C14; $R^6$ is hydrogen; $R^7$ is hydrogen; each $R^8$ is independently a direct bond or —$CH_2$—; each $R^9$ is hydrogen or alkyl; each $R^{9a}$ is hydrogen, alkyl or optionally substituted monocyclic N-heteroaryl; $R^{11}$ is optionally substituted pyridinyl; and $R^{12}$ is optionally substituted piperidinyl.

Of the embodiment of a compound of formula (I), another embodiment is a compound of formula (I) selected from:

N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)nicotinamide;

(1S,3S,4R)-4-((4R,5S)-1,1-dimethyl-4-((1-methylpiperidin-4-ylamino)methyl)-2,3,4,5,6,7-hexahydro-1H-inden-5-yl)-3-(hydroxymethyl)-4-methylcyclohexanol;

(E)-2-cyano-1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylguanidine;

1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-(pyridin-3-yl)urea;

1-ethyl-3-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)urea; and 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylthiourea.

Another embodiment of the invention is a compound of formula (II):

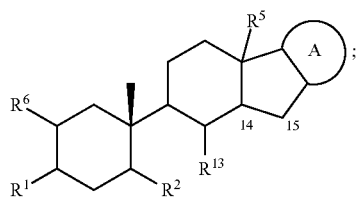

(II)

wherein

is an optionally substituted fused heterocyclyl or an optionally substituted fused heteroaryl; $R^1$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—C(O)$OR^9$, —$R^8$—C(O)$N(R^9)_2$ or —$N(R^9)$C(O)$OR^9$; $R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—$N(R^9)$S(O)$_tR^9$ (where t is 1 or 2), —$R^8$—$N(R^9)$C(=$NR^9$)$N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^5$ is alkyl or $R^5$ is a direct bond to the carbon at C14; $R^6$ is hydrogen, —$R^8$—$OR^9$ or —$R^8$—$N(R^9)_2$; $R^{13}$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—$N(R^9)$S(O)$_tR^9$ (where t is 1 or 2), —$R^8$—$N(R^9)$C(=$NR^9$)$N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; each $R^8$ is independently a direct bond, a straight or branched alkylene chain, a straight or branched alkenylene chain or a straight or branched alkynylene chain; each $R^9$ is hydrogen, alkyl, optionally substituted aryl and optionally substituted aralkyl; and each $R^{10}$ is independently a straight or branched alkylene chain, a straight or branched alkenylene chain or a straight or branched alkynylene chain; or a stereoisomer, enantiomer or tautomer thereof or mixtures thereof, or a pharmaceutically acceptable salt or solvate thereof.

Of the embodiment of a compound of formula (II), one embodiment is a compound of formula (II) wherein

is an optionally substituted fused heterocyclyl or an optionally substituted fused heteroaryl; $R^1$ is —$R^8$—$OR^9$; $R^2$ is —$R^8$—$OR^9$; $R^5$ is alkyl or $R^5$ is a direct bond to the carbon at C14; $R^6$ is hydrogen, —$R^8$—$OR^9$ or —$R^8$—$N(R^9)_2$; $R^{13}$ is —$R^8$—$OR^9$ or —$R^8$—$N(R^9)_2$; each $R^8$ is independently a direct bond or a straight or branched alkylene chain; and each $R^9$ is hydrogen, alkyl, optionally substituted aryl and optionally substituted aralkyl.

Of the embodiment of a compound of formula (II), another embodiment is a compound of formula (II) wherein

is an optionally substituted fused heteroaryl; $R^1$ is —$R^8$—$OR^9$; $R^2$ is —$R^8$—$OR^9$; $R^5$ is alkyl; $R^6$ is hydrogen; $R^{13}$ is —$R^8$—$OR^9$ or —$R^8$—$N(R^9)_2$; each $R^8$ is independently a direct bond or a straight or branched alkylene chain; and each $R^9$ is hydrogen or alkyl.

Of the embodiment of a compound of formula (II), another embodiment is a compound of formula (II) wherein

is an optionally substituted monocyclic N-heteroaryl; $R^1$ is —$R^8$—$OR^9$; $R^2$ is —$R^8$—$OR^9$; $R^5$ is alkyl; $R^6$ is hydrogen; $R^{13}$ is —$R^8$—$OR^9$ or —$R^8$—$N(R^9)_2$; each $R^8$ is independently a direct bond or a straight or branched alkylene chain; and each $R^9$ is hydrogen or alkyl.

Of the embodiment of a compound of formula (II), another embodiment is a compound of formula (II) wherein

is an optionally substituted pyridinyl or an optionally substituted pyrazolyl; $R^1$ is —$R^8$—$OR^9$; $R^2$ is —$R^8$—$OR^9$; $R^5$ is alkyl; $R^6$ is hydrogen; $R^{13}$ is —$R^8$—$OR^9$ or —$R^8$—$N(R^9)_2$; each $R^8$ is independently a direct bond or a straight or branched alkylene chain; and each $R^9$ is hydrogen or alkyl.

Of the embodiment of a compound of formula (II), another embodiment is a compound of formula (II) selected from:

(1S,3S,4R)-4-((4aS,5R,6S,8aS)-5-(aminomethyl)-8a-methyl-2,4,4a,5,6,7,8,8a-octahydroindeno[1,2-c]pyrazol-6-yl)-3-(hydroxymethyl)-4-methylcyclohexanol dihydrochloride;

(1S,3S,4R)-4-((5aS,6R,7S,9aS)-6-(aminomethyl)-9a-methyl-5a,6,7,8,9,9a-hexahydro-5H-indeno[1,2-b]pyridin-7-yl)-3-(hydroxymethyl)-4-methylcyclohexanol; and (1S,3S,4R)-3-(hydroxymethyl)-4-((4aS,5R,6S,8aS)-5-(hydroxymethyl)-8a-methyl-1,4,4a,5,6,7,8,8a-octahydroindeno[1,2-c]pyrazol-6-yl)-4-methylcyclohexanol.

Of the embodiment of a compound of formula (II), another embodiment is a compound of formula (II) wherein

is an optionally substituted fused heterocyclyl; $R^1$ is —$R^8$—$OR^9$; $R^2$ is —$R^8$—$OR^9$; $R^5$ is alkyl; $R^6$ is hydrogen; $R^{13}$ is —$R^8$—$OR^9$ or —$R^8$—$N(R^9)_2$; each $R^8$ is independently a direct bond or a straight or branched alkylene chain; and each $R^9$ is hydrogen or alkyl.

Of the embodiment of a compound of formula (II), another embodiment is a compound of formula (II) wherein

is an optionally substituted fused tetrahydrofuryl; $R^1$ is —$R^8$—$OR^9$; $R^2$ is —$R^8$—$OR^9$; $R^5$ is alkyl; $R^6$ is hydrogen; $R^{13}$ is —$R^8$—$OR^9$ or —$R^8$—$N(R^9)_2$; each $R^8$ is independently a direct bond or a straight or branched alkylene chain; and each $R^9$ is hydrogen or alkyl.

Of the embodiment of a compound of formula (II), another embodiment is a compound of formula (II) selected from:
(1S,3S,4R)-4-((2R,3S,3aR,3bS,5'R,6S,7R,7aS,8aS)-7-(aminomethyl)-3,3b,5'-trimethyltetradecahydrospiro[indeno[2,1-b]furan-2,2'-pyran]-6-yl)-3-(hydroxymethyl)-4-methylcyclohexanol; and
(1S,3S,4R)-3-(hydroxymethyl)-4-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-4-methylcyclohexanol.

Another embodiment of the invention is a compound of formula (III):

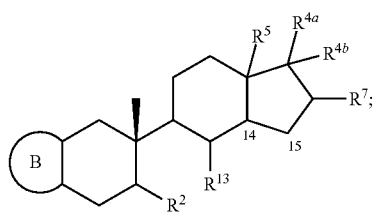

wherein

is an optionally substituted fused heterocyclyl or an optionally substituted heteroaryl; $R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—$OC(O)R^9$, —$R^8$—$C(O)OR^9$, —$R^8$—$C(O)N(R^9)_2$, —$N(R^9)C(O)OR^9$, —$R^8$—$N(R^9)S(O)_tR^9$ (where t is 1 or 2), —$R^8$—$N(R^9)C(=NR^9)N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^{4a}$ and $R^{4b}$ are each independently hydrogen, alkyl, alkenyl or alkynyl; or $R^{4a}$ is hydrogen, alkyl, alkenyl or alkynyl and $R^{4b}$ is a direct bond to the carbon to which $R^7$ is attached; or $R^{4a}$ and $R^{4b}$ together form alkylidene or haloalkylidene; $R^5$ is alkyl or $R^5$ is a direct bond to the carbon at C14; $R^7$ is hydrogen, —$R^8$—$OR^9$, —$R^8$—$N(R^9)_2$, or a direct bond to C15, provided that when $R^7$ is a direct bond to C15, $R^{4b}$ is not a direct bond to the carbon to which $R^7$ is attached; $R^{13}$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—$OC(O)R^9$, —$R^8$—C(O)$OR^9$, —$R^8$—C(O)N($R^9)_2$, —N($R^9$)C(O)$OR^9$, —$R^8$—N($R^9$)S(O)$_tR^9$ (where t is 1 or 2), —$R^8$—N($R^9$)C(=N$R^9$)N($R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; each $R^8$ is independently a direct bond, a straight or branched alkylene chain, a straight or branched alkenylene chain or a straight or branched alkynylene chain; each $R^9$ is hydrogen, alkyl, optionally substituted aryl and optionally substituted aralkyl; and each $R^{10}$ is independently a straight or branched alkylene chain, a straight or branched alkenylene chain or a straight or branched alkynylene chain; or a stereoisomer, enantiomer or tautomer thereof or mixtures thereof, or a pharmaceutically acceptable salt or solvate thereof.

Of the embodiment of a compound of formula (III), one embodiment is a compound of formula (III) wherein

is an optionally substituted fused heterocyclyl or an optionally substituted fused heteroaryl; $R^2$ is —$R^8$—$OR^9$; $R^{4a}$ and $R^{4b}$ are each independently hydrogen, alkyl, alkenyl or alkynyl; or $R^{4a}$ is hydrogen, alkyl, alkenyl or alkynyl and $R^{4b}$ is a direct bond to the carbon to which $R^7$ is attached; or $R^{4a}$ and $R^{4b}$ together form alkylidene or haloalkylidene; $R^5$ is alkyl or $R^5$ is a direct bond to the carbon at C14; $R^7$ is hydrogen, —$R^8$—$OR^9$, —$R^8$—$N(R^9)_2$, or a direct bond to C15, provided that when $R^7$ is a direct bond to C15, $R^{4b}$ is not a direct bond to the carbon to which $R^7$ is attached; $R^{13}$ is —$R^8$—$OR^9$; each $R^8$ is independently a direct bond or a straight or branched alkylene chain; and each $R^9$ is hydrogen, alkyl, optionally substituted aryl and optionally substituted aralkyl.

Of the embodiment of a compound of formula (III), another embodiment is a compound of formula (III) wherein

is an optionally substituted fused heterocyclyl or an optionally substituted fused heteroaryl; $R^2$ is —$R^8$—$OR^9$; $R^{4a}$ and $R^{4b}$ are each independently hydrogen, alkyl, alkenyl or alkynyl; or $R^{4a}$ and $R^{4b}$ together form alkylidene or haloalkylidene; $R^5$ is alkyl or $R^5$ is a direct bond to the carbon at C14; $R^7$ is hydrogen; $R^{13}$ is —$R^8$—$OR^9$; each $R^8$ is independently a direct bond or a straight or branched alkylene chain; and each $R^9$ is hydrogen, alkyl, optionally substituted aryl and optionally substituted aralkyl.

Of the embodiment of a compound of formula (III), another embodiment is a compound of formula (III) wherein

is an optionally substituted fused heteroaryl; $R^2$ is —$R^8$—$OR^9$; $R^{4a}$ and $R^{4b}$ are each independently hydrogen or alkyl; or $R^{4a}$ and $R^{4b}$ together form alkylidene or haloalkylidene; $R^5$ is alkyl or $R^5$ is a direct bond to the carbon at C14; $R^7$ is hydrogen; $R^{13}$ is —$R^8$—$OR^9$; each $R^8$ is independently a direct bond or a straight or branched alkylene chain; and each $R^9$ is hydrogen or alkyl.

Of the embodiment of a compound of formula (III), another embodiment is a compound of formula (III) wherein

is an optionally substituted fused oxaxolyl, pyrazolyl or thiazolyl; $R^2$ is —$R^8$—$OR^9$; $R^{4a}$ and $R^{4b}$ are each independently hydrogen or alkyl; or $R^{4a}$ and $R^{4b}$ together form alkylidene or haloalkylidene; $R^5$ is alkyl or $R^5$ is a direct bond to the carbon at C14; $R^7$ is hydrogen; $R^{13}$ is —$R^8$—$OR^9$; each $R^8$ is independently a direct bond or a straight or branched alkylene chain; and each $R^9$ is hydrogen or alkyl.

Of the embodiment of a compound of formula (III), another embodiment is a compound of formula (III) selected from:
((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol;
((3aS,4R,5S,7aS)-5-((5R,6S)-6-(hydroxymethyl)-5-methyl-4,5,6,7-tetrahydrobenzo[c]isoxazol-5-yl)-7a-methyl-1-methyleneoctahydro-1H-inden-4-yl)methanol;
((5R,6S)-5-((4R,5S)-4-(hydroxymethyl)-1,1-dimethyl-2,3,4,5,6,7-hexahydro-1H-inden-5-yl)-5-methyl-4,5,6,7-tetrahydrobenzo[d]isoxazol-6-yl)methanol; and
((3aS,4R,5S,7aS)-5-((5S,6R)-5-(hydroxymethyl)-2,6-dimethyl-4,5,6,7-tetrahydrobenzo[d]thiazol-6-yl)-7a-methyl-1-methyleneoctahydro-1H-inden-4-yl)methanol.

Another embodiment of the invention is a compound of formula (IV):

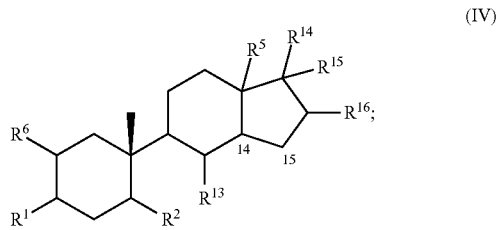

(IV)

wherein $R^1$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—C(O)$OR^9$, —$R^8$—C(O)$N(R^9)_2$ or —$N(R^9)$C(O)$OR^9$; $R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—N($R^9$)S(O)$_tR^9$ (where t is 1 or 2), —$R^8$—$N(R^9)$C(=$NR^9$)$N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^5$ is alkyl or $R^5$ is a direct bond to the carbon at C14; $R^6$ is hydrogen, —$R^8$—$OR^9$ or —$R^8$—$N(R^9)_2$; $R^{13}$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—N($R^9$)—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—N($R^9$)S(O)$_tR^9$ (where t is 1 or 2), —$R^8$—$N(R^9)$C(=$NR^9$)$N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^{14}$ is alkyl, alkenyl, alkynyl, optionally substituted aryl or optionally substituted heteroaryl; $R^{15}$ is alkyl, —$R^8$—$OR^9$ or a direct bond to the carbon to which $R^{16}$ is attached, provided that $R^{15}$ is not alkyl when $R^{14}$ is alkyl, alkenyl or alkynyl; $R^{16}$ is hydrogen, —$R^8$—$OR^9$, —$R^8$—$N(R^9)_2$, or a direct bond to C15, provided that when $R^{16}$ is a direct bond to C15, $R^{15}$ is not a direct bond to the carbon to which $R^{16}$ is attached; and each $R^8$ is independently a direct bond, a straight or branched alkylene chain, a straight or branched alkenylene chain or a straight or branched alkynylene chain; each $R^9$ is hydrogen, alkyl, optionally substituted aryl and optionally substituted aralkyl; and each $R^{10}$ is independently a straight or branched alkylene chain, a straight or branched alkenylene chain or a straight or branched alkynylene chain; or a stereoisomer, enantiomer or tautomer thereof or mixtures thereof, or a pharmaceutically acceptable salt or solvate thereof.

Of the embodiment of a compound of formula (IV), one embodiment is a compound of formula (IV) wherein $R^1$ is —$R^8$—$OR^9$; $R^2$ is —$R^8$—$OR^9$; $R^5$ is alkyl or $R^5$ is a direct bond to the carbon at C14; $R^6$ is hydrogen, —$R^8$—$OR^9$ or —$R^8$—$N(R^9)_2$; $R^{13}$ is —$R^8$—$OR^9$ or —$R^8$—$N(R^9)_2$; $R^{14}$ is alkyl, alkenyl, alkynyl, optionally substituted aryl or optionally substituted heteroaryl; $R^{15}$ is alkyl, —$R^8$—$OR^9$ or a direct bond to the carbon to which $R^{16}$ is attached, provided that $R^{15}$ is not alkyl when $R^{14}$ is alkyl, alkenyl or alkynyl; $R^{16}$ is hydrogen or —$R^8$—$OR^9$, —$R^8$—$N(R^9)_2$; and each $R^8$ is independently a direct bond or a straight or branched alkylene chain; and each $R^9$ is hydrogen, alkyl, optionally substituted aryl and optionally substituted aralkyl.

Of the embodiment of a compound of formula (IV), another embodiment is a compound of formula (IV) wherein $R^1$ is —$R^8$—$OR^9$; $R^2$ is —$R^8$—$OR^9$; $R^5$ is alkyl; $R^6$ is hydrogen; $R^{13}$ is —$R^8$—$OR^9$ or —$R^8$—$N(R^9)_2$; $R^{14}$ is alkyl or alkynyl; $R^{15}$ is —$R^8$—$OR^9$; $R^{16}$ is hydrogen; and each $R^8$ is independently a direct bond or a straight or branched alkylene chain; and each $R^9$ is hydrogen or alkyl.

Of the embodiment of a compound of formula (IV), another embodiment is a compound of formula (IV) selected from:
(1S,3aS,4R,5S,7aS)-4-(aminomethyl)-5-((1R,2S,4S)-4-hydroxy-2-(hydroxymethyl)-1-methylcyclohexyl)-1,7a-dimethyloctahydro-1H-inden-1-ol;
(1S,3aS,4R,5S,7aS)-5-((1R,2S,4S)-4-hydroxy-2-(hydroxymethyl)-1-methylcyclohexyl)-4-(hydroxymethyl)-1,7a-dimethyloctahydro-1H-inden-1-ol; and
(1R,3aS,4R,5S,7aS)-1-ethynyl-5-((1R,2S,4S)-4-hydroxy-2-(hydroxymethyl)-1-methylcyclohexyl)-4-(hydroxymethyl)-7a-methyloctahydro-1H-inden-1-ol.

Of the embodiment of a compound of formula (IV), another embodiment is a compound of formula (IV) wherein $R^1$ is —$R^8$—$OR^9$; $R^2$ is —$R^8$—$OR^9$; $R^5$ is alkyl or $R^5$ is a direct bond to the carbon at C14; $R^6$ is hydrogen; $R^{13}$ is —$R^8$—$OR^9$ or —$R^8$—$N(R^9)_2$; $R^{14}$ is optionally substituted aryl; $R^{15}$ is alkyl, —$R^8$—$OR^9$ or a direct bond to the carbon to which $R^{16}$ is attached; $R^{16}$ is hydrogen or —$R^8$—$OR^9$; and each $R^8$ is independently a direct bond or a straight or branched alkylene chain; and each $R^9$ is hydrogen or alkyl.

Of the embodiment of a compound of formula (IV), another embodiment is a compound of formula (IV) selected from:
(1S,3S,4R)-4-((3aS,6S,7R,7aS)-7-(aminomethyl)-3a-methyl-3-phenyl-3a,4,5,6,7,7a-hexahydro-1H-inden-6-yl)-3-(hydroxymethyl)-4-methylcyclohexano;

(1S,3aS,4R,5S,7aS)-4-(aminomethyl)-5-((1R,2S,4S)-4-hydroxy-2-(hydroxymethyl)-1-methylcyclohexyl)-7a-methyl-1-phenyloctahydro-1H-inden-1-ol;

(1S,2R,4R,5S)-4-(aminomethyl)-5-((1R,2S,4S)-4-hydroxy-2-(hydroxymethyl)-1-methylcyclohexyl)-1-methyl-1-phenyl-2,3,4,5,6,7-hexahydro-1H-inden-2-ol;

(1S,3S,4R)-3-(hydroxymethyl)-4-((3aS,6S,7R,7aS)-7-(hydroxymethyl)-3a-methyl-3-phenyl-3a,4,5,6,7,7a-hexahydro-1H-inden-6-yl)-4-methylcyclohexanol;

(1S,3aS,4R,5S,7aS)-5-((1R,2S,4S)-4-hydroxy-2-(hydroxymethyl)-1-methylcyclohexyl)-4-(hydroxymethyl)-7a-methyl-1-phenyloctahydro-1H-inden-1-ol; and (1S,2R,4R,5S)-5-((1R,2S,4S)-4-hydroxy-2-(hydroxymethyl)-1-methylcyclohexyl)-4-(hydroxymethyl)-1-methyl-1-phenyl-2,3,4,5,6,7-hexahydro-1H-inden-2-ol.

Of the embodiment of a compound of formula (IV), another embodiment is a compound of formula (IV) wherein $R^1$ is —$R^8$—$OR^9$; $R^2$ is —$R^8$—$OR^9$; $R^5$ is alkyl or $R^5$ is a direct bond to the carbon at C14; $R^6$ is hydrogen; $R^{13}$ is —$R^8$—$OR^9$ or —$R^8$—$N(R^9)_2$; $R^{14}$ is optionally substituted heteroaryl; $R^{15}$ is alkyl, —$R^8$—$OR^9$ or a direct bond to the carbon to which $R^{16}$ is attached; $R^{16}$ is hydrogen or —$R^8$—$OR^9$, —$R^8$—$N(R^9)_2$; and each $R^8$ is independently a direct bond or a straight or branched alkylene chain; and each $R^9$ is hydrogen or alkyl.

Of the embodiment of a compound of formula (IV), another embodiment is a compound of formula (IV) selected from:

(1S,3aS,4R,5S,7aS)-4-(aminomethyl)-1-(furan-2-yl)-5-((1R,2S,4S)-4-hydroxy-2-(hydroxymethyl)-1-methylcyclohexyl)-7a-methyloctahydro-1H-inden-1-ol;

(1S,3S,4R)-4-((3aS,6S,7R,7aS)-7-(aminomethyl)-3-(furan-2-yl)-3a-methyl-3a,4,5,6,7,7a-hexahydro-1H-inden-6-yl)-3-(hydroxymethyl)-4-methylcyclohexanol;

(1S,3aS,4R,5S,7aS)-4-(aminomethyl)-5-((1R,2S,4S)-4-hydroxy-2-(hydroxymethyl)-1-methylcyclohexyl)-7a-methyl-1-(thiophen-2-yl)octahydro-1H-inden-1-ol;

(1S,3S,4R)-4-((3aS,6S,7R,7aS)-7-(aminomethyl)-3a-methyl-3-(thiophen-2-yl)-3a,4,5,6,7,7a-hexahydro-1H-inden-6-yl)-3-(hydroxymethyl)-4-methylcyclohexanol;

(1S,3aS,4R,5S,7aS)-4-(aminomethyl)-5-((1R,2S,4S)-4-hydroxy-2-(hydroxymethyl)-1-methylcyclohexyl)-7a-methyl-1-(pyridin-2-yl)octahydro-1H-inden-1-ol;

(1S,3aS,4R,5S,7aS)-4-(aminomethyl)-5-((1R,2S,4S)-4-hydroxy-2-(hydroxymethyl)-1-methylcyclohexyl)-7a-methyl-1-(thiazol-2-yl)octahydro-1H-inden-1-ol;

(1S,3S,4R)-4-((3aS,6S,7R,7aS)-3-(furan-2-yl)-7-(hydroxymethyl)-3a-methyl-3a,4,5,6,7,7a-hexahydro-1H-inden-6-yl)-3-(hydroxymethyl)-4-methylcyclohexanol;

(1S,3aS,4R,5S,7aS)-1-(furan-2-yl)-5-((1R,2S,4S)-4-hydroxy-2-(hydroxymethyl)-1-methylcyclohexyl)-4-(hydroxymethyl)-7a-methyloctahydro-1H-inden-1-ol;

(1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiophen-2-yl)octahydro-1H-inden-1-ol;

(1S,3S,4R)-3-(hydroxymethyl)-4-((3aS,6S,7R,7aS)-7-(hydroxymethyl)-3a-methyl-3-(thiophen-2-yl)-3a,4,5,6,7,7a-hexahydro-1H-inden-6-yl)-4-methylcyclohexanol;

(1S,3aS,4R,5S,7aS)-5-((1R,2S,4S)-4-hydroxy-2-(hydroxymethyl)-1-methylcyclohexyl)-4-(hydroxymethyl)-7a-methyl-1-(pyridin-2-yl)octahydro-1H-inden-1-ol; and (1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiazol-2-yl)octahydro-1H-inden-1-ol.

Another embodiment of the invention is a compound of formula (V):

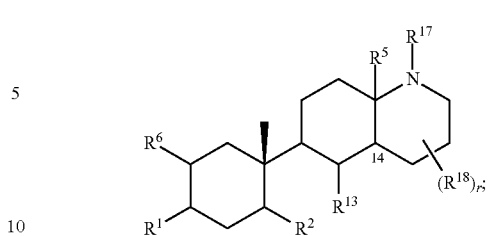

(V)

wherein r is 0, 1, 2 or 3; $R^1$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—N(R^9)—$R^{10}$—$OR^9$, —$R^8$—N(R^9)—$R^{10}$—$N(R^9)_2$, —$R^8$—C(O)$OR^9$, —$R^8$—C(O)N($R^9$)$_2$ or —N($R^9$)C(O)$OR^9$; $R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—N($R^9$)—$R^{10}$—$OR^9$, —$R^8$—N($R^9$)—$R^{10}$—$N(R^9)_2$, —$R^8$—OC(O)$R^9$, —$R^8$—C(O)$OR^9$, —$R^8$—C(O)N($R^9$)$_2$, —N($R^9$)C(O)$OR^9$, —$R^8$—N($R^9$)S(O)$_t$$R^9$ (where t is 1 or 2), —$R^8$—N($R^9$)C(=N$R^9$)N($R^9$)$_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^5$ is alkyl or $R^5$ is a direct bond to the carbon at C14; $R^6$ is hydrogen, —$R^8$—$OR^9$ or —$R^8$—$N(R^9)_2$; $R^{13}$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—N($R^9$)—$R^{10}$—$OR^9$, —$R^8$—N($R^9$)—$R^{10}$—$N(R^9)_2$, —$R^8$—OC(O)$R^9$, —$R^8$—C(O)$OR^9$, —$R^8$—C(O)N($R^9$)$_2$, —N($R^9$)C(O)$OR^9$, —$R^8$—N($R^9$)S(O)$_t$$R^9$ (where t is 1 or 2), —$R^8$—N($R^9$)C(=N$R^9$)N($R^9$)$_2$, alkyl, alkenyl, aralkyl, aralkenyl, heterocyclylalkyl, heteroarylalkyl or heteroarylalkenyl; $R^{17}$ is hydrogen, alkyl, haloalkyl, optionally substituted aryl, optionally substituted aralkyl or —C(O)$OR^9$; $R^{18}$ is hydrogen, halo, haloalkyl, alkyl, optionally substituted aryl, optionally substituted aralkyl, oxo or —$OR^9$; each $R^8$ is independently a direct bond, a straight or branched alkylene chain, a straight or branched alkenylene chain or a straight or branched alkynylene chain; each $R^9$ is hydrogen, alkyl, optionally substituted aryl and optionally substituted aralkyl; and each $R^{10}$ is independently a straight or branched alkylene chain, a straight or branched alkenylene chain or a straight or branched alkynylene chain; or a stereoisomer, enantiomer or tautomer thereof or mixtures thereof, or a pharmaceutically acceptable salt or solvate thereof.

Of the embodiment of a compound of formula (V), one embodiment is a compound of formula (V) wherein r is 0, 1, 2 or 3; $R^1$ is —$R^8$—$OR^9$; $R^2$ is —$R^8$—$OR^9$; $R^5$ is alkyl or $R^5$ is a direct bond to the carbon at C14; $R^6$ is hydrogen, —$R^8$—$OR^9$ or —$R^8$—$N(R^9)_2$; $R^{13}$ is —$R^8$—$OR^9$ or —$R^8$—$N(R^9)_2$; $R^{17}$ is hydrogen, alkyl, haloalkyl, optionally substituted aryl, optionally substituted aralkyl or —C(O)$OR^9$; $R^{18}$ is hydrogen, halo, haloalkyl, alkyl, optionally substituted aryl, optionally substituted aralkyl, oxo or —$OR^9$; each $R^8$ is independently a direct bond, a straight or branched alkylene chain, a straight or branched alkenylene chain or a straight or branched alkynylene chain; and each $R^9$ is hydrogen, alkyl, aryl and aralkyl.

Of the embodiment of a compound of formula (V), another embodiment is a compound of formula (V) wherein r is 1; $R^1$ is —$R^8$—$OR^9$; $R^2$ is —$R^8$—$OR^9$; $R^5$ is alkyl or $R^5$ is a direct bond to the carbon at C14; $R^6$ is hydrogen; $R^{13}$ is —$R^8$—$OR^9$ or —$R^8$—$N(R^9)_2$; $R^{17}$ is hydrogen or alkyl; $R^{18}$ is hydrogen, oxo or —$OR^9$; each $R^8$ is independently a direct bond or a straight or branched alkylene chain; and each $R^9$ is hydrogen or alkyl.

Of the embodiment of a compound of formula (V), another embodiment is a compound of formula (V) which is (4aS,5R,6S,8aS)-5-(aminomethyl)-6-((1R,2S,4S)-4-hydroxy-2-(hydroxymethyl)-1-methylcyclohexyl)-8a-methyl-octahydroquinolin-2(1H)-one.

Another embodiment of the invention is a compound of formula (VI):

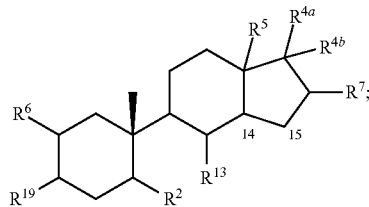

(VI)

wherein: $R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—$N(R^9)$S(O)$_tR^9$ (where t is 1 or 2), —$R^8$—N$(R^9)$C(=$NR^9$)$N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^{4a}$ and $R^{4b}$ are each independently hydrogen, alkyl, alkenyl or alkynyl; or $R^{4a}$ is hydrogen, alkyl, alkenyl or alkynyl and $R^{4b}$ is a direct bond to the carbon to which $R^7$ is attached; or $R^{4a}$ and $R^{4b}$ together form alkylidene or haloalkylidene; $R^5$ is alkyl or $R^5$ is a direct bond to the carbon at C14; $R^6$ is hydrogen, —$R^8$—$OR^9$ or —$R^8$—$N(R^9)_2$; $R^7$ is hydrogen, —$R^8$—$OR^9$, —$R^8$—$N(R^9)_2$, or a direct bond to C15, provided that when $R^7$ is a direct bond to C15, $R^{4b}$ is not a direct bond to the carbon to which $R^7$ is attached; $R^{13}$ is —$R^8$—$OR^9$, —$R^8$—$N(R^9)_2$, —$R^8$—O—$R^{10}$—$OR^9$, —$R^8$—O—$R^{10}$—$N(R^9)_2$, —R—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—$N(R^9)$S(O)$_tR^9$ (where t is 1 or 2), —$R^8$—$N(R^9)$C(=$NR^9$)$N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl; $R^{19}$ is —$R^8$—$N(R^9)$C(O)$R^9$; each $R^8$ is independently a direct bond, a straight or branched alkylene chain, a straight or branched alkenylene chain or a straight or branched alkynylene chain; each $R^9$ is hydrogen, alkyl, optionally substituted aryl and optionally substituted aralkyl; and each $R^{10}$ is independently a straight or branched alkylene chain, a straight or branched alkenylene chain or a straight or branched alkynylene chain; or a stereoisomer, enantiomer or tautomer thereof or mixtures thereof, or a pharmaceutically acceptable salt or solvate thereof.

Of the embodiment of a compound of formula (VI), one embodiment is a compound of formula (VI) wherein $R^2$ is —$R^8$—$OR^9$; $R^{4a}$ and $R^{4b}$ are each independently hydrogen, alkyl, alkenyl or alkynyl; or $R^{4a}$ is hydrogen, alkyl, alkenyl or alkynyl and $R^{4b}$ is a direct bond to the carbon to which $R^7$ is attached; or $R^{4a}$ and $R^{4b}$ together form alkylidene or haloalkylidene; $R^5$ is alkyl or $R^5$ is a direct bond to the carbon at C14; $R^6$ is hydrogen, —$R^8$—$OR^9$ or —$R^8$—$N(R^9)_2$; $R^7$ is hydrogen, —$R^8$—$OR^9$, —$R^8$—$N(R^9)_2$, or a direct bond to C15, provided that when $R^7$ is a direct bond to C15, $R^{4b}$ is not a direct bond to the carbon to which $R^7$ is attached; $R^{13}$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—OC(O)$R^9$, —$R^8$—C(O)$OR^9$, —$R^8$—C(O)$N(R^9)_2$, —$N(R^9)$C(O)$OR^9$, —$R^8$—$N(R^9)$S(O)$_tR^9$ (where t is 1 or 2), or —$R^8$—$N(R^9)$C(=$NR^9$)$N(R^9)_2$; $R^{19}$ is —$R^8$—$N(R^9)$C(O)$R^9$; each $R^8$ is independently a direct bond or a straight or branched alkylene chain; each $R^9$ is hydrogen, alkyl, optionally substituted aryl and optionally substituted aralkyl; and each $R^{10}$ is independently a straight or branched alkylene chain, a straight or branched alkenylene chain or a straight or branched alkynylene chain.

Of the embodiment of a compound of formula (VI), another embodiment is a compound of formula (VI) wherein $R^2$ is —$R^8$—$OR^9$; $R^{4a}$ and $R^{4b}$ together form alkylidene or haloalkylidene; $R^5$ is alkyl or $R^5$ is a direct bond to the carbon at C14; $R^6$ is hydrogen; $R^7$ is hydrogen or a direct bond to C15, provided that when $R^7$ is a direct bond to C15, $R^{4b}$ is not a direct bond to the carbon to which $R^7$ is attached; $R^{13}$ is —$R^8$—$OR^9$, —$R^8$—$N(R^9)_2$, —$N(R^9)$C(O)$OR^9$, —$R^8$—$N(R^9)$S(O)$_tR^9$ (where t is 1 or 2), or —$R^8$—$N(R^9)$C(=$NR^9$)$N(R^9)_2$; $R^{19}$ is —$R^8$—$N(R^9)$C(O)$R^9$; each $R^8$ is independently a direct bond or a straight or branched alkylene chain; and each $R^9$ is hydrogen or alkyl.

Of the embodiment of a compound of formula (VI), another embodiment is a compound of formula (VI) wherein $R^2$ is —$R^8$—$OR^9$; $R^{4a}$ and $R^{4b}$ together form alkylidene or haloalkylidene; $R^5$ is alkyl; $R^6$ is hydrogen; $R^7$ is hydrogen; $R^{13}$ is —$R^8$—$OR^9$; $R^{19}$ is —$R^8$—$N(R^9)$C(O)$R^9$; each $R^8$ is independently a direct bond or a straight or branched alkylene chain; and each $R^9$ is hydrogen or alkyl.

Of the embodiment of a compound of formula (VI), another embodiment is a compound of formula (VI) which is N-((1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl)acetamide.

It is understood that any embodiment of the compounds of the invention, as set forth above, and any specific substituent set forth herein for a particular R group in the compounds of the invention, as set forth above, may be independently combined with other embodiments and/or substituents of compounds of the invention to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention.

Another embodiment of the invention are methods for treating a disease, disorder or condition in a mammal in need thereof is where the disease, disorder or condition is an autoimmune disease, disorder or condition, an inflammatory disease, disorder or condition, or a neoplastic or cell proliferative disease, disorder or condition.

Another embodiment of the methods for treating a disease, disorder or condition in a mammal in need thereof is where the disease, disorder or condition is an autoimmune disease, disorder or condition selected from idiopathic pulmonary fibrosis, an inflammatory bowel disease, rheumatoid arthritis, Still's Disease, Sjögren's Syndrome, systemic lupus erythematosus, multiple sclerosis, psoriasis and systemic sclerosis.

Another embodiment of the methods for treating a disease, disorder or condition in a mammal in need thereof is where the disease, disorder or condition is an inflammatory bowel disease selected from Crohn's Disease and ulcerative colitis.

Another embodiment of the methods for treating a disease, disorder or condition in a mammal in need thereof is where the disease, disorder or condition is an inflammatory disease, disorder or condition selected from acute respiratory distress syndrome, allergic rhinitis, Alzheimer's Disease, asthma, an ocular inflammatory disease, atopic dermatitis, bladder pain syndrome/interstitial cystitis, chronic obstructive pulmonary disease (COPD) including emphysematous, bronchitic, and alpa 1 anti-trypsin deficiency related COPD; dermal contact hypersitivy, eczema, eosiniphilic gastrointestinal disorder, fibromyalgia, gout, hepatic fibrosis, irritable bowel syndrome, ischemic reperfusion disease, kidney fibrosis, pancratitis, Parkisons Disease, post operative inflammation, a seronegative spondyloarthropathy, and vasculitis.

Another embodiment of the methods for treating a disease, disorder or condition in a mammal in need thereof is where the disease, disorder or condition is an ocular inflammatory disease selected from allergic conjunctivitis, dry eye, and uveitis.

Another embodiment of the methods for treating a disease, disorder or condition in a mammal in need thereof is where the disease, disorder or condition is a seronegative spondyloarthropathy selected from anklyosing spondylitis, psoriatic arthritis, and Reiter's Syndrome.

Another embodiment of the methods for treating a disease, disorder or condition in a mammal in need thereof is where the disease, disorder or condition is vasculitis selected from Wegener's Granulomatosis, polyarteritis nodosa, leucocytoclastic vasculitis, Churg-Strauss Syndrome, cryoglobulinemic vasculitis, and giant cell arteritis.

Another embodiment of the methods for treating a disease, disorder or condition in a mammal in need thereof is where the disease, disorder or condition is a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

Another embodiment of the invention is a method of using the compounds of the invention as standards or controls in in vitro or in vivo assays in determining the efficacy of test compounds in modulating SHIP1 activity.

In another embodiment of the invention, the compounds of the invention are isotopically-labeled by having one or more atoms therein replaced by an atom having a different atomic mass or mass number. Such isotopically-labeled (i.e., radiolabelled) compounds of the invention are considered to be within the scope of this invention. Examples of isotopes that can be incorporated into the compounds of the invention include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$ $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action for SHIP1 modulation, or binding affinity to pharmacologically important site of action for SHIP1 modulation. Certain isotopically-labeled compounds of the invention, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of the invention can generally be prepared by conventional techniques known to those skilled in the art or by processes analogous to those described in the Examples as set out below using an appropriate isotopically-labeled reagent in place of the non-labeled reagent previously employed.

In other embodiments, preferred stereochemistry of the compounds of the invention is shown below, using the compound of formula (I) as an example:

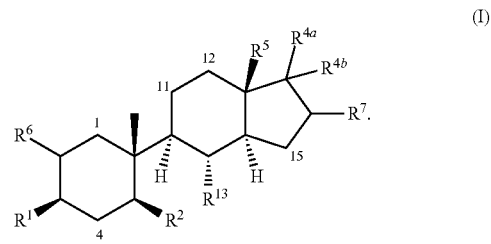

Specific embodiments of the compounds of the invention are described in more detail below in the Preparation of the Compounds of the Invention.

Utility and Testing of the Compounds of the Invention

Compounds of the invention above have activity as SHIP1 modulators and utility over a wide range of therapeutic applications, and may be used to treat any of a variety of diseases, disorders or conditions that would benefit from SHIP1 modulation. For example, such diseases, disorders or conditions include (but are not limited to) autoimmune diseases such as idiopathic pulmonary fibrosis, inflammatory bowel disease (including Crohn's Disease and ulcerative colitis), rheumatoid arthritis, Still's Disease, Sjögren's Syndrome, systemic lupus erythematosus, multiple sclerosis, psoriasis, and systemic sclerosis; inflammatory diseases such as acute respiratory distress syndrome (ARDS), allergic rhinitis, Alzheimer's Disease, asthma, ocular inflammatory diseases (including allergic conjunctivitis, dry eye, and uveitis), chronic obstructive pulmonary disease (COPD) including emphysematous, brochitic, and COPD due to alpha 1 anti-trypsin deficiency, atopic dermatitis, dermal contact hypersensitivity, eczema, eosiniphilic gastrointestinal disorder, fibromyalgia, gout, hepatic fibrosis, irritable bowel syndrome, bladder pain syndrome/interstitial cystitis, post operative inflammation, ischemic reperfusion disease, kidney fibrosis, pancreatitis, Parkinsons Disease, seronegative spondyloarthropathies (including anklyosing spondylitis, psoriatic arthritis, and Reiter's Syndrome), and vasculitis (including Wegener's Granulomatosis, polyarteritis nodosa, leucocytoclastic vasculitis, Churg-Strauss Syndrome, cryoglobulinemic vasculitis and giant cell arteritis); and neoplastic diseases or other cell proliferative disorders such as acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

The effectiveness of the compounds of the invention as a SHIP1 modulator may be determined by any number of known techniques, including the assays set forth in Examples 39-42.

Pharmaceutical Compositions of the Invention and Administration

For the purposes of administration, the compounds of the present invention may be formulated as pharmaceutical compositions. Pharmaceutical compositions comprise one or more compounds of this invention in combination with a pharmaceutically acceptable carrier and/or diluent. The compound is present in the composition in an amount which is effective to treat a particular disorder, that is, in an amount sufficient to achieve SHIP1 modulation activity, and preferably with acceptable toxicity to the patient. Typically, the pharmaceutical compositions of the present invention may include a compound in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds in an appropriate manner, and in accordance with accepted practices, such as those disclosed in *Remington's Pharmaceutical Sciences* (Mack Pub. Co., N.J. current edition).

In another embodiment, the present invention provides a method for modulation SHIP1 generally and, more specifically, to treating the diseases, disorders and conditions as discussed above. Such methods include administering of a compound of the present invention to a mammal, preferably a human, in an amount sufficient to treat the condition. In this context, "treat" includes prophylactic administration. Such methods include systemic administration of a compound of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

Preparation of the Compounds of the Invention

The following Reaction Schemes illustrate methods to make compounds of the present invention, i.e., compounds of formula (I), as set forth above in the Summary of the Invention.

The compounds of the present invention may be prepared by known organic synthesis techniques, including the methods described in more detail in the Examples. In general, the compounds of formula (I) may be made by the following Reaction Schemes, wherein all substituents are as defined above unless indicated otherwise. Although not generally depicted in the following schemes, one skilled in the art will understand that appropriate protecting group strategies may be useful in preparing compounds of formula (I). Protecting group methodology is well known to those skilled in the art (see, for example, Greene, T. W. and Wuts, P. G. M. *Greene's Protective Groups in Organic Synthesis* (2006), 4$^{th}$ Ed. Wiley).

It is also understood that one skilled in the art would be able to make the compounds of the invention by similar methods, by methods known to one skilled in the art, or by methods similar to the methods disclosed in U.S. Pat. Nos. 6,635,629 and 7,601,874. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure,* 6th edition (Wiley, 2007)) or prepared as described herein. Certain starting materials, or their salts thereof, may be prepared according to the methods disclosed in U.S. Pat. Nos. 6,635,629 and 7,601,874, the relevant disclosures therein are incorporated in reference herein, or by methods known to one skilled in the art.

It is also understood that in the following description, combinations of substituents and/or variables of the depicted formulae are permissible only if such contributions result in stable compounds.

It will also be appreciated by those skilled in the art, although protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Although depicted without stereochemistry, one skilled in the art will recognize that the compounds depicted in the following general Reaction Schemes can also be prepared in an optically pure form by utilizing methods known to one skilled in the art, such as the use of stereoselective reagents, chiral starting materials and phase transfer catalysts.

Abbreviations

The following abbreviations may be used herein in the following general reaction schemes and the Examples:
Ac$_2$O for acetic anhydride;
AcOH for acetic acid;
AlMe$_3$ for trimethylaluminum;
Boc for tert-butoxycarbonyl;
BH$_3$.THF for borane tetrahydrofuran complex;
BnBr for benzyl bromide;
Bu$_3$SnH for tributyltin hydride;
n-BuLi for n-butyl lithium;
t-BuOOH for tert-butyl hydroperoxide;

CDI for 1,1'-carbonyldiimidazole;
d for days;
DABCO for 1,4-diazalbicyclo[2.2.2]octane;
DBU for 1,8-diazabicyclo[5.4.0]undec-7-ene;
DCC for N,N'-dicyclohexylcarbodiimide;
DCE for dichloroethane;
DIAD for diisopropyl azodicarboxylate;
Diglyme for diethylene glycol dimethyl ether;
DIPEA/DIEA for N,N-diisopropylethylamine;
DMAP for 4-dimethylaminopyridine;
DMF for N,N-dimethylformamide;
DMSO for dimethyl sulfoxide;
DPPA for diphenylphosphoryl azide;
$Et_2O$ for diethyl ether;
$Et_3N$ for triethylamine;
EtNCO for ethyl isocyanate;
EtOAc for ethyl acetate;
EtOH for ethanol;
h for hours;
$H_2/Pd/C$ for hydrogen on palladium on charcoal;
$H_2NMe.HCl$ for methylamine hydrochloride;
HBTU for O-(benzotriazol-1-yl)-N,N,N',N'-tetramethyluronium hexafluorophosphate;
IBX for 2-iodoxybenzoic acid;
Imid for imidazole;
i-PrOH for iso-propanol;
Imid. for imidazole;
KO$^t$Bu for potassium tert-butoxide;
$LiAlH_4$/LAH for lithium aluminum hydride;
$LiEt_3BH$ for lithium triethylborohydride (Super hydride);
m-CPBA/MCPBA for meta-chloroperoxybenzoic acid;
m for minutes;
MeCN for acetonitrile;
MeI for methyl iodide;
MeNCS for methyl isocyanate;
2-MePhCO$_2$H for o-toluic acid;
3-MePhCO$_2$H for m-toluic acid;
4-MePhCO$_2$H for p-toluic acid;
Me$_4$Phen for 3,4,7,8-tetramethyl-[1,10]-phenanthroline;
MeOCH$_2$PPh$_3$Cl for methoxymethyl triphenylphosphonium chloride;
MeOH for methanol;
MePPh$_3$Br for methyl triphenylphosphonium bromide;
MeSO$_3$SiMe$_3$ for trimethylsilylmethanesulfonate;
MsCl for mesyl chloride;
MW for microwave;
NaOMe for sodium acetate;
NaSEt for sodium ethanethiolate;
NaBH(OAc)$_3$ for sodium triacetoxyborohydride;
n-BuLi for n-butyllithium;
NMO for N-methylmorpholine N-oxide;
NMP for N-methyl-2-pyrrolidone;
NMR for nuclear magnetic resonance;
pTsNHNH$_2$ for para-toluenesulfonyl hydrazide;
PCC for pyridinium chlorochromate;
Pd/C for palladium metal on charcoal;
PhCO$_2$H for benzoic acid;
PPh$_3$ for triphenylphosphine;
Ph$_3$PMeBr for methyltriphenylphosphonium bromide;
PhMe for toluene;
PivCl for trimethylacetyl chloride;
POCl$_3$ for phosphoryl chloride;
PTSA/PTSA.H$_2$O for para-toluenesulfonic acid/para-toluenesulfonic acid monohydrate;
PyBOP for benzotriazol-1-yl-oxytripyrrolidinophosphonium hexafluorophosphate;
Pyr for pyridine;
SEMCl for 2-(trimethylsilyl)ethoxymethyl chloride;
SEM for 2-(trimethylsilyl)ethoxymethyl;
TBAF for tetrabutylammonium fluoride;
TBDPS for tert-butyldiphenylsilyl;
TBDPS for tert-butyldiphenylsilyl;
TBDPSCl for tert-butyldiphenylsilyl chloride;
TBS/TBDMS for tert-butyldimethylsilyl;
TBSCl for tert-butyldimethylsilyl chloride;
TBTU for O-(benzotriazol-1-yl)-N,N,N',N'-tetramethyluronium tetrafluoroborate;
TEA for triethylamine;
TFA for trifluoroacetic acid;
TFAA for trifluoroacetic anhydride;
THF for tetrahydrofuran;
TLC for thin layer chromatography;
TMSOTf for trimethylsilyl triflate;
TPAP for tetrapropylammonium perruthenate;
TPSH for 2,4,6-triisopropylbenzenesulfonyl hydrazide; and
VAZO® for 1,1'-azobis(cyclohexanecarbonitrile).

A. Preparation of Compounds of Formula (I)

Compounds of formula (I-1) are compounds of formula (I), as described above in the Summary of the Invention, where $R^{4a}$ and $R^{4b}$ are each methyl, $R^5$ is a direct bond to the carbon at C14 and $R^3$ is —$R^8$—$N(R^9)$—$R^{12}$ where $R^8$ and $R^9$ are as described above for compounds of formula (I) and $R^{12a}$ is optionally substituted heterocyclyl, and are prepared as described below in Reaction Scheme 1A wherein $R^1$, $R^2$, $R^6$, $R^7$, $R^8$ and $R^9$ are as described above in the Summary of the Invention for compounds of formula (I) and $R^{12a}$ is optionally substituted heterocyclyl, preferably piperidinyl, piperazinyl or morpholinyl:

REACTION SCHEME 1A

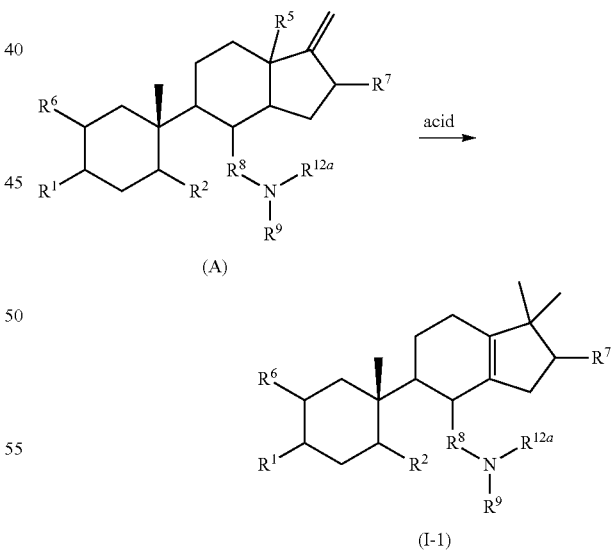

Compounds of formula (A) may be prepared by methods known to one skilled in the art or by methods similar to the methods disclosed in U.S. Pat. No. 7,601,874.

In general, compounds of formula (I-1) are prepared, as described above in Reaction Scheme 1A, by treating a compound of formula (A) with an acid, preferably HCl, to form the compound of formula (I-1).

B. Preparation of Compounds of Formulae (I-2), (I-3), (I-4) and (I-5)

Compounds of formulae (I-1), (I-3), (I-4) and (I-5) are compounds of formula (I), as described above in the Summary of the Invention, where $R^{4a}$ and $R^{4b}$ together form methylene and $R^5$ is a direct bond to the carbon at C14 and $R^3$ is $-R^8-N(R^9)C(O)R^1$, $-R^8-N(R^9)C(=NCN)N(R^{9a})_2$, $-R^8-N(R^9)C(O)N(R^{9a})_2$ or $-R^8-N(R^9)C(S)N(R^{9a})_2$ where each $R^8$, each $R^9$, each $R^{9a}$ and $R^{11}$ are as described above for compounds of formula (I), and are prepared as described below in Reaction Scheme 1A wherein $R^1$, $R^2$, $R^6$, $R^7$, $R^8$, $R^9$, $R^{9a}$ and $R^{11}$ are as described above for compounds of formula (I), A is oxygen or sulfur and $Lg^2$ is a leaving group, such as thiomethyl:

REACTION SCHEME 1B

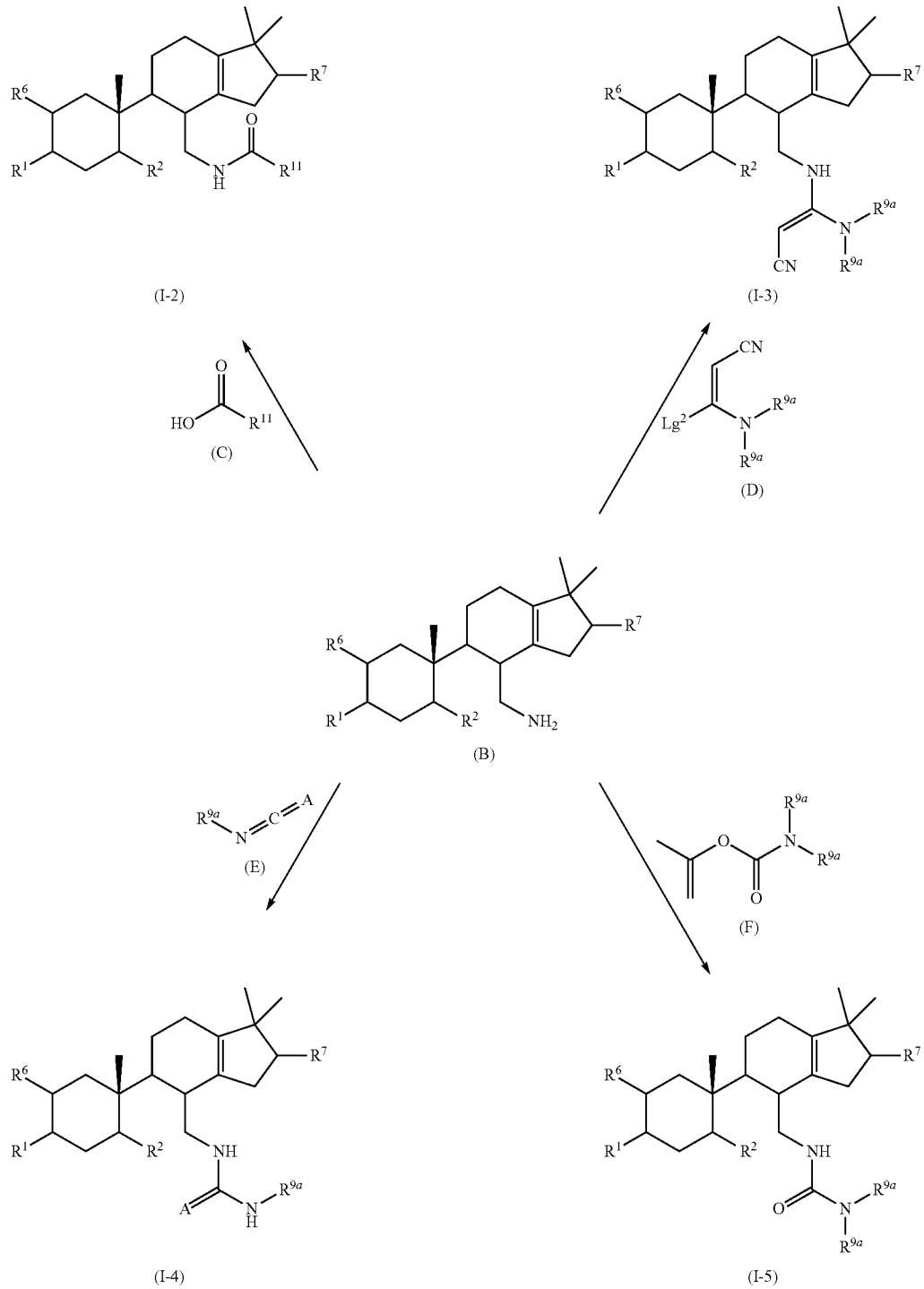

Compounds of formula (B) may be prepared by methods known to one skilled in the art or by methods similar to the methods disclosed in U.S. Pat. No. 7,601,874. Compounds of formulae (C), (D), (E) and (F) are commercially available or can be prepared according to methods known to one skilled in the art.

In general, compounds of formula (I-2) can be prepared, as described above in Reaction Scheme 1B, by treating a compound of formula (B) with a compound of formula (C) under suitable conditions, such as treatment with a coupling reagent in an aprotic solvent, to yield a compound of formula (I-2).

Compounds of formula (I-3) can be prepared, as described above in Reaction Scheme 1B, by treating a compound of formula (B) with a compound of formula (D) with an appropriate promoter or catalyst under basic conditions in an aprotic solvent to yield a compound of formula (I-3).

Compounds of formula (I-4) can be prepared, as described above in Reaction Scheme 1B, by treating a compound of formula (B) with a compound of formula (E) where A is oxygen in an aprotic solvent to yield a compound of formula (I-4) where A is oxygen. Alternatively, a compound of formula (B) can be treated with a compound of formula (E) where A is sulfur in an aprotic solvent to yield a compound of formula (I-4) where A is sulfur.

Compounds of formula (I-5) can be prepared, as described above in Reaction Scheme 1B, by treating a compound of formula (B) with a compound of formula (F) under basic conditions in an aprotic solvent to yield a compound of formula (I-5).

C. Preparation of Compounds of Formula (II-1)

Compounds of formula (II-1) are compounds of formula (II), as described above in the Summary of the Invention, where $R^1$ and $R^2$ are each $-R^8-OH$, $R^{13}$ is $-R^8-NH_2$, and

is a fused pyrazolyl ring, and are prepared as described below in Reaction Scheme 2A, where $R^5$, $R^6$ and each $R^8$ are as described above in the Summary of the Invention for compounds of formula (II), $Pg^1$ is a nitrogen-protecting group, such as tert-butoxycarbonyl, and $Pg^2$ and $Pg^3$ are each independently selected from an oxygen-protecting group, such as, but not limited to, tert-butyldimethylsilyl, tert-butyldiphenylsilyl or acetyl:

REACTION SCHEME 2A

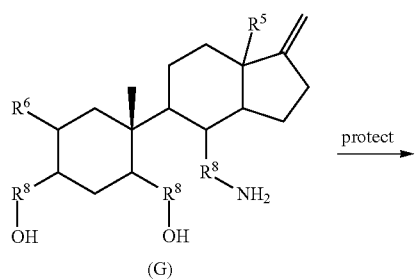

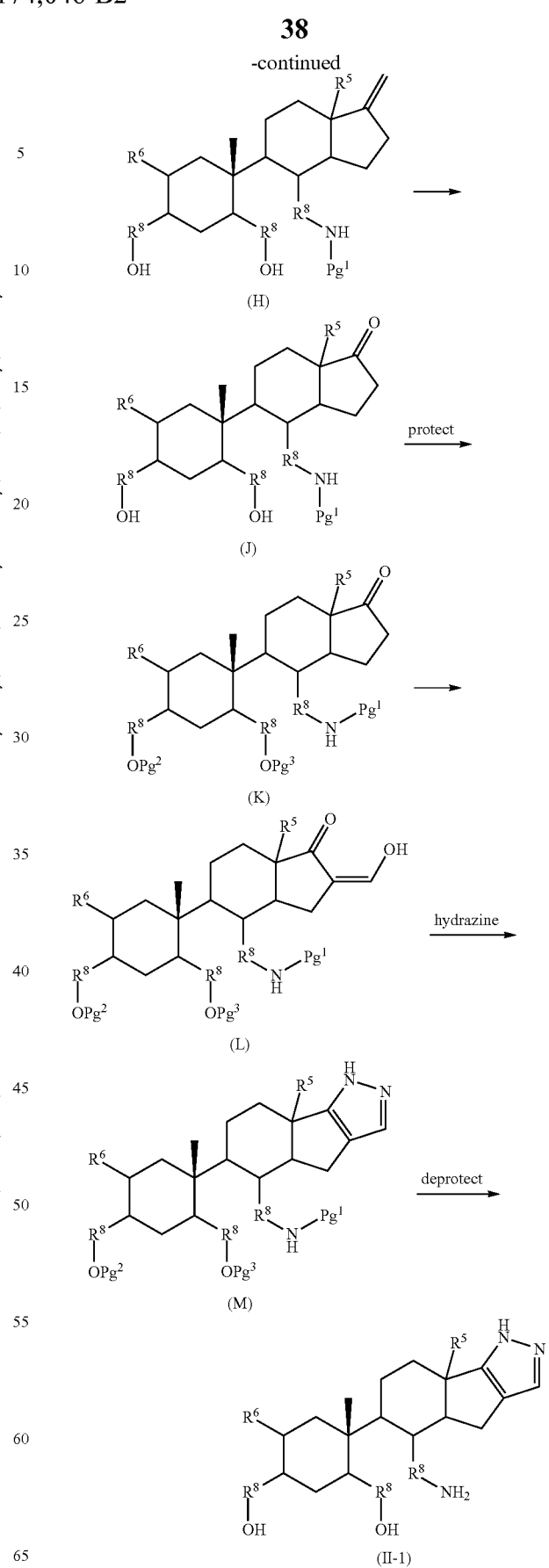

Compounds of formula (G) are prepared by methods known to one skilled in the art or by methods similar to the methods disclosed in U.S. Pat. No. 7,601,874.

In general, compounds of formula (II-1) are prepared, as described above in Reaction Scheme 2A, by first treating a compound of formula (G) under standard nitrogen-protecting conditions, such as treatment with an appropriate nitrogen-protecting group under basic conditions, to yield a compound of formula (H), when is then oxidized under ozonolysis conditions to yield the compound of formula (J). The compound of formula (J) is then treated under standard oxygen-protecting conditions, such as treating the compound of formula (J) with the appropriate oxygen-protecting group under basic conditions in an aprotic solvent, to yield a compound of formula (K). The compound of formula (K) is then treated with an appropriate formic acid ester, such as ethyl formate, under basic conditions in an aprotic solvent, to yield the compound of formula (L), which is then treated with hydrazine in a protic solvent, to yield a compound of formula (M). The compound of formula (M) is then deprotected under standard conditions known to one skilled in the art to yield the compound of formula (II-1).

D. Preparation of Compounds of Formula (II-2)

Compounds of formula (II-2) are compounds of formula (II), as described above in the Summary of the Invention, where $R^1$ is $-R^8-OH$, $R^2$ and $R^{13}$ are each $-CH_2-OH$, and

is a fused pyrazolyl ring, and are prepared as described below in Reaction Scheme 2B, where $R^5$, $R^6$ and $R^8$ are as described above in the Summary of the Invention for compounds of formula (II) and $Pg^2$ is an oxygen-protecting group, such as, but not limited to, tert-butyldimethylsilyl, tert-butyldiphenylsilyl or acetyl:

REACTION SCHEME 2B

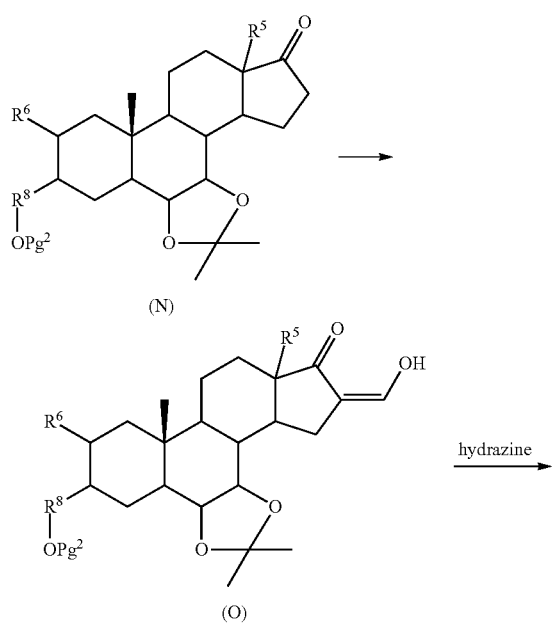

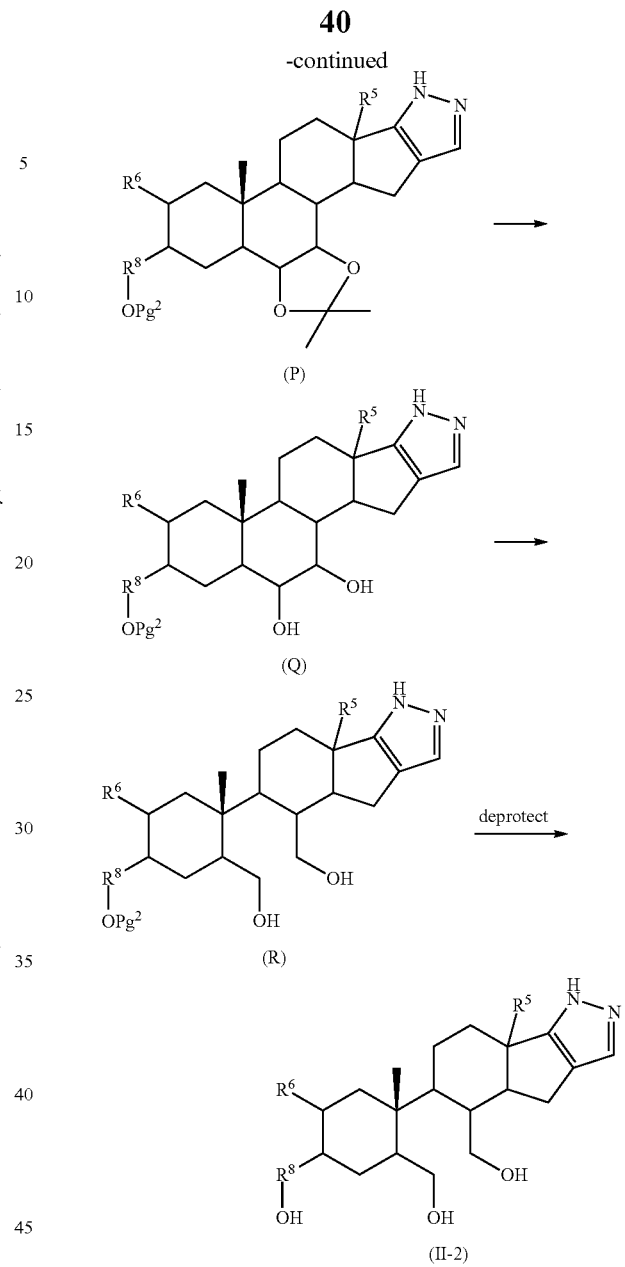

Compounds of formula (N) are prepared by methods known to one skilled in the art or by methods similar to the methods disclosed in U.S. Pat. No. 7,601,874.

In general, compounds of formula (II-2) are prepared, as described above in Reaction Scheme 2B, by first treating a compound of formula (N) an appropriate formic acid ester, such as ethyl formate, under basic conditions in an aprotic solvent, to yield the compound of formula (O), which is then treated with hydrazine in a protic solvent, to yield a compound of formula (P). The compound of formula (P) is then deprotected under standard conditions known to one skilled in the art to yield the compound of formula (Q). Treatment of the compound of formula (Q) with sodium periodate in THF to oxidatively cleave the diol yields a dialdehyde intermediate, which is then reduced with sodium borohydride in THF to yield the compound of formula (R), which is then deprotected under standard conditions in an aprotic solvent, to yield the compound of formula (II-2).

E. Preparation of Compounds of Formula (II-3)

Compounds of formula (II-3) are compounds of formula (II), as described above in the Summary of the Invention, where $R^1$ is —$R^8$—OH, $R^2$ and $R^{13}$ are each —$CH_2$—OH, and

is a fused pyridinyl ring, and are prepared as described below in Reaction Scheme 2C, where $R^5$, $R^6$ and $R^8$ are as described above in the Summary of the Invention for compounds of formula (II), Ac is acetyl and $Pg^2$ and $Pg^3$ are independently selected from an oxygen-protecting group, such as, but not limited to, pivaloyl:

REACTION SCHEME 2C

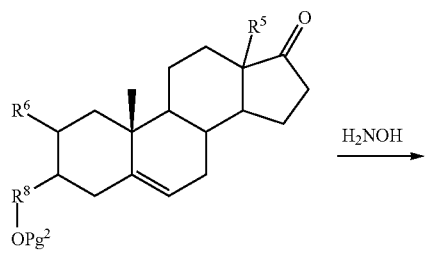
(S)

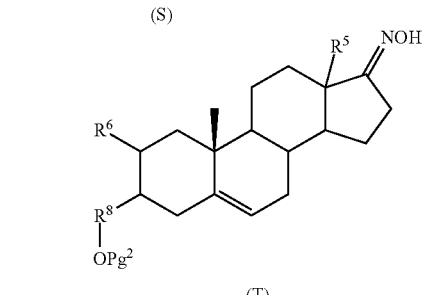
(T)

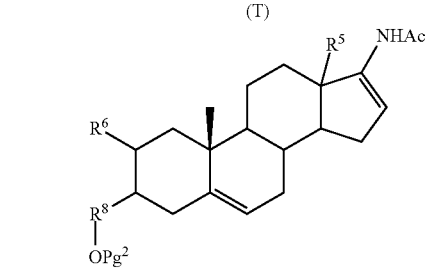
(U)

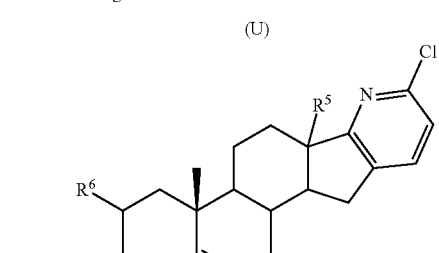
(V)

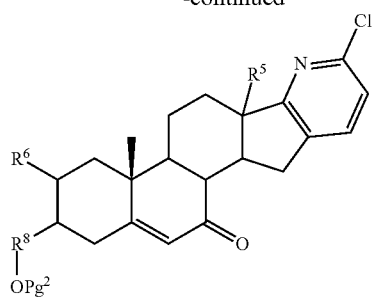
(W)

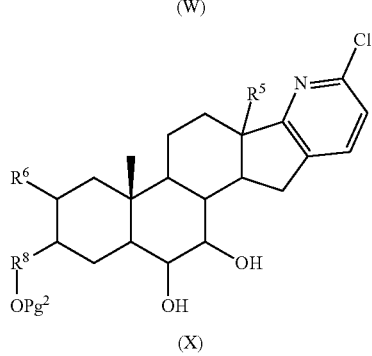
(X)

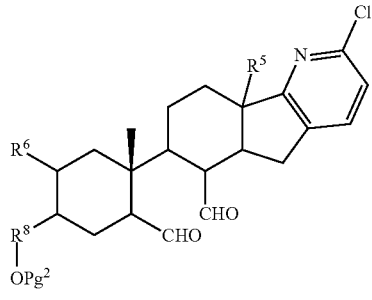
(Y)

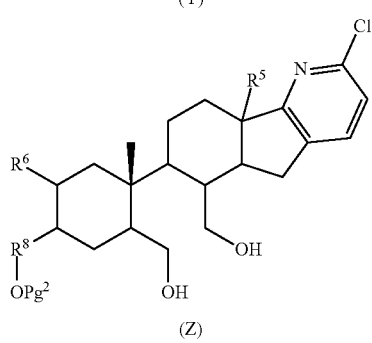
(Z)

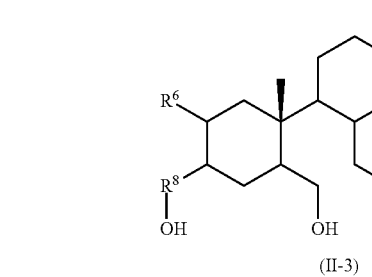
(II-3)

Compounds of formula (S) are prepared by methods known to one skilled in the art or by methods similar to the methods disclosed in U.S. Pat. No. 7,601,874.

In general, compounds of formula (II-3) are prepared, as described above in Reaction Scheme 2C, by first treating a compound of formula (S) with hydroxylamine hydrochloride in a protic solvent to yield a compound of the formula (T). Treatment of a compound of formula (T) under reductive acetylation conditions, such as treatment with phosphoryl chloride in an aprotic solvent, yields a compound of formula (U) which is then condensed under acidic conditions to yield the compound of formula (V). A compound of formula (V) is then the oxidized under allylic oxidation conditions, such as a catalyst and a peroxide, to yield a compound of formula (W) which then undergoes hydroboration under standard conditions to yield a compound of formula (X). Treatment of the compound of formula (X) with sodium periodate in THF to oxidatively cleave the diol yields a dialdehyde intermediate (Y), which is then reduced with sodium borohydride in THF to yield the compound of formula (Z), which is then treated to standard catalytic hydrogenation conditions, such as the use of palladium metal on charcoal under hydrogen, to remove the chloro group and then the protecting groups are removed under standard conditions to yield the compound of formula (II-3).

Alternatively, compounds of formula (Z) may treated under standard oxygen-protecting conditions to yield a compound of formula (II) wherein $R^2$ is —$CH_2$—$OPg^1$ and $R^{13}$ is —$CH_2$—OH which can then be treating under standard leaving group formation conditions, such as treating the compound of formula (G) with the appropriate oxygen-activating group under basic conditions in an aprotic solvent, to yield a compound wherein $R^2$ is —$CH_2$—$OPg^1$ and $R^{13}$ is —$CH_2$—$OLg^1$ where $Lg^1$ is a functional group, such as mesyl or tosyl, which forms a leaving group with the oxygen to which it is attached. This compound can then be treated the appropriate nucleophilic azide in an aprotic solvent to yield a compound wherein $R^{13}$ is —$CH_2$—$N_3$. This compound can be further reduced to form a compound where $R^1$ is —$R^8$—OH, $R^2$ is —$CH_2OH$ and $R^{13}$ is —$CH_2NH_2$.

Compound of formula (II) where (A)

are other optionally substituted fused heterocyclyl rings or other optionally substituted fused heteroaryl rings can be prepared in a similar manner as described above.

F. Preparation of Compounds of Formula (III-1)

Compounds of formula (III-1) are compounds of formula (III), as described above in the Summary of the Invention, where $R^2$ and $R^{13}$ are each —$CH_2$—OH, and (B)

is fused isoxazolyl ring, and are prepared as described below in Reaction Scheme 3A, where $R^{4a}$ and $R^{4b}$, $R^5$ and $R^7$ are as described above in the Summary of the Invention for compounds of formula (III):

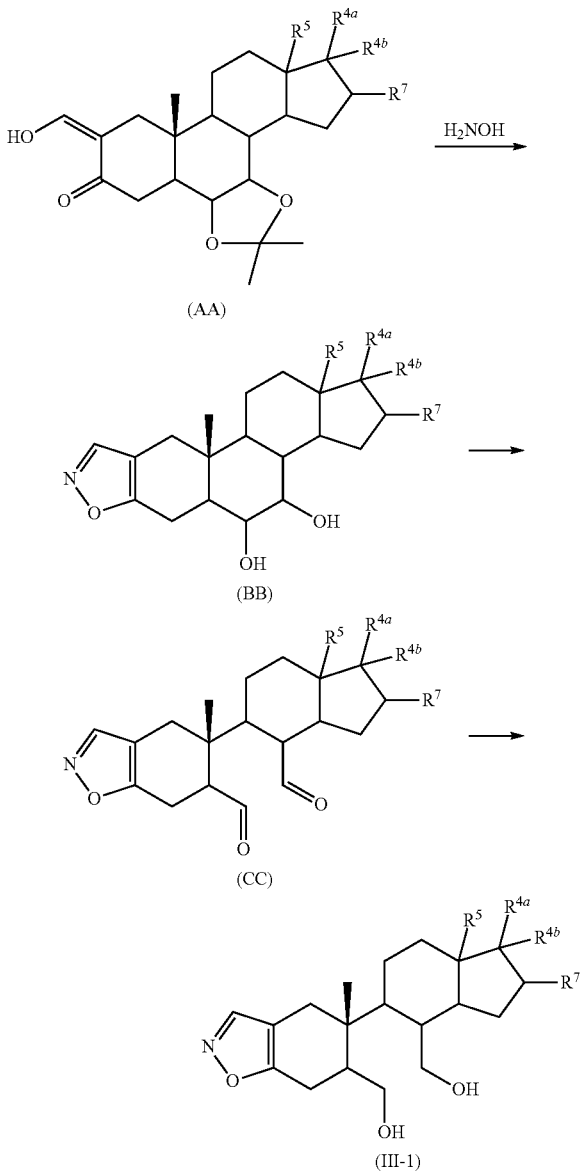

REACTION SCHEME 3A

Compounds of formula (AA) are prepared by methods known to one skilled in the art, or by methods similar to the methods disclosed above in Reaction Scheme 2B for the preparation of compounds of formula (O) or by methods similar to the methods disclosed in U.S. Pat. No. 7,601,874.

In general, compounds of formula (III-1) are prepared, as described above in Reaction Scheme 3A, by first treating a compound of formula (AA) with hydroxylamine hydrochloride under condensation conditions in a protic solvent to yield a compound of formula (BB), which is then treated with sodium periodate in THF to oxidatively cleave the diol to yield the compound of formula (CC), which is then reduced under standard procedures known to one skilled in the art to yield the compound of formula (III-1).

Alternatively, compounds of formula (AA) are treated with hydrazine under acidic conditions in a protic solvent to form a compound wherein

is fused pyrazolyl ring, which can then be treated with acetic acid to form the fused-pyrazolyl compounds corresponding to the compounds of formula (BB) above. Further treatment in a similar manner as compounds of formula (BB) above to form the dialdehyde fuzed-pyrazoly compounds corresponding compound of formula (CC), which can then be reduced under standard procedures to yield compounds of formula (III) where

is fused pyrazolyl ring, and $R^2$ and $R^{13}$ are both —CH$_2$OH.

G. Preparation of Compounds of Formula (III-2)

Compounds of formula (III-2) are compounds of formula (III), as described above in the Summary of the Invention, where $R^2$ and $R^{13}$ are each —CH$_2$—OH, and

is fused thiazolyl or oxazolyl ring, and are prepared as described below in Reaction Scheme 3B, where $R^{4a}$ and $R^{4b}$, $R^5$ and $R^7$ are as described above in the Summary of the Invention for compounds of formula (III), $R^{20a}$ is alkyl, X is halo, preferably bromo or chloro, and A is oxygen or sulfur:

REACTION SCHEME 3B

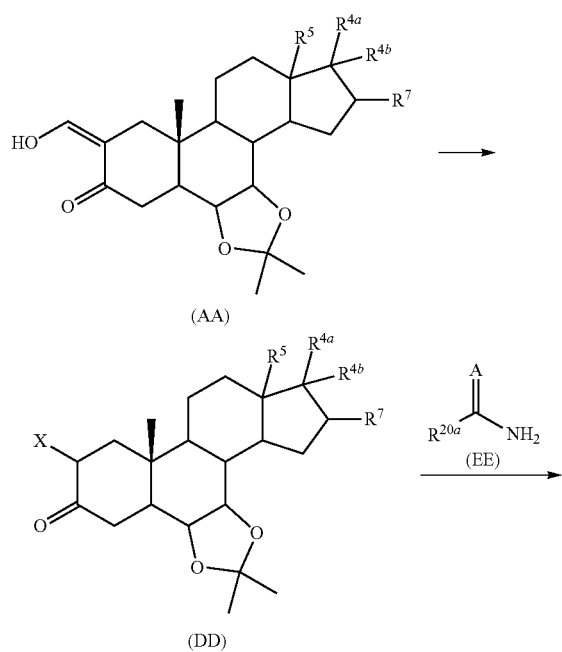

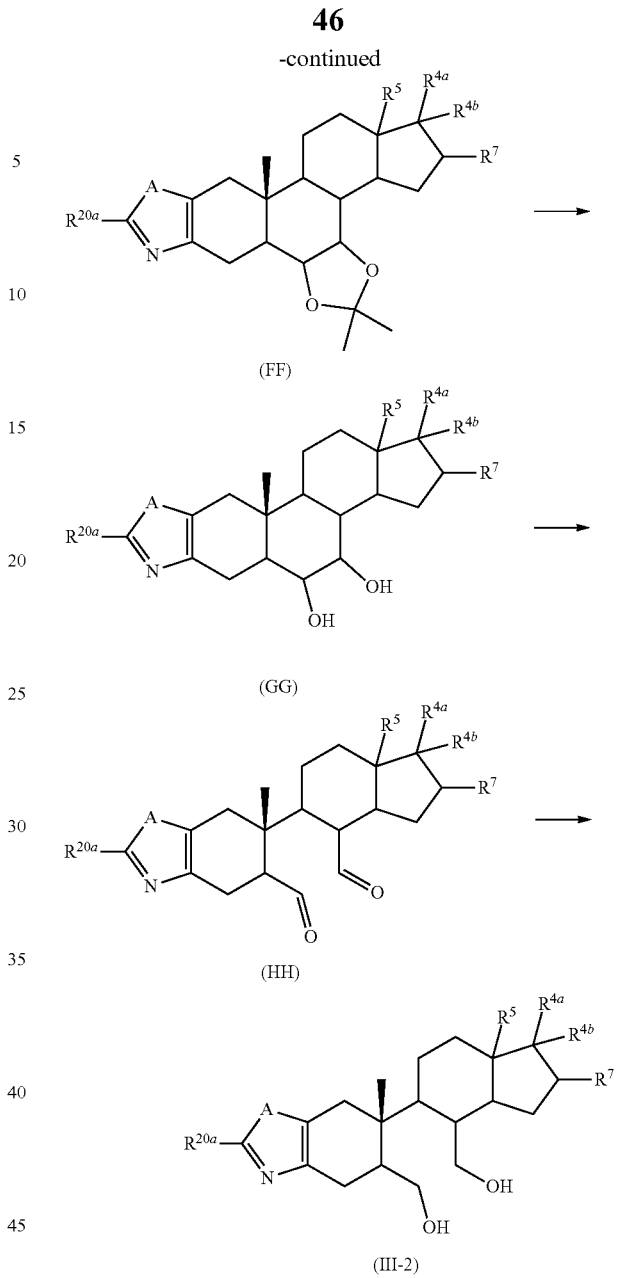

Compounds of formula (AA) are prepared by methods known to one skilled in the art, or by methods similar to the methods disclosed above in Reaction Scheme 2B for the preparation of compounds of formula (O) or by methods similar to the methods disclosed in U.S. Pat. No. 7,601,874.

In general, compounds of formula (III-2) are prepared, as described above in Reaction Scheme 3B, by first treating a compound of formula (AA) with a halogenating agent, such as N-bromosuccinimide, under basic conditions to yield a compound of formula (DD). The compound of formula (DD) is then treated with a compound of formula (EE) under condensation conditions to yield a compound of formula (FF), which is then treated under acidic conditions in a protic solvent to yield a compound of formula (GG), which is then treated with sodium periodate in THF to oxidatively cleave the diol to yield the compound of formula (HH), which is then reduced under standard procedures known to one skilled in the art to yield the compound of formula (III-2).

H. Preparation of Compounds of Formula (IV-1)

Compounds of formula (IV-1) are compounds of formula (IV), as described above in the Summary of the Invention, where $R^1$ is —$R^8$—OH, $R^2$ is —$CH_2OH$, $R^{13}$ is —$CH_2NH_2$, $R^{14}$ is alkynyl, optionally substituted aryl or optionally substituted heteroaryl, and $R^{15}$ is —OH, and are prepared as described below in Reaction Scheme 4A, where $R^5$, $R^8$ and $R^{16}$ are as described above in the Summary of the Invention for compounds of formula (IV), $R^{14a}$ is alkynyl, optionally substituted aryl or optionally substituted heteroaryl, $Pg^2$ and $Pg^3$ are each independently selected from an oxygen-protecting group, such as, but not limited to, tert-butyldimethylsilyl, tert-butyldiphenylsilyl, acetyl or pivaloyl, $Lg^1$ is a which forms a leaving group with the oxygen to which it is attached, such as mesyl or tosyl, and X is bromo or chloro:

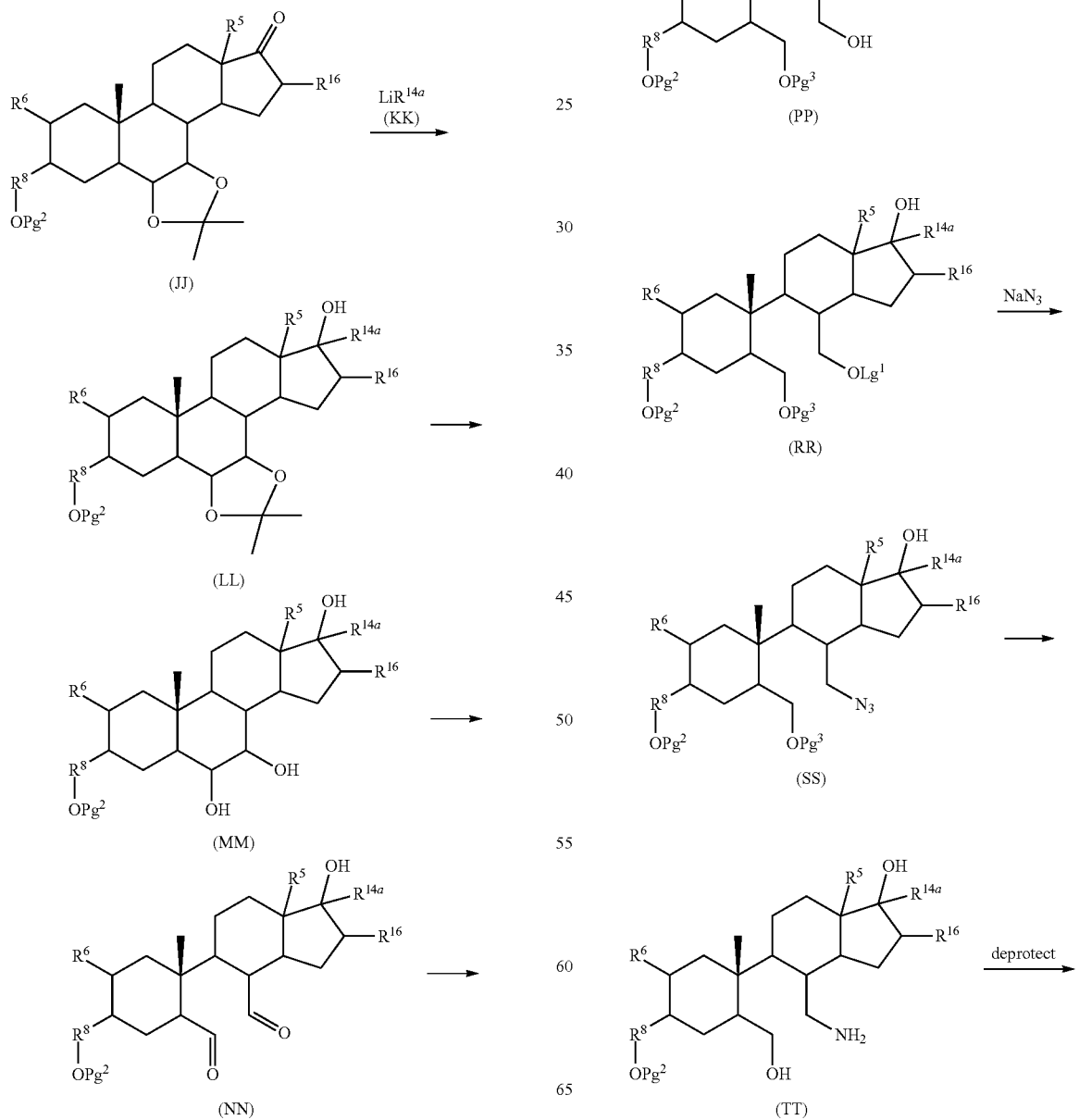

49

-continued

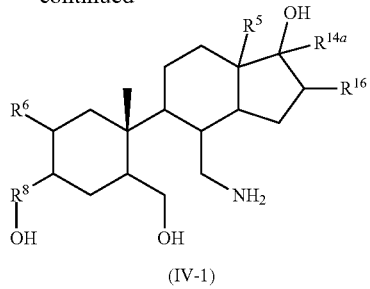

(IV-1)

Compounds of formula (JJ) are prepared by methods known to one skilled in the art or by methods similar to the methods disclosed in U.S. Pat. No. 7,601,874. Compounds of formulae (KK) and (QQ) are commercially available or can be prepared according to methods known to one skill in the art.

In general, compounds of formula (IV-1) are prepared, as described above in Reaction Scheme 4A, by first treating a compound of formula (JJ) with a lithium compound of formula (KK) under standard nucleophilic addition conditions, such as the appropriate lithium species in an aprotic solvent, to yield a compound of formula (LL). The compound of formula (LL) is then treated with acetic acid to remove the acetonide group to yield the compound of formula (MM). Reaction with sodium periodate in an aprotic solvent, such as THF, oxidatively cleaves the diol to yield the compound of formula (NN). Sodium borohydride reduction of the aldehyde groups yields the compound of formula (OO). Selective protection of one of the primary hydroxyls under standard conditions, such as treating the compound of formula (OO) with the appropriate oxygen-protecting group under basic conditions in an aprotic solvent, yields the compound of formula (PP). The compound of formula (PP) is then treated with the compound of formula (QQ) under standard leaving group formation conditions, such as treatment with the appropriate oxygen-activating group under basic conditions in an aprotic solvent, to yield the compound of formula (RR). The compound of formula (RR) is then treated reacted with sodium azide in an aprotic solvent, such as DMF, to yield the compound of formula (SS), which is then reduced under standard reducing conditions, to yield the compound of formula (TT), which is further deprotected to yield the compound of formula (IV-1).

Alternatively, compounds of formula (LL) wherein $Pg^2$ is tert-butyldiphenylsilyl can be treated, for example, with tetrabutylammonium fluoride in an aprotic solvent to yield the free hydroxyl compound, which can then be treated with acetic anhydride to yield a compound of formula (LL) where $Pg^2$ is acetyl, which can be further treated in a similar manner as described above in Reaction Scheme 4A to yield a compound of formula (IV-1).

Alternatively, removal of the $Pg^2$ group from the compounds of formula (OO) under standard conditions, such as treatment of the compound of formula (OO) with tetrabutylammonium fluoride (for example, when $Pg^2$ is tert-butyldiphenylsilyl) or potassium carbonate (for example, when $Pg^2$ is acetyl), yields a compound of formula (IV) as defined above in the Summary of the Invention.

Compounds of formula (IV-1) can be further treated with para-toluenesulfonic acid under standard conditions to form compounds of formula (IV) where $R^{14}$ is optionally substituted aryl or optionally substituted heteroaryl and $R^{15}$ is a direct bond to the carbon to which $R^{16}$ is attached.

50

I. Preparation of Compounds of Formula (IV-2)

Compounds of formula (IV-2) are compounds of formula (IV), as described above in the Summary of the Invention, where $R^1$ is —$R^8$—OH, $R^2$ is —$CH_2OH$, $R^{13}$ is —$CH_2NH_2$, $R^{14}$ is optionally substituted aryl or optionally substituted heteroaryl, $R^{15}$ is a direct bond to the carbon to which $R^{16}$ is attached, and $R^{16}$ is hydrogen, and are prepared as described below in Reaction Scheme 4A, where $R^5$ and $R^8$ are as described above in the Summary of the Invention for compounds of formula (IV), $R^{14a}$ is optionally substituted aryl or optionally substituted heteroaryl, $Pg^2$ and $Pg^3$ are each independently selected from an oxygen-protecting group, such as, but not limited to, tert-butyldimethylsilyl, tert-butyldiphenylsilyl, acetyl or pivaloyl, $Lg^1$ is a which forms a leaving group with the oxygen to which it is attached, such as mesyl or tosyl, and X is bromo or chloro:

REACTION SCHEME 4B

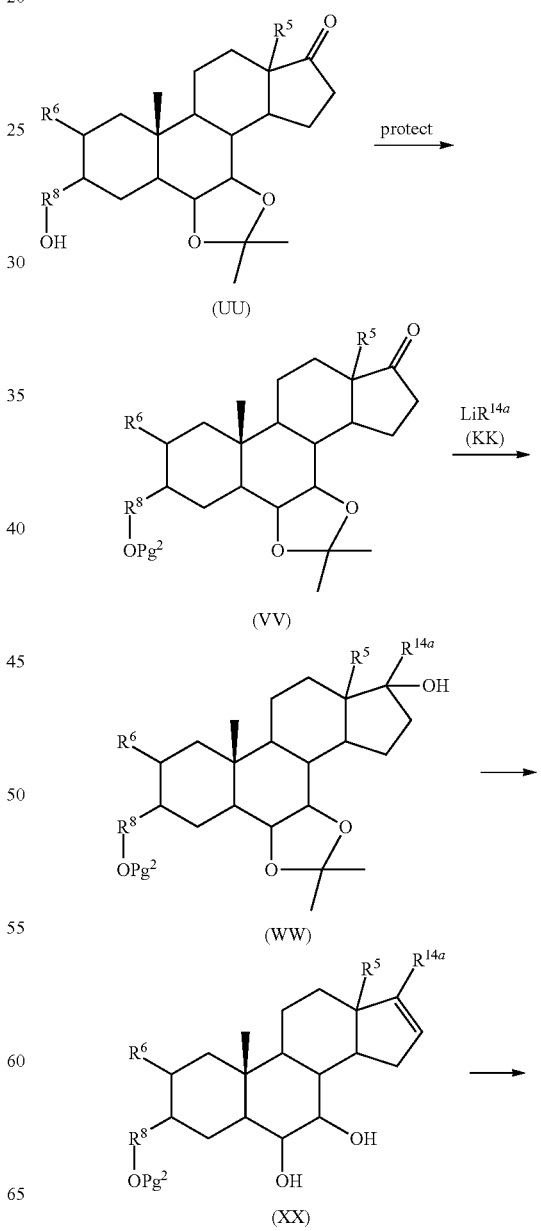

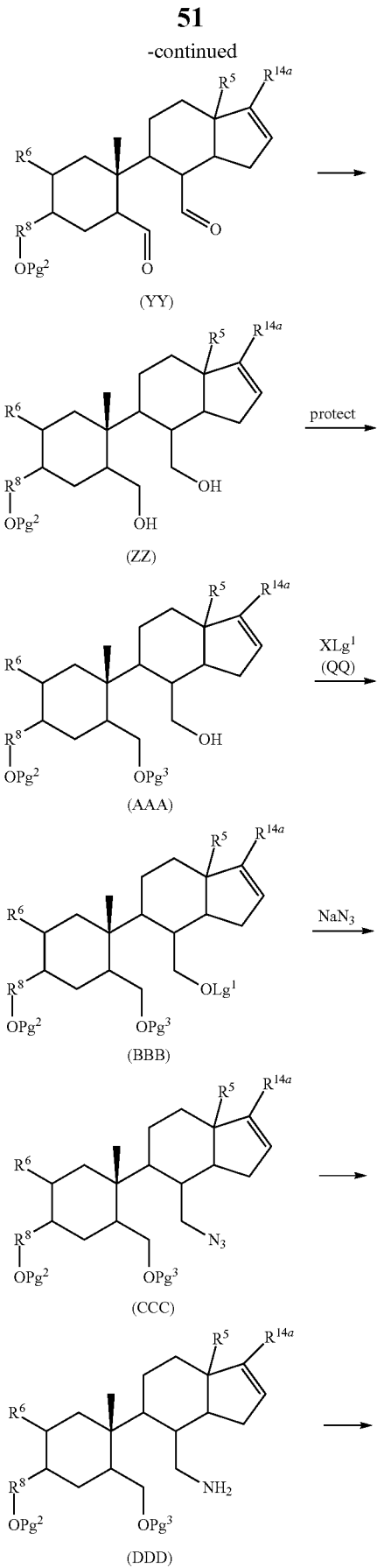

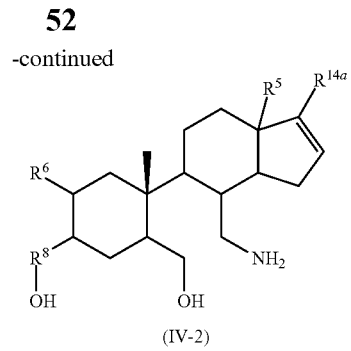

(IV-2)

Compounds of formula (UU) are prepared by methods known to one skilled in the art or by methods similar to the methods disclosed in U.S. Pat. No. 7,601,874. Compounds of formulae (KK) and (QQ) are commercially available or can be prepared according to methods known to one skill in the art.

In general, compounds of formula (IV-2) are prepared, as described above in Reaction Scheme 4B, by first protecting the compound of formula (UU) under standing oxygen-protecting conditions, such as treating the compound of formula (UU) with the appropriate oxygen-protecting group under basic conditions in an aprotic solvent, to yield a compound of formula (VV), which is then treated with a lithium compound of formula (KK) under standard nucleophilic addition conditions, such as the appropriate lithium species in an aprotic solvent, to yield a compound of formula (WW), which is then deprotected under standard procedures to yield the compound of formula (XX). The compound of formula (XX) is then reacted with sodium periodate to yield the compound of formula (YY). Sodium borohydride reduction of the aldehyde groups yields the compound of formula (ZZ). Selective protection of one of the primary hydroxyls under standard conditions, such as such as treating the compound of formula (ZZ) with the appropriate oxygen-protecting group under basic conditions in an aprotic solvent, yields the compound of formula (AAA). The compound of formula (AAA) is then treated with the compound of formula (QQ) under standard leaving group formation conditions, such as treatment with the appropriate oxygen-activating group under basic conditions in an aprotic solvent, to yield the compound of formula (BBB). The compound of formula (BBB) is then treated reacted with sodium azide in an aprotic solvent, such as DMF, to yield the compound of formula (CCC), which is then reduced under standard reducing conditions to yield the compound of formula (DDD), which is then deprotected under standard conditions to yield the compound of formula (IV-2).

Alternatively, removal of the $Pg^2$ group from the compounds of formula (ZZ) under standard conditions, such as treatment of the compound of formula (ZZ) with tetrabutylammonium fluoride (for example, when $Pg^2$ is tert-butyldiphenylsilyl) or potassium carbonate (for example, when $Pg^2$ is acetyl), yields a compound of formula (IV) as defined above in the Summary of the Invention.

J. Preparation of Compounds of Formula (IV-3)

Compounds of formula (IV-3) are compounds of formula (IV), as described above in the Summary of the Invention, where $R^1$ is —$R^8$—OH, $R^2$ is —$CH_2OH$, $R^5$ is a direct bond to the carbon at C14, $R^{13}$ is —$CH_2NH_2$, $R^{14}$ is optionally substituted aryl or optionally substituted heteroaryl, $R^{15}$ is methyl, and $R^{16}$ is hydrogen, and are prepared as described below in Reaction Scheme 4C, where $R^5$ and $R^8$ are as described above in the Summary of the Invention for compounds of formula (IV), $R^{14a}$ is optionally substituted aryl or optionally substituted heteroaryl, $R^{15a}$ is methyl, and $Pg^2$ is selected from an oxygen-protecting group, such as, but not limited to, tert-butyldimethylsilyl, tert-butyldiphenylsilyl, acetyl, preferably acetyl:

REACTION SCHEME 4C

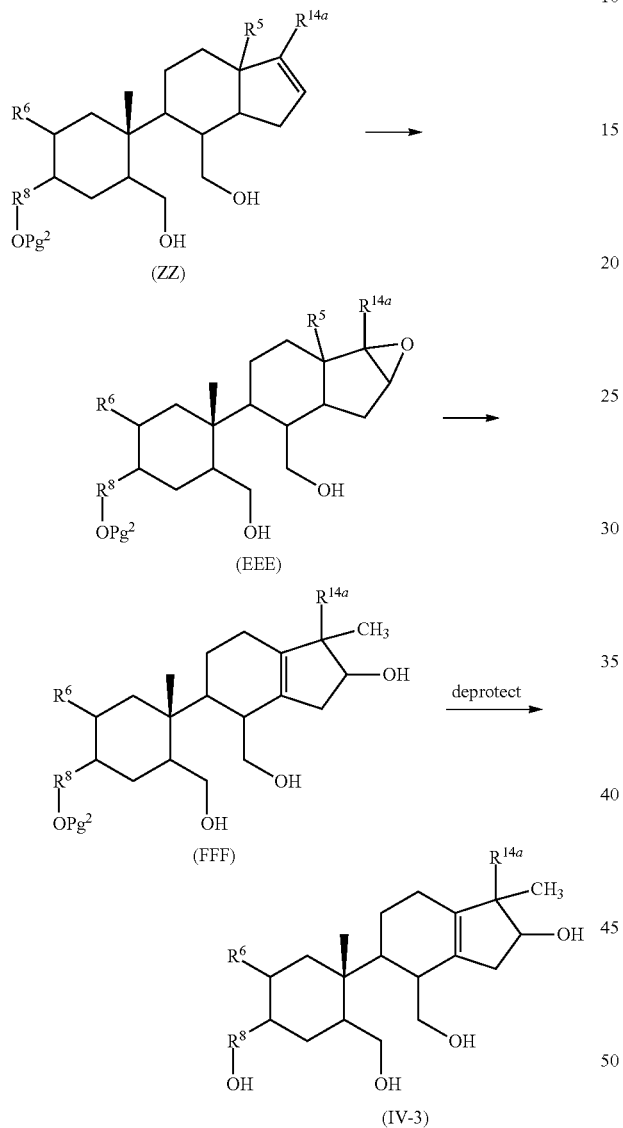

Compounds of formula (ZZ) are prepared by methods known to one skilled in the art or by methods disclosed herein.

In general, compounds of formula (IV-3) are prepared, as described above in Reaction Scheme 4C, by first treating a compound of formula (ZZ) with an oxidizing agent, such as meta-chloroperoxybenzoic acid, in an aprotic solvent to yield a compound of formula (EEE), with is then treated with acetic acid to yield the compound of formula (FFF). The $Pg^2$ protecting group is removed by standard procedures known to one skilled in the art, such as treatment with potassium carbonate in a protic solvent, to yield a compound of formula (IV-3).

K. Preparation of Compounds of Formula (V-1)

Compounds of formula (V-1) are compounds of formula (V), as described above in the Summary of the Invention, where r is 1, $R^1$ and $R^2$ are each —$R^8$—OH, $R^{13}$ is —$R^8$—$NH_2$, $R^{17}$ is hydrogen and $R^{18}$ is oxo, and are prepared as described below in Reaction Scheme 5, where $R^5$, $R^6$ and $R^8$ are as described above in the Summary of the Invention for compounds of formula (V), $Pg^1$ is a nitrogen-protecting group, such as tert-butoxycarbonyl, and $Pg^2$ and $Pg^3$ are each independently selected from an oxygen-protecting group, such as, but not limited to, tert-butyldimethylsilyl, tert-butyldiphenylsilyl or acetyl:

REACTION SCHEME 5

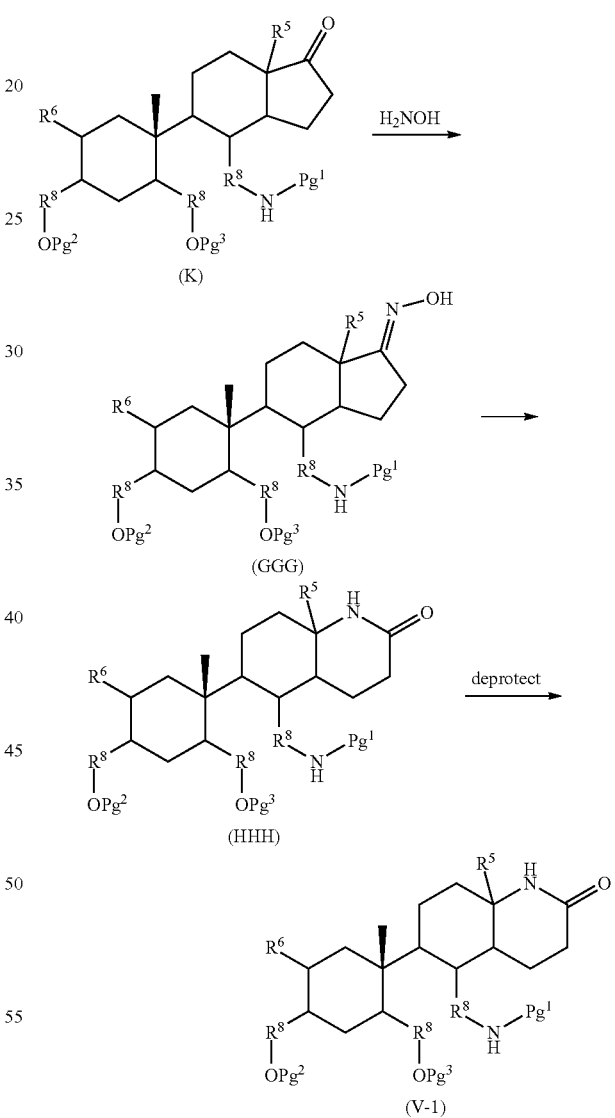

Compounds of formula (K) are prepared by methods known to one skilled in the art or by methods disclosed herein.

In general, compounds of formula (V-1) are prepared, as described above in Reaction Scheme 5, by first treating a compound of formula (K) with hydroxylamine under standard conditions, such as under basic conditions in an aprotic solvent, to yield a compound of formula (GGG). The compound of formula (GGG) is then treated under standard Beckmann rearrangement conditions, such as under acidic conditions in a protic solvent, to yield the compound of formula (HHH), which is deprotected under standard conditions to yield a compound of formula (V-1).

L. Preparation of Compounds of Formula (VI-1))

Compounds of formula (VI-1) are compounds of formula (VI), as described above in the Summary of the Invention, where $R^2$ and $R^{13}$ are each —$CH_2OH$ and $R^{19}$ is —$R^8$—N(H)C(O)$R^9$ where $R^9$ is as described above in the Summary of the Invention for compounds of formula (VI), and are prepared as described below in Reaction Scheme 6, where $R^{4a}$, $R^{4b}$, $R^5$, $R^6$, $R^7$ and $R^8$ are as described above in the Summary of the Invention for compounds of formula (VI), and $Pg^2$ and $Pg^3$ are each acetyl:

REACTION SCHEME 6

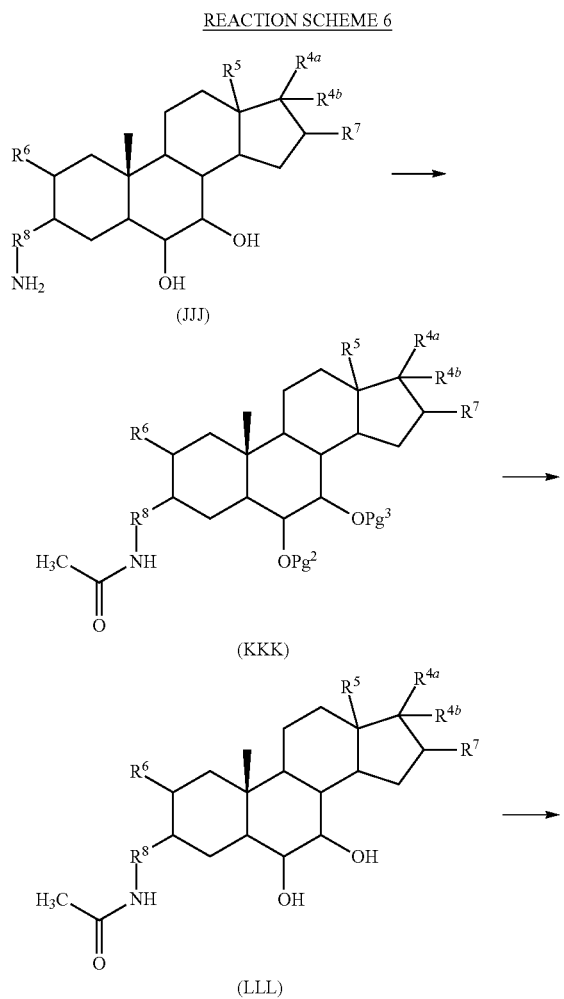

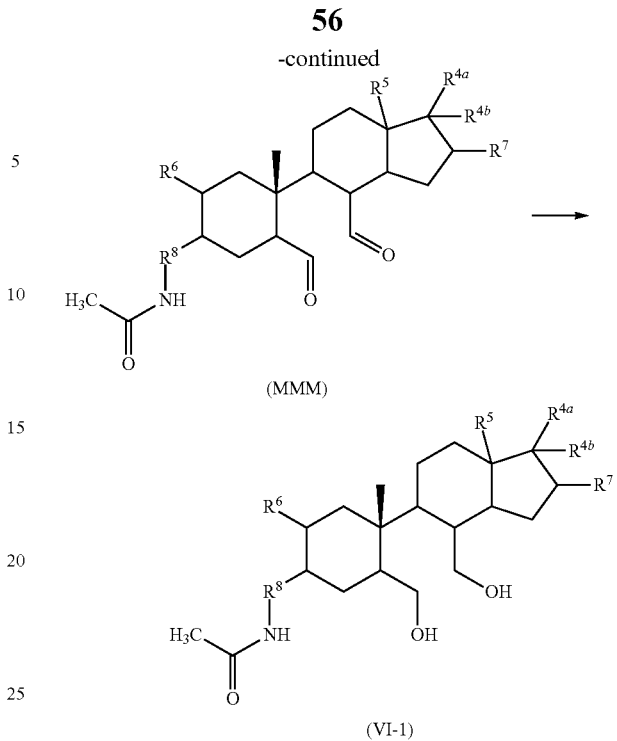

Compounds of formula (JJJ) are prepared by methods known to one skilled in the art or by methods similar to the methods disclosed in U.S. Pat. No. 6,635,629.

In general, compounds of formula (VI-1) are prepared, as described above in Reaction Scheme 6, by first treating a compound of formula (JJJ) with an appropriate acetylating agent, such as acetic anhydride, to yield a compound of formula (KKK). The primary hydroxyls on the compound of formula (KKK) are deprotected under standard conditions, such as under basic conditions in a protic solvent, to yield a compound of formula (LLL). The compound of formula (LLL) is then is then reacted with sodium periodate to yield the compound of formula (MMM). Sodium borohydride reduction of the aldehyde groups yields the compound of formula (VI-1).

All of the compounds described herein as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

Representative compounds of the invention which were prepared by the methods disclosed herein include (but are not limited to) the compounds listed below in Table 1. The compound (Cpd) numbers in this table correspond to the compound numbers in Example 39-42 below (but do not correspond with the compound numbers in Examples 1-38 below).

TABLE 1

| Cpd No. | Compound Name |
| --- | --- |
| Cpd No. 1 | N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)nicotinamide |

TABLE 1-continued

| Cpd No. | Compound Name |
|---|---|
| Cpd No. 2 | (1S,3S,4R)-4-((4R,5S)-1,1-dimethyl-4-((1-methylpiperidin-4-ylamino)methyl)-2,3,4,5,6,7-hexahydro-1H-inden-5-yl)-3-(hydroxymethyl)-4-methylcyclohexanol |
| Cpd No. 3 | (E)-2-cyano-1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylguanidine |
| Cpd No. 4 | 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-(pyridin-3-yl)urea |
| Cpd No. 5 | 1-ethyl-3-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)urea |
| Cpd No. 6 | 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylthiourea |
| Cpd No. 7 | (1S,3S,4R)-4-((4aS,5R,6S,8aS)-5-(aminomethyl)-8a-methyl-2,4,4a,5,6,7,8,8a-octahydroindeno[1,2-c]pyrazol-6-yl)-3-(hydroxymethyl)-4-methylcyclohexanol dihydrochloride |
| Cpd No. 8 | (4aS,5R,6S,8aS)-5-(aminomethyl)-6-((1R,2S,4S)-4-hydroxy-2-(hydroxymethyl)-1-methylcyclohexyl)-8a-methyloctahydroquinolin-2(1H)-one |
| Cpd No. 9 | (1S,3S,4R)-4-((5aS,6R,7S,9aS)-6-(aminomethyl)-9a-methyl-5a,6,7,8,9,9a-hexahydro-5H-indeno[1,2-b]pyridin-7-yl)-3-(hydroxymethyl)-4-methylcyclohexanol |
| Cpd No. 10 | (1S,3S,4R)-4-((3aS,6S,7R,7aS)-7-(aminomethyl)-3a-methyl-3-phenyl-3a,4,5,6,7,7a-hexahydro-1H-inden-6-yl)-3-(hydroxymethyl)-4-methylcyclohexanol hydrochloride |
| Cpd No. 11 | (1S,3aS,4R,5S,7aS)-4-(aminomethyl)-5-((1R,2S,4S)-4-hydroxy-2-(hydroxymethyl)-1-methylcyclohexyl)-7a-methyl-1-phenyloctahydro-1H-inden-1-ol acetate |
| Cpd No. 12 | (1S,3aS,4R,5S,7aS)-4-(aminomethyl)-1-(furan-2-yl)-5-((1R,2S,4S)-4-hydroxy-2-(hydroxymethyl)-1-methylcyclohexyl)-7a-methyloctahydro-1H-inden-1-ol |
| Cpd No. 13 | (1S,3S,4R)-4-((3aS,6S,7R,7aS)-7-(aminomethyl)-3-(furan-2-yl)-3a-methyl-3a,4,5,6,7,7a-hexahydro-1H-inden-6-yl)-3-(hydroxymethyl)-4-methylcyclohexanol |
| Cpd No. 14 | (1S,3S,4R)-4-((2R,3S,3aR,3bS,5'R,6S,7R,7aS,8aS)-7-(aminomethyl)-3,3b,5'-trimethyltetradecahydrospiro[indeno[2,1-b]furan-2,2'-pyran]-6-yl)-3-(hydroxymethyl)-4-methylcyclohexanol acetate |
| Cpd No. 15 | (1S,3aS,4R,5S,7aS)-4-(aminomethyl)-5-((1R,2S,4S)-4-hydroxy-2-(hydroxymethyl)-1-methylcyclohexyl)-7a-methyl-1-(thiophen-2-yl)octahydro-1H-inden-1-ol |
| Cpd No. 16 | (1S,3S,4R)-4-((3aS,6S,7R,7aS)-7-(aminomethyl)-3a-methyl-3-(thiophen-2-yl)-3a,4,5,6,7,7a-hexahydro-1H-inden-6-yl)-3-(hydroxymethyl)-4-methylcyclohexanol |
| Cpd No. 17 | (1S,3aS,4R,5S,7aS)-4-(aminomethyl)-5-((1R,2S,4S)-4-hydroxy-2-(hydroxymethyl)-1-methylcyclohexyl)-7a-methyl-1-(pyridin-2-yl)octahydro-1H-inden-1-ol |
| Cpd No. 18 | (1S,3aS,4R,5S,7aS)-4-(aminomethyl)-5-((1R,2S,4S)-4-hydroxy-2-(hydroxymethyl)-1-methylcyclohexyl)-1,7a-dimethyloctahydro-1H-inden-1-ol |
| Cpd No. 19 | (1S,2R,4R,5S)-4-(aminomethyl)-5-((1R,2S,4S)-4-hydroxy-2-(hydroxymethyl)-1-methylcyclohexyl)-1-methyl-1-phenyl-2,3,4,5,6,7-hexahydro-1H-inden-2-ol |
| Cpd No. 20 | (1S,3aS,4R,5S,7aS)-4-(aminomethyl)-5-((1R,2S,4S)-4-hydroxy-2-(hydroxymethyl)-1-methylcyclohexyl)-7a-methyl-1-(thiazol-2-yl)octahydro-1H-inden-1-ol |
| Cpd No. 21 | ((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol |
| Cpd No. 22 | ((3aS,4R,5S,7aS)-5-((5R,6S)-6-(hydroxymethyl)-5-methyl-4,5,6,7-tetrahydrobenzo[c]isoxazol-5-yl)-7a-methyl-1-methyleneoctahydro-1H-inden-4-yl)methanol |
| Cpd No. 23 | ((5R,6S)-5-((4R,5S)-4-(hydroxymethyl)-1,1-dimethyl-2,3,4,5,6,7-hexahydro-1H-inden-5-yl)-5-methyl-4,5,6,7-tetrahydrobenzo[d]isoxazol-6-yl)methanol |
| Cpd No. 24 | ((3aS,4R,5S,7aS)-5-((5S,6R)-5-(hydroxymethyl)-2,6-dimethyl-4,5,6,7-tetrahydrobenzo[d]thiazol-6-yl)-7a-methyl-1-methyleneoctahydro-1H-inden-4-yl)methanol |
| Cpd No. 25 | (1S,3S,4R)-3-(hydroxymethyl)-4-((3aS,6S,7R,7aS)-7-(hydroxymethyl)-3a-methyl-3-phenyl-3a,4,5,6,7,7a-hexahydro-1H-inden-6-yl)-4-methylcyclohexanol |
| Cpd No. 26 | (1S,3aS,4R,5S,7aS)-5-((1R,2S,4S)-4-hydroxy-2-(hydroxymethyl)-1-methylcyclohexyl)-4-(hydroxymethyl)-7a-methyl-1-phenyloctahydro-1H-inden-1-ol |

TABLE 1-continued

| Cpd No. | Compound Name |
|---|---|
| Cpd No. 27 | (1S,3aS,4R,5S,7aS)-5-((1R,2S,4S)-4-hydroxy-2-(hydroxymethyl)-1-methylcyclohexyl)-4-(hydroxymethyl)-1,7a-dimethyloctahydro-1H-inden-1-ol |
| Cpd No. 28 | (1R,3aS,4R,5S,7aS)-1-ethynyl-5-((1R,2S,4S)-4-hydroxy-2-(hydroxymethyl)-1-methylcyclohexyl)-4-(hydroxymethyl)-7a-methyloctahydro-1H-inden-1-ol |
| Cpd No. 29 | (1S,3S,4R)-3-(hydroxymethyl)-4-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-4-methylcyclohexanol |
| Cpd No. 30 | (1S,3S,4R)-4-((3aS,6S,7R,7aS)-3-(furan-2-yl)-7-(hydroxymethyl)-3a-methyl-3a,4,5,6,7,7a-hexahydro-1H-inden-6-yl)-3-(hydroxymethyl)-4-methylcyclohexanol |
| Cpd No. 31 | (1S,3aS,4R,5S,7aS)-1-(furan-2-yl)-5-((1R,2S,4S)-4-hydroxy-2-(hydroxymethyl)-1-methylcyclohexyl)-4-(hydroxymethyl)-7a-methyloctahydro-1H-inden-1-ol |
| Cpd No. 32 | N-((1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl)acetamide |
| Cpd No. 33 | (1S,3S,4R)-3-(hydroxymethyl)-4-((4aS,5R,6S,8aS)-5-(hydroxymethyl)-8a-methyl-1,4,4a,5,6,7,8,8a-octahydroindeno[1,2-c]pyrazol-6-yl)-4-methylcyclohexanol |
| Cpd No. 34 | (1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiophen-2-yl)octahydro-1H-inden-1-ol |
| Cpd No. 35 | (1S,3S,4R)-3-(hydroxymethyl)-4-((3aS,6S,7R,7aS)-7-(hydroxymethyl)-3a-methyl-3-(thiophen-2-yl)-3a,4,5,6,7,7a-hexahydro-1H-inden-6-yl)-4-methylcyclohexanol |
| Cpd No. 36 | (1S,3aS,4R,5S,7aS)-5-((1R,2S,4S)-4-hydroxy-2-(hydroxymethyl)-1-methylcyclohexyl)-4-(hydroxymethyl)-7a-methyl-1-(pyridin-2-yl)octahydro-1H-inden-1-ol |
| Cpd No. 37 | (1S,2R,4R,5S)-5-((1R,2S,4S)-4-hydroxy-2-(hydroxymethyl)-1-methylcyclohexyl)-4-(hydroxymethyl)-1-methyl-1-phenyl-2,3,4,5,6,7-hexahydro-1H-inden-2-ol |
| Cpd No. 38 | (1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiazol-2-yl)octahydro-1H-inden-1-ol |

The following Examples are provided for purposes of illustration, not limitation. In summary, the following Examples disclose the synthesis of representative compounds of this invention and compounds used in the preparation of compounds of the invention, as well as representative assays for the same.

Example 1

Synthesis of N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)nicotinamide (Compound No. 2)

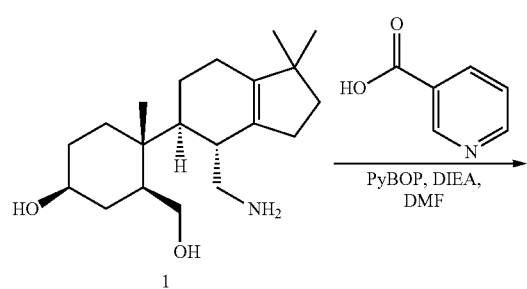

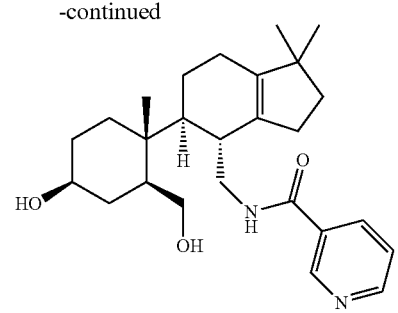

To a solution of (1S,3S,4R)-4-((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 1, 53 mg, 0.16 mmol), PyBOP (104 mg, 0.200 mmol), and nicotinic acid (25 mg, 0.20 mmol) in DMF (1.6 mL) was added DIEA (0.07 mL, 0.4 mmol), and the solution was stirred under argon for 16 h. The mixture was concentrated, and the residue was dissolved in EtOAc (40 mL). The solution was washed with saturated aqueous NaHCO$_3$ (5×10 mL) and brine (2×10 mL) then dried (MgSO$_4$) and concentrated. The residue was purified by chromatography on silica gel (100:10:2 CH$_2$Cl$_2$/MeOH/NH$_4$OH) to give N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)nicotinamide (Compound No. 2, 37 mg, 53%) as a colourless foam. $^1$H NMR (CD$_3$OD): δ 8.94 (s, 1H), 8.68 (d, J=4.5 Hz, 1H), 8.20 (d, J=8.1 Hz, 1H), 7.55 (dd, J=7.4, 5.3 Hz, 1H), 3.77 (m, 1H), 3.56 (dd, J=13, 3.6 Hz, 1H), 3.43 (m, 1H), 3.09-3.24 (m, 2H), 2.52 (m, 1H), 2.38 (m, 1H), 1.13-2.20 (m, 15H), 1.02 (s, 3H), 0.94 (s, 3H), 0.77 (s, 3H); $^{13}$C NMR (CD$_3$OD): δ 167.8, 152.6, 148.9, 144.8, 136.8, 135.0, 132.3, 125.2, 71.4, 63.3, 46.7, 44.2, 43.6, 41.6, 40.3, 38.6, 38.2, 35.7, 34.0, 33.0, 32.2, 27.2, 25.7, 20.9, 20.6, 19.9. ES-MS m/z 427 ([M+1]$^+$).

Example 2

Synthesis of (1S,3S,4R)-4-((4R,5S)-1,1-dimethyl-4-((1-methylpiperidin-4-ylamino)methyl)-2,3,4,5,6,7-hexahydro-1H-inden-5-yl)-3-(hydroxymethyl)-4-methylcyclohexanol (Compound No. 4)

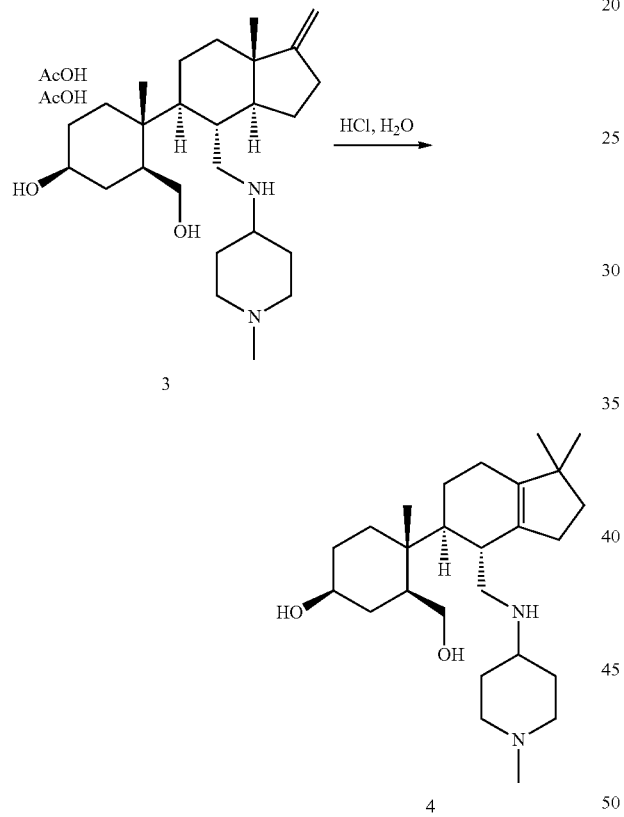

A solution of (1S,3S,4R)-3-(hydroxymethyl)-4-methyl-4-((3aS,4R,5S,7aS)-7a-methyl-1-methylene-4-(((1-methylpiperidin-4-yl)amino)methyl)octahydro-1H-inden-5-yl)cyclohexanol diacetate (Compound No. 3, 153 mg, 0.284 mmol) in 1 N HCl(aq) (6.9 mL) was stirred at 60° C. overnight. The solution was cooled to 0° C., adjusted to pH 12 using 10 N NaOH(aq), and extracted with EtOAc (3×20 mL). The combined organic layers were dried (MgSO$_4$) and concentrated to give (1S,3S,4R)-4-((4R,5S)-1,1-dimethyl-4-((1-methylpiperidin-4-ylamino)methyl)-2,3,4,5,6,7-hexahydro-1H-inden-5-yl)-3-(hydroxymethyl)-4-methylcyclohexanol (Compound No. 4, 80 mg, 67%) as a yellow foam. $^1$H NMR (CD$_3$OD): δ 3.82 (dd, J=11, 2.3 Hz, 1H), 3.43 (m, 1H), 3.21 (m, 1H), 2.88 (m, 2H), 2.73 (dd, J=12, 2.9 Hz, 1H), 2.52 (m, 2H), 2.38 (m, 1H), 2.27 (s, 3H), 1.20-2.20 (m, 22H), 0.99 (s, 3H), 0.92 (s, 3H), 0.90 (s, 3H); $^{13}$C NMR (CD$_3$OD): δ 144.3, 135.5, 71.4, 63.4, 55.4, 55.3 (2C), 50.9, 46.7, 46.1, 43.7, 42.4, 40.2, 38.8, 37.7, 35.7, 34.2, 33.1, 32.7, 32.2 (2C), 27.3, 25.7, 20.9, 20.8, 20.0. ES-MS m/z 419 ([M+1]$^+$).

Example 3

Synthesis of (E)-2-cyano-1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylguanidine (Compound No. 5)

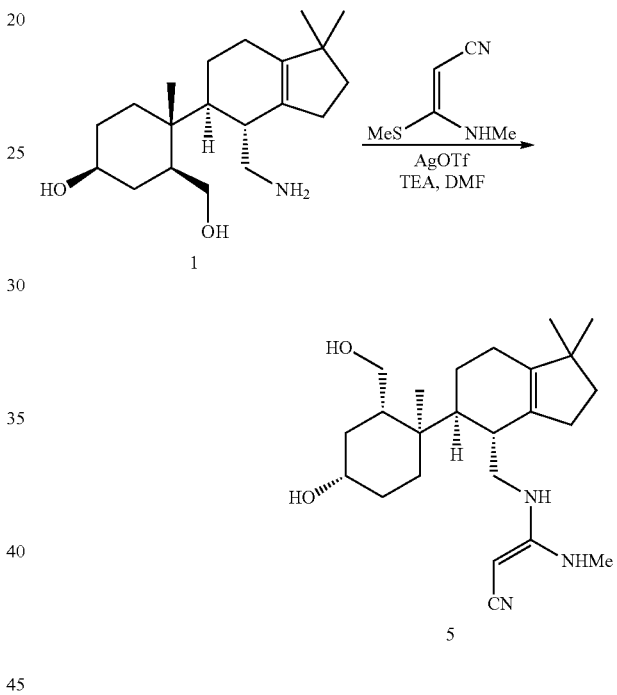

A solution of (1S,3S,4R)-4-((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 1, 71 mg, 0.22 mmol), S-methyl-N-cyano-N'-methyl-carbamimidothioate (34 mg, 0.26 mmol), TEA (150 μL, 1.1 mmol) and AgOTf (95 mg, 0.37 mmol) in DMF (2 mL) was stirred at room temperature for 1 h then was diluted with EtOAc (40 mL) and brine (25 mL). After stirring 2 h, the layers were separated and the aqueous was extracted with EtOAc (30 mL) then the combined organic layers were washed with brine (3×20 mL), dried (Na$_2$SO$_4$) and concentrated. The residue was purified using chromatography on silica gel (4% then 10% the 15% MeOH/CH$_2$Cl$_2$) to afford (E)-2-cyano-1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylguanidine (Compound No. 5, 57 mg, 64%) as a white solid. $^1$H NMR (CD$_3$OD): δ 3.78 (m, 1H), 3.42 (m, 1H), 3.36 (m, 1H), 3.18 (m, 1H), 3.01 (m, 1H), 2.79 (s, 3H), 2.42 (m, 1H), 2.29 (m, 1H), 2.25-1.90 (5H), 1.80 (m, 1H), 1.65 (4H), 1.4-1.1 (5H), 1.00 (s, 3H), 0.90 (s, 3H), 0.80 (s, 3H). ES-MS m/z 403 ([M+1]$^+$).

Example 4

Synthesis of 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-(pyridin-3-yl)urea (Compound No. 6)

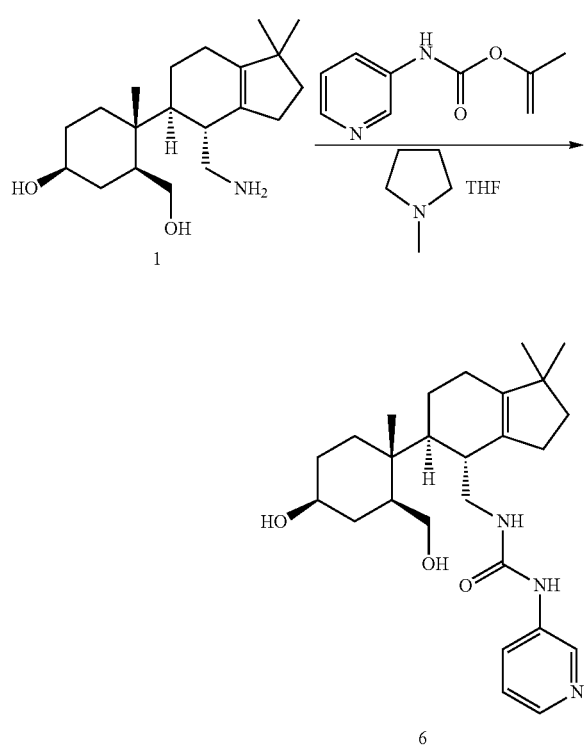

To a solution of (1S,3S,4R)-4-((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 1, 61 mg, 0.19 mmol) and pyridin-3-yl-carbamic acid isopropenyl ester (41 mg, 0.23 mmol, prepared according to Gallou, I. et al., *J. Org. Chem.*, 2005, 70 (17), pp 6960-6963) in THF (1.5 mL) was added 1-methylpyrrolidine (0.02 mL, 0.2 mmol), and the solution was heated to 55° C. under argon for 16 h. The solution was concentrated, and the residue was purified by chromatography on silica gel (100:10:2 CH$_2$Cl$_2$/MeOH/NH$_4$OH) to give 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-(pyridin-3-yl)urea (Compound No. 6, 67 mg, 80%) as a yellow oil. $^1$H NMR (CD$_3$OD): δ 8.53 (d, J=2.4 Hz, 1H), 8.13 (dd, J=1.4, 5.0 Hz, 1H), 7.93 (m, 1H), 7.33 (dd, J=4.8, 8.4 Hz, 1H), 3.80 (dd, J=3.1, 11 Hz, 1H), 3.42 (m, 2H), 3.18 (m, 1H), 3.00 (dd, J=9.6, 14 Hz, 1H), 2.48 (m, 1H), 1.15-2.25 (m, 16H), 1.01 (s, 3H), 0.93 (s, 3H), 0.86 (s, 3H); $^{13}$C NMR (CD$_3$OD): δ 157.8, 144.7, 143.3, 140.8, 138.7, 135.1, 127.7, 125.2, 71.4, 63.3, 46.7, 44.1, 43.6, 41.7, 40.3, 38.7, 38.5, 35.6, 33.9, 33.0, 32.2, 27.2, 25.7, 20.9, 20.7, 19.9. ES-MS m/z 442 ([M+1]$^+$).

Example 5

Synthesis of 1-ethyl-3-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)urea (Compound No. 7)

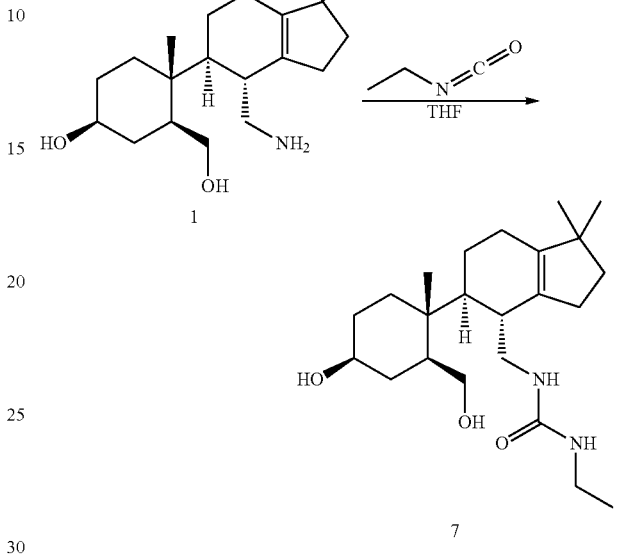

To a solution of (1S,3S,4R)-4-((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 1, 50 mg, 0.16 mmol) in THF (1.6 mL) at 0° C. under argon was added ethyl isocyanate (0.03 mL, 0.4 mmol), and the solution was stirred at room temperature for 3 h then concentrated. The residue was purified by chromatography on silica gel (100:10:2 CH$_2$Cl$_2$/MeOH/NH$_4$OH) to give 1-ethyl-3-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)urea (Compound No. 7, 48 mg, 79%) as a colourless foam. $^1$H NMR (CD$_3$OD): δ 5.93 (m, 1H), 3.80 (dd, J=2.9, 10 Hz, 1H), 3.43 (m, 1H), 3.16 (m, 3H), 2.88 (m, 1H), 2.45 (m, 1H), 1.18-2.22 (m, 17H), 1.08 (t, J=7.2 Hz, 3H), 0.99 (s, 3H), 0.92 (s, 3H), 0.83 (s, 3H); $^{13}$C NMR (CD$_3$OD): δ 161.1, 144.3, 135.4, 71.4, 63.3, 46.7, 44.1, 43.6, 41.4, 40.3, 38.8, 38.6, 35.8, 35.7, 34.0, 33.0, 32.2, 27.3, 25.7, 20.9, 20.7, 19.8, 15.9. ES-MS m/z 393 ([M+1]$^+$).

Example 6

Synthesis of 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylthiourea (Compound No. 8)

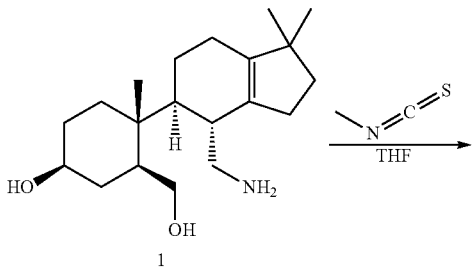

-continued

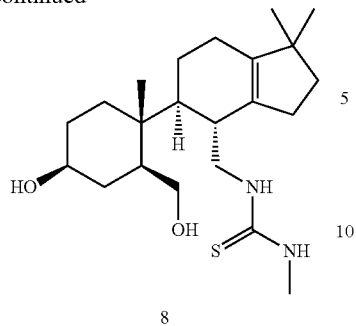

8

To a solution of (1S,3S,4R)-4-(((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 1, 49 mg, 0.15 mmol) in THF (1.5 mL) under argon was added methyl isothiocyanate (24 mg, 0.33 mmol), and the solution was stirred at room temperature for 3 h then concentrated. The residue was purified by chromatography on silica gel (100:10:2 CH$_2$Cl$_2$/MeOH/NH$_4$OH) to give 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)-3-methylthiourea (Compound No. 8, 51 mg, 85%) as a colourless foam. $^1$H NMR (CD$_3$OD): δ 3.80 (m, 1H), 3.69 (m, 1H), 3.44 (m, 1H), 3.16 (m, 1H), 2.89 (s, 3H), 2.46 (m, 2H), 1.18-2.21 (m, 17H), 1.00 (s, 3H), 0.92 (s, 3H), 0.81 (s, 3H); $^{13}$C NMR (CD$_3$OD): δ 183.8, 144.6, 135.2, 71.4, 63.4, 46.7, 43.6, 41.3, 40.3, 38.6, 38.0, 35.7, 33.9, 32.9, 32.2, 30.7, 27.3, 25.7, 20.9, 20.8, 19.8. ES-MS m/z 395 ([M+1]$^+$).

Example 7

Synthesis of (1S,3S,4R)-4-((4aS,5R,6S,8aS)-5-(aminomethyl)-8a-methyl-2,4,4a,5,6,7,8,8a-octahydroindeno[1,2-c]pyrazol-6-yl)-3-(hydroxymethyl)-4-methylcyclohexanol dihydrochloride (Compound No. 15)

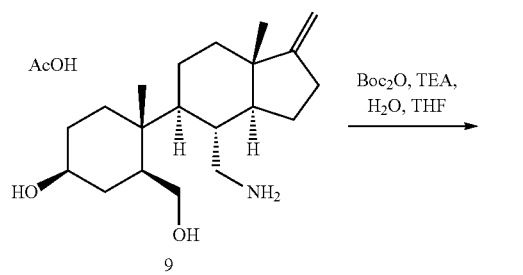

9

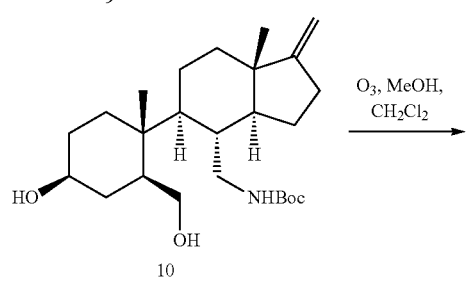

10

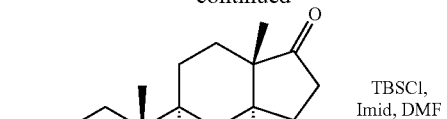

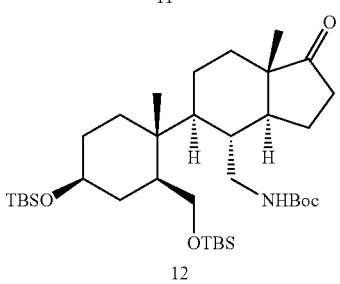

11

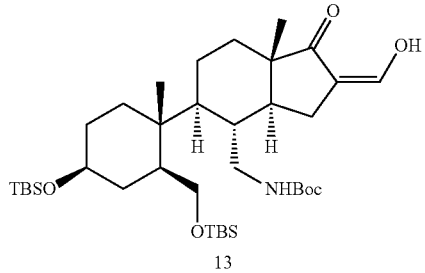

12

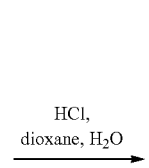

13

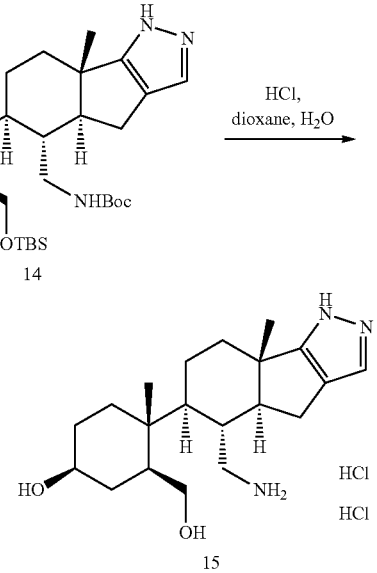

14

15

A. To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 9, 1.45 g, 3.80 mmol) in 10% H$_2$O/THF (19 mL) was added TEA (1.17 mL, 8.39 mmol) and di-tert-butyl dicarbonate (912 mg, 4.18 mmol), and the solution was stirred at room temperature for 20 h. EtOAc (25 mL) was added, and the solution was washed with saturated aqueous NaHCO$_3$ (5×15 mL) and brine (10 mL) then dried (MgSO$_4$) and concentrated to afford tert-butyl (((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)carbamate (Compound No. 10, 1.78 g).

B. A suspension of tert-butyl (((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)carbamate (Compound No. 10, 1.78 g) in 20% MeOH/CH$_2$Cl$_2$ (20 mL) was cooled to −78° C. while O$_2$(g) was passed through the mixture then O$_3$(g) was passed through the mixture at −78° C. for 2 h. Additional MeOH (19 mL) and CH$_2$Cl$_2$ (5 mL) were added, and O$_3$(g) was passed through the mixture for another 40 min followed by a stream of O$_2$(g) for 10 min. The mixture was treated with dimethyl sulfide (1.4 mL, 19 mmol) and stirred at room temperature for 3 h then concentrated. The solution was diluted with EtOAc (50 mL) and washed with brine (4×20 mL) then dried (MgSO$_4$) and concentrated. The residue was purified by chromatography on silica gel (100:8 CH$_2$Cl$_2$/MeOH) to give tert-butyl (((3aS,4R,5S,7aS)-5-((1R,2S,4S)-4-hydroxy-2-(hydroxymethyl)-1-methylcyclohexyl)-7a-methyl-1-oxooctahydro-1H-inden-4-yl)methyl)carbamate (Compound No. 11, 1.45 g, 90% over 2 steps) as a colourless foam.

C. To a solution of tert-butyl (((3aS,4R,5S,7aS)-5-((1R,2S,4S)-4-hydroxy-2-(hydroxymethyl)-1-methylcyclohexyl)-7a-methyl-1-oxooctahydro-1H-inden-4-yl)methyl)carbamate (Compound No. 11, 1.43 g, 3.38 mmol) in DMF (6.8 mL) was added imidazole (644 mg, 9.46 mmol) and TBSCl (1.27 g, 8.43 mmol), and the solution was stirred at room temperature under argon for 15 h. The mixture was diluted with EtOAc (100 mL) and washed with 1 N HCl(aq) (2×30 mL) and brine (5×30 mL) then dried (MgSO$_4$) and concentrated. The residue was purified by chromatography on silica gel (15:85 EtOAc/hexanes) to give tert-butyl (((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-oxooctahydro-1H-inden-4-yl)methyl)carbamate (Compound No. 12, 1.56 g, 71%) as a colourless foam.

D. A solution of tert-butyl (((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-oxooctahydro-1H-inden-4-yl)methyl)carbamate (Compound No. 12, 0.85 g, 1.3 mmol) in THF (2.6 mL) was added to a suspension of sodium hydride (60% dispersion in oil, 209 mg, 5.23 mmol) in THF (2.6 mL) at 0° C. under argon. After stirring for 5 min at 0° C., ethyl formate (0.63 mL, 7.8 mmol) was added and stirred at room temperature for 2.5 h. Saturated aqueous NH$_4$Cl (25 mL) was added followed by EtOAc (20 mL), and the aqueous phase was extracted with EtOAc (15 mL). The combined organic layers were washed with H$_2$O (10 mL) then dried (MgSO$_4$) and concentrated to give tert-butyl (((3aS,4R,5S,7aS,Z)-5-((1R,2S,4S)-4-((tert-butyldimethylsilyl)oxy)-2-(((tert-butyldimethylsilyl)oxy)methyl)-1-methylcyclohexyl)-2-(hydroxymethylene)-7a-methyl-1-oxooctahydro-1H-inden-4-yl)methyl)carbamate (Compound No. 13, 0.89 g) that was used in the next step without further purification.

E. To a solution of tert-butyl (((3aS,4R,5S,7aS,Z)-5-((1R,2S,4S)-4-((tert-butyldimethylsilyl)oxy)-2-(((tert-butyldimethylsilyl)oxy)methyl)-1-methylcyclohexyl)-2-(hydroxymethylene)-7a-methyl-1-oxooctahydro-1H-inden-4-yl)methyl)carbamate (Compound No. 13, 203 mg, 0.298 mmol) in EtOH (6 mL) was added hydrazine hydrate (0.022 mL, 0.45 mmol), and the solution was heated to reflux for 1 h then concentrated. The residue was partitioned between EtOAc (40 mL) and brine (10 mL), and the organic layer was washed with brine (10 mL) then dried (MgSO$_4$) and concentrated. The residue was purified by chromatography on silica gel (1:1 EtOAc/CH$_2$Cl$_2$) to give tert-butyl (((4aS,5R,6S,8aS)-6-((1R,2S,4S)-4-((tert-butyldimethylsilyl)oxy)-2-(((tert-butyldimethylsilyl)oxy)methyl)-1-methylcyclohexyl)-8a-methyl-1,4,4a,5,6,7,8,8a-octahydroindeno[1,2-c]pyrazol-5-yl)methyl)carbamate (Compound No. 14, 124 mg, 61% over 2 steps) as a colourless foam.

F. To a suspension of tert-butyl (((4aS,5R,6S,8aS)-6-((1R,2S,4S)-4-((tert-butyldimethylsilyl)oxy)-2-(((tert-butyldimethylsilyl)oxy)methyl)-1-methylcyclohexyl)-8a-methyl-1,4,4a,5,6,7,8,8a-octahydroindeno[1,2-c]pyrazol-5-yl)methyl)carbamate (Compound No. 14, 60 mg, 0.089 mmol) in 1:1 H$_2$O/1,4-dioxane (2 mL) was added 4 N HCl in dioxane (2 mL), and the solution was stirred at room temperature for 2.3 h then concentrated. Azeotropic removal of remaining H$_2$O was carried out with MeOH (5×20 mL). The residue was dissolved in MeOH (2 mL), and the volume was reduced to about 0.5 mL in vacuo. Et$_2$O (30 mL) was added, giving a pale precipitate, and the supernatant was decanted. More Et$_2$O (30 mL) was added, and the supernatant was decanted (2×). The residue was dried in vacuo to afford (1S,3S,4R)-4-((4aS,5R,6S,8aS)-5-(aminomethyl)-8a-methyl-2,4,4a,5,6,7,8,8a-octahydroindeno[1,2-c]pyrazol-6-yl)-3-(hydroxymethyl)-4-methylcyclohexanol dihydrochloride (Compound No. 15, 31 mg, 84%) as a light yellow solid. $^1$H NMR (DMSO-d6): δ 7.80 (br s, 2H), 7.39 (s, 1H), 3.54 (d, J=11 Hz, 1H), 3.26 (m, 2H), 2.93 (m, 2H), 2.77 (m, 1H), 1.09-2.50 (m, 15H), 0.98 (s, 3H), 0.90 (s, 3H). ES-MS m/z 348 ([M+1]$^+$).

Example 8

Synthesis of (4aS,5R,6S,8aS)-5-(aminomethyl)-6-((1R,2S,4S)-4-hydroxy-2-(hydroxymethyl)-1-methylcyclohexyl)-8a-methyloctahydroquinolin-2(1H)-one (Compound No. 18)

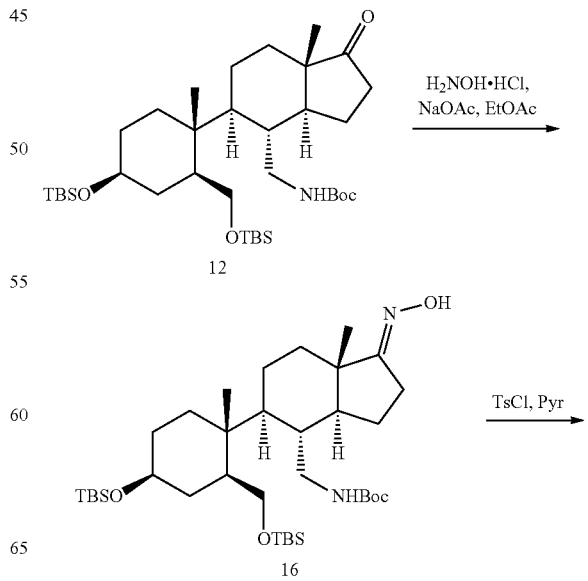

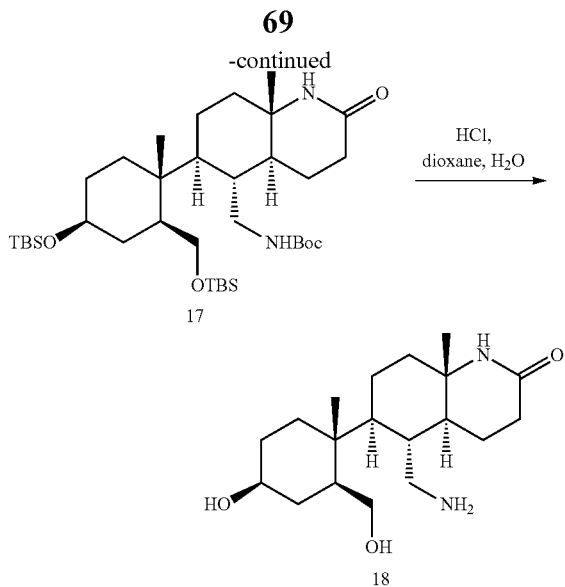

A. A mixture of tert-butyl (((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-oxooctahydro-1H-inden-4-yl)methyl)carbamate (Compound No. 12, 643 mg, 0.986 mmol), hydroxylamine hydrochloride (274 mg, 3.94 mmol), and NaOAc (324 mg, 3.95 mmol) were heated to reflux in EtOH (14 mL) under argon for 2 h then concentrated. The residue was partitioned between $CH_2Cl_2$ (20 mL) and saturated aqueous $NaHCO_3$ (15 mL), and the aqueous layer was extracted with $CH_2Cl_2$ (2×10 mL). The combined organic layers were dried ($MgSO_4$) and concentrated to give tert-butyl (((3aS,4R,5S,7aS, E)-5-((1R,2S,4S)-4-((tert-butyldimethylsilyl)oxy)-2-(((tert-butyldimethylsilyl)oxy)methyl)-1-methylcyclohexyl)-1-(hydroxyimino)-7a-methyloctahydro-1H-inden-4-yl)methyl)carbamate (Compound No. 16, 647 mg) that was used in the next step without further purification.

B. To a solution of tert-butyl (((3aS,4R,5S,7aS, E)-5-((1R,2S,4S)-4-((tert-butyldimethylsilyl)oxy)-2-(((tert-butyldimethylsilyl)oxy)methyl)-1-methylcyclohexyl)-1-(hydroxyimino)-7a-methyloctahydro-1H-inden-4-yl)methyl)carbamate (Compound No. 16, 644 mg, 0.965 mmol) in pyridine (8.0 mL) was added TsCl (202 mg, 1.06 mmol) portionwise over 2 min. After stirring at room temperature for 24 h, additional TsCl (202 mg, 1.06 mmol) was added and stirred for another 6 h. To the mixture was added $H_2O$ (10 mL) then stirred for 30 min. The mixture was diluted with EtOAc (80 mL) then washed with brine (15 mL), dried ($MgSO_4$) and concentrated. Azeotropic removal of remaining pyridine was carried out with PhMe (3×30 mL). The residue was purified by chromatography on silica gel (EtOAc) to give tert-butyl (((4aS,5R,6S,8aS)-6-((1R,2S,4S)-4-((tert-butyldimethylsilyl)oxy)-2-(((tert-butyldimethylsilyl)oxy)methyl)-1-methylcyclohexyl)-8a-methyl-2-oxodecahydroquinolin-5-yl)methyl)carbamate (Compound No. 17, 186 mg, 28% over 2 steps) as a pale solid.

C. To a suspension of tert-butyl (((4aS,5R,6S,8aS)-6-((1R,2S,4S)-4-((tert-butyldimethylsilyl)oxy)-2-(((tert-butyldimethylsilyl)oxy)methyl)-1-methylcyclohexyl)-8a-methyl-2-oxodecahydroquinolin-5-yl)methyl)carbamate (Compound No. 17, 186 mg, 0.279 mmol) in 1:1 $H_2O$/1,4-dioxane (3 mL) was added 4 M HCl in dioxane (3 mL). The mixture was stirred at room temperature for 2.25 h then diluted with $CH_2Cl_2$ (30 mL). The mixture was washed with 1 N NaOH(aq) (10 mL) and saturated aqueous $NaHCO_3$ (20 mL). The combined aqueous layers were concentrated, and azeotropic removal of remaining $H_2O$ was carried out with PhMe (30 mL). The residue was stirred in MeOH (30 mL) then filtered and concentrated. The residue was stirred in 20% $MeOH/CH_2Cl_2$ (30 mL) then filtered and concentrated. The residue was purified by chromatography on silica gel (100:10:2 $CH_2Cl_2/MeOH/NH_4OH$) to afford (4aS,5R,6S,8aS)-5-(aminomethyl)-6-((1R,2S,4S)-4-hydroxy-2-(hydroxymethyl)-1-methylcyclohexyl)-8a-methyloctahydroquinolin-2(1H)-one (Compound No. 18, 38 mg, 40%) as a colourless solid. $^1H$ NMR ($CD_3OD$): δ 3.71 (m, 1H), 3.44 (m, 1H), 3.05-3.19 (m, 2H), 2.87 (m, 1H), 2.42 (m, 2H), 2.16 (m, 1H), 1.26-2.00 (m, 15H), 1.17 (s, 3H), 1.12 (s, 3H); $^{13}C$ NMR ($CD_3OD$): δ 174.5, 71.0, 62.8, 55.2, 45.0, 44.8, 43.8, 40.8, 40.6, 40.3, 38.0, 35.3, 32.0, 31.5, 31.1, 23.9, 21.8, 21.3, 21.1. ES-MS m/z 339 ([M+1]$^+$).

Example 9

Synthesis of (1S,3S,4R)-4-((5aS,6R,7S,9aS)-6-(aminomethyl)-9a-methyl-5a,6,7,8,9,9a-hexahydro-5H-indeno[1,2-b]pyridin-7-yl)-3-(hydroxymethyl)-4-methylcyclohexanol (Compound No. 31)

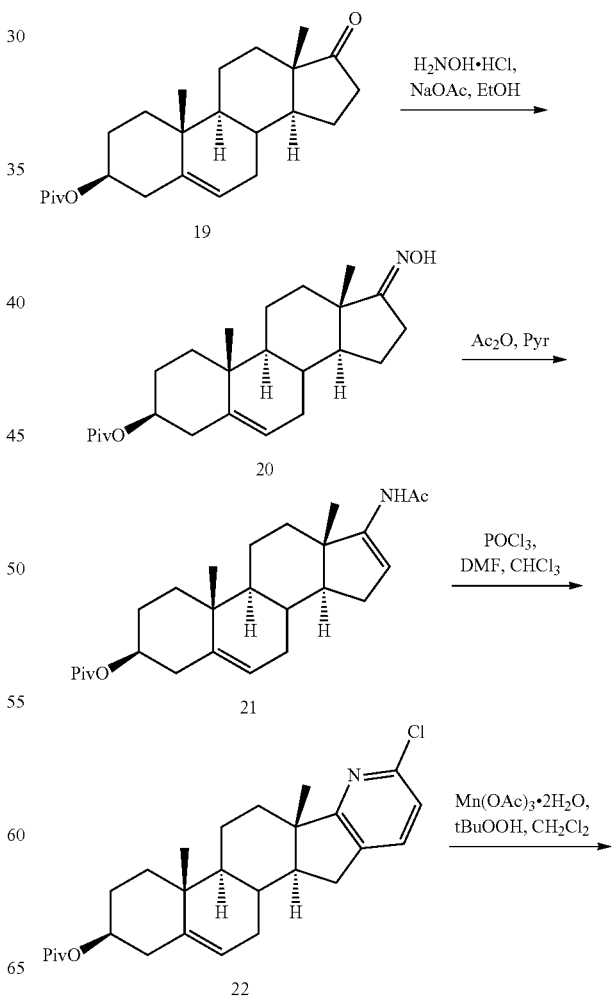

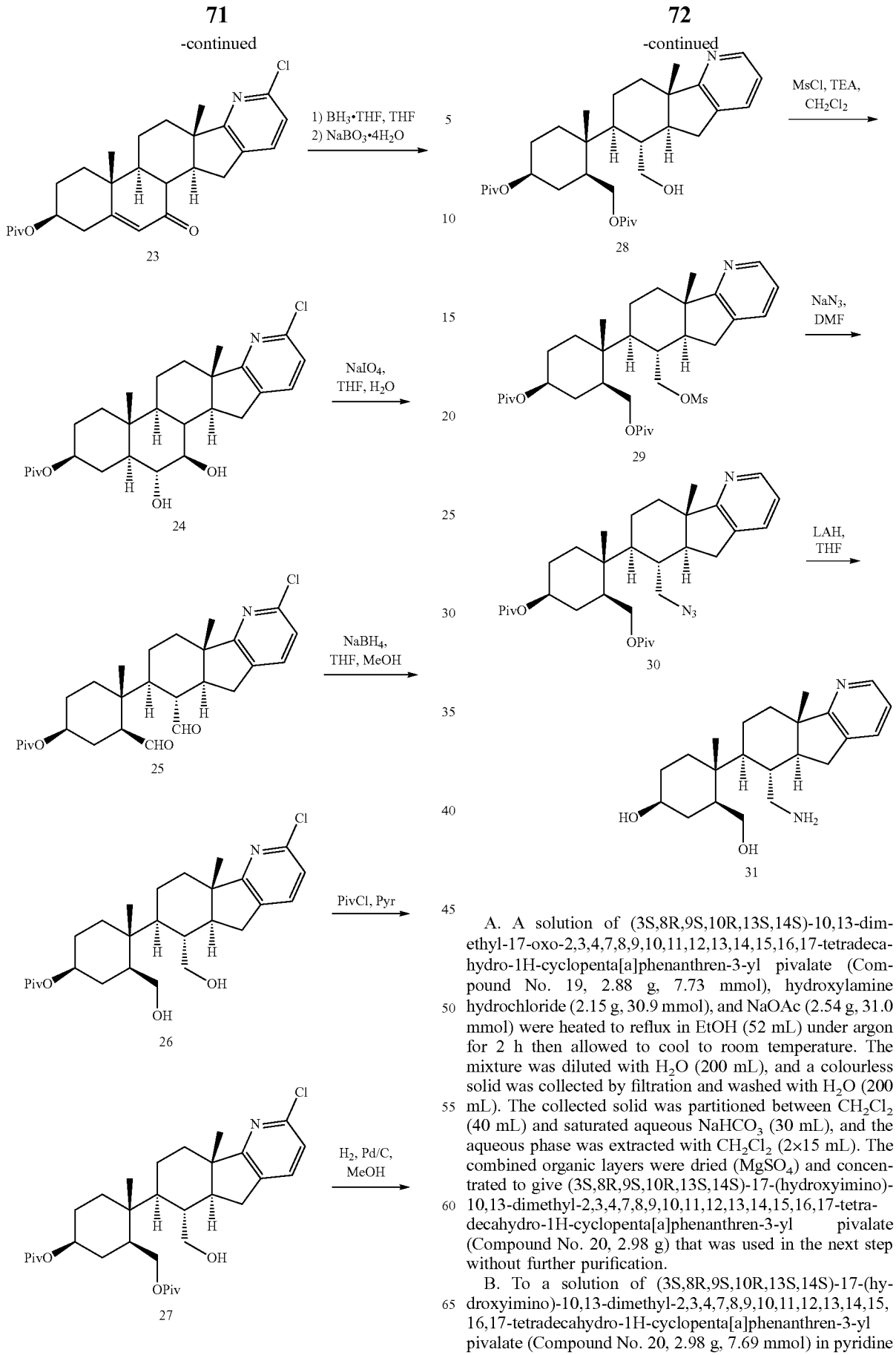

A. A solution of (3S,8R,9S,10R,13S,14S)-10,13-dimethyl-17-oxo-2,3,4,7,8,9,10,11,12,13,14,15,16,17-tetradecahydro-1H-cyclopenta[a]phenanthren-3-yl pivalate (Compound No. 19, 2.88 g, 7.73 mmol), hydroxylamine hydrochloride (2.15 g, 30.9 mmol), and NaOAc (2.54 g, 31.0 mmol) were heated to reflux in EtOH (52 mL) under argon for 2 h then allowed to cool to room temperature. The mixture was diluted with H₂O (200 mL), and a colourless solid was collected by filtration and washed with H₂O (200 mL). The collected solid was partitioned between CH₂Cl₂ (40 mL) and saturated aqueous NaHCO₃ (30 mL), and the aqueous phase was extracted with CH₂Cl₂ (2×15 mL). The combined organic layers were dried (MgSO₄) and concentrated to give (3S,8R,9S,10R,13S,14S)-17-(hydroxyimino)-10,13-dimethyl-2,3,4,7,8,9,10,11,12,13,14,15,16,17-tetradecahydro-1H-cyclopenta[a]phenanthren-3-yl pivalate (Compound No. 20, 2.98 g) that was used in the next step without further purification.

B. To a solution of (3S,8R,9S,10R,13S,14S)-17-(hydroxyimino)-10,13-dimethyl-2,3,4,7,8,9,10,11,12,13,14,15,16,17-tetradecahydro-1H-cyclopenta[a]phenanthren-3-yl pivalate (Compound No. 20, 2.98 g, 7.69 mmol) in pyridine (45 mL) was added Ac$_2$O (30 mL, 320 mmol), and the mixture was heated to reflux under argon for 22 h then concentrated. Et$_2$O (150 mL) was added, and the mixture was washed with 1 M K$_2$CO$_3$(aq) (45 mL). The mixture was filtered through Celite, and the organic layer was washed with H$_2$O (50 mL) and brine (20 mL) then dried (MgSO$_4$) and concentrated. Azeotropic removal of remaining pyridine and Ac$_2$O was carried out with PhMe (3×50 mL). The residue was purified by chromatography on silica gel (30:70-40:60 EtOAc/hexanes) to afford (3S,8R,9S,10R,13S,14S)-17-acetamido-10,13-dimethyl-2,3,4,7,8,9,10,11,12,13,14,15-dodecahydro-1H-cyclopenta[a]phenanthren-3-yl pivalate (Compound No. 21, 1.41 g, 44% over 2 steps) as a pale solid.

C. To DMF at 0° C. under argon was added phosphorus oxychloride (5.7 mL, 61 mmol) and stirred at 0° C. for 15 min. A solution of (3S,8R,9S,10R,13S,14S)-17-acetamido-10,13-dimethyl-2,3,4,7,8,9,10,11,12,13,14,15-dodecahydro-1H-cyclopenta[a]phenanthren-3-yl pivalate (Compound No. 21, 1.41 g, 3.41 mmol) in CHCl$_3$ (85 mL) was added and stirred at 0° C. for 2 h then heated to 65° C. for 3.5 h. The mixture was allowed to cool to room temperature then poured into ice-H$_2$O. To the mixture was added 10 N NaOH(aq) until pH 8 was achieved, and the aqueous phase was extracted with CHCl$_3$ (2×20 mL). The combined organic layers were washed with brine (3×150 mL) then dried (MgSO$_4$) and concentrated. The residue was purified by chromatography on silica gel (5:95 EtOAc/hexanes) to give (4S,6aR,6bS,8aS,13aS,13bR)-10-chloro-6a,8a-dimethyl-3,4,5,6,6a,6b,7,8,8a,13,13a,13b-dodecahydro-1H-naphtho[2',1':4,5]indeno[1,2-b]pyridin-4-yl pivalate (Compound No. 22, 1.00 g, 66%) as colourless crystals.

D. To a solution of (4S,6aR,6bS,8aS,13aS,13bR)-10-chloro-6a,8a-dimethyl-3,4,5,6,6a,6b,7,8,8a,13,13a,13b-dodecahydro-1H-naphtho[2',1':4,5]indeno[1,2-b]pyridin-4-yl pivalate (Compound No. 22, 1.00 g, 2.26 mmol) in CH$_2$Cl$_2$ (16 mL) was added 3 Å molecular sieves (1.1 g) followed by $^t$BuOOH (2.06 mL of a 5.5 M solution in decane, 11.3 mmol). After stirring at room temperature under argon for 25 min, manganese (III) acetate dihydrate (61 mg, 0.23 mmol) was added and stirred at room temperature for 40 h. Celite (0.8 g) was added, and the mixture was filtered. The filtrate was washed with saturated aqueous Na$_2$SO$_3$ (30 mL), and the aqueous phase was extracted with CH$_2$Cl$_2$ (3×10 mL). The combined organic layers were dried (MgSO$_4$) and concentrated. The residue was purified by chromatography on silica gel (15:85 EtOAc/hexanes) to afford (4S,6aR,6bS,8aS,13aS,13bR)-10-chloro-6a,8a-dimethyl-1-oxo-3,4,5,6,6a,6b,7,8,8a,13,13a,13b-dodecahydro-1H-naphtho[2',1':4,5]indeno[1,2-b]pyridin-4-yl pivalate (Compound No. 23, 0.54 g, 52%) as colourless crystals.

E. A solution of (4S,6aR,6bS,8aS,13aS,13bR)-10-chloro-6a,8a-dimethyl-1-oxo-3,4,5,6,6a,6b,7,8,8a,13,13a,13b-dodecahydro-1H-naphtho[2',1':4,5]indeno[1,2-b]pyridin-4-yl pivalate (Compound No. 23, 0.54 g, 1.2 mmol) in THF (3.9 mL) was cooled to 0° C. under argon, and borane (3.6 mL of a 1 M solution in THF, 3.6 mmol) was added over 2 h. The solution was stirred at room temperature for 26 h then cooled to 0° C. and H$_2$O (4 mL) was added dropwise followed by NaBO$_3$·4H$_2$O (547 mg, 3.56 mmol). The mixture was allowed to warm to room temperature with stirring over 19 h then diluted with H$_2$O (6 mL) and EtOAc (15 mL). The aqueous phase was extracted with EtOAc (2×15 mL), and the combined organic layers were dried (MgSO$_4$) and concentrated. The residue was filtered through silica gel (1:1 EtOAc/hexanes) to give (1R,2R,2aS,4S,6aR,6bS,8aS,13aS,13bR)-10-chloro-1,2-dihydroxy-6a,8a-dimethyl-2,2a,3,4,5,6,6a,6b,7,8,8a,13,13a,13b-tetradecahydro-1H-naphtho[2',1':4,5]indeno[1,2-b]pyridin-4-yl pivalate (Compound No. 24, 431 mg) that was used in the next step without further purification.

F. To a solution of (1R,2R,2aS,4S,6aR,6bS,8aS,13aS,13bR)-10-chloro-1,2-dihydroxy-6a,8a-dimethyl-2,2a,3,4,5,6,6a,6b,7,8,8a,13,13a,13b-tetradecahydro-1H-naphtho[2',1':4,5]indeno[1,2-b]pyridin-4-yl pivalate (Compound No. 24, 431 mg) in THF (9.1 mL) was added a suspension of NaIO$_4$ (387 mg, 1.81 mmol) in H$_2$O (1.8 mL), and the mixture was stirred at room temperature for 3 h. The mixture was concentrated, and the residue was partitioned between CH$_2$Cl$_2$ (25 mL) and H$_2$O (10 mL). The aqueous phase was extracted with CH$_2$Cl$_2$ (2×10 mL), and the combined organic layers were washed with brine (15 mL) then dried (MgSO$_4$) and concentrated to give (1S,3S,4R)-4-((5aS,6R,7S,9aS)-2-chloro-6-formyl-9a-methyl-5a,6,7,8,9,9a-hexahydro-5H-indeno[1,2-b]pyridin-7-yl)-3-formyl-4-methylcyclohexyl pivalate (Compound No. 25, 424 mg) that was obtained was used in the next step without further purification.

G. A solution of (1S,3S,4R)-4-((5aS,6R,7S,9aS)-2-chloro-6-formyl-9a-methyl-5a,6,7,8,9,9a-hexahydro-5H-indeno[1,2-b]pyridin-7-yl)-3-formyl-4-methylcyclohexyl pivalate (Compound No. 25, 424 mg) in 3:1 THF/MeOH (9 mL) was cooled to 0° C. under argon and NaBH$_4$ (69 mg, 1.8 mmol) was added. The mixture was stirred for 30 min at 0° C. then at room temperature for 3 h. The mixture was cooled to 0° C., and 80% acetic acid(aq) (1 mL) was added dropwise. The mixture was stirred for 5 min at 0° C. then at room temperature for 15 min. The mixture was concentrated, and the residue was partitioned between EtOAc (40 mL) and 1 N NaOH(aq) (10 mL). The organic layer was washed with brine (10 mL) then dried (MgSO$_4$) and concentrated. The residue was purified by chromatography on silica gel (1:1 EtOAc/CH$_2$Cl$_2$) to afford (1S,3S,4R)-4-((5aS,6R,7S,9aS)-2-chloro-6-(hydroxymethyl)-9a-methyl-5a,6,7,8,9,9a-hexahydro-5H-indeno[1,2-b]pyridin-7-yl)-3-(hydroxymethyl)-4-methylcyclohexyl pivalate (Compound No. 26, 262 mg, 46% over 3 steps) as a colourless oil.

H. To a solution of (1S,3S,4R)-4-((5aS,6R,7S,9aS)-2-chloro-6-(hydroxymethyl)-9a-methyl-5a,6,7,8,9,9a-hexahydro-5H-indeno[1,2-b]pyridin-7-yl)-3-(hydroxymethyl)-4-methylcyclohexyl pivalate (Compound No. 26, 262 mg, 0.548 mmol) in pyridine (5.5 mL) was added pivaloyl chloride (0.074 mL, 0.60 mmol) dropwise then stirred at room temperature under argon for 3 h. Additional pivaloyl chloride (0.030 mL, 0.24 mmol) was added and stirred for an additional 1.5 h. The mixture was diluted with EtOAc (60 mL) and washed with saturated aqueous NaHCO$_3$ (15 mL) and brine (10 mL) then dried (MgSO$_4$) and concentrated. Azeotropic removal of remaining pyridine was carried out with hexanes (3×20 mL). The residue was purified by chromatography on silica gel (10:90 EtOAc/CH$_2$Cl$_2$) to give ((1S,2R,5S)-2-((5aS,6R,7S,9aS)-2-chloro-6-(hydroxymethyl)-9a-methyl-5a,6,7,8,9,9a-hexahydro-5H-indeno[1,2-b]pyridin-7-yl)-2-methyl-5-(pivaloyloxy)cyclohexyl)methyl pivalate (Compound No. 27, 106 mg, 34%) as a colourless oil.

I. To a solution of ((1S,2R,5S)-2-((5aS,6R,7S,9aS)-2-chloro-6-(hydroxymethyl)-9a-methyl-5a,6,7,8,9,9a-hexahydro-5H-indeno[1,2-b]pyridin-7-yl)-2-methyl-5-(pivaloyloxy)cyclohexyl)methyl pivalate (Compound No. 27, 128 mg, 0.228 mmol) in MeOH (8.0 mL) was added 10% Pd/C (35 mg) then shaken under an atmosphere of H$_2$(g) at 30 psi for 2 h. The mixture was filtered through Celite then concentrated to give ((1S,2R,5S)-2-((5aS,6R,7S,9aS)-6-(hydroxymethyl)-9a-methyl-5a,6,7,8,9,9a-hexahydro-5H-indeno[1,2-b]pyridin-7-yl)-2-methyl-5-(pivaloyloxy)cyclohexyl)methyl pivalate (Compound No. 28, 121 mg) that was used in the next step without further purification.

J. To a solution of ((1S,2R,5S)-2-((5aS,6R,7S,9aS)-6-(hydroxymethyl)-9a-methyl-5a,6,7,8,9,9a-hexahydro-5H-indeno[1,2-b]pyridin-7-yl)-2-methyl-5-(pivaloyloxy)cyclohexyl)methyl pivalate (Compound No. 28, 120 mg) and TEA (0.063 mL, 0.45 mmol) in CH$_2$Cl$_2$ (4.5 mL) at 0° C. was added MsCl (0.026 mL, 0.34 mmol), and the solution was stirred under argon at room temperature for 1 h. The solution was concentrated, and the residue was partitioned between EtOAc (40 mL) and saturated aqueous NaHCO$_3$ (10 mL). The organic layer was washed with saturated aqueous NaHCO$_3$ (3×10 mL) and brine (2×10 mL) then dried (MgSO$_4$) and concentrated to give ((1S,2R,5S)-2-methyl-2-((5aS,6R,7S,9aS)-9a-methyl-6-(((methylsulfonyl)oxy)methyl)-5a,6,7,8,9,9a-hexahydro-5H-indeno[1,2-b]pyridin-7-yl)-5-(pivaloyloxy)cyclohexyl)methyl pivalate (Compound No. 29, 143 mg) that was used in the next step without further purification.

K. Sodium azide (44 mg, 0.68 mmol) was added to a solution of ((1S,2R,5S)-2-methyl-2-((5aS,6R,7S,9aS)-9a-methyl-6-(((methylsulfonyl)oxy)methyl)-5a,6,7,8,9,9a-hexahydro-5H-indeno[1,2-b]pyridin-7-yl)-5-(pivaloyloxy)cyclohexyl)methyl pivalate (Compound No. 29, 143 mg) in DMF (1.1 mL), and the mixture was heated to 60° C. under argon for 15 h. The mixture was diluted with EtOAc (40 mL) and H$_2$O (10 mL). The organic layer was washed with brine (5×10 mL) then dried (MgSO$_4$) and concentrated to give ((1S,2R,5S)-2-((5aS,6R,7S,9aS)-6-(azidomethyl)-9a-methyl-5a,6,7,8,9,9a-hexahydro-5H-indeno[1,2-b]pyridin-7-yl)-2-methyl-5-(pivaloyloxy)cyclohexyl)methyl pivalate (Compound No. 30, 108 mg) that was used in the next step without further purification.

L. A solution of ((1S,2R,5S)-2-((5aS,6R,7S,9aS)-6-(azidomethyl)-9a-methyl-5a,6,7,8,9,9a-hexahydro-5H-indeno[1,2-b]pyridin-7-yl)-2-methyl-5-(pivaloyloxy)cyclohexyl)methyl pivalate (Compound No. 30, 108 mg) in THF (1.0 mL) was cooled to 0° C. under argon and LiAlH$_4$ (0.39 mL of a 2 M solution in THF, 0.78 mmol) was added dropwise. After stirring at room temperature for 21 h, the mixture was diluted with THF (2 mL) and stirred for an additional 1.5 h. The mixture was cooled to 0° C. and H$_2$O (0.030 mL) was added followed by 15% NaOH(aq) (0.030 mL) and H$_2$O (0.090 mL). The mixture was stirred at room temperature for 30 min then dried (MgSO$_4$), filtered and concentrated. The residue was purified by chromatography on silica gel (100:10:2 CH$_2$Cl$_2$/MeOH/NH$_4$OH) to afford (1S,3S,4R)-4-((5aS,6R,7S,9aS)-6-(aminomethyl)-9a-methyl-5a,6,7,8,9,9a-hexahydro-5H-indeno[1,2-b]pyridin-7-yl)-3-(hydroxymethyl)-4-methylcyclohexanol (Compound No. 31, 32 mg, 39% over 4 steps) as a colourless solid. $^1$H NMR (CD$_3$OD): δ 8.33 (d, J=4.2 Hz, 1H), 7.61 (d, J=7.5 Hz, 1H), 7.17 (dd, J=7.4, 5.0 Hz, 1H), 3.73 (dd, J=11, 2.9 Hz, 1H), 3.38 (m, 1H), 3.06-3.20 (m, 2H), 2.67-2.87 (m, 4H), 2.09 (m, 2H), 1.80 (m, 2H), 1.17-1.63 (m, 10H), 0.94 (s, 3H), 0.70-0.94 (m, 2H); $^{13}$C NMR (CD$_3$OD): δ 171.6, 148.8, 137.5, 134.3, 123.1, 71.3, 62.7, 50.3, 48.2, 47.7, 43.4, 43.0, 41.9, 38.6, 38.2, 37.9, 35.2, 32.8, 31.7, 31.1, 20.0, 18.1. ES-MS m/z 359 ([M+1]$^+$).

Example 10

Synthesis of (1S,3S,4R)-4-((3aS,6S,7R,7aS)-7-(aminomethyl)-3a-methyl-3-phenyl-3a,4,5,6,7,7a-hexahydro-1H-inden-6-yl)-3-(hydroxymethyl)-4-methylcyclohexanol hydrochloride (Compound No. 44)

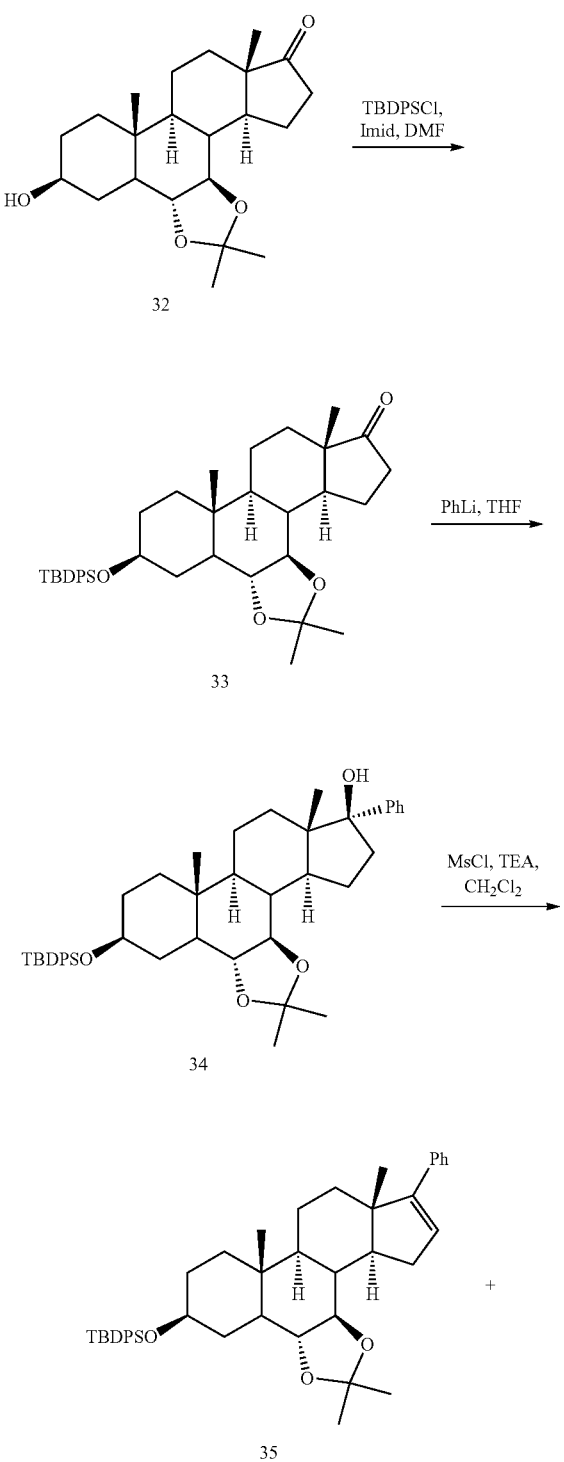

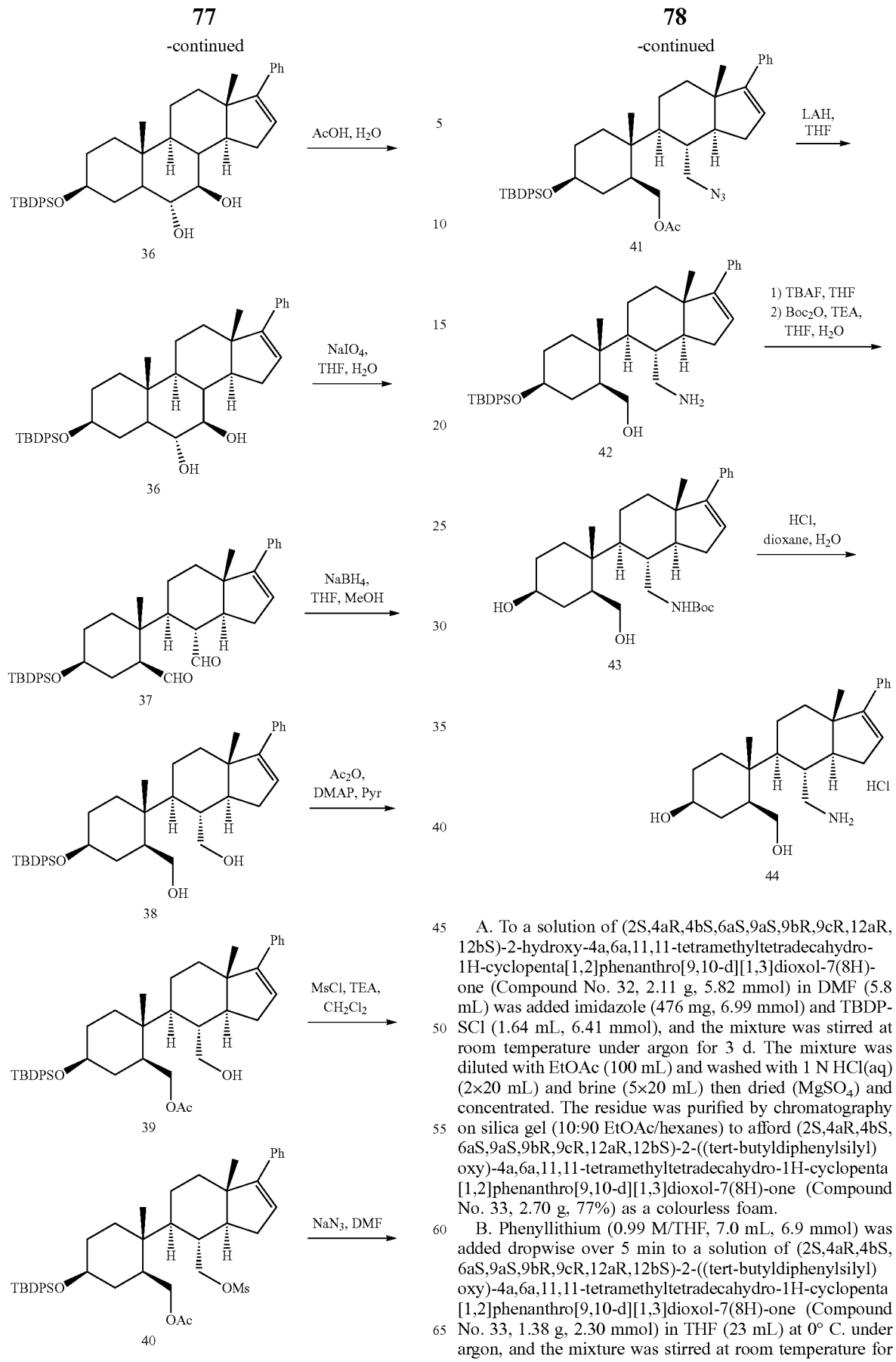

A. To a solution of (2S,4aR,4bS,6aS,9aS,9bR,9cR,12aR,12bS)-2-hydroxy-4a,6a,11,11-tetramethyltetradecahydro-1H-cyclopenta[1,2]phenanthro[9,10-d][1,3]dioxol-7(8H)-one (Compound No. 32, 2.11 g, 5.82 mmol) in DMF (5.8 mL) was added imidazole (476 mg, 6.99 mmol) and TBDPSCl (1.64 mL, 6.41 mmol), and the mixture was stirred at room temperature under argon for 3 d. The mixture was diluted with EtOAc (100 mL) and washed with 1 N HCl(aq) (2×20 mL) and brine (5×20 mL) then dried (MgSO$_4$) and concentrated. The residue was purified by chromatography on silica gel (10:90 EtOAc/hexanes) to afford (2S,4aR,4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 2.70 g, 77%) as a colourless foam.

B. Phenyllithium (0.99 M/THF, 7.0 mL, 6.9 mmol) was added dropwise over 5 min to a solution of (2S,4aR,4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 1.38 g, 2.30 mmol) in THF (23 mL) at 0° C. under argon, and the mixture was stirred at room temperature for 16 h. The mixture was cooled to 0° C. and saturated aqueous NaHCO$_3$ (25 mL) was added. The aqueous layer was extracted with EtOAc (2×20 mL), and the combined organic layers were dried (MgSO$_4$) and concentrated. The residue was purified by chromatography on silica gel (15:85 EtOAc/hexanes) to give (2S,4aR,4bS,6aS,7S,9aS,9bR,9cR,12aR,12bS)-2-((tert-butyldiphenylsilyl)oxy)-4a,6a,11,11-tetramethyl-7-phenylhexadecahydro-1H-cyclopenta[1,2]phenanthro[9,10-d][1,3]dioxol-7-ol (Compound No. 34, 1.40 g).

C. To a solution (2S,4aR,4bS,6aS,7S,9aS,9bR,9cR,12aR,12bS)-2-((tert-butyldiphenylsilyl)oxy)-4a,6a,11,11-tetramethyl-7-phenylhexadecahydro-1H-cyclopenta[1,2]phenanthro[9,10-d][1,3]dioxol-7-ol (Compound No. 34, 1.40 g) and TEA (2.87 mL, 20.6 mmol) in CH$_2$Cl$_2$ (41 mL) at 0° C. was added MsCl (0.80 mL, 10 mmol) dropwise, and the solution was stirred under argon at 0° C. for 40 min. The solution was concentrated, and the residue was purified by chromatography on silica gel (3:97 EtOAc/hexanes) to afford tert-butyldiphenyl(((2S,4aR,4bS,6aS,9aS,9bR,9cR,12aR,12bS)-4a,6a,11,11-tetramethyl-7-phenyl-2,3,4,4a,4b,5,6,6a,9,9a,9b,9c,12a,12b-tetradecahydro-1H-cyclopenta[1,2]phenanthro[9,10-d][1,3]dioxol-2-yl)oxy)silane (Compound No. 35, 0.28 g) as a colourless gum. Further elution with 25:75 EtOAc/hexanes gave (3S,5S,6R,7R,8R,9S,10R,13S,14S)-3-((tert-butyldiphenylsilyl)oxy)-10,13-dimethyl-17-phenyl-2,3,4,5,6,7,8,9,10,11,12,13,14,15-tetradecahydro-1H-cyclopenta[a]phenanthrene-6,7-diol (Compound No. 36, 677 mg) as colourless crystals.

D. A suspension of (3S,5S,6R,7R,8R,9S,10R,13S,14S)-3-((tert-butyldiphenylsilyl)oxy)-10,13-dimethyl-17-phenyl-2,3,4,5,6,7,8,9,10,11,12,13,14,15-tetradecahydro-1H-cyclopenta[a]phenanthrene-6,7-diol (Compound No. 35, 0.28 g) in 80% acetic acid(aq) (5 mL) was heated to 40° C. for 2 h then concentrated. Azeotropic removal of remaining AcOH and H$_2$O was carried out with PhMe (4×20 mL) to give (3S,5S,6R,7R,8R,9S,10R,13S,14S)-3-((tert-butyldiphenylsilyl)oxy)-10,13-dimethyl-17-phenyl-2,3,4,5,6,7,8,9,10,11,12,13,14,15-tetradecahydro-1H-cyclopenta[a]phenanthrene-6,7-diol (Compound No. 36, 289 mg) as a colourless foam.

E. The two batches of (3S,5S,6R,7R,8R,9S,10R,13S,14S)-3-((tert-butyldiphenylsilyl)oxy)-10,13-dimethyl-17-phenyl-2,3,4,5,6,7,8,9,10,11,12,13,14,15-tetradecahydro-1H-cyclopenta[a]phenanthrene-6,7-diol from above (Compound No. 36, 677 mg and 289 mg) were combined and dissolved in THF (16 mL). A suspension of NaIO$_4$ (665 mg, 3.11 mmol) in H$_2$O (1.6 mL) was added, and the mixture was stirred at room temperature for 1.5 h. The mixture was concentrated, and the residue was partitioned between CH$_2$Cl$_2$ (20 mL) and H$_2$O (10 mL). The aqueous phase was extracted with CH$_2$Cl$_2$ (2×10 mL), and the combined organic layers were washed with brine (10 mL) then dried (MgSO$_4$) and concentrated to afford (3aS,6S,7R,7aS)-6-((1R,2S,4S)-4-((tert-butyldiphenylsilyl)oxy)-2-formyl-1-methylcyclohexyl)-3a-methyl-3-phenyl-3a,4,5,6,7,7a-hexahydro-1H-indene-7-carbaldehyde (Compound No. 37, 914 mg) that was used in the next step without further purification.

F. A solution of (3aS,6S,7R,7aS)-6-((1R,2S,4S)-4-((tert-butyldiphenylsilyl)oxy)-2-formyl-1-methylcyclohexyl)-3a-methyl-3-phenyl-3a,4,5,6,7,7a-hexahydro-1H-indene-7-carbaldehyde (Compound No. 37, 914 mg) in 1:1 THF/MeOH (15 mL) was cooled to 0° C. under argon and NaBH$_4$ (112 mg, 2.96 mmol) was added. The mixture was stirred at room temperature for 2 h, cooled to 0° C. and 80% acetic acid(aq) (1.5 mL) was added. The mixture was stirred for 3 min at 0° C. then at room temperature for 15 min. The mixture was concentrated, and the residue was partitioned between EtOAc (40 mL) and 1 N NaOH(aq) (10 mL). The organic layer was washed with 1 N NaOH(aq) until the washings remained basic then washed with brine (10 mL), dried (MgSO$_4$) and concentrated. The residue was purified by chromatography on silica gel (15:85 EtOAc/CH$_2$Cl$_2$) to give ((1S,2R,5S)-5-((tert-butyldiphenylsilyl)oxy)-2-((3aS,6S,7R,7aS)-7-(hydroxymethyl)-3a-methyl-3-phenyl-3a,4,5,6,7,7a-hexahydro-1H-inden-6-yl)-2-methylcyclohexyl)methanol (Compound No. 38, 743 mg, 52% over 5 steps) as a colourless solid.

G. To a solution of ((1S,2R,5S)-5-((tert-butyldiphenylsilyl)oxy)-2-((3aS,6S,7R,7aS)-7-(hydroxymethyl)-3a-methyl-3-phenyl-3a,4,5,6,7,7a-hexahydro-1H-inden-6-yl)-2-methylcyclohexyl)methanol (Compound No. 38, 634 mg, 1.02 mmol) and DMAP (12 mg, 0.098 mmol) in pyridine (6.8 mL) at 0° C. under argon was added Ac$_2$O (0.096 mL, 1.0 mmol) dropwise over 55 min then stirred at 0° C. for 1 h. The mixture was diluted with EtOAc (80 mL) and washed with brine (3×20 mL) then dried (MgSO$_4$) and concentrated. Azeotropic removal of remaining pyridine was carried out with PhMe (3×20 mL). The residue was purified by chromatography on silica gel (20:80 EtOAc/hexanes) to afford ((1S,2R,5S)-5-((tert-butyldiphenylsilyl)oxy)-2-((3aS,6S,7R,7aS)-7-(hydroxymethyl)-3a-methyl-3-phenyl-3a,4,5,6,7,7a-hexahydro-1H-inden-6-yl)-2-methylcyclohexyl)methyl acetate (Compound No. 39, 450 mg, 66%) as a colourless foam.

H. To a solution of ((1S,2R,5S)-5-((tert-butyldiphenylsilyl)oxy)-2-((3aS,6S,7R,7aS)-7-(hydroxymethyl)-3a-methyl-3-phenyl-3a,4,5,6,7,7a-hexahydro-1H-inden-6-yl)-2-methylcyclohexyl)methyl acetate (Compound No. 39, 450 mg, 0.677 mmol) and TEA (0.28 mL, 2.0 mmol) in CH$_2$Cl$_2$ (6.8 mL) at 0° C. was added MsCl (0.079 mL, 1.0 mmol), and the solution was stirred under argon at room temperature for 45 min. The solution was concentrated, and the residue was partitioned between EtOAc (40 mL) and saturated aqueous NaHCO$_3$ (15 mL). The organic layer was washed with saturated aqueous NaHCO$_3$ (3×15 mL) and brine (10 mL) then dried (MgSO$_4$) and concentrated to give ((1S,2R,5S)-5-((tert-butyldiphenylsilyl)oxy)-2-methyl-2-((3aS,6S,7R,7aS)-3a-methyl-7-(((methylsulfonyl)oxy)methyl)-3-phenyl-3a,4,5,6,7,7a-hexahydro-1H-inden-6-yl)cyclohexyl)methyl acetate (Compound No. 40, 508 mg) that was used in the next step without further purification.

I. Sodium azide (132 mg, 2.03 mmol) was added to a solution of ((1S,2R,5S)-5-((tert-butyldiphenylsilyl)oxy)-2-methyl-2-((3aS,6S,7R,7aS)-3a-methyl-7-(((methylsulfonyl)oxy)methyl)-3-phenyl-3a,4,5,6,7,7a-hexahydro-1H-inden-6-yl)cyclohexyl)methyl acetate (Compound No. 40, 508 mg) in DMF (4.5 mL), and the mixture was heated to 60° C. under argon for 18 h. The mixture was diluted with EtOAc (100 mL) and washed with H$_2$O (20 mL) and brine (5×15 mL) then dried (MgSO$_4$) and concentrated to give ((1S,2R,5S)-2-((3aS,6S,7R,7aS)-7-(azidomethyl)-3a-methyl-3-phenyl-3a,4,5,6,7,7a-hexahydro-1H-inden-6-yl)-5-((tert-butyl-diphenylsilyl)oxy)-2-methylcyclohexyl)methyl acetate (Compound No. 41, 467 mg) that was used in the next step without further purification.

J. A solution of ((1S,2R,5S)-2-((3aS,6S,7R,7aS)-7-(az-idomethyl)-3a-methyl-3-phenyl-3a,4,5,6,7,7a-hexahydro-1H-inden-6-yl)-5-((tert-butyldiphenylsilyl)oxy)-2-methylcyclohexyl)methyl acetate (Compound No. 41, 467 mg) in THF (12 mL) was cooled to 0° C. under argon, and LiAlH$_4$ (1.7 mL of a 2 M solution in THF, 3.4 mmol) was added dropwise. The mixture was allowed to warm to room temperature over 1 h then stirred at room temperature for 3 d. The mixture was diluted with THF (5 mL) and stirred for an additional 10 min. The mixture was cooled to 0° C. and H$_2$O (0.076 mL) was added followed by 15% NaOH(aq) (0.076 mL) and H$_2$O (0.23 mL). The mixture was stirred at room temperature for 30 min then dried (MgSO$_4$), filtered and concentrated. The residue was purified by chromatography on silica gel (6:94 MeOH/CH$_2$Cl$_2$) to afford ((1S,2R,5S)-2-((3aS,6S,7R,7aS)-7-(aminomethyl)-3a-methyl-3-phenyl-3a,4,5,6,7,7a-hexahydro-1H-inden-6-yl)-5-((tert-butyldiphenylsilyl)oxy)-2-methylcyclohexyl)methanol (Compound No. 42, 195 mg).

K. TBAF (0.47 mL of a 1 M solution in THF, 0.47 mmol) was added to a solution of ((1S,2R,5S)-2-((3aS,6S,7R,7aS)-7-(aminomethyl)-3a-methyl-3-phenyl-3a,4,5,6,7,7a-hexahydro-1H-inden-6-yl)-5-((tert-butyldiphenylsilyl)oxy)-2-methylcyclohexyl)methanol (Compound No. 42, 195 mg) in THF (6.3 mL) at room temperature under argon then stirred for 18 h. The solution was concentrated, and the residue was purified by chromatography on silica gel (100:10:2 EtOAc/MeOH/NH$_4$OH). The residue (79 mg), di-tert-butyl dicarbonate (58 mg, 0.27 mmol), and TEA (0.043 mL, 0.31 mmol) in 10% H$_2$O/THF (4.1 mL) was stirred at room temperature for 18 h then concentrated. The residue was dissolved in EtOAc (40 mL), and the solution was washed with saturated aqueous NaHCO$_3$ (10 mL) and brine (4×10 mL) then dried (MgSO$_4$) and concentrated. The residue was purified by chromatography on silica gel (5:95 MeOH/CH$_2$Cl$_2$) to give tert-butyl (((3aS,6S,7R,7aS)-6-((1R,2S,4S)-4-hydroxy-2-(hydroxymethyl)-1-methylcyclohexyl)-3a-methyl-3-phenyl-3a,4,5,6,7,7a-hexahydro-1H-inden-7-yl)methyl)carbamate (Compound No. 43, 81 mg, 25% over 5 steps) as a colourless solid.

L. To a solution of tert-butyl tert-butyl (((3aS,6S,7R,7aS)-6-((1R,2S,4S)-4-hydroxy-2-(hydroxymethyl)-1-methylcyclohexyl)-3a-methyl-3-phenyl-3a,4,5,6,7,7a-hexahydro-1H-inden-7-yl)methyl)carbamate (Compound No. 43, 80 mg, 0.17 mmol) in 1:1 H$_2$O/1,4-dioxane (3 mL) was added 4 N HCl in dioxane (3 mL), and the solution was stirred at room temperature for 4.5 h then concentrated. Azeotropic removal of remaining H$_2$O was carried out with MeOH (5×20 mL), and the residue was dissolved in MeOH (0.4 mL). Et$_2$O (30 mL) was added, giving a yellow precipitate, and the supernatant was decanted. Additional ether (30 mL) was added, and the supernatant was decanted (3×). The residue was dried in vacuo to afford (1S,3S,4R)-4-((3aS,6S,7R,7aS)-7-(aminomethyl)-3a-methyl-3-phenyl-3a,4,5,6,7,7a-hexahydro-1H-inden-6-yl)-3-(hydroxymethyl)-4-methylcyclohexanol hydrochloride (Compound No. 44, 30 mg, 43%) as a yellow solid. $^1$H NMR (CD$_3$OD): δ 7.21-7.37 (m, 5H), 5.93 (s, 1H), 3.71 (m, 1H), 3.47 (m, 2H), 3.16 (m, 2H), 2.38 (m, 1H), 1.25-2.17 (m, 15H), 1.09 (s, 6H); $^{13}$C NMR (CD$_3$OD): δ 156.0, 137.6, 129.1 (2C), 127.9, 127.6 (2C), 126.7, 70.8, 62.7, 54.4, 48.0, 45.5, 44.5, 44.1, 38.2, 36.5, 35.8, 34.8, 33.1, 32.6, 32.0, 23.9, 22.5, 17.3. ES-MS m/z 384 ([M+1]$^+$).

Example 11

Synthesis of (1S,3aS,4R,5S,7aS)-4-(aminomethyl)-5-((1R,2S,4S)-4-hydroxy-2-(hydroxymethyl)-1-methylcyclohexyl)-7a-methyl-1-phenyloctahydro-1H-inden-1-ol acetate (Compound No. 54)

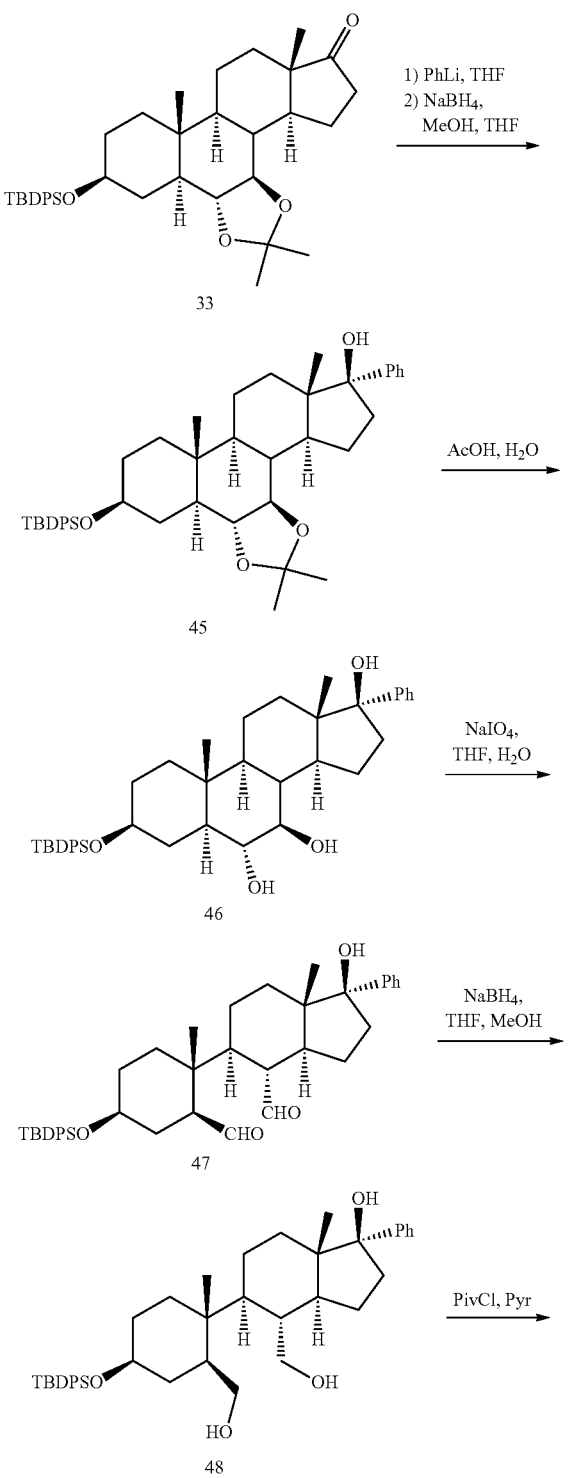

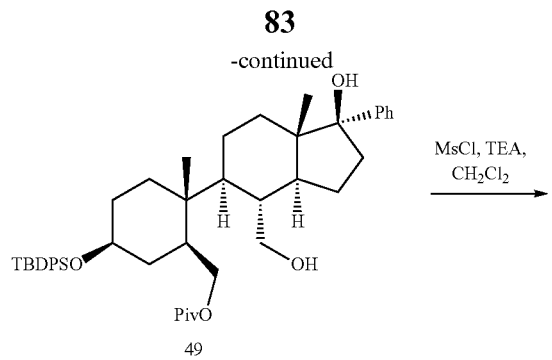

49

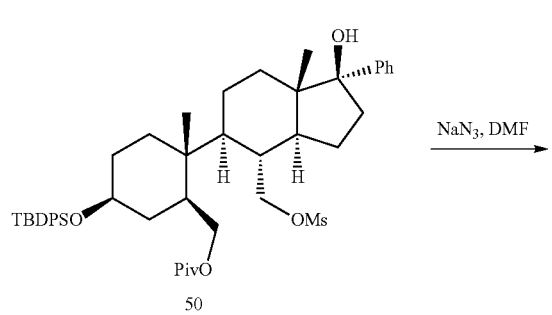

50

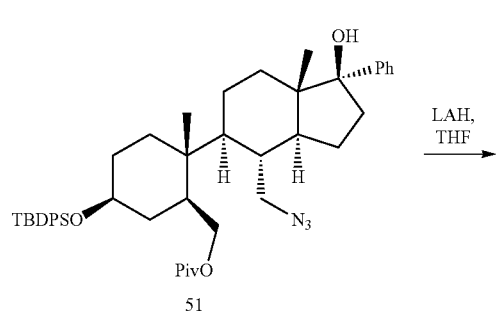

51

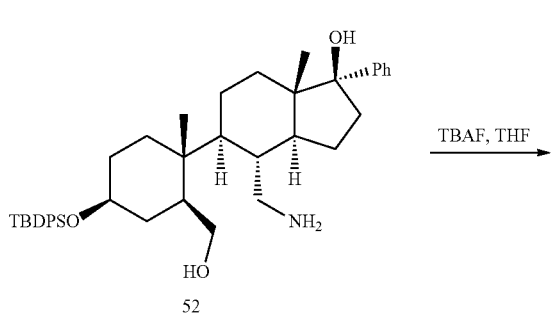

52

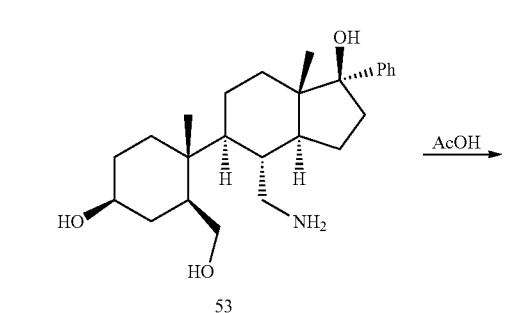

53

MsCl, TEA, CH$_2$Cl$_2$ →

NaN$_3$, DMF →

LAH, THF →

TBAF, THF →

AcOH →

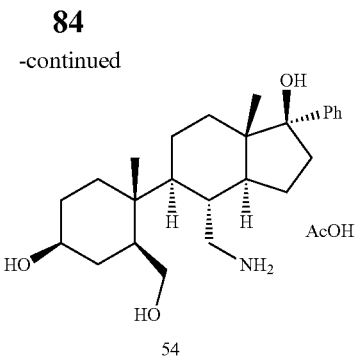

54

A. Phenyllithium (5.50 mL of a 0.99 M solution in THF, 5.45 mmol) was added dropwise to a solution of (2S,4aR, 4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 1.09 g, 1.81 mmol) in THF (18 mL) at 0° C. under argon, and the mixture was stirred at room temperature for 20 h. The mixture was cooled to 0° C. and brine (20 mL) was added followed by EtOAc (20 mL). The aqueous layer was extracted with EtOAc (15 mL), and the combined organic layers were dried (MgSO$_4$) and concentrated. The residue was partially purified by chromatography on silica gel (15:85 EtOAc/hexanes) to give a colourless foam (1.11 g). To facilitate purification, the foam (1.11 g) was dissolved in MeOH (10 mL) and THF (2 mL), and NaBH$_4$ (62 mg, 1.6 mmol) was added. The mixture was stirred at room temperature under argon for 1.5 h then acetone (5 mL) was added and the mixture was concentrated. The residue was dissolved in EtOAc (50 mL) and washed with brine (15 mL) then dried (MgSO$_4$) and concentrated. The residue was purified by chromatography on silica gel (15:85 EtOAc/hexanes) to give (2S,4aR,4bS,6aS, 7S,9aS,9bR,9cR,12aR,12bS)-2-((tert-butyldiphenylsilyl)oxy)-4a,6a,11,11-tetramethyl-7-phenylhexadecahydro-1H-cyclopenta[1,2]phenanthro[9,10-d][1,3]dioxol-7-ol (Compound No. 45, 851 mg, 69% over 2 steps) as a colourless foam.

B. A suspension of (2S,4aR,4bS,6aS,7S,9aS,9bR,9cR, 12aR,12bS)-2-((tert-butyldiphenylsilyl)oxy)-4a,6a,11,11-tetramethyl-7-phenylhexadecahydro-1H-cyclopenta[1,2]phenanthro[9,10-d][1,3]dioxol-7-ol (Compound No. 45, 851 mg, 1.25 mmol) in 80% acetic acid(aq) (12.5 mL) was heated to 40° C. for 2 h then concentrated. Azeotropic removal of remaining AcOH and H$_2$O was carried out with PhMe (2×30 mL), and the residue was purified by chromatography on silica gel (1:1 EtOAc/hexanes) to give (3S,5S, 6R,7R,8R,9S,10R,13S,14S,17S)-3-((tert-butyldiphenylsilyl)oxy)-10,13-dimethyl-17-phenylhexadecahydro-1H-cyclopenta[a]phenanthrene-6,7,17-triol (Compound No. 46, 641 mg, 80%) as a colourless foam.

C. A suspension of NaIO$_4$ (373 mg, 1.74 mmol) in H$_2$O (0.9 mL) was added to a solution of (3S,5S,6R,7R,8R,9S, 10R,13S,14S,17S)-3-((tert-butyldiphenylsilyl)oxy)-10,13-dimethyl-17-phenylhexadecahydro-1H-cyclopenta[a] phenanthrene-6,7,17-triol (Compound No. 46, 557 mg, 0.872 mmol) in THF (8.7 mL), and the mixture was stirred at room temperature for 1.5 h. The mixture was concentrated, and the residue was partitioned between CH$_2$Cl$_2$ (20 mL) and H$_2$O (10 mL). The aqueous phase was extracted with CH$_2$Cl$_2$ (10 mL), and the combined organic layers were dried (MgSO$_4$) and concentrated. The (1S,3aS,4R,5S,7aS)-5-((1R,2S,4S)-4-((tert-butyldiphenylsilyl)oxy)-2-formyl-1-methylcyclohexyl)-1-hydroxy-7a-methyl-1-phenyloctahydro-1H-indene-4-carbaldehyde (Compound No. 47, 593 mg) that was obtained was used in the next step without further purification.

D. A solution of (1S,3aS,4R,5S,7aS)-5-((1R,2S,4S)-4-((tert-butyldiphenylsilyl)oxy)-2-formyl-1-methylcyclohexyl)-1-hydroxy-7a-methyl-1-phenyloctahydro-1H-indene-4-carbaldehyde (Compound No. 47, 593 mg) in 3:1 THF/MeOH (8 mL) was cooled to 0° C. under argon and NaBH$_4$ (66 mg, 1.7 mmol) was added. The mixture was stirred at 0° C. for 40 min then at room temperature for 2 h. Acetone (5 mL) was added and the mixture was concentrated. The residue was dissolved in EtOAc (50 mL) and washed with brine (15 mL) then dried (MgSO$_4$) and concentrated. The (1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-7a-methyl-1-phenyloctahydro-1H-inden-1-ol (Compound No. 48, 558 mg) that was obtained was used in the next step without further purification.

E. To a solution of (1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-7a-methyl-1-phenyloctahydro-1H-inden-1-ol (Compound No. 48, 478 mg) in pyridine (5.0 mL) at 0° C. under argon was added pivaloyl chloride (0.096 mL, 0.78 mmol) dropwise then stirred at room temperature for 1.5 h. Additional pivaloyl chloride (0.030 mL, 0.24 mmol) was added dropwise at room temperature, and the mixture was stirred at room temperature for 1.5 h. The mixture was diluted with EtOAc (50 mL) and washed with saturated aqueous NaHCO$_3$ (25 mL) and brine (15 mL) then dried (MgSO$_4$) and concentrated. Azeotropic removal of remaining pyridine was carried out with hexanes (3×20 mL). The residue was purified by chromatography on silica gel (25:75 EtOAc/hexanes) to give ((1S,2R,5S)-5-((tert-butyldiphenylsilyl)oxy)-2-((1S,3aS,4R,5S,7aS)-1-hydroxy-4-(hydroxymethyl)-7a-methyl-1-phenyloctahydro-1H-inden-5-yl)-2-methylcyclohexyl)methyl pivalate (Compound No. 49, 281 mg, 52% over 3 steps) as a colourless foam.

F. To a solution of ((1S,2R,5S)-5-((tert-butyldiphenylsilyl)oxy)-2-((1S,3aS,4R,5S,7aS)-1-hydroxy-4-(hydroxymethyl)-7a-methyl-1-phenyloctahydro-1H-inden-5-yl)-2-methylcyclohexyl)methyl pivalate (Compound No. 49, 281 mg, 0.388 mmol) and TEA (0.15 mL, 1.1 mmol) in CH$_2$Cl$_2$ (5.0 mL) at 0° C. was added a solution of MsCl (80 mg, 0.70 mmol) in CH$_2$Cl$_2$ (0.5 mL), and the solution was stirred under argon at room temperature for 2.5 h. The solution was concentrated, and the residue was dissolved in EtOAc (40 mL). The solution was washed with saturated aqueous NaHCO$_3$ (5×10 mL) and brine (10 mL) then dried (MgSO$_4$) and concentrated. Azeotropic removal of impurities was carried out with PhMe (2×20 mL). The ((1S,2R,5S)-5-((tert-butyldiphenylsilyl)oxy)-2-((1S,3aS,4R,5S,7aS)-1-hydroxy-7a-methyl-4-(((methylsulfonyl)oxy)methyl)-1-phenyloctahydro-1H-inden-5-yl)-2-methylcyclohexyl)methyl pivalate (Compound No. 50, 392 mg) that was obtained was used in the next step without further purification.

G. NaN$_3$ (76 mg, 1.2 mmol) was added to a solution of ((1S,2R,5S)-5-((tert-butyldiphenylsilyl)oxy)-2-((1S,3aS,4R,5S,7aS)-1-hydroxy-7a-methyl-4-(((methylsulfonyl)oxy)methyl)-1-phenyloctahydro-1H-inden-5-yl)-2-methylcyclohexyl)methyl pivalate (Compound No. 50, 392 mg) in DMF (3.9 mL), and the mixture was heated to 60° C. under argon for 18 h. The mixture was diluted with EtOAc (60 mL) and washed with H$_2$O (20 mL) and brine (5×20 mL) then dried (MgSO$_4$) and concentrated to give ((1S,2R,5S)-2-((1S,3aS,4R,5S,7aS)-4-(azidomethyl)-1-hydroxy-7a-methyl-1-phenyloctahydro-1H-inden-5-yl)-5-((tert-butyldiphenylsilyl)oxy)-2-methylcyclohexyl)methyl pivalate (Compound No. 51, 315 mg) as a pale foam that was used in the next step without further purification.

H. A solution of ((1S,2R,5S)-2-((1S,3aS,4R,5S,7aS)-4-(azidomethyl)-1-hydroxy-7a-methyl-1-phenyloctahydro-1H-inden-5-yl)-5-((tert-butyldiphenylsilyl)oxy)-2-methylcyclohexyl)methyl pivalate (Compound No. 51, 315 mg) in THF (4 mL) was cooled to 0° C. under argon, and LiAlH$_4$ (0.78 mL of a 2 M solution in THF, 1.6 mmol) was added. The mixture was stirred at room temperature for 2 h then diluted with THF (4 mL) and stirred for an additional 68 h. The mixture was cooled to 0° C. and H$_2$O (0.060 mL) was added followed by 15% NaOH(aq) (0.060 mL) and H$_2$O (0.18 mL). The mixture was stirred at room temperature for 30 min then dried (MgSO$_4$), filtered and concentrated. The residue was partially purified by chromatography on silica gel (1:99-10:90 MeOH/CH$_2$Cl$_2$) to give (1S,3aS,4R,5S,7aS)-4-(aminomethyl)-5-((1R,2S,4S)-4-((tert-butyldiphenylsilyl)oxy)-2-(hydroxymethyl)-1-methylcyclohexyl)-7a-methyl-1-phenyloctahydro-1H-inden-1-ol (Compound No. 52, 112 mg) as a pale oil.

I. TBAF (0.35 mL of a 1 M solution in THF, 0.35 mmol) was added to a solution of (1S,3aS,4R,5S,7aS)-4-(aminomethyl)-5-((1R,2S,4S)-4-((tert-butyldiphenylsilyl)oxy)-2-(hydroxymethyl)-1-methylcyclohexyl)-7a-methyl-1-phenyloctahydro-1H-inden-1-ol (Compound No. 52, 112 mg) in THF (3.5 mL) at room temperature under argon then stirred for 25 h. The solution was concentrated, and the residue was partially purified by chromatography on silica gel (100:10:2 EtOAc/MeOH/NH$_4$OH) to give (1S,3aS,4R,5S,7aS)-4-(aminomethyl)-5-((1R,2S,4S)-4-hydroxy-2-(hydroxymethyl)-1-methylcyclohexyl)-7a-methyl-1-phenyloctahydro-1H-inden-1-ol (Compound No. 53, 39 mg) as a colourless solid.

J. A solution of (1S,3aS,4R,5S,7aS)-4-(aminomethyl)-5-((1R,2S,4S)-4-hydroxy-2-(hydroxymethyl)-1-methylcyclohexyl)-7a-methyl-1-phenyloctahydro-1H-inden-1-ol (Compound No. 53, 39 mg) was dissolved in AcOH (6 mL) and allowed to stand at room temperature for 1 h. The solution was concentrated followed by azeotropic removal of AcOH using 1:5 MeOH/PhMe (12 mL). The residue was dissolved in MeOH (0.5 mL) and Et$_2$O (30 mL) was added to give a precipitate. The mixture was allowed to stand at room temperature overnight then the supernatant was removed by decantation. Azeotropic removal of remaining volatiles using Et$_2$O (3×10 mL) afforded (1S,3aS,4R,5S,7aS)-4-(aminomethyl)-5-((1R,2S,4S)-4-hydroxy-2-(hydroxymethyl)-1-methylcyclohexyl)-7a-methyl-1-phenyloctahydro-1H-inden-1-ol acetate (Compound No 54, 37 mg, 21% over 5 steps) as a colourless solid. $^1$H NMR (CD$_3$OD): δ 7.43 (d, J=7.2 Hz, 2H), 7.31 (t, J=7.4 Hz, 2H), 7.22 (m, 1H), 3.46 (m, 2H), 3.28 (m, 1H), 2.99 (m, 2H), 2.41 (m, 1H), 2.14 (m, 2H), 1.16-1.94 (m, 17H), 1.08 (s, 3H), 0.98 (s, 3H), 0.42 (m, 1H). ES-MS m/z 402 ([M+1]$^+$).

Example 12
Synthesis of (1S,3aS,4R,5S,7aS)-4-(aminomethyl)-1-(furan-2-yl)-5-((1R,2S,4S)-4-hydroxy-2-(hydroxymethyl)-1-methylcyclohexyl)-7a-methyloctahydro-1H-inden-1-ol (Compound No. 63)
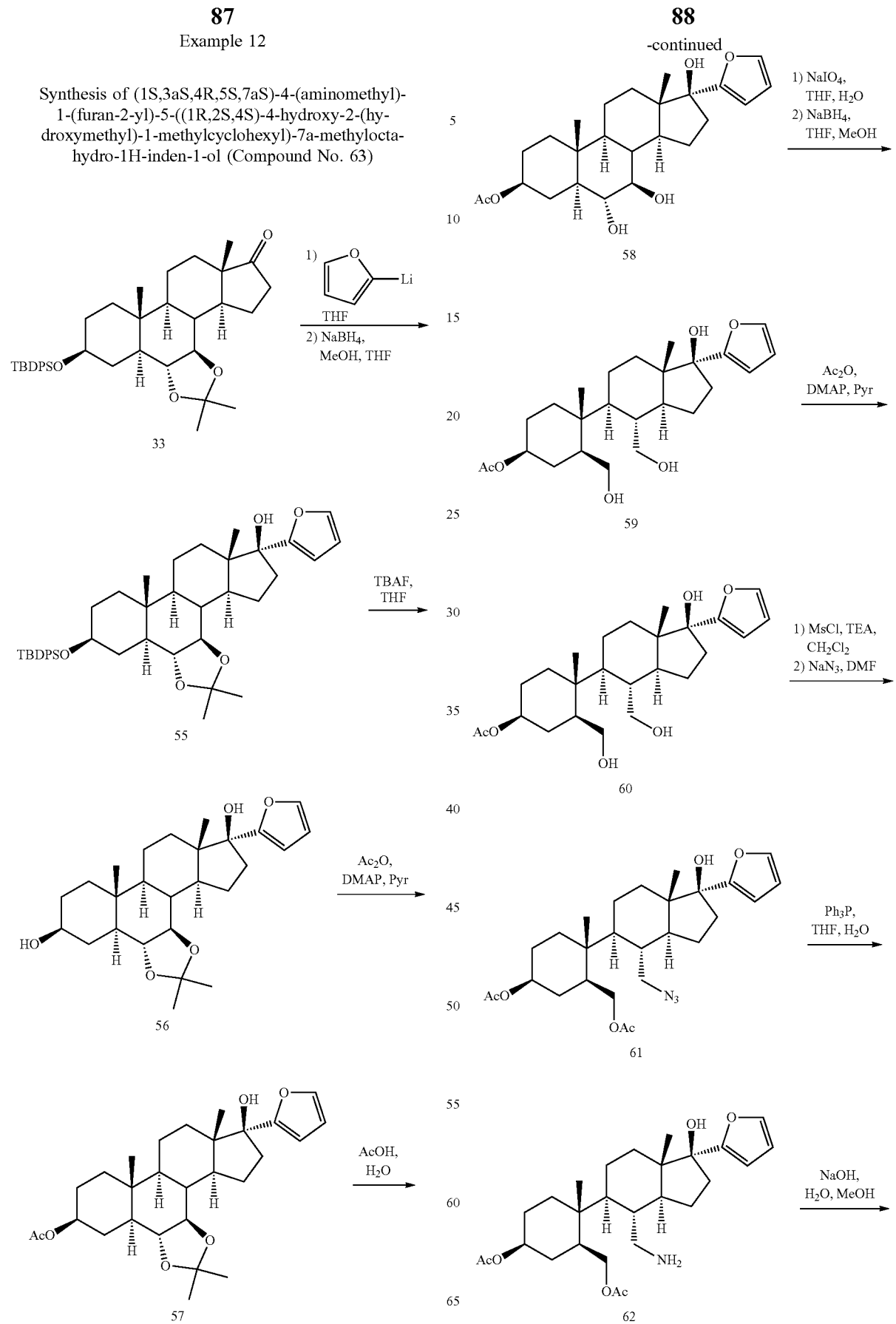

-continued

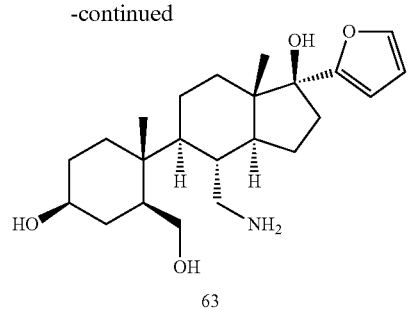

63

A. n-Butyllithium (4.4 mL of a 1.7 M solution in hexanes, 7.5 mmol) was added to a solution of furan (591 mg, 8.68 mmol) in THF (14 mL) at 0° C. under argon, and the mixture was stirred at room temperature for 30 min. The mixture was cooled to 0° C. and a solution of (2S,4aR,4bS,6aS,9aS,9bR, 9cR,12aR,12bS)-2-((tert-butyldiphenylsilyl)oxy)-4a,6a,11, 11-tetramethyltetradecahydro-1H-cyclopenta[1,2]phenanthro[9,10-d][1,3]dioxol-7(8H)-one (Compound No. 33, 1.49 g, 2.48 mmol) in THF (11 mL) was added. The mixture was stirred at room temperature for 17 h then $H_2O$ (5 mL) and brine (15 mL) were added followed by EtOAc (25 mL). The aqueous layer was extracted with EtOAc (2×20 mL), and the combined organic layers were dried ($MgSO_4$) and concentrated. To facilitate purification, the residue was dissolved in 5:1 MeOH/THF (24 mL), and $NaBH_4$ (94 mg, 2.5 mmol) was added. The mixture was stirred at room temperature under argon for 1.8 h then acetone (5 mL) was added and the mixture was concentrated. The residue was dissolved in EtOAc (60 mL) and washed with brine (15 mL). The aqueous layer was extracted with EtOAc (15 mL), and the combined organic layers were dried ($MgSO_4$) and concentrated. The residue was purified by chromatography on silica gel (20:80 EtOAc/hexanes) to give (2S,4aR,4bS,6aS,7S, 9aS,9bR,9cR,12aR,12bS)-2-((tert-butyldiphenylsilyl)oxy)-7-(furan-2-yl)-4a,6a,11,11-tetramethylhexadecahydro-1H-cyclopenta[1,2]phenanthro[9,10-d][1,3]dioxol-7-ol (Compound No. 55, 1.41 g, 85%) as a pale foam.

B. TBAF (4.2 mL of a 1 M solution in THF, 4.2 mmol) was added to a solution of (2S,4aR,4bS,6aS,7S,9aS,9bR, 9cR,12aR,12bS)-2-((tert-butyldiphenylsilyl)oxy)-7-(furan-2-yl)-4a,6a,11,11-tetramethylhexadecahydro-1H-cyclopenta [1,2]phenanthro[9,10-d][1,3]dioxol-7-ol (Compound No, 55, 1.41 g, 2.11 mmol) in THF (21 mL) at room temperature under argon then stirred for 39 h. The solution was concentrated, and the residue was purified by chromatography on silica gel (60:40 EtOAc/hexanes) to give (2S,4aR,4bS,6aS, 7S,9aS,9bR,9cR,12aR,12bS)-7-(furan-2-yl)-4a,6a,11,11-tetramethylhexadecahydro-1H-cyclopenta[1,2]phenanthro[9, 10-d][1,3]dioxole-2,7-diol (Compound No. 56, 878 mg, 97%) as a colourless foam.

C. To a solution of (2S,4aR,4bS,6aS,7S,9aS,9bR,9cR, 12aR,12bS)-7-(furan-2-yl)-4a,6a,11,11-tetramethylhexadecahydro-1H-cyclopenta[1,2]phenanthro[9,10-d][1,3]dioxole-2,7-diol (Compound No. 56, 878 mg, 2.04 mmol) and DMAP (25 mg, 0.20 mmol) in pyridine (10 mL) at 0° C. under argon was added a solution of $Ac_2O$ (292 mg, 2.86 mmol) in pyridine (10 mL) over 1.75 h then stirred at 0° C. for 4.5 h. The mixture was diluted with PhMe (10 mL) and concentrated. Azeotropic removal of remaining pyridine was carried out with PhMe (3×20 mL). The light green foam, (2S,4aR,4bS,6aS,7S,9aS,9bR,9cR,12aR,12bS)-7-(furan-2-yl)-7-hydroxy-4a,6a,11,11-tetramethylhexadecahydro-1H-cyclopenta[1,2]phenanthro[9,10-d][1,3]dioxol-2-yl acetate (Compound No. 57), that was obtained was used in the next step without further purification.

D. A suspension of (2S,4aR,4bS,6aS,7S,9aS,9bR,9cR, 12aR,12bS)-7-(furan-2-yl)-7-hydroxy-4a,6a,11,11-tetramethylhexadecahydro-1H-cyclopenta[1,2]phenanthro[9,10-d] [1,3]dioxol-2-yl acetate (Compound No. 57) in 80% acetic acid(aq) (20 mL) was heated to 40° C. for 1.5 h then concentrated. Azeotropic removal of remaining AcOH and $H_2O$ was carried out with PhMe (3×30 mL), and the residue was purified by chromatography on silica gel (50:50-60:40 EtOAc/$CH_2Cl_2$) to give (3S,5S,6R,7R,8R,9S,10R,13S,14S, 17S)-17-(furan-2-yl)-6,7,17-trihydroxy-10,13-dimethylhexadecahydro-1H-cyclopenta[a]phenanthren-3-yl acetate (Compound No. 58, 641 mg, 73% over 2 steps) as a colourless foam.

E. $NaIO_4$ (634 mg, 2.96 mmol) was added to a solution of (3S,5S,6R,7R,8R,9S,10R,13S,14S,17S)-17-(furan-2-yl)-6, 7,17-trihydroxy-10,13-dimethylhexadecahydro-1H-cyclopenta[a]phenanthren-3-yl acetate (Compound No. 58, 641 mg, 1.48 mmol) in 10:1 THF/$H_2O$ (16.5 mL), and the mixture was stirred at room temperature for 2 h. The mixture was concentrated, and the residue was partitioned between $CH_2Cl_2$ (20 mL) and $H_2O$ (10 mL). The aqueous phase was extracted with $CH_2Cl_2$ (2×10 mL), and the combined organic layers were dried ($MgSO_4$) and concentrated. The resulting colourless foam (657 mg) was dissolved in 3:1 THF/MeOH (15 mL) and cooled to 0° C. under argon. $NaBH_4$ (112 mg, 2.96 mmol) was added, and the mixture was stirred at 0° C. for 30 min then at room temperature for 2.5 h. Acetone (6 mL) was added and the mixture was concentrated. The residue was partitioned between $CH_2Cl_2$ (20 mL) and $H_2O$ (15 mL), and the aqueous phase was extracted with $CH_2Cl_2$ (2×10 mL). The combined organic layers were dried ($MgSO_4$) and concentrated. The colourless foam, (1S,3S,4R)-4-((1S,3aS,4R,5S,7aS)-1-(furan-2-yl)-1-hydroxy-4-(hydroxymethyl)-7a-methyloctahydro-1H-inden-5-yl)-3-(hydroxymethyl)-4-methylcyclohexyl acetate (Compound No. 59, 638 mg), that was obtained was used in the next step without further purification.

F. To a solution of (1S,3S,4R)-4-((1S,3aS,4R,5S,7aS)-1-(furan-2-yl)-1-hydroxy-4-(hydroxymethyl)-7a-methyloctahydro-1H-inden-5-yl)-3-(hydroxymethyl)-4-methylcyclohexyl acetate (Compound No. 59, 638 mg) and DMAP (18 mg, 0.15 mmol) in pyridine (7.5 mL) at 0° C. under argon was added a solution of $Ac_2O$ (180 mg, 1.76 mmol) in pyridine (7.5 mL) over 2 h then stirred at 0° C. for 1 h. The mixture was concentrated, and azeotropic removal of remaining pyridine was carried out with PhMe (3×20 mL). The residue was purified by chromatography on silica gel (20:80-40:60 EtOAc/$CH_2Cl_2$) to give ((1S,2R,5S)-5-acetoxy-2-((1S,3aS,4R,5S,7aS)-1-(furan-2-yl)-1-hydroxy-4-(hydroxymethyl)-7a-methyloctahydro-1H-inden-5-yl)-2-methylcyclohexyl)methyl acetate (Compound No. 60, 509 mg, 72% over 3 steps) as a colourless foam.

G. To a solution of ((1S,2R,5S)-5-acetoxy-2-((1S,3aS,4R, 5S,7aS)-1-(furan-2-yl)-1-hydroxy-4-(hydroxymethyl)-7a-methyloctahydro-1H-inden-5-yl)-2-methylcyclohexyl) methyl acetate (Compound No. 60, 509 mg, 1.07 mmol) and TEA (0.19 mL, 1.4 mmol) in $CH_2Cl_2$ (11 mL) at 0° C. was added MsCl (0.091 mL, 1.2 mmol), and the solution was stirred under argon at room temperature for 1 h. The solution was diluted with $CH_2Cl_2$ (20 mL) and washed with saturated aqueous $NaHCO_3$ (15 mL). The aqueous phase was extracted with $CH_2Cl_2$ (10 mL), and the combined organic layers were dried ($MgSO_4$) and concentrated. Azeotropic removal of impurities was carried out with PhMe (3×20 mL), and the resulting yellow oil (798 mg) was dissolved in DMF (5.3 mL). NaN₃ (208 mg, 3.20 mmol) was added, and the mixture was heated to 60° C. under argon for 16 h. The mixture was partitioned between EtOAc (80 mL), H₂O (10 mL) and brine (10 mL). The organic layer was washed with brine (2×20 mL) then dried (MgSO₄) and concentrated. The residue was purified by chromatography on silica gel (10:90 EtOAc/CH₂Cl₂) to give ((1S,2R,5S)-5-acetoxy-2-((1S,3aS, 4R,5S,7aS)-4-(azidomethyl)-1-(furan-2-yl)-1-hydroxy-7a-methyloctahydro-1H-inden-5-yl)-2-methylcyclohexyl) methyl acetate (Compound No. 61, 485 mg, 90% over 2 steps) as a colourless gum.

H. Triphenylphosphine (292 mg, 1.11 mmol) was added to a solution of ((1S,2R,5S)-5-acetoxy-2-((1S,3aS,4R,5S, 7aS)-4-(azidomethyl)-1-(furan-2-yl)-1-hydroxy-7a-methyl-octahydro-1H-inden-5-yl)-2-methylcyclohexyl)methyl acetate (Compound No. 17, 279 mg, 0.556 mmol) in 10:1 THF/H₂O (6.2 mL) then heated to 50° C. under argon for 17 h. The mixture was concentrated, and azeotropic removal of remaining H₂O was carried out with MeOH (2×20 mL). The residue was purified by chromatography on silica gel (5:95 MeOH/CH₂Cl₂ then 100:5:1 CH₂Cl₂/MeOH/NH₄OH) to give ((1S,2R,5S)-5-acetoxy-2-((1S,3aS,4R,5S,7aS)-4-(aminomethyl)-1-(furan-2-yl)-1-hydroxy-7a-methylocta-hydro-1H-inden-5-yl)-2-methylcyclohexyl)methyl acetate (Compound No. 62, 244 mg, 92%) as a colourless gum.

I. To a suspension of ((1S,2R,5S)-5-acetoxy-2-((1S,3aS, 4R,5S,7aS)-4-(aminomethyl)-1-(furan-2-yl)-1-hydroxy-7a-methyloctahydro-1H-inden-5-yl)-2-methylcyclohexyl) methyl acetate (Compound No. 62, 212 mg, 0.446 mmol) in MeOH (4.5 mL) was added 10 N NaOH(aq) (0.45 mL, 4.5 mmol) and heated to 40° C. for 16 h. The mixture was concentrated, and the residue was partitioned between EtOAc (20 mL), H₂O (10 mL) and brine (10 mL). The aqueous layer was extracted with 1:9 MeOH/CH₂Cl₂ (5×10 mL), and the combined organic layers were dried (MgSO₄) and concentrated. The residue was purified by chromatography on silica gel (100:10:2 CH₂Cl₂/MeOH/NH₄OH) to give (1S,3aS,4R,5S,7aS)-4-(aminomethyl)-1-(furan-2-yl)-5-((1R,2S,4S)-4-hydroxy-2-(hydroxymethyl)-1-methylcyclohexyl)-7a-methyloctahydro-1H-inden-1-ol (Compound No. 63, 145 mg, 83%) as a colourless solid. ¹H NMR (CD₃OD): δ 7.42 (m, 1H), 6.35 (m, 1H), 6.29 (m, 1H), 3.59 (m, 1H), 3.42 (m, 1H), 3.05 (m, 2H), 2.69 (m, 1H), 2.29 (m, 1H), 1.95-2.13 (m, 2H), 1.17-1.83 (m, 14H), 1.03 (s, 3H), 0.98 (s, 3H), 0.52 (m, 1H). ES-MS m/z 392 ([M+1]⁺).

Example 13

Synthesis of (1S,3S,4R)-4-((3aS,6S,7R,7aS)-7-(aminomethyl)-3-(furan-2-yl)-3a-methyl-3a,4,5,6,7, 7a-hexahydro-1H-inden-6-yl)-3-(hydroxymethyl)-4-methylcyclohexanol (Compound No. 64)

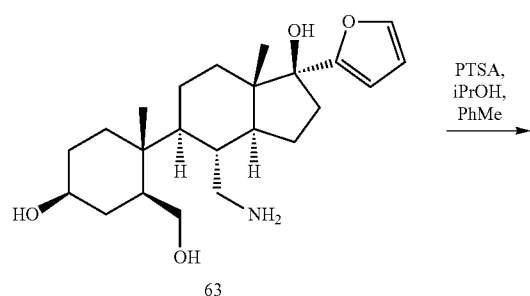

63

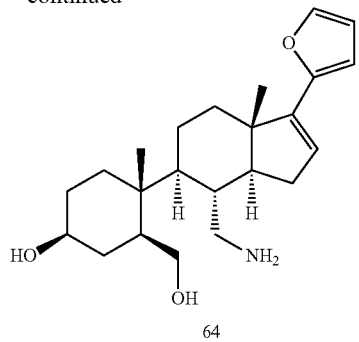

64

To a solution of (1S,3aS,4R,5S,7aS)-4-(aminomethyl)-1-(furan-2-yl)-5-((1R,2S,4S)-4-hydroxy-2-(hydroxymethyl)-1-methylcyclohexyl)-7a-methyloctahydro-1H-inden-1-ol (Compound No. 63, 93 mg, 0.24 mmol) in 15:85 iPrOH/PhMe (6 mL) was added p-toluenesulfonic acid monohydrate (55 mg, 0.29 mmol) then heated to 100° C. for 6 h. The mixture was washed with 1 N NaOH(aq) (15 mL), and the aqueous phase was extracted with 1:9 MeOH/CH₂Cl₂ (5×10 mL). The combined organic layers were dried (MgSO₄) and concentrated, and the residue was purified by chromatography on silica gel (100:10:2 CH₂Cl₂/MeOH/NH₄OH) to give (1S,3S,4R)-4-((3aS,6S,7R,7aS)-7-(aminomethyl)-3-(furan-2-yl)-3a-methyl-3a,4,5,6,7,7a-hexahydro-1H-inden-6-yl)-3-(hydroxymethyl)-4-methylcyclohexanol (Compound No. 64, 30 mg, 34%) as a yellow solid. ¹H NMR (CD₃OD): δ 7.40 (s, 1H), 6.38 (m, 1H), 6.32 (m, 1H), 6.03 (br s, 1H), 3.75 (m, 1H), 3.46 (m, 1H), 3.13 (m, 2H), 2.76 (m, 1H), 2.37 (m, 1H), 1.22-2.23 (m, 15H), 1.11 (s, 3H), 0.99 (s, 3H). ES-MS m/z 374 ([M+1]⁺).

Example 14

Synthesis of (1S,3S,4R)-4-((2R,3S,3aR,3bS,5'R,6S, 7R,7aS,8aS)-7-(aminomethyl)-3,3b,5'-trimethyltetra-decahydrospiro[indeno[2,1-b]furan-2,2'-pyran]-6-yl)-3-(hydroxymethyl)-4-methylcyclohexanol acetate (Compound No. 76)

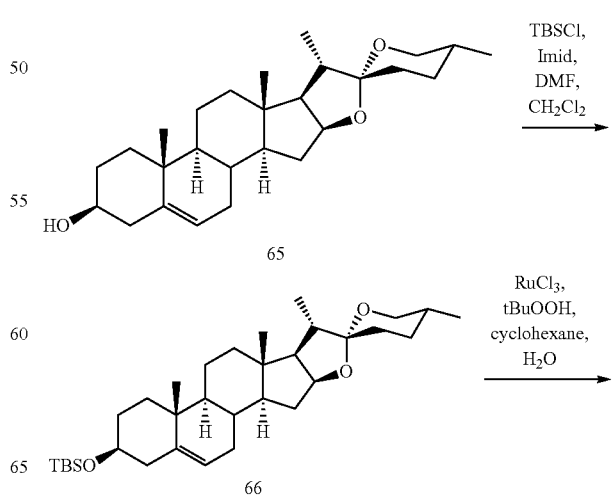

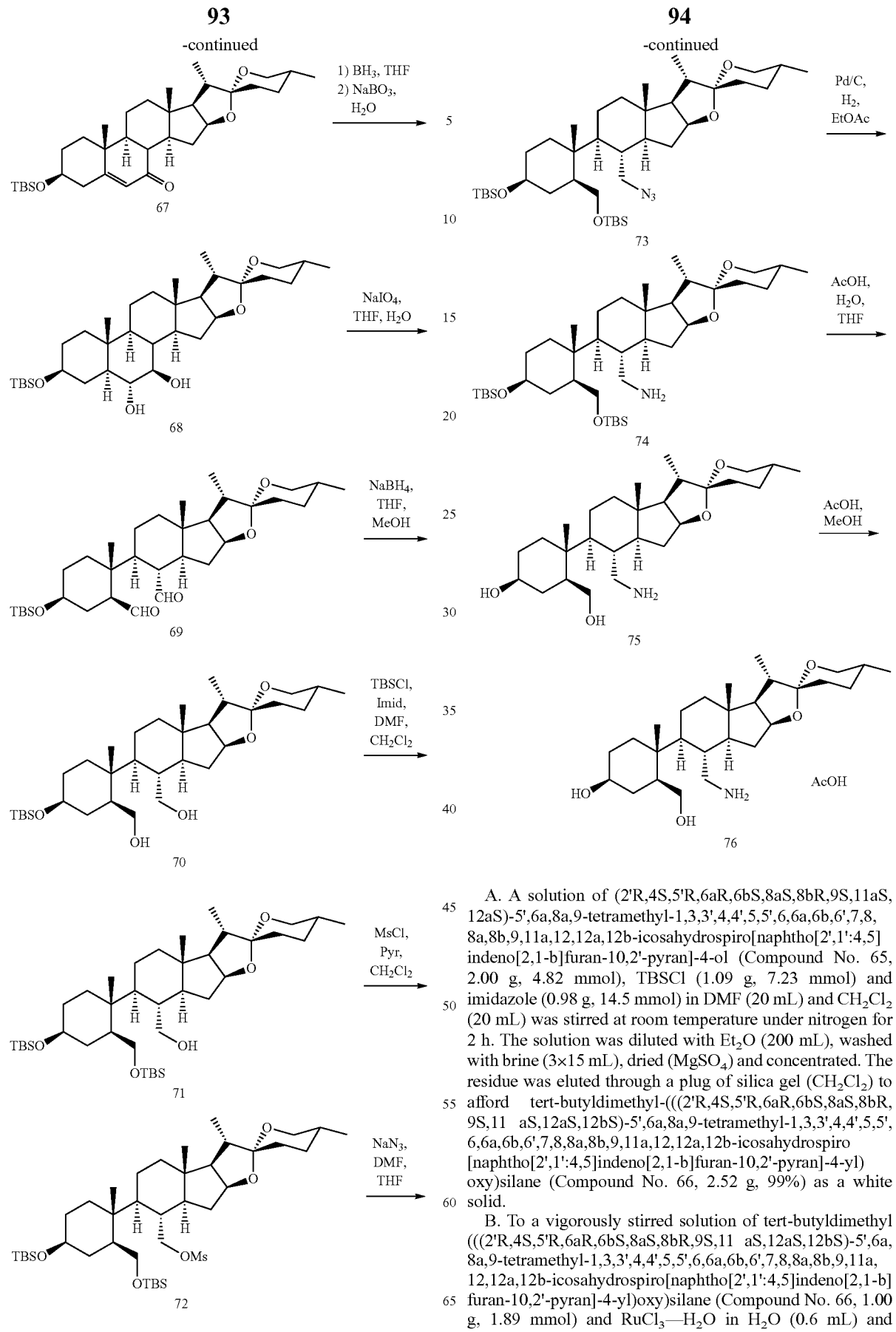

A. A solution of (2'R,4S,5'R,6aR,6bS,8aS,8bR,9S,11aS,12aS)-5',6a,8a,9-tetramethyl-1,3,3',4,4',5,5',6,6a,6b,6',7,8,8a,8b,9,11a,12,12a,12b-icosahydrospiro[naphtho[2',1':4,5]indeno[2,1-b]furan-10,2'-pyran]-4-ol (Compound No. 65, 2.00 g, 4.82 mmol), TBSCl (1.09 g, 7.23 mmol) and imidazole (0.98 g, 14.5 mmol) in DMF (20 mL) and $CH_2Cl_2$ (20 mL) was stirred at room temperature under nitrogen for 2 h. The solution was diluted with $Et_2O$ (200 mL), washed with brine (3×15 mL), dried ($MgSO_4$) and concentrated. The residue was eluted through a plug of silica gel ($CH_2Cl_2$) to afford tert-butyldimethyl-(((2'R,4S,5'R,6aR,6bS,8aS,8bR,9S,11 aS,12aS,12bS)-5',6a,8a,9-tetramethyl-1,3,3',4,4',5,5',6,6a,6b,6',7,8,8a,8b,9,11a,12,12a,12b-icosahydrospiro[naphtho[2',1':4,5]indeno[2,1-b]furan-10,2'-pyran]-4-yl)oxy)silane (Compound No. 66, 2.52 g, 99%) as a white solid.

B. To a vigorously stirred solution of tert-butyldimethyl(((2'R,4S,5'R,6aR,6bS,8aS,8bR,9S,11 aS,12aS,12bS)-5',6a,8a,9-tetramethyl-1,3,3',4,4',5,5',6,6a,6b,6',7,8,8a,8b,9,11a,12,12a,12b-icosahydrospiro[naphtho[2',1':4,5]indeno[2,1-b]furan-10,2'-pyran]-4-yl)oxy)silane (Compound No. 66, 1.00 g, 1.89 mmol) and $RuCl_3$—$H_2O$ in $H_2O$ (0.6 mL) and cyclohexane (10 mL), immersed in a room temperature $H_2O$ bath, was added ᵗBuOOH (2.6 mL of a 70% solution in H$_2$O, 18.9 mmol) in approximately 0.5 mL portions over 1 h. After 18 h to the mixture was added a solution of Na$_2$SO$_3$ (2.4 g) in H$_2$O (20 mL). After 30 minutes the mixture was extracted with EtOAc (100 mL), washed with brine (3×15 mL), dried (MgSO$_4$) and concentrated. The residue was purified using chromatography on silica gel (5% EtOAc/hexanes with 1% CH$_2$Cl$_2$) to afford 2'R,4S,5'R,6aR,6bS,8aS,8bR,9S,11aS,12aS,12bS)-4-((tert-butyldimethylsilyl)oxy)-5',6a,8a,9-tetramethyl-3',4,4',5,5',6,6a,6b,6',7,8,8a,8b,9,11a,12,12a,12b-octadecahydrospiro[naphtho[2',1':4,5]indeno[2,1-b]furan-10,2'-pyran]-1 (3H)-one (Compound No. 67, 448 mg, 43%) as a white solid.

C. To a solution of 2'R,4S,5'R,6aR,6bS,8aS,8bR,9S,11aS,12aS,12bS)-4-((tert-butyldimethylsilyl)oxy)-5',6a,8a,9-tetramethyl-3',4,4',5,5',6,6a,6b,6',7,8,8a,8b,9,11a,12,12a,12b-octadecahydrospiro[naphtho[2',1':4,5]indeno[2,1-b]furan-10,2'-pyran]-1 (3H)-one (Compound No. 67 1.47 g, 2.71 mmol) in THF (8 mL) at 0° C. under nitrogen was added borane (5.4 mL of a 1M solution in THF, 5.4 mmol) over a period of 1 h. After 6.5 h the reaction was cooled in ice and quenched with H$_2$O (0.8 mL) then added NaBO$_3$·4H$_2$O (0.83 g) and stirred the mixture at room temperature for 3 d. The mixture was diluted with EtOAc (200 mL), washed with brine (2×20 mL), dried (MgSO$_4$) and concentrated. The residue was purified using chromatography on silica gel (20% then 30% EtOAc/hexanes with 1% CH$_2$Cl$_2$) to afford (1R,2R,2aS,2'R,4S,5'R,6aR,6bS,8aS,8bR,9S,11aS,12aS,12bR)-4-((tert-butyldimethylsilyl)oxy)-5',6a,8a,9-tetramethyldocosahydrospiro[naphtho[2',1':4,5]indeno[2,1-b]furan-10,2'-pyran]-1,2-diol (Compound No. 68, 0.91 g, 60%) as a white foam.

D. A solution of (1R,2R,2aS,2'R,4S,5'R,6aR,6bS,8aS,8bR,9S,11aS,12aS,12bR)-4-((tert-butyldimethylsilyl)oxy)-5',6a,8a,9-tetramethyldocosahydrospiro[naphtho[2',1':4,5]indeno[2,1-b]furan-10,2'-pyran]-1,2-diol (Compound No. 110, 0.91 g, 1.62 mmol) and NaIO$_4$ (0.69 g, 3.2 mmol) in THF (20 mL) and H$_2$O (3 mL) was stirred at room temperature for 45 minutes. The solution was diluted with H$_2$O (30 mL), extracted with CH$_2$Cl$_2$ (2×50 mL), washed with brine (20 mL), dried (MgSO$_4$) and concentrated to afford (2R,3S,3aR,3bS,5'R,6S,7R,7aS,8aS)-6-((1R,2S,4S)-4-((tert-butyldimethylsilyl)oxy)-2-formyl-1-methylcyclohexyl)-3,3b,5'-trimethyltetradecahydrospiro[indeno[2,1-b]furan-2,2'-pyran]-7-carbaldehyde (Compound No. 69, 0.91 g) as a white solid.

E. A solution of (2R,3S,3aR,3bS,5'R,6S,7R,7aS,8aS)-6-((1R,2S,4S)-4-((tert-butyldimethylsilyl)oxy)-2-formyl-1-methylcyclohexyl)-3,3b,5'-trimethyltetradecahydrospiro[indeno[2,1-b]furan-2,2'-pyran]-7-carbaldehyde (Compound No. 69, 0.92 g, 1.62 mmol) and NaBH$_4$ (123 mg, 3.2 mmol) in MeOH (4 mL) and THF (16 mL) was stirred overnight in a cool H$_2$O bath. The reaction was cooled in ice and quenched with saturated NaHCO$_3$ solution (10 mL), stirring 10 minutes at room temperature. The mixture was diluted with EtOAc (200 mL), washed with brine (3×15 mL), dried (MgSO$_4$) and concentrated. The residue was purified using chromatography on silica gel (40% then 50% EtOAc/hexanes) to afford ((1S,2R,5S)-5-((tert-butyldimethylsilyl)oxy)-2-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-2-methylcyclohexyl)methanol (Compound No. 70, 0.62 g, 68%) as a white solid.

F. A solution of ((1S,2R,5S)-5-((tert-butyldimethylsilyl)oxy)-2-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-2-methylcyclohexyl)methanol (Compound No. 70, 0.31 g, 0.55 mmol) and TBSCl (91 mg, 0.60 mmol) and imidazole (82 mg, 1.2 mmol) in DMF (5 mL) and CH$_2$Cl$_2$ (5 mL) was stirred at room temperature under nitrogen for 1 h. The solution was diluted with Et$_2$O (100 mL), washed with brine (3×15 mL), dried (MgSO$_4$) and concentrated. The residue was purified using chromatography on silica gel (15% EtOAc/hexanes) to afford ((2R,3S,3aR,3bS,5'R,6S,7R,7aS,8aS)-6-((1R,2S,4S)-4-((tert-butyldimethylsilyl)oxy)-2-(((tert-butyldimethylsilyl)oxy)methyl)-1-methylcyclohexyl)-3,3b,5'-trimethyltetradecahydrospiro[indeno[2,1-b]furan-2,2'-pyran]-7-yl)methanol (Compound No. 71, 0.26 g, 70%).

G. A solution of ((2R,3S,3aR,3bS,5'R,6S,7R,7aS,8aS)-6-((1R,2S,4S)-4-((tert-butyldimethylsilyl)oxy)-2-(((tert-butyldimethylsilyl)oxy)methyl)-1-methylcyclohexyl)-3,3b,5'-trimethyltetradecahydrospiro[indeno[2,1-b]furan-2,2'-pyran]-7-yl)methanol (Compound No. 71, 0.26 g, 0.38 mmol) and MsCl (0.16 mL, 2.1 mmol) in pyridine (5 mL) and CH$_2$Cl$_2$ (5 mL) was stirred at room temperature under nitrogen for 3 h. The solution was cooled in ice, quenched with saturated NaHCO$_3$ solution (8 mL) for 15 minutes, diluted with EtOAc (100 mL), washed with brine (3×15 mL), dried (MgSO$_4$) and concentrated to afford ((2R,3S,3aR,3bS,5'R,6S,7R,7aS,8aS)-6-((1R,2S,4S)-4-((tert-butyldimethylsilyl)oxy)-2-(((tert-butyldimethylsilyl)oxy)methyl)-1-methylcyclohexyl)-3,3b,5'-trimethyltetradecahydrospiro[indeno[2,1-b]furan-2,2'-pyran]-7-yl)methyl methanesulfonate (Compound No. 72, 0.28 g) as an off-white solid.

H. A solution of ((2R,3S,3aR,3bS,5'R,6S,7R,7aS,8aS)-6-((1R,2S,4S)-4-((tert-butyldimethylsilyl)oxy)-2-(((tert-butyldimethylsilyl)oxy)methyl)-1-methylcyclohexyl)-3,3b,5'-trimethyltetradecahydrospiro[indeno[2,1-b]furan-2,2'-pyran]-7-yl)methyl methanesulfonate (Compound No. 72, 0.28 g, 0.38 mmol) and NaN$_3$ (102 mg, 1.57 mmol) in DMF (5 mL) and THF (1 mL) at 60° C. was stirred overnight under nitrogen. The solution was diluted with Et$_2$O (100 mL), washed with brine (3×15 mL), dried (MgSO$_4$) and concentrated to afford (((1S,3S,4R)-4-((2R,3S,3aR,3bS,5'R,6S,7R,7aS,8aS)-7-(azidomethyl)-3,3b,5'-trimethyltetradecahydrospiro[indeno[2,1-b]furan-2,2'-pyran]-6-yl)-3-(((tert-butyldimethylsilyl)oxy)methyl)-4-methylcyclohexyl)oxy)(tert-butyl)dimethylsilane (Compound No. 73, 0.26 g) as a white solid.

I. A solution of (((1S,3S,4R)-4-((2R,3S,3aR,3bS,5'R,6S,7R,7aS,8aS)-7-(azidomethyl)-3,3b,5'-trimethyltetradecahydrospiro[indeno[2,1-b]furan-2,2'-pyran]-6-yl)-3-(((tert-butyldimethylsilyl)oxy)methyl)-4-methylcyclohexyl)oxy)(tert-butyl)dimethylsilane (Compound No. 73, 0.26 g, 0.37 mmol) and Pd (catalytic amount of a 10% solution on carbon) in EtOAc (40 mL) was stirred for 3 d at room temperature under hydrogen (balloon). The solution was filtered through Celite (EtOAc and MeOH) and concentrated. The residue was purified using chromatography on silica gel (5% MeOH/CH$_2$Cl$_2$ then 8% MeOH/CH$_2$Cl$_2$ with 1% TEA) to afford ((2R,3S,3aR,3bS,5'R,6S,7R,7aS,8aS)-6-((1R,2S,4S)-4-((tert-butyldimethylsilyl)oxy)-2-(((tert-butyldimethylsilyl)oxy)methyl)-1-methylcyclohexyl)-3,3b,5'-trimethyltetradecahydrospiro[indeno[2,1-b]furan-2,2'-pyran]-7-yl)methanamine (Compound No. 74, 185 mg, 74%) as a colourless film.

J. A solution of ((2R,3S,3aR,3bS,5'R,6S,7R,7aS,8aS)-6-((1R,2S,4S)-4-((tert-butyldimethylsilyl)oxy)-2-(((tert-butyldimethylsilyl)oxy)methyl)-1-methylcyclohexyl)-3,3b,5'-trimethyltetradecahydrospiro[indeno[2,1-b]furan-2,2'-pyran]-7-yl)methanamine (Compound No. 74, 185 mg, 0.273 mmol) in AcOH (16 mL) and H$_2$O (4 mL) was stirred at room temperature for 13 d then was concentrated. The residue was purified using chromatography on silica gel (10% MeOH/EtOAc then 10% MeOH/EtOAc with 5% NH₄OH then 20% MeOH/EtOAc with 5% NH₄OH) to afford (1S,3S,4R)-4-((2R,3S,3aR,3bS,5′R,6S,7R,7aS,8aS)-7-(aminomethyl)-3,3b,5′-trimethyltetradecahydrospiro[indeno[2,1-b]furan-2,2′-pyran]-6-yl)-3-(hydroxymethyl)-4-methylcyclohexanol (Compound No. 75, 75 mg, 61%) as a white solid.

K. A solution of (1S,3S,4R)-4-((2R,3S,3aR,3bS,5′R,6S,7R,7aS,8aS)-7-(aminomethyl)-3,3b,5′-trimethyltetradecahydrospiro[indeno[2,1-b]furan-2,2′-pyran]-6-yl)-3-(hydroxymethyl)-4-methylcyclohexanol (Compound No. 75, 75 mg, 0.17 mmol) in MeOH (1 mL) and AcOH (1 mL) was stirred at room temperature for 15 minutes then was concentrated. The residue was twice taken up in MeOH (0.5 mL) and MeCN (5 mL) and concentrated. The residue was freeze dried from H₂O (5 mL) to afford (1S,3S,4R)-4-((2R,3S,3aR,3bS,5′R,6S,7R,7aS,8aS)-7-(aminomethyl)-3,3b,5′-trimethyltetradecahydrospiro[indeno[2,1-b]furan-2,2′-pyran]-6-yl)-3-(hydroxymethyl)-4-methylcyclohexanol acetate (Compound No. 76, 81 mg, 96%) as an off-white solid. ¹H NMR (CD₃OD): δ 4.43 (m, 1H), 3.68 (m, 1H), 3.45 (2H), 3.3 (2H), 3.13 (m, 1H), 3.00 (m, 1H), 2.10 (2H), 1.92 (s, 3H), 1.85-1.15 (21H), 1.08 (s, 3H), 0.98 (d, 3H), 0.85 (s, 3H), 0.80 (d, 3H).

Example 15

Synthesis of (1S,3aS,4R,5S,7aS)-4-(aminomethyl)-5-((1R,2S,4S)-4-hydroxy-2-(hydroxymethyl)-1-methylcyclohexyl)-7a-methyl-1-(thiophen-2-yl)octahydro-1H-inden-1-ol (Compound No. 85)

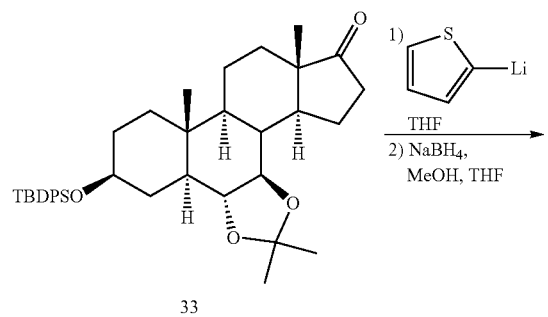

33

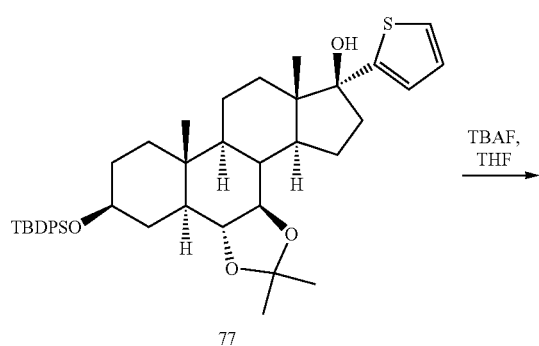

77

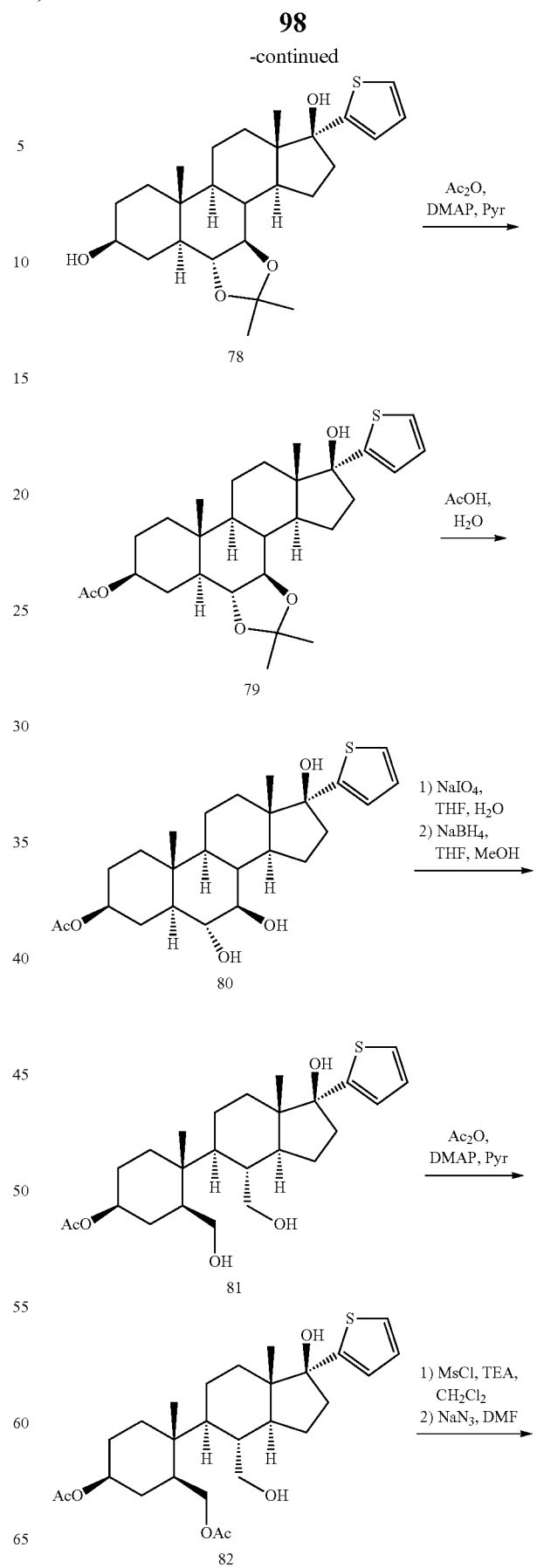

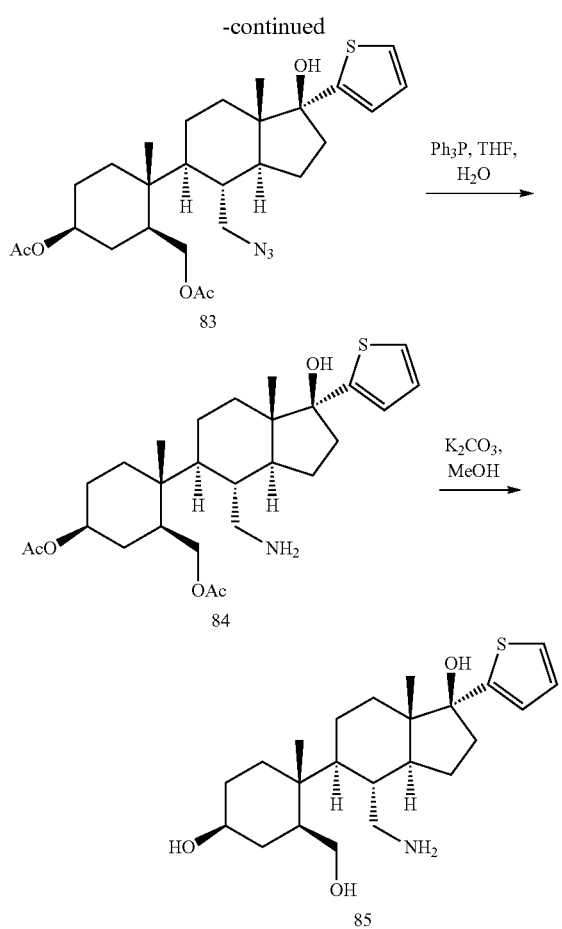

A. n-Butyllithium (4.4 mL of a 1.7 M solution in hexanes, 7.5 mmol) was added to a solution of thiophene (740 mg, 8.79 mmol) in THF (15 mL) at 0° C. under argon, and the mixture was stirred at room temperature for 30 min. The mixture was cooled to 0° C. and a solution of (2S,4aR,4bS, 6aS,9aS,9bR,9cR,12aR,12bS)-2-((tert-butyldiphenylsilyl) oxy)-4a,6a,11,11-tetramethyltetradecahydro-1H-cyclopenta [1,2]phenanthro[9,10-d][1,3]dioxol-7(8H)-one (Compound No. 33, 1.51 g, 2.51 mmol) in THF (10 mL) was added. The mixture was stirred at room temperature for 20 h then H₂O (5 mL) and brine (15 mL) were added followed by EtOAc (25 mL). The aqueous layer was extracted with EtOAc (2×20 mL), and the combined organic layers were dried (MgSO₄) and concentrated. To facilitate purification, the residue was dissolved in 2:1 MeOH/THF (30 mL), and NaBH₄ (48 mg, 1.3 mmol) was added. The mixture was stirred at room temperature under argon for 1.5 h then acetone (5 mL) was added and the mixture was concentrated. The residue was dissolved in EtOAc (60 mL) and washed with brine (20 mL). The aqueous layer was extracted with EtOAc (2×10 mL), and the combined organic layers were dried (MgSO₄) and concentrated. The residue was purified by chromatography on silica gel (15:85 EtOAc/hexanes) to give (2S,4aR,4bS,6aS,7S,9aS,9bR,9cR,12aR, 12bS)-2-((tert-butyldiphenylsilyl)oxy)-4a,6a,11,11-tetramethyl-7-(thiophen-2-yl)hexadecahydro-1H-cyclopenta[1,2] phenanthro[9,10-d][1,3]dioxol-7-ol (Compound No. 77, 1.36 g, 79%) as a yellow foam.

B. TBAF (4.0 mL of a 1 M solution in THF, 4.0 mmol) was added to a solution of (2S,4aR,4bS,6aS,7S,9aS,9bR, 9cR,12aR,12bS)-2-((tert-butyldiphenylsilyl)oxy)-4a,6a,11, 11-tetramethyl-7-(thiophen-2-yl)hexadecahydro-1H-cyclopenta[1,2]phenanthro[9,10-d][1,3]dioxol-7-ol (Compound No. 77, 1.36 g, 1.99 mmol) in THF (20 mL) and heated to 40° C. under argon for 16 h then stirred at room temperature for 3 d. The solution was concentrated, and the residue was purified by chromatography on silica gel (50:50-80:20 EtOAc/hexanes) to give (2S,4aR,4bS,6aS,7S,9aS,9bR,9cR, 12aR,12bS)-4a,6a,11,11-tetramethyl-7-(thiophen-2-yl) hexadecahydro-1H-cyclopenta[1,2]phenanthro[9,10-d][1,3] dioxole-2,7-diol (Compound No. 78, 828 mg, 93%) as a light yellow foam.

C. To a solution of (2S,4aR,4bS,6aS,7S,9aS,9bR,9cR, 12aR,12bS)-4a,6a,11,11-tetramethyl-7-(thiophen-2-yl) hexadecahydro-1H-cyclopenta[1,2]phenanthro[9,10-d][1,3] dioxole-2,7-diol (Compound No. 78, 828 mg, 1.85 mmol) and DMAP (23 mg, 0.19 mmol) in pyridine (14 mL) at 0° C. under argon was added a solution of Ac₂O (284 mg, 2.78 mmol) in pyridine (5 mL) then stirred at 0° C. for 20 min followed by stirring at room temperature for 17 h. The mixture was concentrated, and azeotropic removal of remaining pyridine was carried out with PhMe (3×30 mL). The yellow foam, (2S,4aR,4bS,6aS,7S,9aS,9bR,9cR,12aR, 12bS)-7-hydroxy-4a,6a,11,11-tetramethyl-7-(thiophen-2-yl) hexadecahydro-1H-cyclopenta[1,2]phenanthro[9,10-d][1,3] dioxol-2-yl acetate (Compound No. 79, 920 mg), that was obtained was used in the next step without further purification.

D. A suspension of (2S,4aR,4bS,6aS,7S,9aS,9bR,9cR, 12aR,12bS)-7-hydroxy-4a,6a,11,11-tetramethyl-7-(thiophen-2-yl)hexadecahydro-1H-cyclopenta[1,2]phenanthro[9, 10-d][1,3]dioxol-2-yl acetate (Compound No. 79, 920 mg) in 80% acetic acid(aq) (18 mL) was heated to 40° C. for 1.5 h then concentrated. Azeotropic removal of remaining AcOH and H₂O was carried out with PhMe (3×25 mL), and the residue was purified by chromatography on silica gel (1:1 EtOAc/CH₂Cl₂) to give (3S,5S,6R,7R,8R,9S,10R,13S, 14S,17S)-6,7,17-trihydroxy-10,13-dimethyl-17-(thiophen-2-yl)hexadecahydro-1H-cyclopenta[a]phenanthren-3-yl acetate (Compound No. 80, 430 mg, 52% over 2 steps) as a light yellow foam.

E. NaIO₄ (280 mg, 1.31 mmol) was added to a solution of (3S,5S,6R,7R,8R,9S,10R,13S,14S,17S)-6,7,17-trihydroxy-10,13-dimethyl-17-(thiophen-2-yl)hexadecahydro-1H-cyclopenta[a]phenanthren-3-yl acetate (Compound No. 80, 294 mg, 0.655 mmol) in 12:1 THF/H₂O (8.7 mL), and the mixture was stirred at room temperature for 2.3 h. The mixture was concentrated, and the residue was partitioned between CH₂Cl₂ (20 mL) and H₂O (10 mL). The aqueous phase was extracted with CH₂Cl₂ (2×10 mL), and the combined organic layers were dried (MgSO₄) and concentrated. The resulting light yellow oil (358 mg) was dissolved in 3:1 THF/MeOH (8 mL) and cooled to 0° C. under argon. NaBH₄ (50 mg, 1.3 mmol) was added, and the mixture was stirred at 0° C. for 30 min then at room temperature for 2 h. Acetone (5 mL) was added and the mixture was concentrated. The residue was partitioned between CH₂Cl₂ (20 mL) and H₂O (10 mL), and the aqueous phase was extracted with CH₂Cl₂ (2×10 mL). The combined organic layers were dried (MgSO₄) and concentrated. The pale foam, (1S,3S,4R)-4-((1S,3aS,4R,5S,7aS)-1-hydroxy-4-(hydroxymethyl)-7a-methyl-1-(thiophen-2-yl)octahydro-1H-inden-5-yl)-3-(hydroxymethyl)-4-methylcyclohexyl acetate (Compound No. 81, 319 mg), that was obtained was used in the next step without further purification.

F. To a solution of (1S,3S,4R)-4-((1S,3aS,4R,5S,7aS)-1-hydroxy-4-(hydroxymethyl)-7a-methyl-1-(thiophen-2-yl)

octahydro-1H-inden-5-yl)-3-(hydroxymethyl)-4-methylcyclohexyl acetate (Compound No. 81, 263 mg) and DMAP (7 mg, 0.06 mmol) in pyridine (2.7 mL) at 0° C. under argon was added a solution of Ac$_2$O (66 mg, 0.65 mmol) in pyridine (2.7 mL) over 1.75 h then stirred at 0° C. for 1.5 h. The mixture was concentrated, and azeotropic removal of remaining pyridine was carried out with PhMe (3×20 mL). The residue was purified by chromatography on silica gel (20:80 EtOAc/CH$_2$Cl$_2$) to give ((1S,2R,5S)-5-acetoxy-2-((1S,3aS,4R,5S,7aS)-1-hydroxy-4-(hydroxymethyl)-7a-methyl-1-(thiophen-2-yl)octahydro-1H-inden-5-yl)-2-methylcyclohexyl)methyl acetate (Compound No. 82, 177 mg, 67% over 3 steps) as a colourless foam.

G. To a solution of ((1S,2R,5S)-5-acetoxy-2-((1S,3aS,4R,5S,7aS)-1-hydroxy-4-(hydroxymethyl)-7a-methyl-1-(thiophen-2-yl)octahydro-1H-inden-5-yl)-2-methylcyclohexyl)methyl acetate (Compound No. 82, 177 mg, 0.359 mmol) and TEA (0.065 mL, 0.47 mmol) in CH$_2$Cl$_2$ (6 mL) at 0° C. was added MsCl (0.031 mL, 0.40 mmol), and the solution was stirred under argon at room temperature for 1 h. The solution was diluted with CH$_2$Cl$_2$ (10 mL) and washed with saturated aqueous NaHCO$_3$ (10 mL). The aqueous phase was extracted with CH$_2$Cl$_2$ (2×10 mL), and the combined organic layers were dried (MgSO$_4$) and concentrated. Azeotropic removal of impurities was carried out with PhMe (3×20 mL), and the resulting pale oil (257 mg) was dissolved in DMF (1.8 mL). NaN$_3$ (70 mg, 1.1 mmol) was added, and the mixture was heated to 60° C. under argon for 17 h. The mixture was concentrated then partitioned between EtOAc (45 mL), H$_2$O (5 mL) and brine (5 mL). The organic layer was washed with brine (2×10 mL) then dried (MgSO$_4$) and concentrated. The residue was purified by chromatography on silica gel (10:90 EtOAc/CH$_2$Cl$_2$) to give ((1S,2R,5S)-5-acetoxy-2-((1S,3aS,4R,5S,7aS)-4-(azidomethyl)-1-hydroxy-7a-methyl-1-(thiophen-2-yl)octahydro-1H-inden-5-yl)-2-methylcyclohexyl)methyl acetate (Compound No. 83, 149 mg, 80% over 2 steps) as a colourless film.

H. Triphenylphosphine (151 mg, 0.576 mmol) was added to a solution of ((1S,2R,5S)-5-acetoxy-2-((1S,3aS,4R,5S,7aS)-4-(azidomethyl)-1-hydroxy-7a-methyl-1-(thiophen-2-yl)octahydro-1H-inden-5-yl)-2-methylcyclohexyl)methyl acetate (Compound No. 83, 149 mg, 0.288 mmol) in 10:1 THF/H$_2$O (3.2 mL) then heated to 50° C. for 22 h. The mixture was concentrated, and azeotropic removal of remaining H$_2$O was carried out with MeOH (2×20 mL). The residue was purified by chromatography on silica gel (5:95 MeOH/CH$_2$Cl$_2$ then 100:5:1 CH$_2$Cl$_2$/MeOH/NH$_4$OH) to give ((1S,2R,5S)-5-acetoxy-2-((1S,3aS,4R,5S,7aS)-4-(aminomethyl)-1-hydroxy-7a-methyl-1-(thiophen-2-yl)octahydro-1H-inden-5-yl)-2-methylcyclohexyl)methyl acetate (Compound No. 84, 139 mg, 98%) as a colourless solid.

I. To a solution of ((1S,2R,5S)-5-acetoxy-2-((1S,3aS,4R,5S,7aS)-4-(aminomethyl)-1-hydroxy-7a-methyl-1-(thiophen-2-yl)octahydro-1H-inden-5-yl)-2-methylcyclohexyl)methyl acetate (Compound No. 84, 139 mg, 0.283 mmol) in MeOH (7 mL) was added potassium carbonate (78 mg, 0.56 mmol) and stirred at room temperature for 15.5 h. The mixture was concentrated, and the residue was purified by chromatography on silica gel (100:10:2 CH$_2$Cl$_2$/MeOH/NH$_4$OH) to give (1S,3aS,4R,5S,7aS)-4-(aminomethyl)-5-((1R,2S,4S)-4-hydroxy-2-(hydroxymethyl)-1-methylcyclohexyl)-7a-methyl-1-(thiophen-2-yl)octahydro-1H-inden-1-ol (Compound No. 85, 107 mg, 93%) as a colourless solid. $^1$H NMR (CD$_3$OD): δ 7.24 (m, 1H), 6.95 (m, 2H), 3.56 (m, 1H), 3.42 (m, 1H), 3.05 (m, 2H), 2.73 (m, 1H), 2.35 (m, 1H), 2.08-2.23 (m, 2H), 1.17-1.93 (m, 14H), 1.02 (s, 3H), 1.01 (s, 3H), 0.57 (m, 1H). ES-MS m/z 408 ([M+1]$^+$).

Example 16

Synthesis of (1S,3S,4R)-4-((3aS,6S,7R,7aS)-7-(aminomethyl)-3a-methyl-3-(thiophen-2-yl)-3a,4,5,6,7,7a-hexahydro-1H-inden-6-yl)-3-(hydroxymethyl)-4-methylcyclohexanol (Compound No. 86)

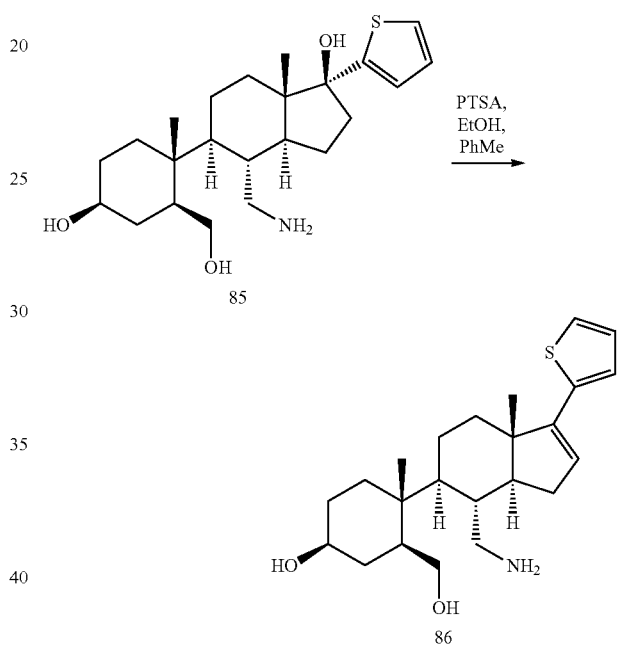

To a solution of (1S,3aS,4R,5S,7aS)-4-(aminomethyl)-5-((1R,2S,4S)-4-hydroxy-2-(hydroxymethyl)-1-methylcyclohexyl)-7a-methyl-1-(thiophen-2-yl)octahydro-1H-inden-1-ol (Compound No. 85, 76 mg, 0.19 mmol) in 16:84 EtOH/PhMe (6 mL) was added p-toluenesulfonic acid monohydrate (43 mg, 0.23 mmol) then heated to 80° C. for 1.5 h. The mixture was washed with 1 N NaOH(aq) (15 mL), and the aqueous phase was extracted with 1:9 MeOH/CH$_2$Cl$_2$ (5×10 mL). The combined organic layers were dried (MgSO$_4$) and concentrated, and the residue was purified by chromatography on silica gel (100:10:2 CH$_2$Cl$_2$/MeOH/NH$_4$OH) to give (1S,3S,4R)-4-((3aS,6S,7R,7aS)-7-(aminomethyl)-3a-methyl-3-(thiophen-2-yl)-3a,4,5,6,7,7a-hexahydro-1H-inden-6-yl)-3-(hydroxymethyl)-4-methylcyclohexanol (Compound No. 86, 66 mg, 90%) as a colourless solid. $^1$H NMR (CD$_3$OD): δ 7.21 (d, J=4.8 Hz, 1H), 7.05 (d, J=3.6 Hz, 1H), 6.96 (dd, J=5.0, 3.5 Hz, 1H), 5.95 (s, 1H), 3.75 (m, 1H), 3.46 (m, 1H), 3.13 (m, 2H), 2.75 (m, 1H), 1.22-2.36 (m, 16H), 1.11 (s, 3H), 1.03 (s, 3H). ES-MS m/z 390 ([M+1]$^+$).

Example 17
Synthesis of (1S,3aS,4R,5S,7aS)-4-(aminomethyl)-5-((1R,2S,4S)-4-hydroxy-2-(hydroxymethyl)-1-methylcyclohexyl)-7a-methyl-1-(pyridin-2-yl)octahydro-1H-inden-1-ol (Compound No. 95)
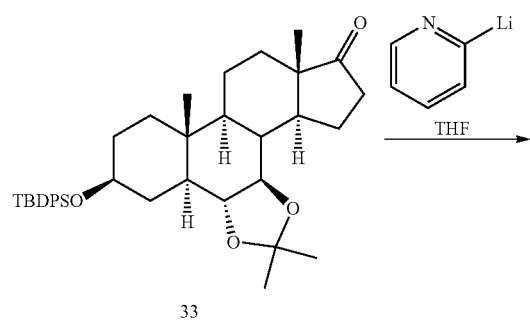
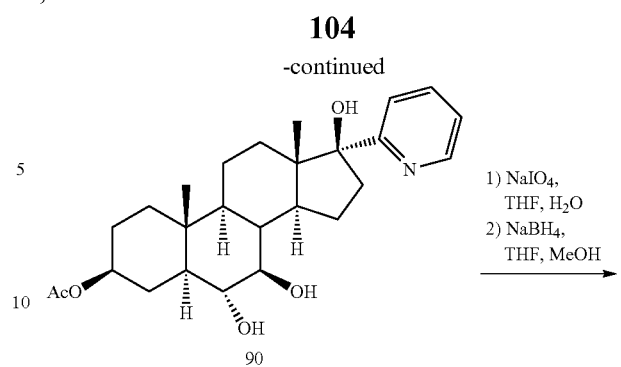
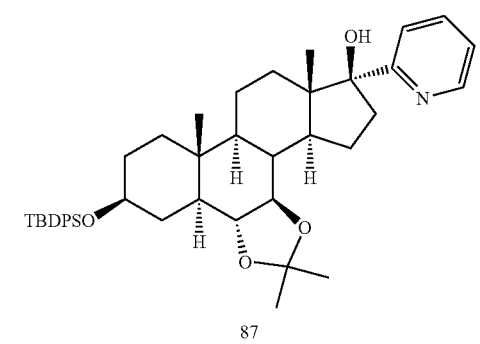
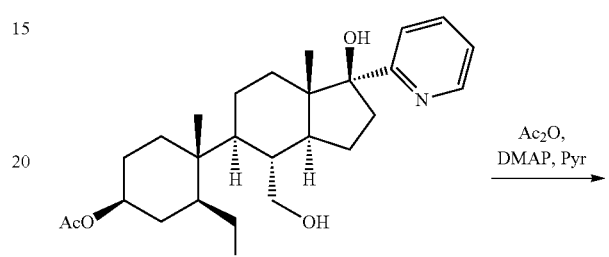
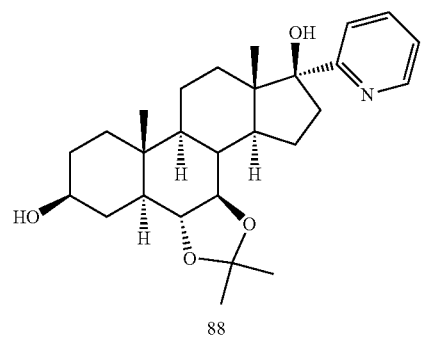
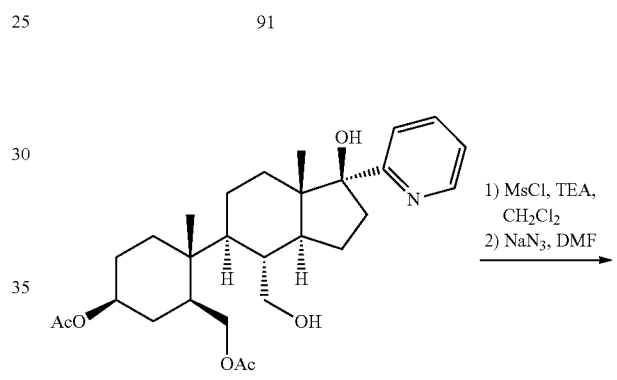
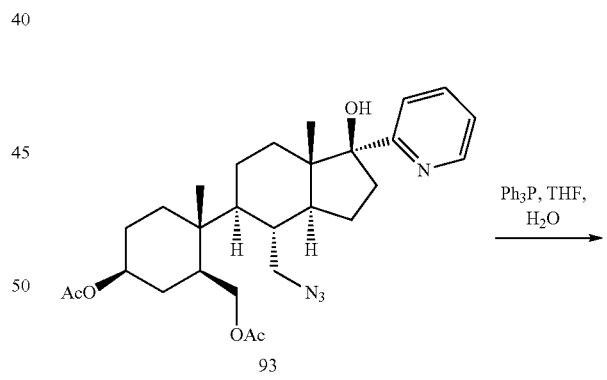
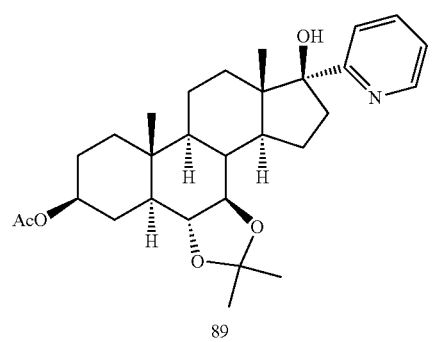
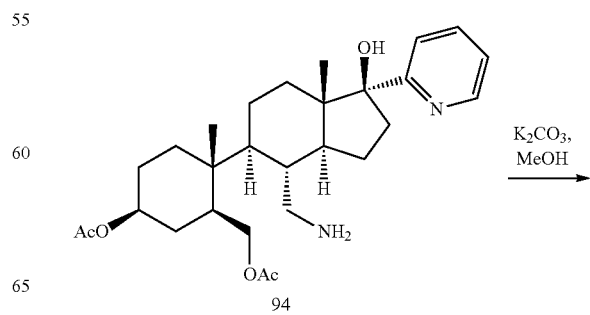

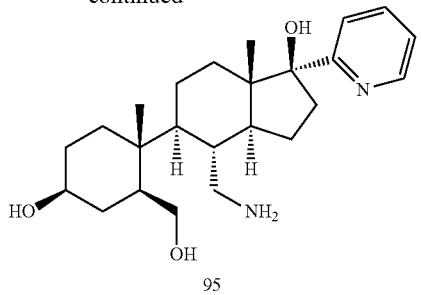

95

A. n-Butyllithium (6.1 mL of a 1.6 M solution in hexanes, 9.8 mmol) was cooled to −78° C. under argon, and a solution of 2-bromopyridine (1.79 g, 11.3 mmol) in THF (4 mL) was added. The mixture was stirred at −78° C. for 20 min then a solution of (2S,4aR,4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 1.95 g, 3.25 mmol) in THF (12 mL) was added. The mixture was stirred at 0° C. for 3.5 h then at room temperature for 16 h followed by the addition of H$_2$O (1 mL). The mixture was filtered through silica gel (1:1 EtOAc/hexanes) and concentrated. The residue was purified by chromatography on silica gel (15:85 EtOAc/hexanes) to give (2S,4aR,4bS,6aS,7S,9aS,9bR,9cR,12aR,12bS)-2-((tert-butyldiphenylsilyl)oxy)-4a,6a,11,11-tetramethyl-7-(pyridin-2-yl)hexadecahydro-1H-cyclopenta[1,2]phenanthro[9,10-d][1,3]dioxol-7-ol (Compound No. 87, 0.94 g, 43%) as a yellow foam.

B. TBAF (3.62 mL of a 1 M solution in THF, 3.62 mmol) was added to a solution of (2S,4aR,4bS,6aS,7S,9aS,9bR,9cR,12aR,12bS)-2-((tert-butyldiphenylsilyl)oxy)-4a,6a,11,11-tetramethyl-7-(pyridin-2-yl)hexadecahydro-1H-cyclopenta[1,2]phenanthro[9,10-d][1,3]dioxol-7-ol (Compound No. 87, 1.23 g, 1.81 mmol) in THF (9.0 mL) and heated to 50° C. under argon for 20 h. The solution was concentrated, and the residue was purified by chromatography on silica gel (80:20 EtOAc/hexanes) to give (2S,4aR,4bS,6aS,7S,9aS,9bR,9cR,12aR,12bS)-4a,6a,11,11-tetramethyl-7-(pyridin-2-yl)hexadecahydro-1H-cyclopenta[1,2]phenanthro[9,10-d][1,3]dioxole-2,7-diol (Compound No. 28, 728 mg, 91%) as a yellow foam.

C. To a solution of (2S,4aR,4bS,6aS,7S,9aS,9bR,9cR,12aR,12bS)-4a,6a,11,11-tetramethyl-7-(pyridin-2-yl)hexadecahydro-1H-cyclopenta[1,2]phenanthro[9,10-d][1,3]dioxole-2,7-diol (Compound No. 88, 728 mg, 1.65 mmol) and DMAP (20 mg, 0.16 mmol) in pyridine (12 mL) at 0° C. under argon was added a solution of Ac$_2$O (252 mg, 2.47 mmol) in pyridine (4 mL) then stirred at room temperature for 19 h. The mixture was concentrated, and azeotropic removal of remaining pyridine was carried out with PhMe (3×25 mL). The yellow foam, (2S,4aR,4bS,6aS,7S,9aS,9bR,9cR,12aR,12bS)-7-hydroxy-4a,6a,11,11-tetramethyl-7-(pyridin-2-yl)hexadecahydro-1H-cyclopenta[1,2]phenanthro[9,10-d][1,3]dioxol-2-yl acetate (Compound No. 89, 817 mg), that was obtained was used in the next step without further purification.

D. A suspension of (2S,4aR,4bS,6aS,7S,9aS,9bR,9cR,12aR,12bS)-7-hydroxy-4a,6a,11,11-tetramethyl-7-(pyridin-2-yl)hexadecahydro-1H-cyclopenta[1,2]phenanthro[9,10-d][1,3]dioxol-2-yl acetate (Compound No. 89, 817 mg) in 80% acetic acid(aq) (16.3 mL) was heated to 40° C. for 1.5 h then concentrated. Azeotropic removal of remaining AcOH and H$_2$O was carried out with PhMe (3×25 mL), and the residue was purified by chromatography on silica gel (EtOAc) to give (3S,5S,6R,7R,8R,9S,10R,13S,14S,17S)-6,7,17-trihydroxy-10,13-dimethyl-17-(pyridin-2-yl)hexadecahydro-1H-cyclopenta[a]phenanthren-3-yl acetate (Compound No. 90, 658 mg, 90% over 2 steps) as a pale foam.

E. NaIO$_4$ (357 mg, 1.67 mmol) was added to a solution of (3S,5S,6R,7R,8R,9S,10R,13S,14S,17S)-6,7,17-trihydroxy-10,13-dimethyl-17-(pyridin-2-yl)hexadecahydro-1H-cyclopenta[a]phenanthren-3-yl acetate (Compound No. 90, 370 mg, 0.834 mmol) in 10:1 THF/H$_2$O (8.8 mL), and the mixture was stirred at room temperature for 2.25 h. The mixture was concentrated, and the residue was partitioned between CH$_2$Cl$_2$ (15 mL) and H$_2$O (15 mL). The aqueous phase was extracted with CH$_2$Cl$_2$ (2×10 mL), and the combined organic layers were dried (MgSO$_4$) and concentrated. The resulting colourless foam (413 mg) was dissolved in 3:1 THF/MeOH (8 mL) and cooled to 0° C. under argon. NaBH$_4$ (63 mg, 1.7 mmol) was added, and the mixture was stirred at room temperature for 3.5 h. Acetone (5 mL) was added and the mixture was concentrated. The residue was partitioned between CH$_2$Cl$_2$ (15 mL) and H$_2$O (10 mL), and the aqueous phase was extracted with CH$_2$Cl$_2$ (2×10 mL). The combined organic layers were dried (MgSO$_4$) and concentrated. The pale foam, (1S,3S,4R)-4-((1S,3aS,4R,5S,7aS)-1-hydroxy-4-(hydroxymethyl)-7a-methyl-1-(pyridin-2-yl)octahydro-1H-inden-5-yl)-3-(hydroxymethyl)-4-methylcyclohexyl acetate (Compound No. 91, 399 mg), that was obtained was used in the next step without further purification.

F. To a solution of (1S,3S,4R)-4-((1S,3aS,4R,5S,7aS)-1-hydroxy-4-(hydroxymethyl)-7a-methyl-1-(pyridin-2-yl)octahydro-1H-inden-5-yl)-3-(hydroxymethyl)-4-methylcyclohexyl acetate (Compound No. 91, 332 mg) and DMAP (8 mg, 0.07 mmol) in pyridine (3.9 mL) at 0° C. under argon was added a solution of Ac$_2$O (85 mg, 0.83 mmol) in pyridine (3.0 mL) over 2 h then stirred at 0° C. for 1 h. The mixture was concentrated, and azeotropic removal of remaining pyridine was carried out with PhMe (3×20 mL). The residue was partially purified by chromatography on silica gel (4:96 MeOH/CH$_2$Cl$_2$) to give ((1S,2R,5S)-5-acetoxy-2-((1S,3aS,4R,5S,7aS)-1-hydroxy-4-(hydroxymethyl)-7a-methyl-1-(pyridin-2-yl)octahydro-1H-inden-5-yl)-2-methylcyclohexyl)methyl acetate (Compound No. 92, 335 mg) as a colourless gum.

G. To a solution of ((1S,2R,5S)-5-acetoxy-2-((1S,3aS,4R,5S,7aS)-1-hydroxy-4-(hydroxymethyl)-7a-methyl-1-(pyridin-2-yl)octahydro-1H-inden-5-yl)-2-methylcyclohexyl) methyl acetate (Compound No. 92, 335 mg) and TEA (0.12 mL, 0.86 mmol) in CH$_2$Cl$_2$ (6.9 mL) at 0° C. was added MsCl (0.059 mL, 0.76 mmol), and the solution was stirred under argon at room temperature for 1.5 h. The solution was diluted with CH$_2$Cl$_2$ (10 mL) and washed with saturated aqueous NaHCO$_3$ (10 mL). The aqueous phase was extracted with CH$_2$Cl$_2$ (2×10 mL), and the combined organic layers were dried (MgSO$_4$) and concentrated. Azeotropic removal of impurities was carried out with PhMe (3×10 mL), and the resulting light yellow foam (403 mg) was dissolved in DMF (2.3 mL). NaN$_3$ (134 mg, 2.06 mmol) was added, and the mixture was heated to 60° C. under argon for 16.5 h. The mixture was concentrated then partitioned between EtOAc (50 mL), H$_2$O (5 mL) and brine (5 mL). The aqueous phase was extracted with EtOAc (2×10 mL), and the combined organic layers were dried (MgSO$_4$) and concentrated. The residue was filtered through silica gel (2:98 MeOH/CH$_2$Cl$_2$) to give ((1S,2R,5S)-5-acetoxy-2-((1S,3aS,4R,5S,7aS)-4-(azidomethyl)-1-hydroxy-7a-methyl-1-(pyridin-2-yl)octahydro-1H-inden-5-yl)-2-methylcyclohexyl)

methyl acetate (Compound No. 93, 272 mg) as a colourless foam that was used in the next step without further purification.

H. Triphenylphosphine (278 mg, 1.06 mmol) was added to a solution of ((1S,2R,5S)-5-acetoxy-2-((1S,3aS,4R,5S,7aS)-4-(azidomethyl)-1-hydroxy-7a-methyl-1-(pyridin-2-yl)octahydro-1H-inden-5-yl)-2-methylcyclohexyl)methyl acetate (Compound No. 93, 272 mg) in 11:1 THF/H$_2$O (5.8 mL) then heated to 50° C. for 19 h. The mixture was concentrated, and azeotropic removal of remaining H$_2$O was carried out with MeOH (2×20 mL). The residue was purified by chromatography on silica gel (5:95 MeOH/CH$_2$Cl$_2$ then 100:5:1 CH$_2$Cl$_2$/MeOH/NH$_4$OH) to give ((1S,2R,5S)-5-acetoxy-2-((1S,3aS,4R,5S,7aS)-4-(aminomethyl)-1-hydroxy-7a-methyl-1-(pyridin-2-yl)octahydro-1H-inden-5-yl)-2-methylcyclohexyl)methyl acetate (Compound No. 94, 206 mg, 61% over 6 steps) as a colourless foam.

I. To a solution of ((1S,2R,5S)-5-acetoxy-2-((1S,3aS,4R,5S,7aS)-4-(aminomethyl)-1-hydroxy-7a-methyl-1-(pyridin-2-yl)octahydro-1H-inden-5-yl)-2-methylcyclohexyl)methyl acetate (Compound No. 94, 137 mg, 0.282 mmol) in MeOH (5.6 mL) was added potassium carbonate (78 mg, 0.56 mmol) and heated to 40° C. for 1.5 h. The mixture was concentrated, and the residue was purified by chromatography on silica gel (100:10:2 CH$_2$Cl$_2$/MeOH/NH$_4$OH) to give (1S,3aS,4R,5S,7aS)-4-(aminomethyl)-5-((1R,2S,4S)-4-hydroxy-2-(hydroxymethyl)-1-methylcyclohexyl)-7a-methyl-1-(pyridin-2-yl)octahydro-1H-inden-1-ol (Compound No. 95, 110 mg, 97%) as a colourless solid. $^1$H NMR (CD$_3$OD): δ 8.50 (d, J=4.8 Hz, 1H), 7.77 (m, 1H), 7.65 (d, J=8.1 Hz, 1H), 7.26 (m, 1H), 3.46 (m, 2H), 3.03 (m, 2H), 2.71 (m, 1H), 2.50 (m, 1H), 1.94-2.09 (m, 3H), 1.12-1.83 (m, 13H), 1.06 (s, 3H), 1.00 (s, 3H), 0.11 (m, 1H). ES-MS m/z 403 ([M+1]$^+$).

Example 18

Synthesis of (1S,3aS,4R,5S,7aS)-4-(aminomethyl)-5-((1R,2S,4S)-4-hydroxy-2-(hydroxymethyl)-1-methylcyclohexyl)-1,7a-dimethyloctahydro-1H-inden-1-ol (Compound No. 103)

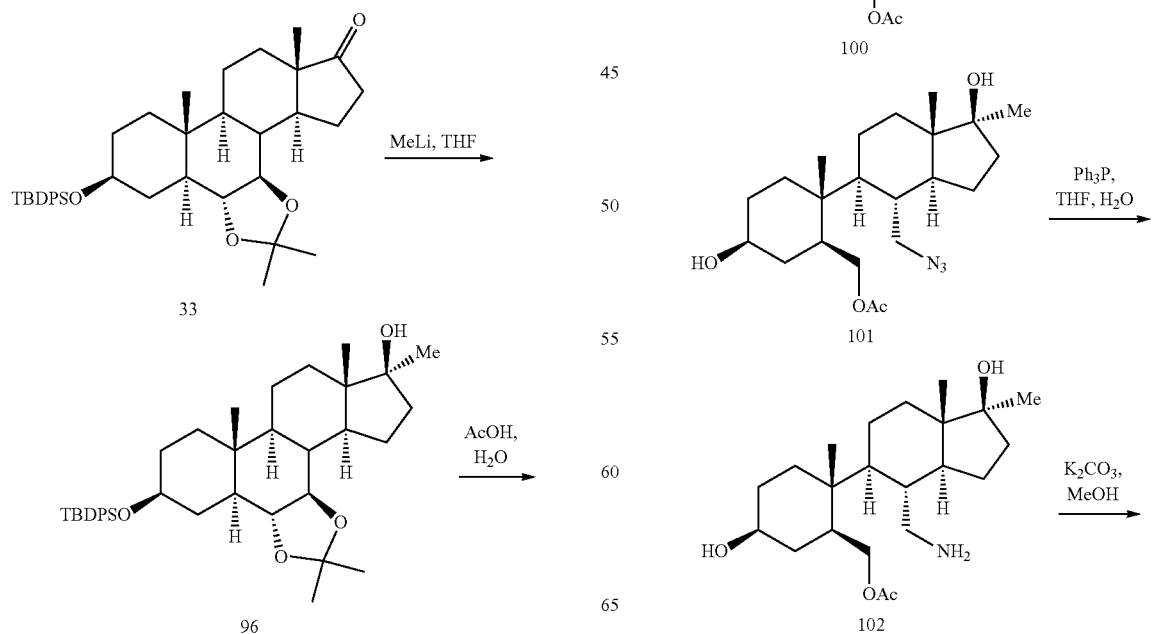

-continued

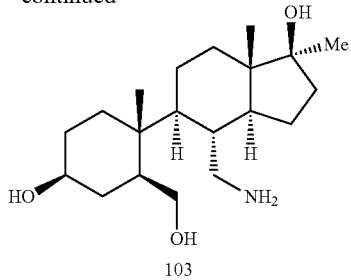

103

A. Methyllithium (5.3 mL of a 1.1 M solution in Et$_2$O, 5.8 mmol) was added dropwise to a solution of (2S,4aR,4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 1.16 g, 1.96 mmol) in THF (19 mL) at −78° C. under argon. The mixture was stirred at −78° C. for 1.5 h, 0° C. for 40 min then at room temperature for 2.5 h. The mixture was cooled to 0° C. and brine (20 mL) was carefully added followed by EtOAc (20 mL). The aqueous layer was extracted with EtOAc (20 mL), and the combined organic layers were dried (MgSO$_4$) and concentrated. The residue was purified by chromatography on silica gel (25:75 EtOAc/hexanes) to give (2S,4aR,4bS,6aS,7S,9aS,9bR,9cR,12aR,12bS)-2-((tert-butyldiphenylsilyl)oxy)-4a,6a,7,11,11-pentamethylhexadecahydro-1H-cyclopenta[1,2]phenanthro[9,10-d][1,3]dioxol-7-ol (Compound No. 96, 814 mg, 68%) as a colourless foam.

B. A suspension of (2S,4aR,4bS,6aS,7S,9aS,9bR,9cR,12aR,12bS)-2-((tert-butyldiphenylsilyl)oxy)-4a,6a,7,11,11-pentamethylhexadecahydro-1H-cyclopenta[1,2]phenanthro[9,10-d][1,3]dioxol-7-ol (Compound No. 96, 814 mg, 1.32 mmol) in 80% acetic acid(aq) (13 mL) was heated to 40° C. for 2.7 h then concentrated. Azeotropic removal of remaining AcOH and H$_2$O was carried out with PhMe (3×25 mL), and the colourless foam, (3S,5S,6R,7R,8R,9S,10R,13S,14S,17S)-3-((tert-butyldiphenylsilyl)oxy)-10,13,17-trimethylhexadecahydro-1H-cyclopenta[a]phenanthrene-6,7,17-triol (Compound No. 97, 824 mg), that was obtained was used in the next step without further purification.

C. A suspension of NaIO$_4$ (552 mg, 2.58 mmol) in H$_2$O (1.3 mL) was added to a solution of (3S,5S,6R,7R,8R,9S,10R,13S,14S,17S)-3-((tert-butyldiphenylsilyl)oxy)-10,13,17-trimethylhexadecahydro-1H-cyclopenta[a]phenanthrene-6,7,17-triol (Compound No. 97, 745 mg) in THF (13 mL), and the mixture was stirred at room temperature for 2 h. The mixture was concentrated, and the residue was partitioned between CH$_2$Cl$_2$ (20 mL) and H$_2$O (10 mL). The aqueous phase was extracted with CH$_2$Cl$_2$ (2×10 mL), and the combined organic layers were dried (MgSO$_4$) and concentrated. The resulting colourless foam (768 mg) was dissolved in 3:1 THF/MeOH (12 mL) and cooled to 0° C. under argon. NaBH$_4$ (91 mg, 2.4 mmol) was added, and the mixture was stirred at 0° C. for 30 min then at room temperature for 2 h. Acetone (5 mL) was added and the mixture was concentrated. The residue was partitioned between EtOAc (50 mL) and brine (15 mL), and the organic layer was washed with brine (15 mL) then dried (MgSO$_4$) and concentrated. The colourless foam, (1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-1,7a-dimethyloctahydro-1H-inden-1-ol (Compound No. 98, 720 mg), that was obtained was used in the next step without further purification.

D. To a solution of (1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-1,7a-dimethyloctahydro-1H-inden-1-ol (Compound No. 98, 633 mg) and DMAP (13 mg, 0.11 mmol) in pyridine (5 mL) at 0° C. under argon was added a solution of Ac$_2$O (108 mg, 1.06 mmol) in pyridine (5 mL) over 2 h then stirred at 0° C. for 1 h. Ice-H$_2$O (15 mL) was added followed by EtOAc (50 mL), and the organic layer was washed with brine (2×15 mL) then concentrated. Azeotropic removal of remaining pyridine was carried out with PhMe (3×20 mL). The residue was purified by chromatography on silica gel (40:60 EtOAc/CH$_2$Cl$_2$) to give ((1S,2R,5S)-5-((tert-butyldiphenylsilyl)oxy)-2-((1S,3aS,4R,5S,7aS)-1-hydroxy-4-(hydroxymethyl)-1,7a-dimethyloctahydro-1H-inden-5-yl)-2-methylcyclohexyl)methyl acetate (Compound No. 99, 402 mg, 62% over 4 steps) as a colourless foam.

E. To a solution of ((1S,2R,5S)-5-((tert-butyldiphenylsilyl)oxy)-2-((1S,3aS,4R,5S,7aS)-1-hydroxy-4-(hydroxymethyl)-1,7a-dimethyloctahydro-1H-inden-5-yl)-2-methylcyclohexyl)methyl acetate (Compound No. 99, 402 mg, 0.647 mmol) and TEA (0.14 mL, 1.0 mmol) in CH$_2$Cl$_2$ (9 mL) at −78° C. under argon was added MsCl (0.055 mL, 0.71 mmol), and the solution was stirred at −78° C. for 10 min then at room temperature for 1 h. Additional MsCl (0.015 mL, 0.19 mmol) was added and stirred at room temperature for 1.5 h. The solution was concentrated, and the residue was partitioned between EtOAc (40 mL) and saturated aqueous NaHCO$_3$ (15 mL). The organic layer was washed with saturated aqueous NaHCO$_3$ (3×15 mL) and brine (10 mL) then dried (MgSO$_4$) and concentrated. Azeotropic removal of impurities was carried out with PhMe (3×15 mL), and the resulting pale oil (529 mg) was dissolved in DMF (3.2 mL). NaN$_3$ (126 mg, 1.94 mmol) was added, and the mixture was heated to 60° C. under argon for 21 h. The mixture was diluted with EtOAc (40 mL) and H$_2$O (10 mL), and the organic layer was washed with brine (5×10 mL) then dried (MgSO$_4$) and concentrated. The residue was purified by chromatography on silica gel (25:75 EtOAc/hexanes) to give ((1S,2R,5S)-2-((1S,3aS,4R,5S,7aS)-4-(azidomethyl)-1-hydroxy-1,7a-dimethyloctahydro-1H-inden-5-yl)-5-((tert-butyldiphenylsilyl)oxy)-2-methylcyclohexyl)methyl acetate (Compound No. 100, 259 mg, 62% over 2 steps) as a colourless foam.

F. TBAF (0.53 mL of a 1 M solution in THF, 0.53 mmol) was added to a solution of ((1S,2R,5S)-2-((1S,3aS,4R,5S,7aS)-4-(azidomethyl)-1-hydroxy-1,7a-dimethyloctahydro-1H-inden-5-yl)-5-((tert-butyldiphenylsilyl)oxy)-2-methylcyclohexyl)methyl acetate (Compound No. 100, 172 mg, 0.266 mmol) in THF (5.3 mL) and stirred at room temperature for 41 h. The solution was concentrated, and the residue was purified by chromatography on silica gel (80:20 EtOAc/hexanes) to give ((1S,2R,5S)-2-((1S,3aS,4R,5S,7aS)-4-(azidomethyl)-1-hydroxy-1,7a-dimethyloctahydro-1H-inden-5-yl)-5-hydroxy-2-methylcyclohexyl)methyl acetate (Compound No. 101, 109 mg, 100%) as a colourless film.

G. Triphenylphosphine (140 mg, 0.534 mmol) was added to a solution of ((1S,2R,5S)-2-((1S,3aS,4R,5S,7aS)-4-(azidomethyl)-1-hydroxy-1,7a-dimethyloctahydro-1H-inden-5-yl)-5-hydroxy-2-methylcyclohexyl)methyl acetate (Compound No. 101, 109 mg, 0.267 mmol) in 9:1 THF/H$_2$O (3.0 mL) then heated to 50° C. for 22 h. The mixture was concentrated, and azeotropic removal of remaining H$_2$O was carried out with MeOH (2×20 mL). The residue was purified by chromatography on silica gel (5:95 MeOH/CH$_2$Cl$_2$ then 100:10:2 CH$_2$Cl$_2$/MeOH/NH$_4$OH) to give ((1S,2R,5S)-2-((1S,3aS,4R,5S,7aS)-4-(aminomethyl)-1-hydroxy-1,7a-dimethyloctahydro-1H-inden-5-yl)-5-hydroxy-2-methylcyclohexyl)methyl acetate (Compound No. 102, 99 mg, 97%) as a colourless film.

H. To a solution of ((1S,2R,5S)-2-((1S,3aS,4R,5S,7aS)-4-(aminomethyl)-1-hydroxy-1,7a-dimethyloctahydro-1H-inden-5-yl)-5-hydroxy-2-methylcyclohexyl)methyl acetate (Compound No. 102, 99 mg, 0.26 mmol) in MeOH (5.2 mL) was added potassium carbonate (72 mg, 0.52 mmol) and heated to 40° C. for 2 h. The mixture was concentrated, and the residue was purified by chromatography on silica gel (100:10:2 CH$_2$Cl$_2$/MeOH/NH$_4$OH) to give (1S,3aS,4R,5S,7aS)-4-(aminomethyl)-5-((1R,2S,4S)-4-hydroxy-2-(hydroxymethyl)-1-methylcyclohexyl)-1,7a-dimethyloctahydro-1H-inden-1-ol (Compound No. 103, 48 mg, 55%) as a colourless solid. $^1$H NMR (CD$_3$OD): δ 3.72 (m, 1H), 3.45 (m, 1H), 3.10 (m, 2H), 2.66 (m, 1H), 2.14 (m, 1H), 1.22-1.89 (m, 20H), 1.08 (s, 3H), 0.86 (s, 3H). ES-MS m/z 340 ([M+1]$^+$).

Example 19

Synthesis of (1S,2R,4R,5S)-4-(aminomethyl)-5-((1R,2S,4S)-4-hydroxy-2-(hydroxymethyl)-1-methylcyclohexyl)-1-methyl-1-phenyl-2,3,4,5,6,7-hexahydro-1H-inden-2-ol (Compound No. 115)

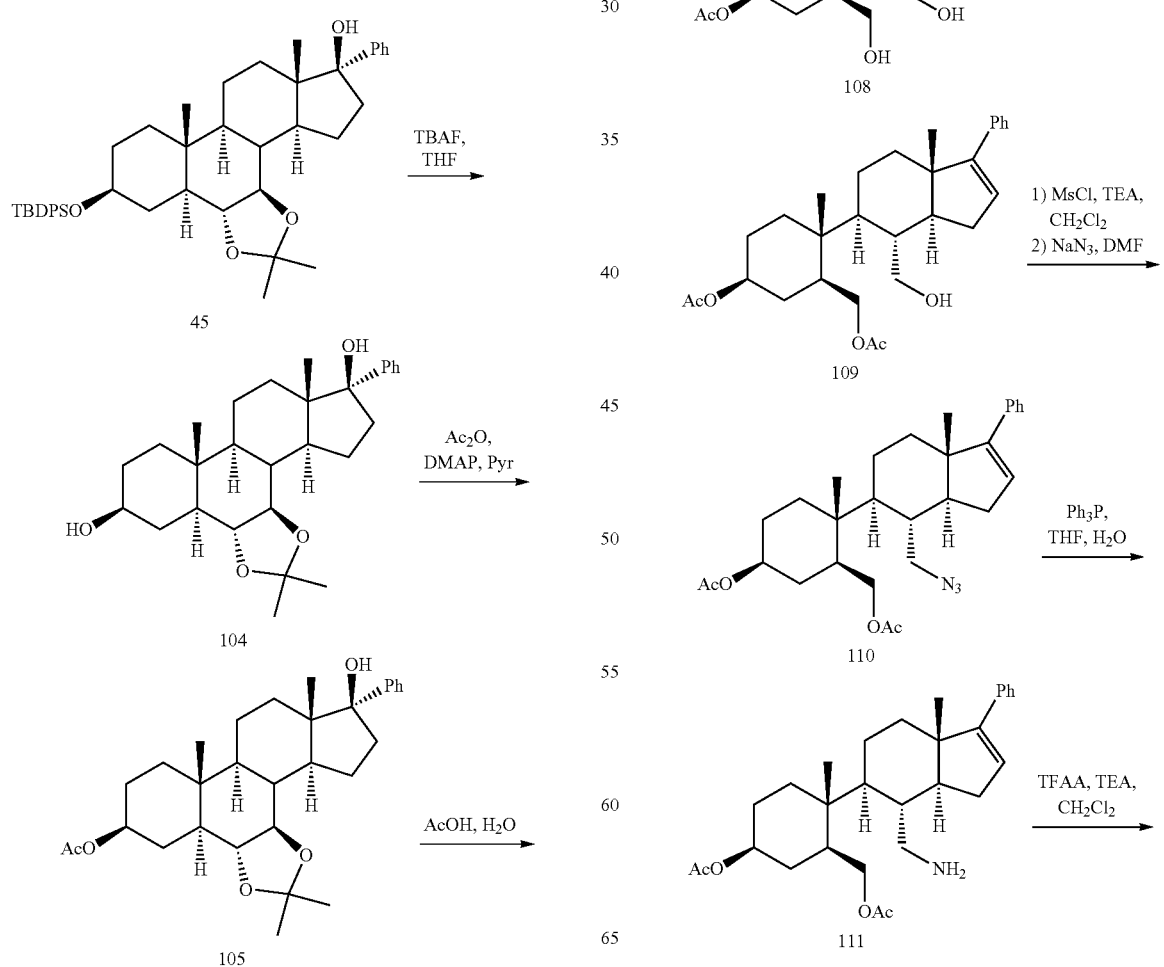

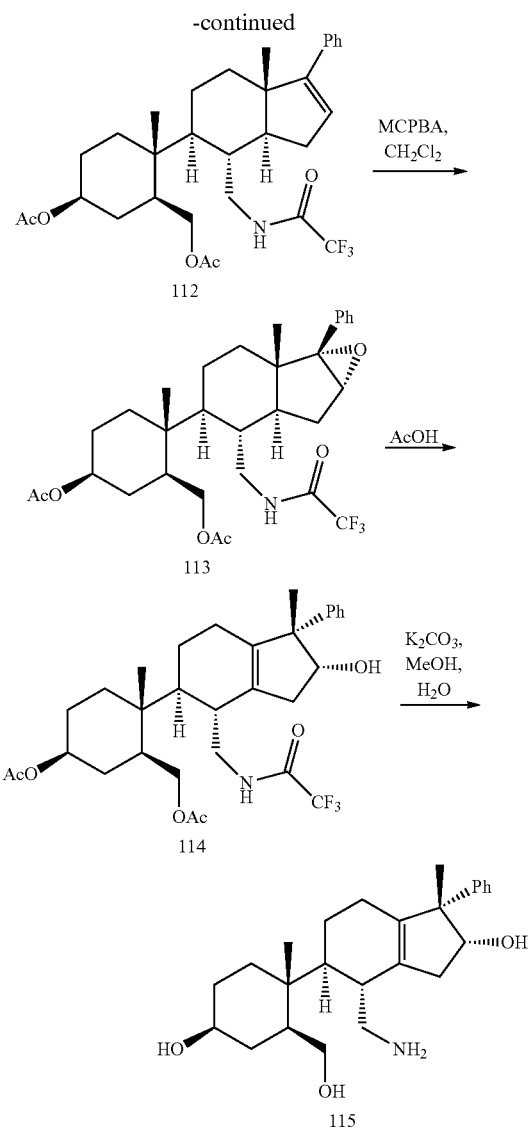

A. TBAF (3.0 mL of a 1 M solution in THF, 3.0 mmol) was added to a solution of (2S,4aR,4bS,6aS,7S,9aS,9bR,9cR,12aR,12bS)-2-((tert-butyldiphenylsilyl)oxy)-4a,6a,11,11-tetramethyl-7-phenylhexadecahydro-1H-cyclopenta[1,2]phenanthro[9,10-d][1,3]dioxol-7-ol (Compound No. 45, 1.01 g, 1.49 mmol) in THF (15 mL) and heated to 50° C. for 20 h. The solution was concentrated, and the residue was purified by chromatography on silica gel (50:50-60:40 EtOAc/hexanes) to give (2S,4aR,4bS,6aS,7S,9aS,9bR,9cR,12aR,12bS)-4a,6a,11,11-tetramethyl-7-phenylhexadecahydro-1H-cyclopenta[1,2]phenanthro[9,10-d][1,3]dioxole-2,7-diol (Compound No. 104, 492 mg, 75%) as a colourless foam.

B. To a solution of (2S,4aR,4bS,6aS,7S,9aS,9bR,9cR,12aR,12bS)-4a,6a,11,11-tetramethyl-7-phenylhexadecahydro-1H-cyclopenta[1,2]phenanthro[9,10-d][1,3]dioxole-2,7-diol (Compound No. 104, 487 mg, 1.11 mmol) and DMAP (14 mg, 0.11 mmol) in pyridine (4.5 mL) at 0° C. under argon was added a solution of Ac$_2$O (226 mg, 2.21 mmol) in pyridine (1.0 mL) then stirred at room temperature for 3 h. The solution was concentrated, and azeotropic removal of remaining pyridine was carried out with PhMe (3×20 mL). The residue was purified by chromatography on silica gel (25:75 EtOAc/hexanes) to give (2S,4aR,4bS,6aS,7S,9aS,9bR,9cR,12aR,12bS)-7-hydroxy-4a,6a,11,11-tetramethyl-7-phenylhexadecahydro-1H-cyclopenta[1,2]phenanthro[9,10-d][1,3]dioxol-2-yl acetate (Compound No. 105, 516 mg, 97%) as a colourless gum.

C. A suspension of (2S,4aR,4bS,6aS,7S,9aS,9bR,9cR,12aR,12bS)-7-hydroxy-4a,6a,11,11-tetramethyl-7-phenylhexadecahydro-1H-cyclopenta[1,2]phenanthro[9,10-d][1,3]dioxol-2-yl acetate (Compound No. 105, 516 mg, 1.07 mmol) in 80% acetic acid(aq) (10 mL) was heated to 40° C. for 1.5 h then concentrated. Azeotropic removal of remaining AcOH and H$_2$O was carried out with PhMe (3×30 mL), and the colourless solid (3S,5S,6R,7R,8R,9S,10R,13S,14S,17S)-6,7,17-trihydroxy-10,13-dimethyl-17-phenylhexadecahydro-1H-cyclopenta[a]phenanthren-3-yl acetate (Compound No. 106) that was obtained was used in the next step without further purification.

D. To a solution of (3S,5S,6R,7R,8R,9S,10R,13S,14S,17S)-6,7,17-trihydroxy-10,13-dimethyl-17-phenylhexadecahydro-1H-cyclopenta[a]phenanthren-3-yl acetate (Compound No. 106) in PhMe (11 mL) was added p-toluenesulfonic acid monohydrate (61 mg, 0.32 mmol) then heated to 70° C. for 3.5 h. The mixture was concentrated, dissolved in CH$_2$Cl$_2$ (20 mL), and washed with saturated aqueous NaHCO$_3$ (20 mL). The aqueous phase was extracted with CH$_2$Cl$_2$ (2×10 mL), and the combined organic layers were dried (MgSO$_4$) and concentrated. The residue was partially purified by chromatography on silica gel (40:60 EtOAc/CH$_2$Cl$_2$) to give (3S,5S,6R,7R,8R,9S,10R,13S,14S)-6,7-dihydroxy-10,13-dimethyl-17-phenyl-2,3,4,5,6,7,8,9,10,11,12,13,14,15-tetradecahydro-1H-cyclopenta[a]phenanthren-3-yl acetate (Compound No. 107, 200 mg) as a pale foam.

E. NaIO$_4$ (202 mg, 0.944 mmol) was added to a solution of (3S,5S,6R,7R,8R,9S,10R,13S,14S)-6,7-dihydroxy-10,13-dimethyl-17-phenyl-2,3,4,5,6,7,8,9,10,11,12,13,14,15-tetradecahydro-1H-cyclopenta[a]phenanthren-3-yl acetate (Compound No. 107, 200 mg) in 10:1 THF/H$_2$O (7.4 mL), and the mixture was stirred at room temperature for 2 h. The mixture was concentrated, and the residue was partitioned between CH$_2$Cl$_2$ (15 mL) and H$_2$O (10 mL). The aqueous phase was extracted with CH$_2$Cl$_2$ (2×10 mL), and the combined organic layers were dried (MgSO$_4$) and concentrated. The resulting colourless foam was dissolved in 3:1 THF/MeOH (6.7 mL) and NaBH$_4$ (36 mg, 0.95 mmol) was added. The mixture was stirred at room temperature under argon for 16 h. Acetone (5 mL) was added and the mixture was concentrated. The residue was dissolved in 1:9 MeOH/CH$_2$Cl$_2$ (10 mL) and washed with H$_2$O (10 mL). The aqueous phase was extracted with 1:9 MeOH/CH$_2$Cl$_2$ (2×10 mL), and the combined organic layers were dried (MgSO$_4$) and concentrated. The colourless film, (1S,3S,4R)-3-(hydroxymethyl)-4-((3aS,6S,7R,7aS)-7-(hydroxymethyl)-3a-methyl-3-phenyl-3a,4,5,6,7,7a-hexahydro-1H-inden-6-yl)-4-methylcyclohexyl acetate (Compound No. 108, 224 mg), that was obtained was used in the next step without further purification.

F. To a solution of (1S,3S,4R)-3-(hydroxymethyl)-4-((3aS,6S,7R,7aS)-7-(hydroxymethyl)-3a-methyl-3-phenyl-3a,4,5,6,7,7a-hexahydro-1H-inden-6-yl)-4-methylcyclohexyl acetate (Compound No. 108, 320 mg) and DMAP (9 mg, 0.07 mmol) in pyridine (4 mL) at 0° C. under argon was added a solution of Ac$_2$O (86 mg, 0.84 mmol) in pyridine (3 mL) over 2 h then stirred at 0° C. for 2 h. The mixture was concentrated, and azeotropic removal of remaining pyridine was carried out with PhMe (3×20 mL). The residue was purified by chromatography on silica gel (7:93-15:85

EtOAc/CH$_2$Cl$_2$) to give ((1S,2R,5S)-5-acetoxy-2-((3aS,6S,7R,7aS)-7-(hydroxymethyl)-3a-methyl-3-phenyl-3a,4,5,6,7,7a-hexahydro-1H-inden-6-yl)-2-methylcyclohexyl)methyl acetate (Compound No. 109, 173 mg, 29% over 5 steps) as a colourless gum.

G. To a solution of ((1S,2R,5S)-5-acetoxy-2-((3aS,6S,7R,7aS)-7-(hydroxymethyl)-3a-methyl-3-phenyl-3a,4,5,6,7,7a-hexahydro-1H-inden-6-yl)-2-methylcyclohexyl)methyl acetate (Compound No. 109, 173 mg, 0.369 mmol) and TEA (0.10 mL, 0.72 mmol) in CH$_2$Cl$_2$ (3.7 mL) at 0° C. under argon was added MsCl (0.043 mL, 0.55 mmol), and the solution was stirred at room temperature for 1.5 h. The solution was diluted with CH$_2$Cl$_2$ (10 mL) and washed with saturated aqueous NaHCO$_3$ (10 mL). The aqueous phase was extracted with CH$_2$Cl$_2$ (2×10 mL), and the combined organic layers were dried (MgSO$_4$) and concentrated. Azeotropic removal of impurities was carried out with PhMe (3×15 mL), and the residue was dissolved in DMF (1.5 mL). NaN$_3$ (72 mg, 1.1 mmol) was added, and the mixture was heated to 60C under argon for 19 h. The mixture was concentrated, and the residue was partitioned between EtOAc (15 mL) and H$_2$O (10 mL). The aqueous phase was extracted with EtOAc (2×10 mL), and the combined organic layers were dried (MgSO$_4$) and concentrated. The residue was purified by chromatography on silica gel (CH$_2$Cl$_2$) to give ((1S,2R,5S)-5-acetoxy-2-((3aS,6S,7R,7aS)-7-(azidomethyl)-3a-methyl-3-phenyl-3a,4,5,6,7,7a-hexahydro-1H-inden-6-yl)-2-methylcyclohexyl)methyl acetate (Compound No. 110,131 mg, 72% over 2 steps) as a colourless film.

H. Triphenylphosphine (139 mg, 0.530 mmol) was added to a solution of ((1S,2R,5S)-5-acetoxy-2-((3aS,6S,7R,7aS)-7-(azidomethyl)-3a-methyl-3-phenyl-3a,4,5,6,7,7a-hexahydro-1H-inden-6-yl)-2-methylcyclohexyl)methyl acetate (Compound No. 110,131 mg, 0.265 mmol) in 11:1 THF/H$_2$O (3.6 mL) then heated to 50° C. for 19.5 h. The mixture was concentrated, and azeotropic removal of remaining H$_2$O was carried out with MeOH (2×10 mL). The residue was partially purified by chromatography on silica gel (5:95 MeOH/CH$_2$Cl$_2$ then 100:5:1 CH$_2$Cl$_2$/MeOH/NH$_4$OH) to give ((1S,2R,5S)-5-acetoxy-2-((3aS,6S,7R,7aS)-7-(aminomethyl)-3a-methyl-3-phenyl-3a,4,5,6,7,7a-hexahydro-1H-inden-6-yl)-2-methylcyclohexyl)methyl acetate (Compound No. 111, 175 mg) as a colourless gum.

I. To a solution of ((1S,2R,5S)-5-acetoxy-2-((3aS,6S,7R,7aS)-7-(aminomethyl)-3a-methyl-3-phenyl-3a,4,5,6,7,7a-hexahydro-1H-inden-6-yl)-2-methylcyclohexyl)methyl acetate (Compound No. 111, 175 mg) and TEA (0.074 mL, 0.53 mmol) in CH$_2$Cl$_2$ (5.3 mL) was added trifluoro Ac$_2$O (0.055 mL, 0.40 mmol), and the solution was stirred at room temperature for 1 h. The mixture was concentrated, and azeotropic removal of remaining trifluoro Ac$_2$O was carried out with CH$_2$Cl$_2$ (10 mL). The residue was dissolved in CH$_2$Cl$_2$ (15 mL) and washed with saturated aqueous NaHCO$_3$ (10 mL). The aqueous phase was extracted with CH$_2$Cl$_2$ (2×10 mL), and the combined organic layers were dried (MgSO$_4$) and concentrated. The residue was purified by chromatography on silica gel (20:80 EtOAc/hexanes) to give ((1S,2R,5S)-5-acetoxy-2-methyl-2-((3aS,6S,7R,7aS)-3a-methyl-3-phenyl-7-((2,2,2-trifluoroacetamido)methyl)-3a,4,5,6,7,7a-hexahydro-1H-inden-6-yl)cyclohexyl)methyl acetate (Compound No. 112, 108 mg, 72% over 2 steps) as a colourless film.

J. MCPBA (77%, 86 mg, 0.38 mmol) was added to a solution of ((1S,2R,5S)-5-acetoxy-2-methyl-2-((3aS,6S,7R,7aS)-3a-methyl-3-phenyl-7-((2,2,2-trifluoroacetamido)methyl)-3a,4,5,6,7,7a-hexahydro-1H-inden-6-yl)cyclohexyl)methyl acetate (Compound No. 112, 108 mg, 0.192 mmol) in CH$_2$Cl$_2$ (3.8 mL), and the mixture was stirred at room temperature for 1 h. The mixture was diluted with CH$_2$Cl$_2$ (20 mL) and washed with saturated aqueous Na$_2$SO$_3$ (10 mL) followed by saturated aqueous NaHCO$_3$ (10 mL) and H$_2$O (10 mL). The organic layer was dried (MgSO$_4$) and concentrated to give a colourless solid, ((1S,2R,5S)-5-acetoxy-2-methyl-2-((1aR,1bS,4S,5R,5aS,6aR)-1b-methyl-1a-phenyl-5-((2,2,2-trifluoroacetamido)methyl)octahydro-1aH-indeno[1,2-b]oxiren-4-yl)cyclohexyl)methyl acetate (Compound No. 113, 111 mg), that was used in the next step without further purification.

K. A solution of ((1S,2R,5S)-5-acetoxy-2-methyl-2-((1aR,1bS,4S,5R,5aS,6aR)-1b-methyl-1a-phenyl-5-((2,2,2-trifluoroacetamido)methyl)octahydro-1aH-indeno[1,2-b]oxiren-4-yl)cyclohexyl)methyl acetate (Compound No. 113, 111 mg) in AcOH (4 mL) was stirred at room temperature for 17.5 h then heated to 40° C. for 7.5 h and concentrated. Azeotropic removal of remaining AcOH was carried out with PhMe (3×10 mL), and the residue was purified by chromatography on silica gel (35:65-50:50 EtOAc/hexanes) to give ((1S,2R,5S)-5-acetoxy-2-((1S,2R,4R,5S)-2-hydroxy-1-methyl-1-phenyl-4-((2,2,2-trifluoroacetamido)methyl)-2,3,4,5,6,7-hexahydro-1H-inden-5-yl)-2-methylcyclohexyl)methyl acetate (Compound No. 114, 68 mg, 61% over 2 steps) as a colourless film.

L. To a solution of ((1S,2R,5S)-5-acetoxy-2-((1S,2R,4R,5S)-2-hydroxy-1-methyl-1-phenyl-4-((2,2,2-trifluoroacetamido)methyl)-2,3,4,5,6,7-hexahydro-1H-inden-5-yl)-2-methylcyclohexyl)methyl acetate (Compound No. 114, 68 mg, 0.12 mmol) in 10:1 MeOH/H$_2$O (2.3 mL) was added potassium carbonate (97 mg, 0.70 mmol) and heated to 50° C. for 26 h. The mixture was filtered and concentrated, and azeotropic removal of remaining H$_2$O was carried out with MeOH (2×10 mL). The residue was purified by chromatography on silica gel (100:10:1 CH$_2$Cl$_2$/MeOH/NH$_4$OH) to give (1S,2R,4R,5S)-4-(aminomethyl)-5-((1R,2S,4S)-4-hydroxy-2-(hydroxymethyl)-1-methylcyclohexyl)-1-methyl-1-phenyl-2,3,4,5,6,7-hexahydro-1H-inden-2-ol (Compound No. 115, 39 mg, 83%) as a pale solid. $^1$H NMR (CD$_3$OD): δ 7.15-7.31 (m, 5H), 4.06 (m, 1H), 3.84 (m, 1H), 3.47 (m, 1H), 3.23 (m, 1H), 2.94 (m, 1H), 2.69 (m, 1H), 2.19-2.45 (m, 4H), 1.25-2.02 (m, 14H), 0.95 (s, 3H). ES-MS m/z 400 ([M+1]$^+$).

Example 20

Synthesis of (1S,3aS,4R,5S,7aS)-4-(aminomethyl)-5-((1R,2S,4S)-4-hydroxy-2-(hydroxymethyl)-1-methylcyclohexyl)-7a-methyl-1-(thiazol-2-yl)octahydro-1H-inden-1-ol (Compound No. 123)

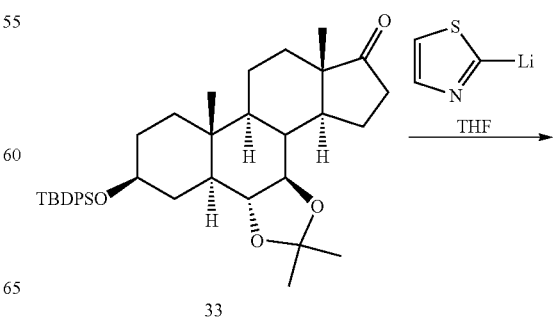

33

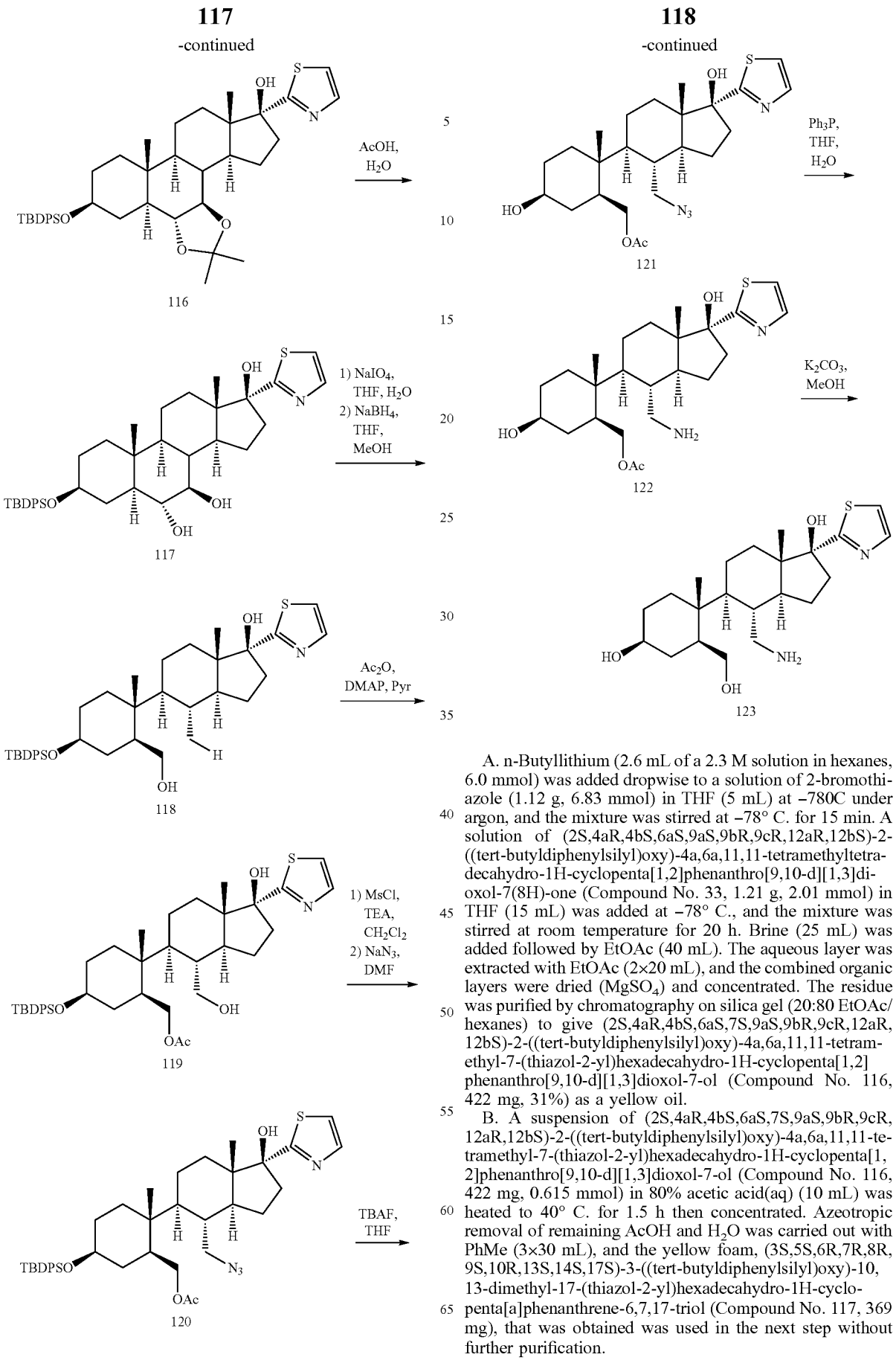

A. n-Butyllithium (2.6 mL of a 2.3 M solution in hexanes, 6.0 mmol) was added dropwise to a solution of 2-bromothiazole (1.12 g, 6.83 mmol) in THF (5 mL) at −78OC under argon, and the mixture was stirred at −78° C. for 15 min. A solution of (2S,4aR,4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 1.21 g, 2.01 mmol) in THF (15 mL) was added at −78° C., and the mixture was stirred at room temperature for 20 h. Brine (25 mL) was added followed by EtOAc (40 mL). The aqueous layer was extracted with EtOAc (2×20 mL), and the combined organic layers were dried (MgSO$_4$) and concentrated. The residue was purified by chromatography on silica gel (20:80 EtOAc/hexanes) to give (2S,4aR,4bS,6aS,7S,9aS,9bR,9cR,12aR,12bS)-2-((tert-butyldiphenylsilyl)oxy)-4a,6a,11,11-tetramethyl-7-(thiazol-2-yl)hexadecahydro-1H-cyclopenta[1,2]phenanthro[9,10-d][1,3]dioxol-7-ol (Compound No. 116, 422 mg, 31%) as a yellow oil.

B. A suspension of (2S,4aR,4bS,6aS,7S,9aS,9bR,9cR,12aR,12bS)-2-((tert-butyldiphenylsilyl)oxy)-4a,6a,11,11-tetramethyl-7-(thiazol-2-yl)hexadecahydro-1H-cyclopenta[1,2]phenanthro[9,10-d][1,3]dioxol-7-ol (Compound No. 116, 422 mg, 0.615 mmol) in 80% acetic acid(aq) (10 mL) was heated to 40° C. for 1.5 h then concentrated. Azeotropic removal of remaining AcOH and H$_2$O was carried out with PhMe (3×30 mL), and the yellow foam, (3S,5S,6R,7R,8R,9S,10R,13S,14S,17S)-3-((tert-butyldiphenylsilyl)oxy)-10,13-dimethyl-17-(thiazol-2-yl)hexadecahydro-1H-cyclopenta[a]phenanthrene-6,7,17-triol (Compound No. 117, 369 mg), that was obtained was used in the next step without further purification.

C. NaIO₄ (205 mg, 0.958 mmol) was added to a solution of (3S,5S,6R,7R,8R,9S,10R,13S,14S,17S)-3-((tert-butyldiphenylsilyl)oxy)-10,13-dimethyl-17-(thiazol-2-yl)hexadecahydro-1H-cyclopenta[a]phenanthrene-6,7,17-triol (Compound No. 117, 309 mg) in 10:1 THF/H₂O (5.5 mL), and the mixture was stirred at room temperature for 2 h. The mixture was concentrated, and the residue was partitioned between CH₂Cl₂ (20 mL) and H₂O (15 mL). The aqueous phase was extracted with CH₂Cl₂ (2×10 mL), and the combined organic layers were dried (MgSO₄) and concentrated. The resulting yellow oil (382 mg) was dissolved in 3:1 THF/MeOH (5 mL) and NaBH₄ (36 mg, 0.95 mmol) was added. The mixture was stirred at room temperature for 2 h and acetone (4 mL) was added. The mixture was concentrated, and the residue was partitioned between CH₂Cl₂ (20 mL) and H₂O (15 mL). The aqueous phase was extracted with CH₂Cl₂ (2×10 mL), and the combined organic layers were dried (MgSO₄) and concentrated to give a yellow foam, 1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-7a-methyl-1-(thiazol-2-yl)octahydro-1H-inden-1-ol (Compound No. 118, 303 mg), that was used in the next step without further purification.

D. To a solution of 1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-7a-methyl-1-(thiazol-2-yl)octahydro-1H-inden-1-ol (Compound No. 118, 303 mg) and DMAP (6 mg, 0.05 mmol) in pyridine (3.0 mL) at 0° C. under argon was added a solution of Ac₂O (57 mg, 0.56 mmol) in pyridine (2.8 mL) over 1.8 h then stirred at 0° C. for 1.5 h. The mixture was concentrated, and azeotropic removal of remaining pyridine was carried out with PhMe (3×10 mL). The residue was purified by chromatography on silica gel (1:99-3:97 MeOH/CH₂Cl₂) to give ((1S,2R,5S)-5-((tert-butyldiphenylsilyl)oxy)-2-((1S,3aS,4R,5S,7aS)-1-hydroxy-4-(hydroxymethyl)-7a-methyl-1-(thiazol-2-yl)octahydro-1H-inden-5-yl)-2-methylcyclohexyl)methyl acetate (Compound No. 119, 192 mg, 54% over 4 steps) as a yellow solid.

E. To a solution of ((1S,2R,5S)-5-((tert-butyldiphenylsilyl)oxy)-2-((1S,3aS,4R,5S,7aS)-1-hydroxy-4-(hydroxymethyl)-7a-methyl-1-(thiazol-2-yl)octahydro-1H-inden-5-yl)-2-methylcyclohexyl)methyl acetate (Compound No. 119, 192 mg, 0.278 mmol) and TEA (0.050 mL, 0.36 mmol) in CH₂Cl₂ (2.8 mL) at 0° C. under argon was added MsCl (0.024 mL, 0.31 mmol), and the solution was stirred at room temperature for 1.3 h. The solution was diluted with CH₂Cl₂ (15 mL) and washed with saturated aqueous NaHCO₃ (10 mL). The aqueous phase was extracted with CH₂Cl₂ (2×10 mL), and the combined organic layers were dried (MgSO₄) and concentrated. Azeotropic removal of impurities was carried out with PhMe (3×10 mL), and the resulting pale solid (283 mg) was dissolved in DMF (1.4 mL). NaN₃ (54 mg, 0.83 mmol) was added, and the mixture was heated to 60° C. under argon for 18 h. The mixture was concentrated, and the residue was partitioned between EtOAc (20 mL) and H₂O (10 mL). Brine (5 mL) was added, and the aqueous phase was extracted with EtOAc (15 mL). The combined organic layers were dried (MgSO₄) and concentrated to give a light yellow foam, ((1S,2R,5S)-2-((1S,3aS,4R,5S,7aS)-4-(azidomethyl)-1-hydroxy-7a-methyl-1-(thiazol-2-yl)octahydro-1H-inden-5-yl)-5-((tert-butyldiphenylsilyl)oxy)-2-methylcyclohexyl)methyl acetate (Compound No. 120, 216 mg), that was used in the next step without further purification.

F. TBAF (0.56 mL of a 1 M solution in THF, 0.56 mmol) was added to a solution of ((1S,2R,5S)-2-((1S,3aS,4R,5S,7aS)-4-(azidomethyl)-1-hydroxy-7a-methyl-1-(thiazol-2-yl)octahydro-1H-inden-5-yl)-5-((tert-butyldiphenylsilyl)oxy)-2-methylcyclohexyl)methyl acetate (Compound No. 120, 216 mg) in THF (5.6 mL) and stirred at room temperature for 3 d. The solution was concentrated, and the residue was purified by chromatography on silica gel (60:40 EtOAc/hexanes) to give ((1S,2R,5S)-2-((1S,3aS,4R,5S,7aS)-4-(azidomethyl)-1-hydroxy-7a-methyl-1-(thiazol-2-yl)octahydro-1H-inden-5-yl)-5-hydroxy-2-methylcyclohexyl)methyl acetate (Compound No. 58, 81 mg, 61% over 3 steps) as a colourless film (Compound No. 121, 81 mg, 61% over 3 steps).

G. Triphenylphosphine (89 mg, 0.34 mmol) was added to a solution of ((1S,2R,5S)-2-((1S,3aS,4R,5S,7aS)-4-(azidomethyl)-1-hydroxy-7a-methyl-1-(thiazol-2-yl)octahydro-1H-inden-5-yl)-5-hydroxy-2-methylcyclohexyl)methyl acetate (Compound No. 121, 81 mg, 0.17 mmol) in 10:1 THF/H₂O (1.9 mL) then heated to 50° C. for 16 h. The mixture was concentrated, and the residue was purified by chromatography on silica gel (5:95 MeOH/CH₂Cl₂ then 100:10:2 CH₂Cl₂/MeOH/NH₄OH) to give ((1S,2R,5S)-2-((1S,3aS,4R,5S,7aS)-4-(aminomethyl)-1-hydroxy-7a-methyl-1-(thiazol-2-yl)octahydro-1H-inden-5-yl)-5-hydroxy-2-methylcyclohexyl)methyl acetate (Compound No. 122, 52 mg, 68%) as a colourless solid.

H. To a solution of ((1S,2R,5S)-2-((1S,3aS,4R,5S,7aS)-4-(aminomethyl)-1-hydroxy-7a-methyl-1-(thiazol-2-yl)octahydro-1H-inden-5-yl)-5-hydroxy-2-methylcyclohexyl)methyl acetate (Compound No. 122, 52 mg, 0.12 mmol) in MeOH (2.3 mL) was added potassium carbonate (32 mg, 0.23 mmol) and heated to 40° C. for 1 h. The mixture was concentrated, and the residue was purified by chromatography on silica gel (100:10:2 CH₂Cl₂/MeOH/NH₄OH) to give (1S,3aS,4R,5S,7aS)-4-(aminomethyl)-5-((1R,2S,4S)-4-hydroxy-2-(hydroxymethyl)-1-methylcyclohexyl)-7a-methyl-1-(thiazol-2-yl)octahydro-1H-inden-1-ol (Compound No. 123, 42 mg, 89%) as a colourless solid. ¹H NMR (CD₃OD): δ 7.72 (d, J=3.0 Hz, 1H), 7.49 (d, J=3.3 Hz, 1H), 3.55 (m, 1H), 3.41 (m, 1H), 3.04 (m, 2H), 2.71 (m, 1H), 2.44 (m, 1H), 1.89-2.12 (m, 4H), 1.17-1.76 (m, 12H), 1.03 (s, 6H), 0.28 (m, 1H). ES-MS m/z 409 ([M+1]⁺).

Example 21

Synthesis of ((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol (Compound No. 130)

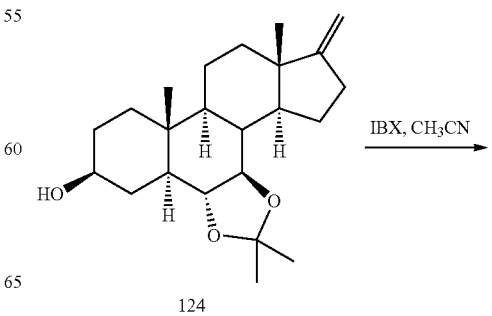

124

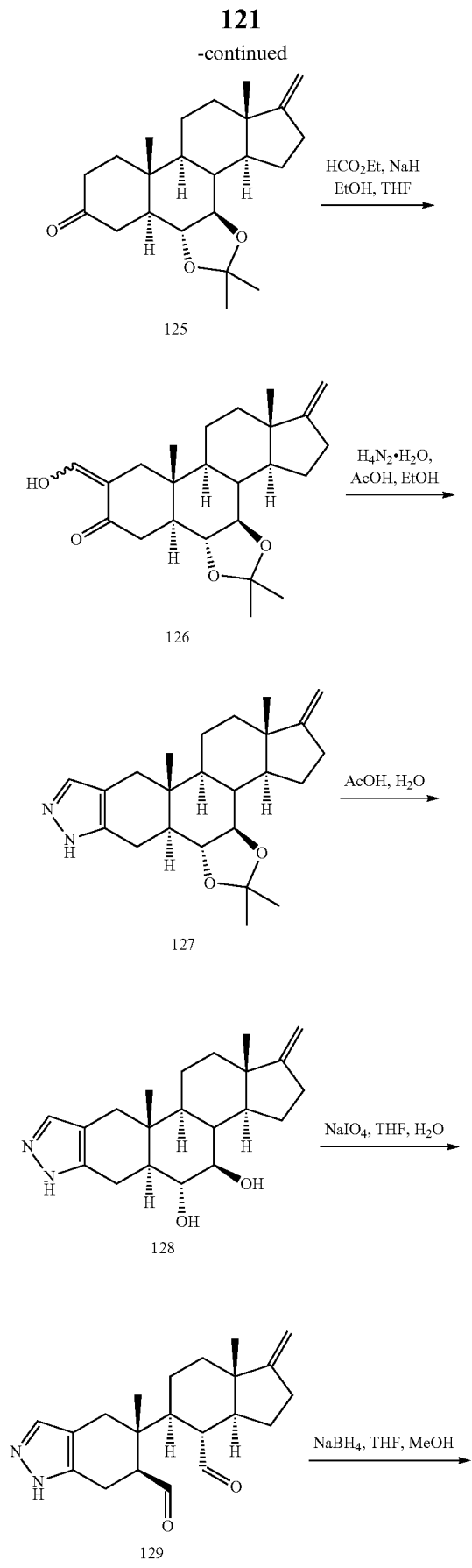

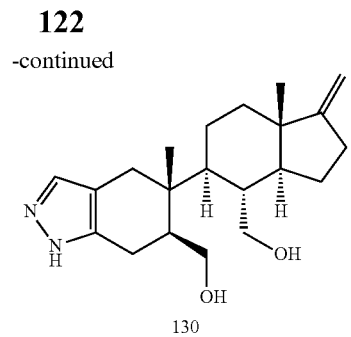

130

A. A mixture of (2S,4aR,4bS,6aS,9aS,9bR,9cR,12aR, 12bS)-4a,6a,11,11-tetramethyl-7-methylenehexadecahydro-1H-cyclopenta[1,2]phenanthro[9,10-d][1,3]dioxol-2-ol (Compound No. 124, 2.05 g, 5.55 mmol) and IBX (3.88 g, 13.9 mmol) in MeCN (80 mL) under argon was stirred at 65° C. for 4.5 h. The mixture was cooled to room temperature, filtered through Celite and concentrated to afford (4aR,4bS, 6aS,9aS,9bR,9cR,12aR,12bS)-4a,6a,11,11-tetramethyl-7-methylenetetradecahydro-1H-cyclopenta[1,2]phenanthro[9, 10-d][1,3]dioxol-2(3H)-one (Compound No. 125, 1.99 g, 98%) as an off-white foam.

B. A mixture of (4aR,4bS,6aS,9aS,9bR,9cR,12aR,12bS)-4a,6a,11,11-tetramethyl-7-methylenetetradecahydro-1H-cyclopenta[1,2]phenanthro[9,10-d][1,3]dioxol-2(3H)-one (Compound No. 125, 250 mg, 0.7 mmol), ethyl formate (113 µL, 1.4 mmol), NaH (60% solution, 56 mg, 1.4 mmol) and EtOH (2 drops) in THF (10 mL) under argon was stirred at reflux for 100 min. The resultant mixture was cooled to room temperature, diluted with saturated NaHCO$_3$ solution (10 mL), extracted with EtOAc (3×10 mL), dried (Na$_2$SO$_4$) and concentrated. The residue was purified using chromatography on silica gel (9:1 hexanes:EtOAc) to afford (4aR,4bS, 6aS,9aS,9bR,9cR,12aR,12bS)-3-(hydroxymethylene)-4a, 6a,11,11-tetramethyl-7-methylenetetradecahydro-1H-cyclopenta[1,2]phenanthro[9,10-d][1,3]dioxol-2(3H)-one (Compound No. 126, 128 mg, 47%) as an off-white solid.

C. A mixture of (4aR,4bS,6aS,9aS,9bR,9cR,12aR,12bS)-3-(hydroxymethylene)-4a,6a,11,11-tetramethyl-7-methylenetetradecahydro-1H-cyclopenta[1,2]phenanthro[9,10-d][1,3]dioxol-2(3H)-one (Compound No. 126, 127 mg, 0.33 mmol), hydrazine hydrate (24 µL, 0.5 mmol) and AcOH (38 µL, 0.66 mmol) in EtOH (15 mL) under argon was stirred at room temperature for 18 h. The resultant mixture was concentrated and reconstituted in EtOAc (50 mL), washed successively with H$_2$O (2×25 mL) and brine (25 mL), dried (Na$_2$SO$_4$) and concentrated. The residue was purified using chromatography on silica gel (1:1 to 1:0 EtOAc:hexanes) to afford (3aS,3bR,3cR,6aR,6bS,11aR,11bS,13aS)-5,5,11a, 13a-tetramethyl-1-methylene-1,2,3,3a,3b,3c,6a,6b,7,8,11, 11a,11b,12,13,13a-hexadecahydrocyclopenta[5,6][1,3]dioxolo[4',5':3,4]naphtho[1,2-f]indazole (Compound No. 127, 130 mg) as a white solid.

D. A mixture of (3aS,3bR,3cR,6aR,6bS,11aR,11bS, 13aS)-5,5,11a,13a-tetramethyl-1-methylene-1,2,3,3a,3b,3c, 6a,6b,7,8,11,11a,11b,12,13,13a-hexadecahydrocyclopenta [5,6][1,3]dioxolo[4',5':3,4]naphtho[1,2-f]indazole (Compound No. 127, 130 mg) in H$_2$O (0.4 mL) and AcOH (1.6 mL) was stirred at room temperature for 4.5 h. The reaction mixture was concentrated and reconstituted in MeOH (25 mL) and 1 M NaOH solution (25 mL). This mixture was extracted with CH$_2$Cl$_2$ (3×50 mL), dried (Na$_2$SO$_4$) and concentrated. The residue was purified using chromatography on silica gel (9:1 EtOAc:MeOH) to afford (3aS,3bR,4R,5R,5aS,10aR,10bS,12aS)-10a,12a-dimethyl- 1-methylene-1,2,3,3a,3b,4,5,5a,6,7,10,10a,10b,11,12,12a-hexadecahydrocyclopenta[5,6]naphtho[1,2-f]indazole-4,5-diol (Compound No. 128, 99 mg, 85% over 2 steps) as a white solid.

E. A mixture of (3aS,3bR,4R,5R,5aS,10aR,10bS,12aS)-10a,12a-dimethyl-1-methylene-1,2,3,3a,3b,4,5,5a,6,7,10,10a,10b,11,12,12a-hexadecahydrocyclopenta[5,6]naphtho[1,2-f]indazole-4,5-diol (Compound No. 128, 77 mg, 0.23 mmol) and NaIO$_4$ (97 mg, 0.46 mmol) in THF (2 mL) and H$_2$O (1 mL) was stirred at room temperature for 4.25 h. The mixture was partitioned between EtOAc (25 mL) and H$_2$O (15 mL) and the organic layer was washed with brine (2×15 mL), dried (Na$_2$SO$_4$) and concentrated to give (5R,6S)-5-((3aS,4R,5S,7aS)-4-formyl-7a-methyl-1-methyleneoctahydro-1H-inden-5-yl)-5-methyl-4,5,6,7-tetrahydro-1H-indazole-6-carbaldehyde (Compound No. 129, 80 mg) as a white solid.

F. A mixture of (5R,6S)-5-((3aS,4R,5S,7aS)-4-formyl-7a-methyl-1-methyleneoctahydro-1H-inden-5-yl)-5-methyl-4,5,6,7-tetrahydro-1H-indazole-6-carbaldehyde (Compound No. 129, 80 mg) and NaBH$_4$ (22 mg, 0.57 mmol) in THF (3 mL) and MeOH (1 mL) under argon was stirred at room temperature for 1 h. The resultant mixture was cooled to 0° C. and 80% AcOH (0.4 mL) was added. After 10 min at room temperature, the mixture was diluted with EtOAc (25 mL), washed successively with saturated NaHCO$_3$ solution (2×15 mL) and brine (10 mL), dried (Na$_2$SO$_4$) and concentrated. The residue was purified using chromatography on silica gel (9:1 EtOAc:MeOH) to afford ((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol (Compound No. 130, 72 mg, 92% over 2 steps) as a white solid. $^1$H NMR (300 MHz, CD$_3$OD) δ 7.25 (s, 1H), 4.60 (s, 2H), 4.03 (d, J=9.6 Hz, 1H), 3.93 (d, J=9.6 Hz, 1H), 3.69 (d, J=11.3 Hz, 1H), 3.35-3.20 (m, 3H), 3.15 (dd, J=5.6 Hz, 16.9, 1H), 2.69-2.45 (m, 2H), 2.28-2.24 (m, 2H), 1.79-1.16 (m, 8H), 1.08 (s, 3H), 0.82 (s, 3H); $^{13}$C NMR (75 MHz, CD$_3$OD) δ 162.9, 101.5, 63.7, 62.8, 51.4, 44.7, 44.4, 41.4, 38.97, 37.1, 30.1, 25.6, 24.4, 23.7, 20.8, 18.8; MS m/z: 345.2 [M+H]$^+$.

Example 22

Synthesis of ((3aS,4R,5S,7aS)-5-((5R,6S)-6-(hydroxymethyl)-5-methyl-4,5,6,7-tetrahydrobenzo[c]isoxazol-5-yl)-7a-methyl-1-methyleneoctahydro-1H-inden-4-yl)methanol (Compound No. 133)

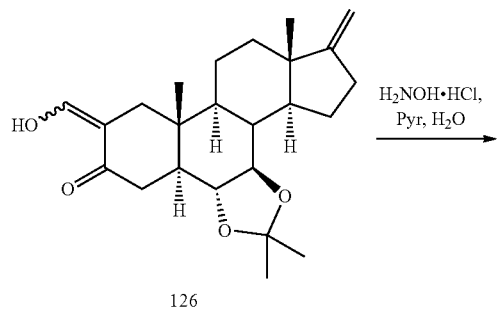

126

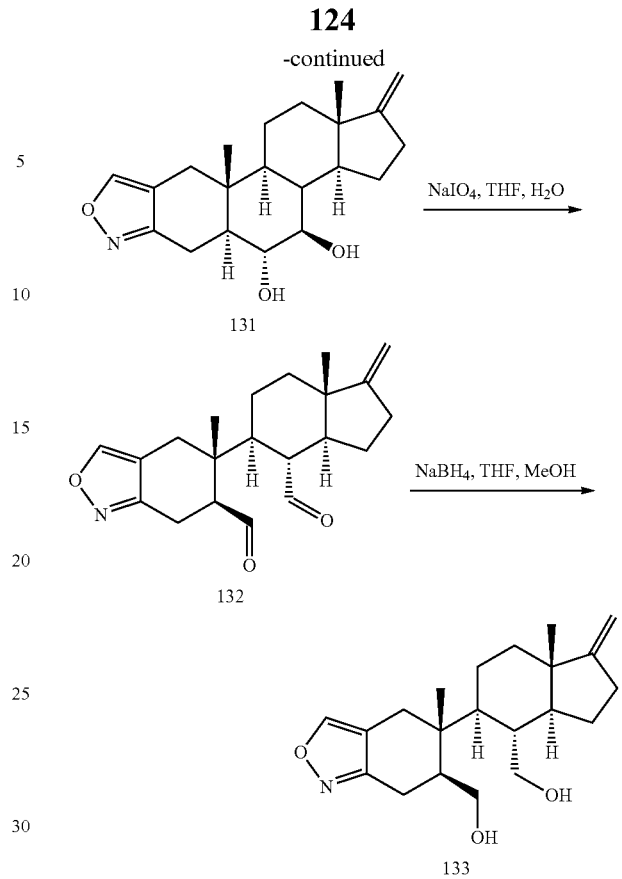

131

132

133

A. A mixture (4aR,4bS,6aS,9aS,9bR,9cR,12aR,12bS)-3-(hydroxymethylene)-4a,6a,11,11-tetramethyl-7-methylenetetradecahydro-1H-cyclopenta[1,2]phenanthro[9,10-d][1,3]dioxol-2(3H)-one (Compound No. 126, 149 mg, 0.39 mmol) and hydroxylamine hydrochloride (80 mg, 1.2 mmol) in pyridine (3 mL) and H$_2$O (0.3 mL) was stirred at reflux for 3.75 h. The resultant mixture was cooled to room temperature and diluted with H$_2$O (15 mL), extracted successively with CH$_2$Cl$_2$ (3×15 mL) and EtOAc (15 mL). The combined organic layers were dried (Na$_2$SO$_4$), concentrated and azeotroped from PhMe (2×10 mL). The residue was purified using chromatography on silica gel (2:1 EtOAc:hexanes) to afford (3aS,3bR,4R,5R,5aS,10aR,10bS,12aS)-10a,12a-dimethyl-1-methylene-2,3,3a,3b,4,5,5a,6,10,10a,10b,11,12,12a-tetradecahydro-1H-cyclopenta[7,8]phenanthro[2,3-c]isoxazole-4,5-diol (Compound No. 131, 130 mg, 98%) as a white solid.

B. A mixture of (3aS,3bR,4R,5R,5aS,10aR,10bS,12aS)-10a,12a-dimethyl-1-methylene-2,3,3a,3b,4,5,5a,6,10,10a,10b,11,12,12a-tetradecahydro-1H-cyclopenta[7,8]phenanthro[2,3-c]isoxazole-4,5-diol (Compound No. 131, 103 mg, 0.30 mmol) and NaIO$_4$ (160 mg, 0.75 mmol) in THF (3 mL) and H$_2$O (1.5 mL) was stirred at room temperature for 4.25 h. The mixture was diluted with EtOAc (25 mL) and H$_2$O (15 mL), washed with brine (2×15 mL), dried (Na$_2$SO$_4$) and concentrated to afford (5R,6S)-5-((3aS,4R,5S,7aS)-4-formyl-7a-methyl-1-methyleneoctahydro-1H-inden-5-yl)-5-methyl-4,5,6,7-tetrahydrobenzo[c]isoxazole-6-carbaldehyde (Compound No. 132) as a white solid.

C. A mixture of (5R,6S)-5-((3aS,4R,5S,7aS)-4-formyl-7a-methyl-1-methyleneoctahydro-1H-inden-5-yl)-5-methyl-4,5,6,7-tetrahydrobenzo[c]isoxazole-6-carbaldehyde (Compound No. 132) and NaBH$_4$ (34 mg, 0.90 mmol)

in THF (3 mL) and MeOH (1 mL) under argon was stirred at room temperature for 1.25 h. The reaction was quenched with NH₄Cl solution (0.5 mL), diluted with EtOAc (25 mL), washed successively with saturated NaHCO₃ solution (2×15 mL) and brine (10 mL), dried (Na₂SO₄) and concentrated. The residue was purified using chromatography on silica gel (2:1 EtOAc:hexanes) to afford ((3aS,4R,5S,7aS)-5-((5R,6S)-6-(hydroxymethyl)-5-methyl-4,5,6,7-tetrahydrobenzo[c]isoxazol-5-yl)-7a-methyl-1-methyleneoctahydro-1H-inden-4-yl)methanol (Compound No. 133, 88 mg, 85% over 2 steps) as a white solid. ¹H NMR (300 MHz, CDCl₃) δ 8.07 (s, 1H), 4.60 (d, J=10.3 Hz, 2H), 4.06-3.95 (m, 2H), 3.74 (d, J=11.5 Hz, 1H), 3.43 (m, 1H), 3.36 (dd, J=18.0, 5.7 Hz, 1H), 2.83 (dd, J=17.7, 5.8 Hz, 1H), 2.66 (d, J=16.3 Hz, 1H), 2.54-2.19 (m, 5H), 1.82-1.14 (m, 8H), 1.10 (s, 3H), 0.77 (s, 3H). ¹³C NMR (75 MHz, CDCl₃) δ 161.3, 159.5, 153.4, 114.1, 101.2, 62.5, 62.3, 49.9, 43.7, 43.6, 42.8, 40.2, 37.6, 35.8, 31.6, 29.2, 27.3, 24.7, 23.4, 22.7, 21.3, 20.5, 18.3, 14.2; MS m/z: 346.2 [M+H]⁺.

Example 23

Synthesis of ((5R,6S)-5-((4R,5S)-4-(hydroxymethyl)-1,1-dimethyl-2,3,4,5,6,7-hexahydro-1H-inden-5-yl)-5-methyl-4,5,6,7-tetrahydrobenzo[d]isoxazol-6-yl) methanol (Compound No. 136)

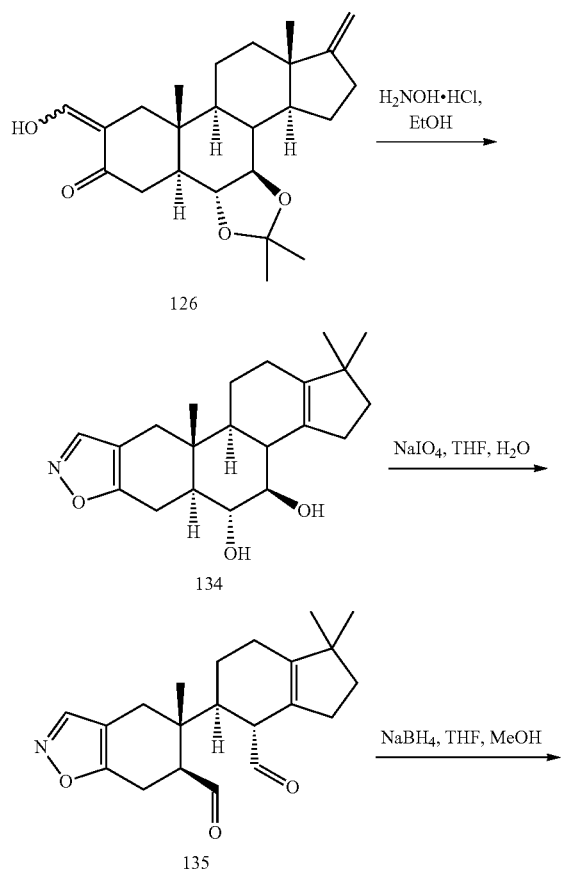

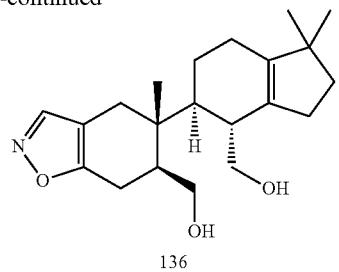

136

A. A mixture of (4aR,4bS,6aS,9aS,9bR,9cR,12aR,12bS)-3-(hydroxymethylene)-4a,6a,11,11-tetramethyl-7-methylenetetradecahydro-1H-cyclopenta[1,2]phenanthro[9,10-d][1,3]dioxol-2(3H)-one (Compound No. 126, 111 mg, 0.29 mmol) and hydroxylamine hydrochloride (60 mg, 0.86 mmol) in EtOH (3 mL) was stirred at reflux for 3.25 h. The resultant mixture was cooled to room temperature, concentrated and reconstituted in EtOAc (10 mL) and CH₂Cl₂ (15 mL). The resultant mixture was washed with saturated NaHCO₃ solution (2×10 mL), dried (Na₂SO₄) and concentrated. The residue was purified using chromatography on silica gel (1:1 EtOAc:hexanes) to afford (3bR,4R,5R,5aS,10aR,10bS)-1,1,10a-trimethyl-2,3,3b,4,5,5a,6,10,10a,10b,11,12-dodecahydro-1H-cyclopenta[7,8]phenanthro[3,2-d]isoxazole-4,5-diol (Compound No. 134, 84 mg, 85%) as a colourless oil.

B. A mixture of (3bR,4R,5R,5aS,10aR,10bS)-1,1,10a-trimethyl-2,3,3b,4,5,5a,6,10,10a,10b,11,12-dodecahydro-1H-cyclopenta[7,8]phenanthro[3,2-d]isoxazole-4,5-diol (Compound No. 134, 99 mg, 0.29 mmol) and NaIO₄ (154 mg, 0.72 mmol) in THF (3 mL) and H₂O (1.5 mL) was stirred at room temperature for 4 h. The mixture was diluted with EtOAc (25 mL) and H₂O (15 mL), washed with brine (2×15 mL), dried (Na₂SO₄) and concentrated to afford (5R,6S)-5-((4R,5S)-4-formyl-1,1-dimethyl-2,3,4,5,6,7-hexahydro-1H-inden-5-yl)-5-methyl-4,5,6,7-tetrahydrobenzo[d]isoxazole-6-carbaldehyde (Compound No. 135) as a white solid.

C. A mixture of (5R,6S)-5-((4R,5S)-4-formyl-1,1-dimethyl-2,3,4,5,6,7-hexahydro-1H-inden-5-yl)-5-methyl-4,5,6,7-tetrahydrobenzo[d]isoxazole-6-carbaldehyde (Compound No. 135) and NaBH₄ (27 mg, 0.72 mmol) in THF (3 mL) and MeOH (1 mL) under argon was stirred at room temperature for 1 h. The reaction was quenched with NH₄Cl solution (0.5 mL). After stirring for 10 min at room temperature, the mixture was diluted with EtOAc (25 mL), washed successively with saturated NaHCO₃ solution (2×15 mL) and brine (15 mL), dried (Na₂SO₄) and concentrated. The residue was purified using chromatography on silica gel (2:1 EtOAc:hexanes) to afford ((5R,6S)-5-((4R,5S)-4-(hydroxymethyl)-1,1-dimethyl-2,3,4,5,6,7-hexahydro-1H-inden-5-yl)-5-methyl-4,5,6,7-tetrahydrobenzo[d]isoxazol-6-yl)methanol (Compound No. 136, 78 mg, 78% over 2 steps) as a white solid. ¹H NMR (300 MHz, CDCl₃) δ 8.00 (s, 1H), 4.04-4.01 (m, 1H), 3.72-3.69 (m 1H), 3.50-3.45 (m, 1H), 3.20 (dd, J=18.1, 5.6 Hz, 1H), 2.64 (dd, J=17.7, 7.9 Hz, 1H), 2.48-1.26 (m, 14H), 0.99 (s, 3H), 0.93 (s, 3H), 0.86 (s, 3H); ¹³C NMR (75 MHz, CDCl₃) δ 166.8, 149.7, 144.7, 132.3, 111.1, 64.7, 62.5, 45.87, 42.1, 39.7, 39.1, 38.5, 37.2, 37.2, 37.2, 32.3, 28.2, 27.0, 25.5, 23.2, 20.2, 20.1, 19.6; MS m/z: 346.2 [M+H]⁺.

Example 24

Synthesis of ((3aS,4R,5S,7aS)-5-((5S,6R)-5-(hydroxymethyl)-2,6-dimethyl-4,5,6,7-tetrahydrobenzo[d]thiazol-6-yl)-7a-methyl-1-methyleneoctahydro-1H-inden-4-yl)methanol (Compound No. 141)

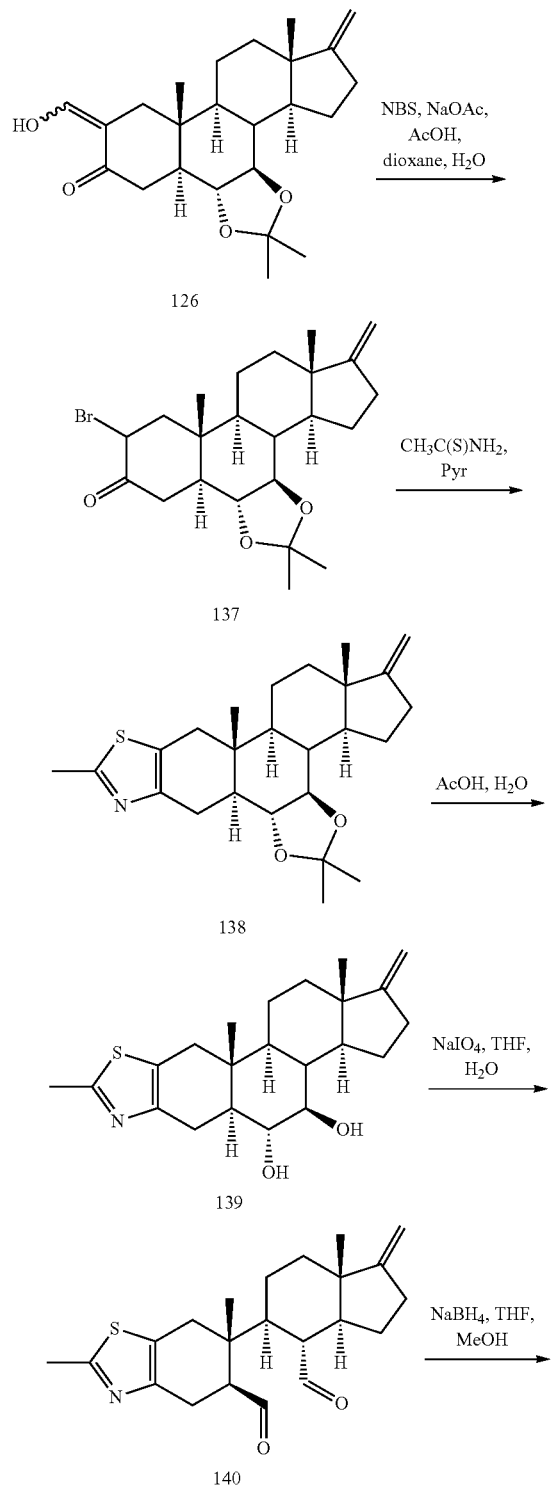

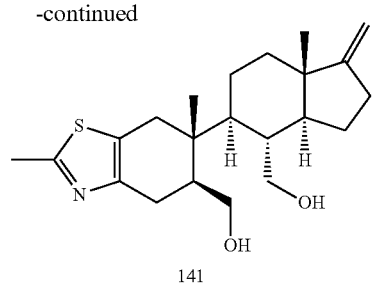

141

A. A mixture of (4aR,4bS,6aS,9aS,9bR,9cR,12aR,12bS)-3-(hydroxymethylene)-4a,6a,11,11-tetramethyl-7-methylenetetradecahydro-1H-cyclopenta[1,2]phenanthro[9,10-d][1,3]dioxol-2(3H)-one (Compound No. 126, 0.81 g, 2.1 mmol), NBS (392 mg, 2.2 mmol), NaOAc (173 mg, 2.1 mmol) and AcOH (120 μL, 2.1 mmol) in dioxane (22 mL) and H₂O (2.2 mL) was stirred at room temperature for 24 h. The reaction was partitioned between EtOAc (150 mL) and H₂O (150 mL) and the aqueous layer was extracted with EtOAc (2×75 mL). The combined organic layers were washed with brine (75 mL), dried (Na₂SO₄) and concentrated. The residue was purified using chromatography on silica gel (9:1 hexanes:EtOAc) to afford (4aR,4bS,6aS,9aS,9bR,9cR,12aR,12bS)-3-bromo-4a,6a,11,11-tetramethyl-7-methylenetetradecahydro-1H-cyclopenta[1,2]phenanthro[9,10-d][1,3]dioxol-2(3H)-one (Compound No. 137, 0.59 g, 64%) as a thick colourless oil.

B. A mixture of (4aR,4bS,6aS,9aS,9bR,9cR,12aR,12bS)-3-bromo-4a,6a,11,11-tetramethyl-7-methylenetetradecahydro-1H-cyclopenta[1,2]phenanthro[9,10-d][1,3]dioxol-2(3H)-one (Compound No. 137, 120 mg, 0.27 mmol) and thioacetamide (82 mg, 1.1 mmol) in pyridine (6 mL) under argon was stirred at 65° C. for 24 h. The reaction was cooled to room temperature and saturated NaHCO₃ solution (20 mL) was added. The resultant mixture was extracted with EtOAc (3×15 mL), dried (Na₂SO₄), concentrated and azeotroped from PhMe. The residue was purified using chromatography on silica gel (2:1 hexanes:EtOAc) to afford (3aS,3bR,3cR,6aR,6bS,11aR,11bS,13aS)-5,5,9,11a,13a-pentamethyl-1-methylene-2,3,3a,3b,3c,6a,6b,7,11,11a,11b,12,13,13a-tetradecahydro-1H-cyclopenta[7,8][1,3]dioxolo[4',5':9,10]phenanthro[2,3-d]thiazole (Compound No. 138, 77 mg, 68%) as a colourless oil.

C. A mixture of (3aS,3bR,3cR,6aR,6bS,11aR,11bS,13aS)-5,5,9,11a,13a-pentamethyl-1-methylene-2,3,3a,3b,3c,6a,6b,7,11,11a,11b,12,13,13a-tetradecahydro-1H-cyclopenta[7,8][1,3]dioxolo[4',5':9,10]phenanthro[2,3-d]thiazole (Compound No. 138, 77 mg, 0.19 mmol) in H₂O (1 mL) and AcOH (5 mL) was stirred at room temperature for 90 min. The reaction mixture was concentrated and partitioned between EtOAc (30 mL) and 1 M NaOH solution (20 mL). This mixture was extracted with EtOAc (3×20 mL) and the combined organic layers were dried (Na₂SO₄) and concentrated. The residue was purified using chromatography on silica gel (19:1 EtOAc:MeOH) to afford (3aS,3bR,4R,5R,5aR,10aR,10bS,12aS)-8,10a,12a-trimethyl-1-methylene-2,3,3a,3b,4,5,5a,6,10,10a,10b,11,12,12a-tetradecahydro-1H-cyclopenta[7,8]phenanthro[2,3-d]thiazole-4,5-diol (Compound No. 139, 69 mg, 98%) as a white solid.

D. A mixture of (3aS,3bR,4R,5R,5aR,10aR,10bS,12aS)-8,10a,12a-trimethyl-1-methylene-2,3,3a,3b,4,5,5a,6,10,10a,10b,11,12,12a-tetradecahydro-1H-cyclopenta[7,8]phenanthro[2,3-d]thiazole-4,5-diol (Compound No. 139, 64 mg, 0.17 mmol) and NaIO₄ (73 mg, 0.34 mmol) in THF (3 mL)

and H₂O (1.5 mL) was stirred at room temperature for 4 h. The mixture was partitioned between EtOAc (25 mL) and H₂O (15 mL), washed with brine (2×15 mL), dried (Na₂SO₄) and concentrated to afford (5S,6R)-6-((3aS,4R, 5S,7aS)-4-formyl-7a-methyl-1-methyleneoctahydro-1H-inden-5-yl)-2,6-dimethyl-4,5,6,7-tetrahydrobenzo[d]thiazole-5-carbaldehyde (Compound No. 140) as a white solid.

E. A mixture of (5S,6R)-6-((3aS,4R,5S,7aS)-4-formyl-7a-methyl-1-methyleneoctahydro-1H-inden-5-yl)-2,6-dimethyl-4,5,6,7-tetrahydrobenzo[d]thiazole-5-carbaldehyde (Compound No. 140) and NaBH₄ (20 mg, 0.51 mmol) in THF (3 mL) and MeOH (1 mL) under argon was stirred at room temperature for 90 min. The reaction was quenched with NH₄Cl solution (0.5 mL), diluted with EtOAc (25 mL), washed successively with saturated NaHCO₃ solution (2×15 mL) and brine (15 mL), dried (Na₂SO₄) and concentrated. The residue was purified using chromatography on silica gel (19:1 EtOAc:MeOH) to afford ((3aS,4R,5S,7aS)-5-((5S, 6R)-5-(hydroxymethyl)-2,6-dimethyl-4,5,6,7-tetrahydrobenzo[d]thiazol-6-yl)-7a-methyl-1-methyleneoctahydro-1H-inden-4-yl)methanol (Compound No. 141, 35 mg, 55% over 2 steps) as a white solid. ¹H NMR (300 MHz, CDCl₃) δ 4.61 (m, 2H), 4.06 (d, J=11.1 Hz, 1H), 3.96 (d, J=9.8 Hz, 1H), 3.74 (m, 1H), 3.44 (m, 1H), 3.25 (dd, J=16.9, 4.8 Hz, 1H), 2.83 (d, J=16.1 Hz, 1H), 2.62 (s, 3H), 2.54-2.28 (m, 3H), 1.86-1.19 (m, 11H), 1.11 (s, 3H), 0.80 (s, 3H). ¹³C NMR (75 MHz, CDCl₃) δ163.4, 161.3, 148.4, 126.9, 101.3, 63.4, 62.7, 50.1, 43.8, 43.0, 42.9, 40.3, 38.6, 35.9, 32.2, 31.7, 29.3, 28.0, 24.9, 23.6, 22.8, 20.8, 19.2, 18.5, 14.2; MS m/z: 376.2 [M+H]⁺.

Example 25

Synthesis of (1S,3S,4R)-3-(hydroxymethyl)-4-((3aS, 6S,7R,7aS)-7-(hydroxymethyl)-3a-methyl-3-phenyl-3a,4,5,6,7,7a-hexahydro-1H-inden-6-yl)-4-methylcyclohexanol (Compound No. 142)

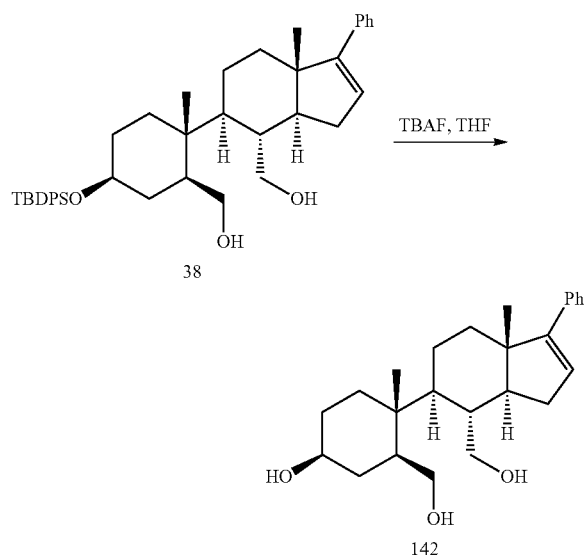

TBAF (0.20 mL of a 1 M solution in THF, 0.20 mmol) was added to a solution of ((1S,2R,5S)-5-((tert-butyldiphenylsilyl)oxy)-2-((3aS,6S,7R,7aS)-7-(hydroxymethyl)-3a-methyl-3-phenyl-3a,4,5,6,7,7a-hexahydro-1H-inden-6-yl)-2-methylcyclohexyl)methanol (Compound No. 38, 80 mg, 0.13 mmol) in THF (2.5 mL) at room temperature under argon then stirred for 26 h. The solution was concentrated, and the residue was purified by chromatography on silica gel (5:95 MeOH/EtOAc) to afford (1S,3S,4R)-3-(hydroxymethyl)-4-((3aS,6S,7R,7aS)-7-(hydroxymethyl)-3a-methyl-3-phenyl-3a,4,5,6,7,7a-hexahydro-1H-inden-6-yl)-4-methylcyclohexanol (Compound No. 142, 43 mg, 88%) as a colourless solid. ¹H NMR (CD₃OD): δ 7.36 (m, 2H), 7.16-7.29 (m, 3H), 5.91 (m, 1H), 3.98 (m, 1H), 3.71 (m, 2H), 3.46 (m, 1H), 3.14 (m, 1H), 2.40 (m, 1H), 2.00-2.17 (m, 4H), 1.22-1.81 (m, 11H), 1.13 (s, 3H), 1.05 (s, 3H); ¹³C NMR (CD₃OD): δ 156.3, 138.6, 129.1 (2C), 127.7 (3C), 127.6, 71.2, 63.3, 62.9, 55.0, 48.0, 45.5, 44.5, 39.6, 38.1, 37.2, 35.2, 33.0, 32.1, 24.3, 21.6, 16.8. ES-MS m/z 385 ([M+1]⁺).

Example 26

Synthesis of (1S,3aS,4R,5S,7aS)-5-((1R,2S,4S)-4-hydroxy-2-(hydroxymethyl)-1-methylcyclohexyl)-4-(hydroxymethyl)-7a-methyl-1-phenyloctahydro-1H-inden-1-ol (Compound No. 143)

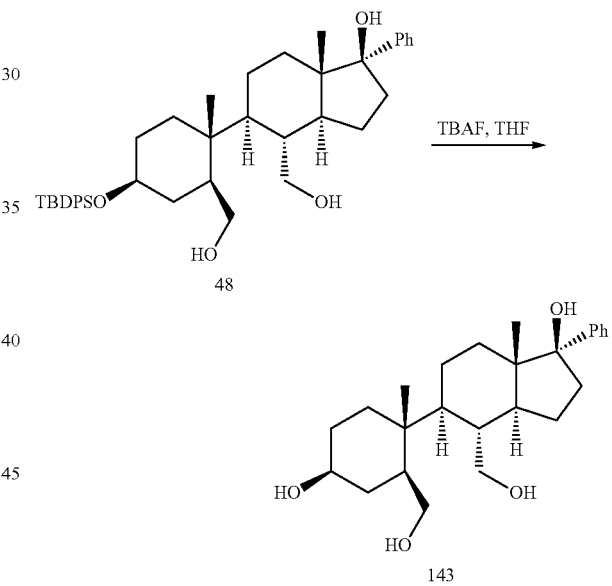

TBAF (0.25 mL of a 1 M solution in THF, 0.25 mmol) was added to a solution of (1S,3aS,4R,5S,7aS)-5-((1R,2S, 4S)-4-((tert-butyldiphenylsilyl)oxy)-2-(hydroxymethyl)-1-methylcyclohexyl)-4-(hydroxymethyl)-7a-methyl-1-phenyloctahydro-1H-inden-1-ol (Compound No. 48, 80 mg, 0.12 mmol) in THF (2.5 mL) and stirred at room temperature for 20 h. The solution was concentrated, and the residue was purified by chromatography on silica gel (5:95 MeOH/EtOAc) to give (1S,3aS,4R,5S,7aS)-5-((1R,2S,4S)-4-hydroxy-2-(hydroxymethyl)-1-methylcyclohexyl)-4-(hydroxymethyl)-7a-methyl-1-phenyloctahydro-1H-inden-1-ol (Compound No. 143, 47 mg, 94%) as a colourless solid. ¹H NMR (CD₃OD): δ 7.39 (m, 2H), 7.29 (m, 2H), 7.20 (m, 1H), 3.89 (m, 1H), 3.41-3.63 (m, 3H), 3.00 (m, 1H), 2.35 (m, 1H), 1.94-2.17 (m, 3H), 1.15-1.75 (m, 13H), 1.04 (s, 3H), 1.02 (s, 3H), 0.36 (m, 1H). ES-MS m/z 425 ([M+23]⁺).

Example 27

Synthesis of (1S,3aS,4R,5S,7aS)-5-((1R,2S,4S)-4-hydroxy-2-(hydroxymethyl)-1-methylcyclohexyl)-4-(hydroxymethyl)-1,7a-dimethyloctahydro-1H-inden-1-ol (Compound No. 144)

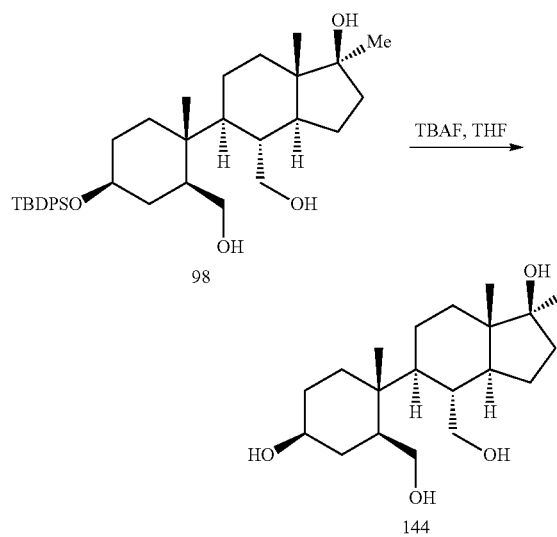

TBAF (0.30 mL of a 1 M solution in THF, 0.30 mmol) was added to a solution of (1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-1,7a-dimethyloctahydro-1H-inden-1-ol (Compound No. 98, 87 mg) in THF (3.0 mL) and stirred at room temperature for 22 h. The solution was concentrated, and the residue was purified by chromatography on silica gel (7:93 MeOH/EtOAc) to give (1S,3aS,4R,5S,7aS)-5-((1R,2S,4S)-4-hydroxy-2-(hydroxymethyl)-1-methylcyclohexyl)-4-(hydroxymethyl)-1,7a-dimethyloctahydro-1H-inden-1-ol (Compound No. 144, 45 mg, 92%) as a colourless solid. $^1$H NMR (CD$_3$OD): δ 3.89 (m, 1H), 3.72 (m, 1H), 3.56 (m, 1H), 3.45 (m, 1H), 3.13 (m, 1H), 2.15 (m, 1H), 1.25-1.88 (m, 17H), 1.21 (s, 3H), 1.10 (s, 3H), 0.85 (s, 3H). ES-MS m/z 341 ([M+1]$^+$).

Example 28

Synthesis of (1R,3aS,4R,5S,7aS)-1-ethynyl-5-((1R,2S,4S)-4-hydroxy-2-(hydroxymethyl)-1-methylcyclohexyl)-4-(hydroxymethyl)-7a-methyloctahydro-1H-inden-1-ol (Compound No. 148)

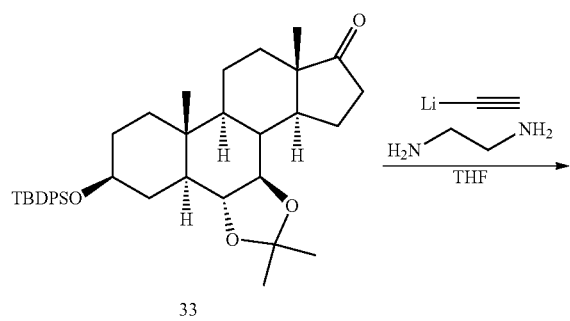

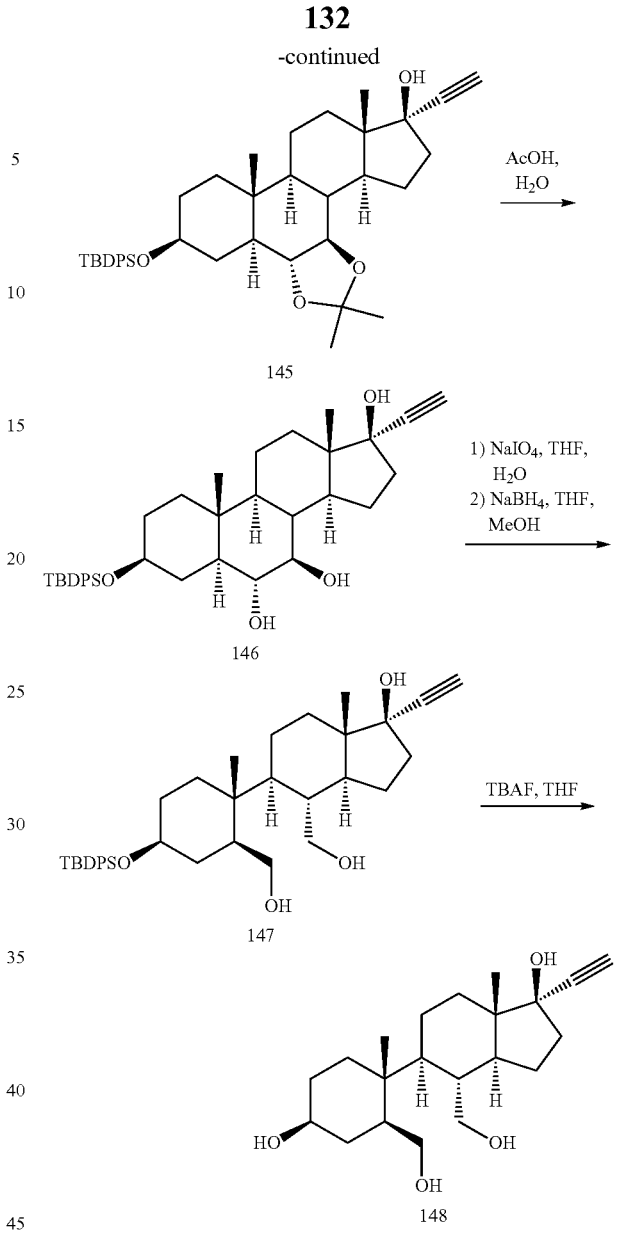

A. Lithium acetylide ethylenediamine complex (1.17 g, 11.4 mmol) was added to a solution of (2S,4aR,4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 1.15 g, 1.91 mmol) in THF (9.6 mL) and stirred at room temperature under argon for 19 h. Brine (12 mL) and H$_2$O (5 mL) were added followed by EtOAc (10 mL). The aqueous layer was extracted with EtOAc (2×10 mL), and the combined organic layers were dried (MgSO$_4$) and concentrated. The residue was purified by chromatography on silica gel (20:80 EtOAc/hexanes) to give (2S,4aR,4bS,6aS,7R,9aS,9bR,9cR,12aR,12bS)-2-((tert-butyldiphenylsilyl)oxy)-7-ethynyl-4a,6a,11,11-tetramethylhexadecahydro-1H-cyclopenta[1,2]phenanthro[9,10-d][1,3]dioxol-7-ol (Compound No. 145, 0.59 g, 49%) as a colourless oil.

B. A suspension of (2S,4aR,4bS,6aS,7R,9aS,9bR,9cR,12aR,12bS)-2-((tert-butyldiphenylsilyl)oxy)-7-ethynyl-4a,6a,11,11-tetramethylhexadecahydro-1H-cyclopenta[1,2]phenanthro[9,10-d][1,3]dioxol-7-ol (Compound No. 145, 0.59 g, 0.94 mmol) in 80% acetic acid(aq) (15 mL) was heated to 40 C for 2.5 h then concentrated. Azeotropic removal of remaining AcOH and H₂O was carried out with PhMe (3×30 mL), and the pale foam, (3S,5S,6R,7R,8R,9S,10R,13S,14S,17R)-3-((tert-butyldiphenylsilyl)oxy)-17-ethynyl-10,13-dimethylhexadecahydro-1H-cyclopenta[a]phenanthrene-6,7,17-triol (Compound No. 146, 0.50 g), that was obtained was used in the next step without further purification.

C. A suspension of NaIO₄ (313 mg, 1.46 mmol) in H₂O (0.7 mL) was added to a solution of (3S,5S,6R,7R,8R,9S,10R,13S,14S,17R)-3-((tert-butyldiphenylsilyl)oxy)-17-ethynyl-10,13-dimethylhexadecahydro-1H-cyclopenta[a]phenanthrene-6,7,17-triol (Compound No. 146, 0.43 g) in THF (7.3 mL), and the mixture was stirred at room temperature for 2 h. The mixture was concentrated, and the residue was partitioned between CH₂Cl₂ (20 mL) and H₂O (10 mL). The aqueous phase was extracted with CH₂Cl₂ (2×10 mL), and the combined organic layers were dried (MgSO₄) and concentrated. The resulting colourless foam (420 mg) was dissolved in 3:1 THF/MeOH (7.2 mL) and cooled to 0° C. under argon. NaBH₄ (55 mg, 1.5 mmol) was added, and the mixture was stirred at 0° C. for 30 min then at room temperature for 2.5 h. Acetone (5 mL) was added and the mixture was concentrated. The residue was dissolved in EtOAc (40 mL) and washed with brine (2×15 mL) then dried (MgSO₄) and concentrated. The residue was purified by chromatography on silica gel (1:1 EtOAc/hexanes) to give (1R,3aS,4R,5S,7aS)-5-((1R,2S,4S)-4-((tert-butyldiphenylsilyl)oxy)-2-(hydroxymethyl)-1-methylcyclohexyl)-1-ethynyl-4-(hydroxymethyl)-7a-methyloctahydro-1H-inden-1-ol (Compound No. 147, 338 mg, 70% over 3 steps) as a colourless foam.

D. TBAF (0.23 mL of a 1 M solution in THF, 0.23 mmol) was added to a solution of (1R,3aS,4R,5S,7aS)-5-((1R,2S,4S)-4-((tert-butyldiphenylsilyl)oxy)-2-(hydroxymethyl)-1-methylcyclohexyl)-1-ethynyl-4-(hydroxymethyl)-7a-methyloctahydro-1H-inden-1-ol (Compound No. 147, 69 mg, 0.12 mmol) in THF (2.3 mL) and stirred at room temperature for 3 d. The solution was concentrated, and the residue was purified by chromatography on silica gel (7:93 MeOH/EtOAc) to give (1R,3aS,4R,5S,7aS)-1-ethynyl-5-((1R,2S,4S)-4-hydroxy-2-(hydroxymethyl)-1-methylcyclohexyl)-4-(hydroxymethyl)-7a-methyloctahydro-1H-inden-1-ol (Compound No. 148, 41 mg, 100%) as a colourless solid. ¹H NMR (CD₃OD): 53.89 (m, 1H), 3.72 (m, 1H), 3.56 (m, 1H), 3.45 (m, 1H), 3.14 (m, 1H), 2.87 (s, 1H), 1.22-2.26 (m, 18H), 1.10 (s, 3H), 0.83 (s, 3H). ES-MS m/z 351 ([M+1]⁺).

Example 29

Synthesis of (1S,3S,4R)-3-(hydroxymethyl)-4-((2R,3S,3aR,3bS,5'R,6S,7R,7aS,8aS)-7-(hydroxymethyl)-3,3b,5'-trimethyltetradecahydrospiro[indeno[2,1-b]furan-2,2'-pyran]-6-yl)-4-methylcyclohexanol (Compound No. 154)

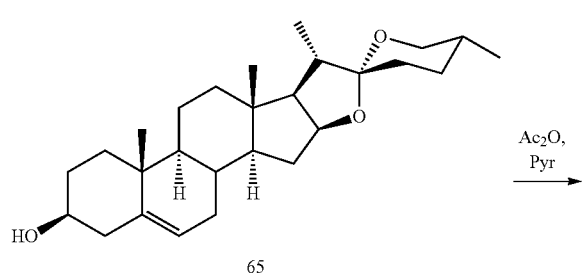

A. A solution of (2'R,4S,5'R,6aR,6bS,8aS,8bR,9S,11aS,12aS)-5',6a,8a,9-tetramethyl-1,3,3',4,4',5,5',6,6a,6b,6',7,8,8a,8b,9,11a,12,12a,12b-icosahydrospiro[naphtho[2',1':4,5]indeno[2,1-b]furan-10,2'-pyran]-4-ol (Compound No. 65, 1.00 g, 2.41 mmol) and Ac$_2$O (0.46 mL, 4.82 mmol) in pyridine (10 mL) initially at 0° C. was stirred under nitrogen for 3 d. The mixture was cooled in ice then quenched with saturated NaHCO$_3$ solution (5 mL), stirring at room temperature for 30 minutes. The solution was diluted with EtOAc (100 mL), washed with brine (3×15 mL), dried (MgSO$_4$) and concentrated to afford (2'R,4S,5'R,6aR,6bS, 8aS,8bR,9S,11 aS,12aS,12bS)-5',6a,8a,9-tetramethyl-1,3,3', 4,4',5,5',6,6a,6b,6',7,8,8a,8b,9,11a,12,12a,12b-icosahydrospiro[naphtho[2',1':4,5]indeno[2,1-b]furan-10,2'-pyran]-4-yl acetate (Compound No. 149, 0.98 g) as an off-white solid.

B. To a solution of (2'R,4S,5'R,6aR,6bS,8aS,8bR,9S, 11aS,12aS,12bS)-5',6a,8a,9-tetramethyl-1,3,3',4,4',5,5',6,6a, 6b,6',7,8,8a,8b,9,11a,12,12a,12b-icosahydrospiro[naphtho [2',1':4,5]indeno[2,1-b]furan-10,2'-pyran]-4-yl acetate (Compound No. 149, 0.98 g, 2.15 mmol) and CuI (4 mg, 0.02 mmol) in cyclohexane (13 mL) under nitrogen was added 'BuOOH (3.0 mL of a 5M solution in decane, 15 mmol) and the resulting solution was heated overnight in a 70° C. oil bath. Excess oxidant was quenched for 10 minutes with a solution of Na$_2$S$_2$O$_5$ (1.89 g) in H$_2$O (20 mL) then the mixture was extracted with EtOAc (100 mL), washed successively with saturated NaHCO$_3$ solution (15 mL) and brine (3×15 mL), dried (MgSO$_4$) and concentrated. The residue was purified using chromatography on silica gel (20% EtOAc/hexanes) to afford (2'R,4S,5'R,6aR,6bS,8aS, 8bR,9S,11aS,12aS,12bS)-5',6a,8a,9-tetramethyl-1-oxo-1,3, 3',4,4',5,5',6,6a,6b,6',7,8,8a,8b,9,11a,12,12a,12b-icosahydrospiro[naphtho[2',1':4,5]indeno[2,1-b]furan-10,2'-pyran]-4-yl acetate (Compound No. 150, 0.37 g, 37%) as a white solid.

C. To a solution of (2'R,4S,5'R,6aR,6bS,8aS,8bR,9S, 11aS,12aS,12bS)-5',6a,8a,9-tetramethyl-1-oxo-1,3,3',4,4',5, 5',6,6a,6b,6',7,8,8a,8b,9,11a,12,12a,12b-icosahydrospiro [naphtho[2',1':4,5]indeno[2,1-b]furan-10,2'-pyran]-4-yl acetate (Compound No. 150, 0.37 g, 0.79 mmol) in THF (5 mL) at 0° C. under nitrogen was added borane (1.6 mL of a 1M solution in THF, 1.6 mmol). After overnight the reaction was cooled in ice and quenched with H$_2$O (0.5 mL) then added NaBO$_3$-4H$_2$O (0.25 g) and heated the mixture at 60° C. for 1 h. The mixture was diluted with EtOAc (100 mL), washed with brine (3×15 mL), dried (MgSO$_4$) and concentrated. The residue was purified using chromatography on silica gel (50% EtOAc/hexanes) to afford (1R,2R,2aS,2'R, 4S,5'R,6aR,6bS,8aS,8bR,9S,11 aS,12aS,12bR)-1,2-dihydroxy-5',6a,8a,9-tetramethyldocosahydrospiro[naphtho[2', 1':4,5]indeno[2,1-b]furan-10,2'-pyran]-4-yl acetate (Compound No. 151, 0.19 g, 49%) as a white foam.

D. A solution of (1R,2R,2aS,2'R,4S,5'R,6aR,6bS,8aS, 8bR,9S,11 aS,12aS,12bR)-1,2-dihydroxy-5',6a,8a,9-tetramethyldocosahydrospiro[naphtho[2',1':4,5]indeno[2,1-b] furan-10,2'-pyran]-4-yl acetate (Compound No. 151, 0.19 g, 0.39 mmol) and NaIO$_4$ (0.17 g, 0.77 mmol) in THF (6 mL) and H$_2$O (1 mL) was stirred at room temperature for 3 h. The solution was diluted with H$_2$O (20 mL), extracted with CH$_2$Cl$_2$ (2×50 mL), washed with brine (10 mL), dried (MgSO$_4$) and concentrated. The residue was purified using chromatography on silica gel (30% EtOAc/hexanes) to afford (1S,3S,4R)-3-formyl-4-((2R,3S,3aR,3bS,5'R,6S,7R, 7aS,8aS)-7-formyl-3,3b,5'-trimethyltetradecahydrospiro[indeno[2,1-b]furan-2,2'-pyran]-6-yl)-4-methylcyclohexyl acetate (Compound No. 152, 147 mg) as a white foam.

E. A solution of (1S,3S,4R)-3-formyl-4-((2R,3S,3aR,3bS, 5'R,6S,7R,7aS,8aS)-7-formyl-3,3b,5'-trimethyltetradecahydrospiro[indeno[2,1-b]furan-2,2'-pyran]-6-yl)-4-methylcyclohexyl acetate (Compound No. 152, 147 mg, 0.302 mmol) and NaBH$_4$ (23 mg, 0.60 mmol) in MeOH (1 mL) and THF (4 mL) was stirred at room temperature for 3 h. The reaction was cooled in ice and quenched with AcOH (0.5 mL), stirring 15 minutes at room temperature then was concentrated. The residue was taken up in EtOAc (100 mL), washed successively with saturated NaHCO$_3$ solution (2×5 mL) and brine (3×15 mL), dried (MgSO$_4$) and concentrated. The residue was purified using chromatography on silica gel (50% then 75% EtOAc/hexanes) to afford (1S,3S,4R)-3-(hydroxymethyl)-4-((2R,3S,3aR,3bS,5'R,6S,7R,7aS,8aS)-7-(hydroxymethyl)-3,3b,5'-trimethyltetradecahydrospiro [indeno[2,1-b]furan-2,2'-pyran]-6-yl)-4-methylcyclohexyl acetate (Compound No. 153, 0.13 g, 88%) as a white solid.

F. A solution of (1S,3S,4R)-3-(hydroxymethyl)-4-((2R, 3S,3aR,3bS,5'R,6S,7R,7aS,8aS)-7-(hydroxymethyl)-3,3b, 5'-trimethyltetradecahydrospiro[indeno[2,1-b]furan-2,2'-pyran]-6-yl)-4-methylcyclohexyl acetate (Compound No. 153, 0.13 g, 0.26 mmol) and NaOH (23 mg, 0.53 mmol) in MeOH (10 mL) was stirred at room temperature for 2 d then was acidified with AcOH (1.5 mL) and concentrated. The residue was purified using chromatography on silica gel (1% then 5% MeOH/EtOAc) to afford (1S,3S,4R)-3-(hydroxymethyl)-4-((2R,3S,3aR,3bS,5'R,6S,7R,7aS,8aS)-7-(hydroxymethyl)-3,3b,5'-trimethyltetradecahydrospiro[indeno [2,1-b]furan-2,2'-pyran]-6-yl)-4-methylcyclohexanol (Compound No. 154, 97 mg, 82%) as a white solid. $^1$H NMR (CD$_3$OD): δ 4.42 (m, 1H), 3.91 (m, 1H), 3.70 (m, 1H), 3.58 (m, 1H), 3.44 (2H), 3.32 (m, 1H), 3.12 (m, 1H), 2.15 (2H), 1.92 (m, 1H), 1.85-1.15 (20H), 1.12 (s, 3H), 0.98 (d, 3H), 0.82 (s, 3H), 0.80 (d, 3H). ES-MS m/z 451 ([M+1]$^+$).

Example 30

Synthesis of (1S,3S,4R)-4-((3aS,6S,7R,7aS)-3-(furan-2-yl)-7-(hydroxymethyl)-3a-methyl-3a,4,5,6, 7,7a-hexahydro-1H-inden-6-yl)-3-(hydroxymethyl)-4-methylcyclohexanol (Compound No. 158)

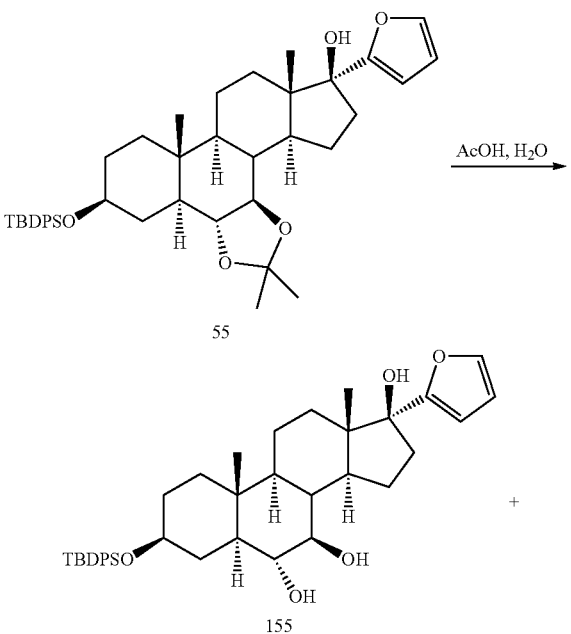

-continued

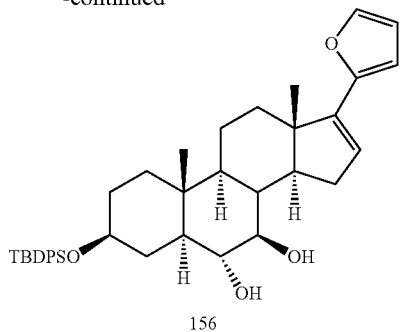

156

1) NaIO₄,
   THF, H₂O
2) NaBH₄,
   THF, MeOH

156 ⟶

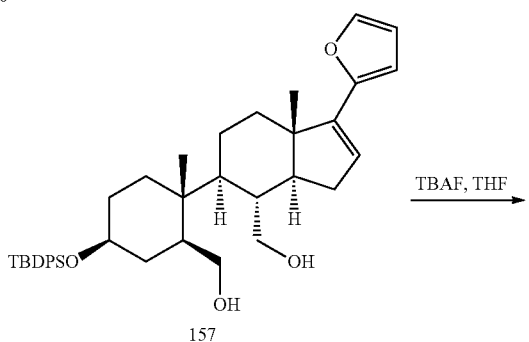

157

TBAF, THF ⟶

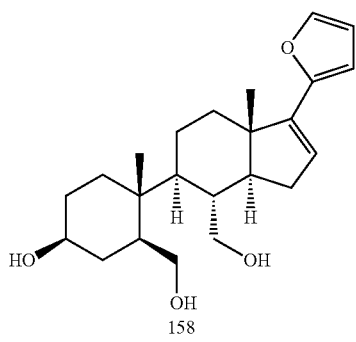

158

A. A suspension of (2S,4aR,4bS,6aS,7S,9aS,9bR,9cR,12aR,12bS)-2-((tert-butyldiphenylsilyl)oxy)-7-(furan-2-yl)-4a,6a,11,11-tetramethylhexadecahydro-1H-cyclopenta[1,2]phenanthro[9,10-d][1,3]dioxol-7-ol (Compound No. 55, 1.15 g, 1.72 mmol) in 80% acetic acid(aq) (16 mL) was heated to 40° C. for 2.5 h then concentrated. Azeotropic removal of remaining AcOH and H₂O was carried out with PhMe (3×30 mL), and the residue was purified by chromatography on silica gel (30:70-50:50 EtOAc/hexanes) to give (3S,5S,6R,7R,8R,9S,10R,13S,14S,17S)-3-((tert-butyldiphenylsilyl)oxy)-17-(furan-2-yl)-10,13-dimethylhexadecahydro-1H-cyclopenta[a]phenanthrene-6,7,17-triol (Compound No. 155, 333 mg, 31%) as a purple foam and (3S,5S,6R,7R,8R,9S,10R,13S,14S)-3-((tert-butyldiphenylsilyl)oxy)-17-(furan-2-yl)-10,13-dimethyl-2,3,4,5,6,7,8,9,10,11,12,13,14,15-tetradecahydro-1H-cyclopenta[a]phenanthrene-6,7-diol (Compound No. 156, 615 mg, 59%) as a pink foam.

B. A suspension of NaIO₄ (373 mg, 1.74 mmol) in H₂O (0.9 mL) was added to a solution of (3S,5S,6R,7R,8R,9S,10R,13S,14S)-3-((tert-butyldiphenylsilyl)oxy)-17-(furan-2-yl)-10,13-dimethyl-2,3,4,5,6,7,8,9,10,11,12,13,14,15-tetradecahydro-1H-cyclopenta[a]phenanthrene-6,7-diol (Compound No. 156, 533 mg, 0.872 mmol) in THF (8.7 mL), and the mixture was stirred at room temperature for 1.5 h. The mixture was concentrated, and the residue was partitioned between CH₂Cl₂ (20 mL) and H₂O (15 mL). The aqueous phase was extracted with CH₂Cl₂ (2×10 mL), and the combined organic layers were dried (MgSO₄) and concentrated. The resulting pink foam (559 mg) was dissolved in 3:1 THF/MeOH (8.7 mL) and cooled to 0° C. under argon. NaBH₄ (66 mg, 1.7 mmol) was added, and the mixture was stirred at 0° C. for 30 min then at room temperature for 2 h. Acetone (5 mL) was added and the mixture was concentrated. The residue was dissolved in EtOAc (40 mL) and washed with brine (2×15 mL) then dried (MgSO₄) and concentrated. The residue was partially purified by chromatography on silica gel (1:1 EtOAc/hexanes) to give ((1S,2R,5S)-5-((tert-butyldiphenylsilyl)oxy)-2-((3aS,6S,7R,7aS)-3-(furan-2-yl)-7-(hydroxymethyl)-3a-methyl-3a,4,5,6,7,7a-hexahydro-1H-inden-6-yl)-2-methylcyclohexyl)methanol (Compound No. 157, 515 mg) as a pink solid.

C. TBAF (0.28 mL of a 1 M solution in THF, 0.28 mmol) was added to a solution of ((1S,2R,5S)-5-((tert-butyldiphenylsilyl)oxy)-2-((3aS,6S,7R,7aS)-3-(furan-2-yl)-7-(hydroxymethyl)-3a-methyl-3a,4,5,6,7,7a-hexahydro-1H-inden-6-yl)-2-methylcyclohexyl)methanol (Compound No. 157, 87 mg) in THF (2.8 mL) and stirred at room temperature for 3 d. The solution was concentrated, and the residue was purified by chromatography on silica gel (7:93 MeOH/EtOAc) to give (1S,3S,4R)-4-((3aS,6S,7R,7aS)-3-(furan-2-yl)-7-(hydroxymethyl)-3a-methyl-3a,4,5,6,7,7a-hexahydro-1H-inden-6-yl)-3-(hydroxymethyl)-4-methylcyclohexanol (Compound No. 158, 49 mg, 89% over 3 steps) as colourless crystals. ¹H NMR (CD₃OD): δ 7.39 (d, J=1.8 Hz, 1H), 6.37 (dd, J=3.3, 1.8 Hz, 1H), 6.30 (d, J=3.3 Hz, 1H), 6.02 (dd, J=3.0, 1.8 Hz, 1H), 3.96 (m, 1H), 3.71 (m, 2H), 3.46 (m, 1H), 3.14 (m, 1H), 2.43 (m, 1H), 1.22-2.22 (m, 15H), 1.13 (s, 3H), 0.97 (s, 3H). ES-MS m/z 357 ([M−17]⁺).

Example 31

Synthesis of (1S,3aS,4R,5S,7aS)-1-(furan-2-yl)-5-((1R,2S,4S)-4-hydroxy-2-(hydroxymethyl)-1-methylcyclohexyl)-4-(hydroxymethyl)-7a-methyloctahydro-1H-inden-1-ol (Compound No. 160)

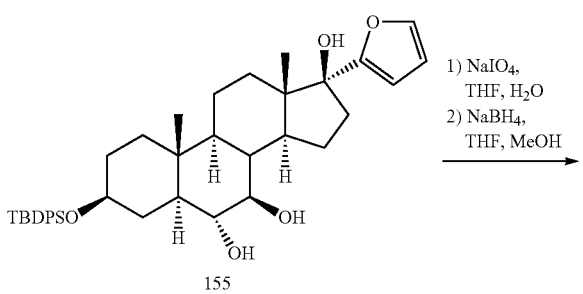

155

1) NaIO₄,
   THF, H₂O
2) NaBH₄,
   THF, MeOH

139

-continued

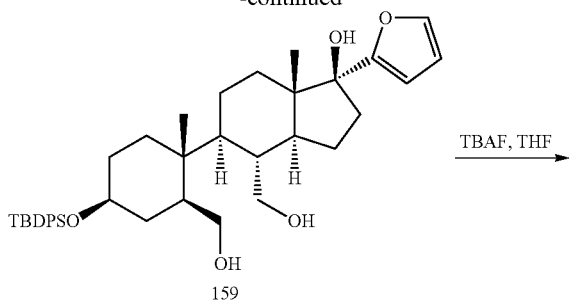

A. A suspension of NaIO₄ (162 mg, 0.757 mmol) in H₂O (0.4 mL) was added to a solution of (3S,5S,6R,7R,8R,9S,10R,13S,14S,17S)-3-((tert-butyldiphenylsilyl)oxy)-17-(furan-2-yl)-10,13-dimethylhexadecahydro-1H-cyclopenta[a]phenanthrene-6,7,17-triol (Compound No. 155, 238 mg, 0.378 mmol) in THF (4 mL), and the mixture was stirred at room temperature for 1.5 h. The mixture was concentrated, and the residue was partitioned between CH₂Cl₂ (20 mL) and H₂O (10 mL). The aqueous phase was extracted with CH₂Cl₂ (2×10 mL), and the combined organic layers were dried (MgSO₄) and concentrated. The resulting purple foam (247 mg) was dissolved in 3:1 THF/MeOH (4 mL) and cooled to 0° C. under argon. NaBH₄ (29 mg, 0.77 mmol) was added, and the mixture was stirred at 0° C. for 30 min then at room temperature for 2 h. Acetone (5 mL) was added and the mixture was concentrated. The residue was dissolved in EtOAc (40 mL) and washed with brine (2×15 mL) then dried (MgSO₄) and concentrated. The residue was purified by chromatography on silica gel (1:1 EtOAc/hexanes) to give (1S,3aS,4R,5S,7aS)-5-((1R,2S,4S)-4-((tert-butyldiphenylsilyl)oxy)-2-(hydroxymethyl)-1-methylcyclohexyl)-1-(furan-2-yl)-4-(hydroxymethyl)-7a-methyloctahydro-1H-inden-1-ol (Compound No. 159, 219 mg, 92% over 2 steps) as a pale solid.

B. TBAF (0.24 mL of a 1 M solution in THF, 0.24 mmol) was added to a solution of (1S,3aS,4R,5S,7aS)-5-((1R,2S,4S)-4-((tert-butyldiphenylsilyl)oxy)-2-(hydroxymethyl)-1-methylcyclohexyl)-1-(furan-2-yl)-4-(hydroxymethyl)-7a-methyloctahydro-1H-inden-1-ol (Compound No. 159, 75 mg, 0.12 mmol) in THF (2.4 mL) and stirred at room temperature for 3 d. The solution was concentrated, and the residue was purified by chromatography on silica gel (7:93 MeOH/EtOAc) to give (1S,3aS,4R,5S,7aS)-1-(furan-2-yl)-5-((1R,2S,4S)-4-hydroxy-2-(hydroxymethyl)-1-methylcyclohexyl)-4-(hydroxymethyl)-7a-methyloctahydro-1H-inden-1-ol (Compound No. 160, 47 mg, 100%) as a colourless solid. ¹H NMR (CD₃OD): δ 7.42 (m, 1H), 6.35 (m, 1H), 6.23 (d, J=3.0 Hz, 1H), 3.89 (m, 1H), 3.59 (m, 2H), 3.42 (m, 1H), 3.06 (m, 1H), 2.26 (m, 1H), 1.17-2.13 (m, 16H), 1.05 (s, 3H), 0.96 (s, 3H), 0.52 (m, 1H). ES-MS m/z 391 ([M−1]⁻).

140

Example 32

Synthesis of N-((1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl)acetamide (Compound No. 165)

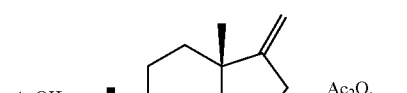

A. A mixture of (3S,6R,7R,9S,10R,13S,14S)-3-amino-10,13-dimethyl-17-methylenehexadecahydro-1H-cyclopenta[a]phenanthrene-6,7-diol acetate (Compound No. 161, 1.05 g, 2.74 mmol), Ac$_2$O (1.3 mL, 13.7 mmol) and DMAP (33 mg, 0.27 mmol) in pyridine (40 mL) under argon was stirred at room temperature for 20 h. The mixture was partitioned between H$_2$O (50 mL) and EtOAc (200 mL). The organic layer was washed with brine (3×50 mL), dried (Na$_2$SO$_4$), concentrated and azeotroped from PhMe (2×50 mL) to afford (3S,5S,6R,7R,8R,9S,10R,13S,14S)-3-acetamido-10,13-dimethyl-17-methylenehexadecahydro-1H-cyclopenta[a]phenanthrene-6,7-diyl diacetate (Compound No. 162) as a foam.

B. A mixture of (3S,5S,6R,7R,8R,9S,10R,13S,14S)-3-acetamido-10,13-dimethyl-17-methylenehexadecahydro-1H-cyclopenta[a]phenanthrene-6,7-diyl diacetate (Compound No. 162) and NaOMe (5.4 M in MeOH, 3 mL, 16.4 mmol) in MeOH (40 mL) under argon was stirred at room temperature for 24 h. H$_2$O (50 mL) was added and the organics were removed by distillation. The mixture was diluted with EtOAc (150 mL), washed successively with saturated NaHCO$_3$ solution (3×30 mL) and brine (30 mL), dried (Na$_2$SO$_4$) and concentrated to afford the diol N-((3S,5S,6R,7R,8R,9S,10R,13S,14S)-6,7-dihydroxy-10,13-dimethyl-17-methylenehexadecahydro-1H-cyclopenta[a]phenanthren-3-yl)acetamide (Compound No. 163, 0.89 g, 90% over 2 steps) as an off-white solid.

C. A mixture of N-((3S,5S,6R,7R,8R,9S,10R,13S,14S)-6,7-dihydroxy-10,13-dimethyl-17-methylenehexadecahydro-1H-cyclopenta[a]phenanthren-3-yl)acetamide (Compound No. 163, 0.75 g, 2.08 mmol) and NaIO$_4$ (888 mg, 4.15 mmol) in THF (20 mL) and H$_2$O (5 mL) was stirred at room temperature for 1 h. The mixture was diluted with H$_2$O (50 mL) and extracted with CH$_2$Cl$_2$ (3×50 mL). The combined organic layers were washed with brine (2×50 mL), dried (Na$_2$SO$_4$) and concentrated to afford N-((1S,3S,4R)-3-formyl-4-((3aS,4R,5S,7aS)-4-formyl-7a-methyl-1-methyleneoctahydro-1H-inden-5-yl)-4-methylcyclohexyl)acetamide (Compound No. 164) as a white foam (0.83 g).

D. A mixture of N-((1S,3S,4R)-3-formyl-4-((3aS,4R,5S,7aS)-4-formyl-7a-methyl-1-methyleneoctahydro-1H-inden-5-yl)-4-methylcyclohexyl)acetamide (Compound No. 164, 0.83 g) and NaBH$_4$ (157 mg, 4.16 mmol) in THF (25 mL) and MeOH (8 mL) under argon was stirred at room temperature for 2 h. The reaction was cooled to 0° C. and quenched with 80% AcOH (2 mL). After 10 min at room temperature, the mixture was concentrated and reconstituted in EtOAc (100 mL). The mixture was washed successively with saturated NaHCO$_3$ solution (2×50 mL) and brine (50 mL), dried (Na$_2$SO$_4$) and concentrated. The residue was purified using chromatography on silica gel (9:1 EtOAc:MeOH) to afford N-((1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl)acetamide (Compound No. 165, 0.54 g, 72% over 2 steps) as a white solid. $^1$H NMR (300 MHz, CD$_3$OD) δ 4.62 (s, 2H), 3.94-3.90 (m, 1H), 3.75-3.55 (m, 3H), 3.13-3.06 (m, 1H), 2.54-2.45 (m, 1H), 2.31-2.20 (m, 1H), 2.10-2.06 (m, 1H), 1.91 (s, 3H), 1.85-1.18 (m, 15H), 1.11 (s, 3H), 0.81 (s, 3H); $^{13}$C NMR (75 MHz, CD$_3$OD) δ 172.2, 162.8, 101.5, 62.5, 51.3, 45.8, 45.4, 45.4, 44.6, 40.9, 37.85 37.1, 32.2, 32.1, 30.1, 29.4, 29.3, 25.7, 24.1, 24.1, 24.1, 22.7, 21.3, 18.7, 18.6; MS m/z: 364.3 [M+H]$^+$.

Example 33

Synthesis of (1S,3S,4R)-3-(hydroxymethyl)-4-((4aS,5R,6S,8aS)-5-(hydroxymethyl)-8a-methyl-1,4,4a,5,6,7,8,8a-octahydroindeno[1,2-c]pyrazol-6-yl)-4-methylcyclohexanol (Compound No. 170)

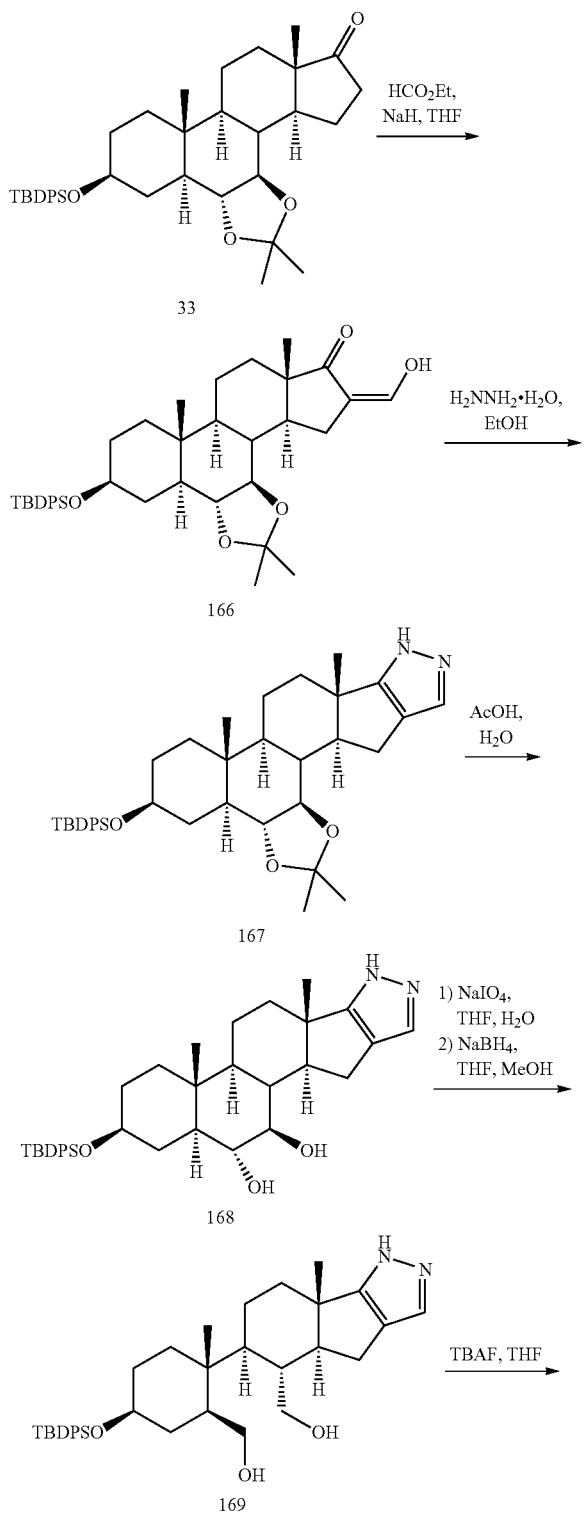

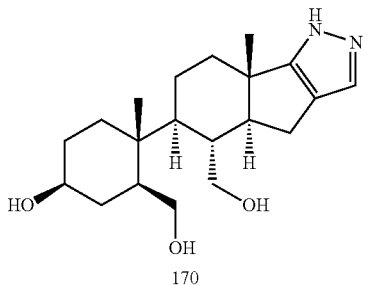

170

A. A solution of (2S,4aR,4bS,6aS,9aS,9bR,9cR,12aR,12bS)-2-((tert-butyldiphenylsilyl)oxy)-4a,6a,11,11-tetramethyltetradecahydro-1H-cyclopenta[1,2]phenanthro[9,10-d][1,3]dioxol-7(8H)-one (Compound No. 33, 907 mg, 1.51 mmol) in THF (3.0 mL) was added to a suspension of NaH (242 mg of a 60% solution, 6.05 mmol) in THF (3.0 mL) at 0° C. under argon. The mixture was stirred at 0° C. for 15 min then ethyl formate (0.73 mL, 9.1 mmol) was added and stirred at room temperature for 3 h. The mixture was diluted with H₂O (20 mL) and EtOAc (40 mL), and the aqueous phase was extracted with EtOAc (3×15 mL). The combined organic layers were dried (MgSO₄) and concentrated to give (2S,4aR,4bS,6aS,9aS,9bR,9cR,12aR,12bS,Z)-2-((tert-butyldiphenylsilyl)oxy)-8-(hydroxymethylene)-4a,6a,11,11-tetramethyltetradecahydro-1H-cyclopenta[1,2]phenanthro[9,10-d][1,3]dioxol-7(8H)-one (Compound No. 166, 1.12 g) that was used in the next step without further purification.

B. To a suspension of (2S,4aR,4bS,6aS,9aS,9bR,9cR,12aR,12bS,Z)-2-((tert-butyldiphenylsilyl)oxy)-8-(hydroxymethylene)-4a,6a,11,11-tetramethyl tetradecahydro-1H-cyclopenta[1,2]phenanthro[9,10-d][1,3]dioxol-7(8H)-one (Compound No. 166, 1.12 g) in EtOH (30 mL) was added hydrazine monohydrate (0.11 mL, 2.3 mmol), and the mixture was heated to reflux under argon for 1 h then concentrated. The residue was dissolved in CH₂Cl₂ (40 mL) and washed with H₂O (15 mL). The aqueous phase was extracted with CH₂Cl₂ (10 mL), and the combined organic layers were dried (MgSO₄) and concentrated. The yellow foam, (3aR,3bS,5S,7aR,7bS,9aS,13aS,13bR,13cR)-5-((tert-butyldiphenylsilyl)oxy)-2,2,7a,9a-tetramethyl-3a,3b,4,5,6,7,7a,7b,8,9,9a,10,13,13a,13b,13c-hexadecahydro-[1,3]dioxolo[4",5":3',4']naphtho[2',1':4,5]indeno[1,2-c]pyrazole (Compound No. 167, 1.05 g) that was obtained was used in the next step without further purification.

C. A suspension of (3aR,3bS,5S,7aR,7bS,9aS,13aS,13bR,13cR)-5-((tert-butyldiphenylsilyl)oxy)-2,2,7a,9a-tetramethyl-3a,3b,4,5,6,7,7a,7b,8,9,9a,10,13,13a,13b,13c-hexadecahydro-[1,3]dioxolo[4",5":3',4']naphtho[2',1':4,5]indeno[1,2-c]pyrazole (Compound No. 167, 1.05 g) in 80% acetic acid(aq) (20 mL) was heated to 40° C. for 2 h then concentrated. Azeotropic removal of remaining AcOH and H₂O was carried out with PhMe (2×40 mL). The residue was partitioned between EtOAc (25 mL) and 1 N NaOH(aq) (20 mL), and the aqueous phase was extracted with EtOAc (2×15 mL). The combined organic layers were dried (MgSO₄) and concentrated, and the residue was purified by chromatography on silica gel (5:95 MeOH/CH₂Cl₂) to give (1R,2R,2aS,4S,6aR,6bS,8aS,12aS,12bR)-4-((tert-butyldiphenylsilyl)oxy)-6a,8a-dimethyl-1,2,2a,3,4,5,6,6a,6b,7,8,8a,9,12,12a,12b-hexadecahydronaphtho[2',1':4,5]indeno[1,2-c]pyrazole-1,2-diol (Compound No. 168, 341 mg, 39% over 3 steps) as a light yellow solid.

D. A suspension of NaIO₄ (178 mg, 0.832 mmol) in H₂O (0.4 mL) was added to a solution of (1R,2R,2aS,4S,6aR,6bS,8aS,12aS,12bR)-4-((tert-butyldiphenylsilyl)oxy)-6a,8a-dimethyl-1,2,2a,3,4,5,6,6a,6b,7,8,8a,9,12,12a,12b-hexadecahydronaphtho[2',1':4,5]indeno[1,2-c]pyrazole-1,2-diol (Compound No. 168, 243 mg, 0.415 mmol) in THF (4.2 mL), and the mixture was stirred at room temperature for 1.5 h. The mixture was concentrated, and the residue was partitioned between CH₂Cl₂ (20 mL) and H₂O (10 mL). The aqueous phase was extracted with CH₂Cl₂ (2×10 mL), and the combined organic layers were dried (MgSO₄) and concentrated. The resulting yellow solid (314 mg) was dissolved in 3:1 THF/MeOH (4 mL) and cooled to 0° C. under argon. NaBH₄ (31 mg, 0.82 mmol) was added, and the mixture was stirred at 0° C. for 30 min then at room temperature for 2.5 h. Acetone (5 mL) was added and the mixture was concentrated. The residue was partitioned between CH₂Cl₂ (20 mL) and H₂O (10 mL), and the aqueous phase was extracted with CH₂Cl₂ (2×10 mL). The combined organic layers were dried (MgSO₄) and concentrated to give ((1S,2R,5S)-5-((tert-butyldiphenylsilyl)oxy)-2-((4aS,5R,6S,8aS)-5-(hydroxymethyl)-8a-methyl-1,4,4a,5,6,7,8,8a-octahydroindeno[1,2-c]pyrazol-6-yl)-2-methylcyclohexyl)methanol (Compound No. 169, 252 mg) that was used in the next step without further purification.

E. TBAF (0.83 mL of a 1 M solution in THF, 0.83 mmol) was added to a solution of ((1S,2R,5S)-5-((tert-butyldiphenylsilyl)oxy)-2-((4aS,5R,6S,8aS)-5-(hydroxymethyl)-8a-methyl-1,4,4a,5,6,7,8,8a-octahydroindeno[1,2-c]pyrazol-6-yl)-2-methylcyclohexyl)methanol (Compound No. 169, 252 mg) in THF (8.3 mL) and stirred at room temperature for 21 h. The solution was concentrated, and the residue was partially purified by chromatography on silica gel (200:5:1 acetone/MeOH/NH₄OH) to give a colourless solid (87 mg). The solid (87 mg) was dissolved in MeOH (1.4 mL), and 4 N HCl in dioxane (0.3 mL) was added then concentrated. Azeotropic removal of solvent using MeOH (10 mL) gave a residue that was dissolved in MeOH (0.4 mL). Et₂O (40 mL) was added to give a precipitate, and the supernatant was decanted. More Et₂O was added and the supernatant was decanted (3×20 mL). The residue was dissolved in H₂O (7 mL) and extracted with CH₂Cl₂ (3×8 mL). The aqueous phase was concentrated, and azeotropic removal of remaining H₂O was carried out using PhMe to give (1S,3S,4R)-3-(hydroxymethyl)-4-((4aS,5R,6S,8aS)-5-(hydroxymethyl)-8a-methyl-1,4,4a,5,6,7,8,8a-octahydroindeno[1,2-c]pyrazol-6-yl)-4-methylcyclohexanol (Compound No. 170, 80 mg, 55% over 3 steps) as a light yellow solid. ¹H NMR (CD₃OD): δ 7.87 (br s, 1H), 4.00 (m, 1H), 3.70 (m, 2H), 3.46 (br s, 1H), 3.15 (m, 1H), 2.90 (br s, 1H), 2.52 (br s, 2H), 2.17 (m, 2H), 1.13-1.93 (m, 17H). ES-MS m/z 349 ([M+1]⁺).

Example 34

Synthesis of (1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiophen-2-yl)octahydro-1H-inden-1-ol (Compound No. 171)

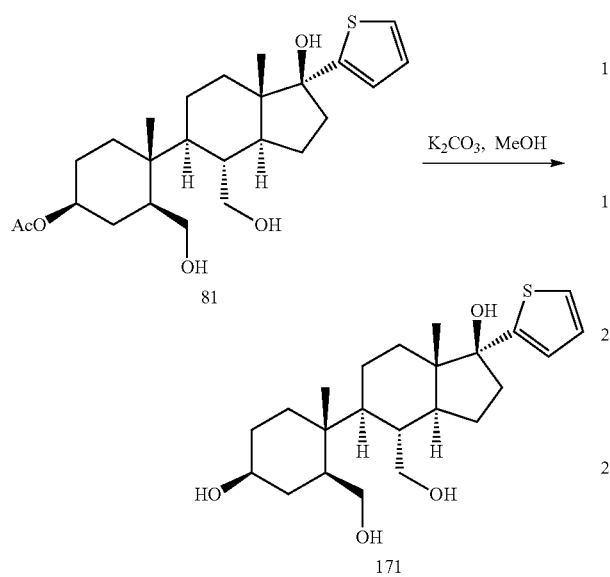

To a solution of (1S,3S,4R)-4-((1S,3aS,4R,5S,7aS)-1-hydroxy-4-(hydroxymethyl)-7a-methyl-1-(thiophen-2-yl)octahydro-1H-inden-5-yl)-3-(hydroxymethyl)-4-methylcyclohexyl acetate (Compound No. 81, 56 mg) in MeOH (2.5 mL) was added potassium carbonate (34 mg, 0.25 mmol) and stirred at room temperature for 2.5 h. The mixture was concentrated, and the residue was purified by chromatography on silica gel (10:90 MeOH/CH$_2$Cl$_2$) to give (1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiophen-2-yl)octahydro-1H-inden-1-ol (Compound No. 171, 44 mg, 94%) as a colourless solid. $^1$H NMR (CD$_3$OD): 57.23 (m, 1H), 6.94 (m, 1H), 6.89 (m, 1H), 3.91 (m, 1H), 3.59 (m, 2H), 3.42 (m, 1H), 3.04 (m, 1H), 1.17-2.35 (m, 17H), 1.05 (s, 3H), 0.99 (s, 3H), 0.57 (m, 1H). ES-MS m/z 467 ([M−1+60]$^-$).

Example 35

Synthesis of (1S,3S,4R)-3-(hydroxymethyl)-4-((3aS, 6S,7R,7aS)-7-(hydroxymethyl)-3a-methyl-3-(thiophen-2-yl)-3a,4,5,6,7,7a-hexahydro-1H-inden-6-yl)-4-methylcyclohexanol (Compound No. 174)

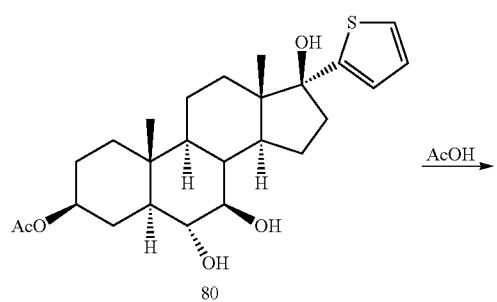

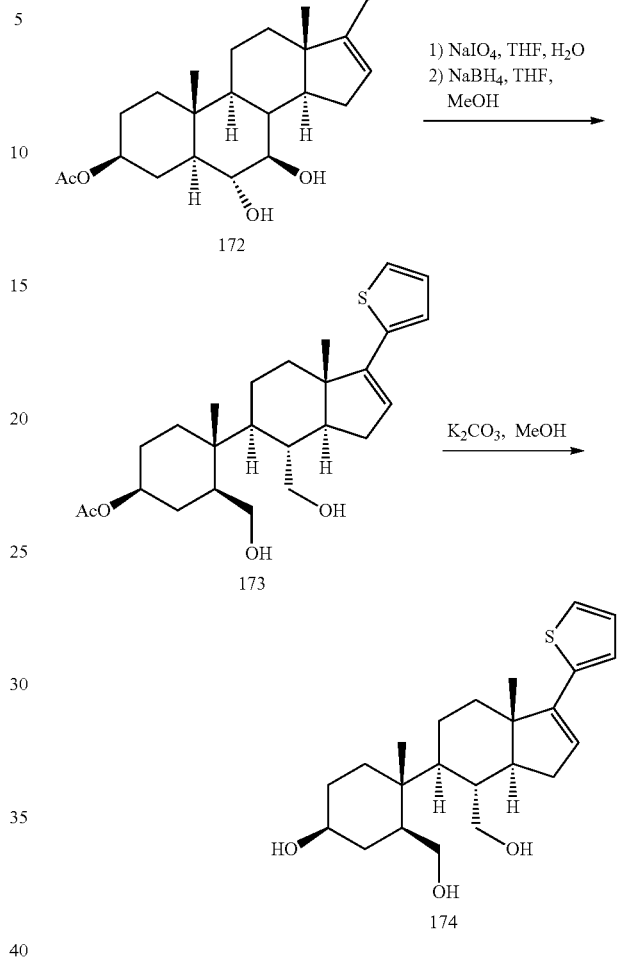

A. A solution of (3S,5S,6R,7R,8R,9S,10R,13S,14S,17S)-6,7,17-trihydroxy-10,13-dimethyl-17-(thiophen-2-yl)hexadecahydro-1H-cyclopenta[a]phenanthren-3-yl acetate (Compound No. 80, 353 mg, 0.787 mmol) in AcOH (8 mL) was heated to 50° C. for 20 h then to 75° C. for 5 d. The solution was concentrated, and azeotropic removal of remaining AcOH was carried out with PhMe (3×20 mL). The residue was purified by chromatography on silica gel (15:85-50:50 EtOAc/CH$_2$Cl$_2$) to give (3S,5S,6R,7R,8R,9S, 10R,13S,14S)-6,7-dihydroxy-10,13-dimethyl-17-(thiophen-2-yl)-2,3,4,5,6,7,8,9,10,11,12,13,14,15-tetradecahydro-1H-cyclopenta[a]phenanthren-3-yl acetate (Compound No. 172, 79 mg, 23%) as a pale film.

B. NaIO$_4$ (78 mg, 0.36 mmol) was added to a solution of (3S,5S,6R,7R,8R,9S,10R,13S,14S)-6,7-dihydroxy-10,13-dimethyl-17-(thiophen-2-yl)-2,3,4,5,6,7,8,9,10,11,12,13,14, 15-tetradecahydro-1H-cyclopenta[a]phenanthren-3-yl acetate (Compound No. 172, 79 mg, 0.18 mmol) in 9:1 THF/H$_2$O (5.1 mL), and the mixture was stirred at room temperature for 2.5 h. The mixture was concentrated, and the residue was partitioned between CH$_2$Cl$_2$ (15 mL) and H$_2$O (10 mL). The aqueous phase was extracted with CH$_2$Cl$_2$ (2×10 mL), and the combined organic layers were dried (MgSO$_4$) and concentrated. The resulting yellow film (88 mg) was dissolved in 3:1 THF/MeOH (4.6 mL) and stirred at room temperature while NaBH$_4$ (14 mg, 0.37 mmol) was added. The mixture was stirred for 2.25 h then acetone (5 mL) was added and the mixture was concentrated. The residue was partitioned between $CH_2Cl_2$ (15 mL) and $H_2O$ (10 mL), and the aqueous phase was extracted with $CH_2Cl_2$ (2×10 mL). The combined organic layers were dried ($MgSO_4$) and concentrated. The colourless solid, (1S,3S,4R)-3-(hydroxymethyl)-4-((3aS,6S,7R,7aS)-7-(hydroxymethyl)-3a-methyl-3-(thiophen-2-yl)-3a,4,5,6,7,7a-hexahydro-1H-inden-6-yl)-4-methylcyclohexyl acetate (Compound No. 173, 80 mg), that was obtained was used in the next step without further purification.

C. To a solution of (1S,3S,4R)-3-(hydroxymethyl)-4-((3aS,6S,7R,7aS)-7-(hydroxymethyl)-3a-methyl-3-(thiophen-2-yl)-3a,4,5,6,7,7a-hexahydro-1H-inden-6-yl)-4-methylcyclohexyl acetate (Compound No. 173, 80 mg) in MeOH (4.5 mL) was added potassium carbonate (50 mg, 0.36 mmol) and stirred at room temperature for 15 h. The mixture was concentrated, and the residue was purified by chromatography on silica gel (10:90 MeOH/$CH_2Cl_2$) to give (1S,3S,4R)-3-(hydroxymethyl)-4-((3aS,6S,7R,7aS)-7-(hydroxymethyl)-3a-methyl-3-(thiophen-2-yl)-3a,4,5,6,7,7a-hexahydro-1H-inden-6-yl)-4-methylcyclohexanol (Compound No. 174, 44 mg, 61% over 3 steps) as a colourless solid. $^1$H NMR ($CD_3OD$): δ 7.20 (d, J=4.8 Hz, 1H), 7.05 (d, J=3.0 Hz, 1H), 6.96 (dd, J=5.1, 3.6 Hz, 1H), 5.96 (s, 1H), 3.96 (m, 1H), 3.71 (m, 2H), 3.46 (m, 1H), 3.14 (m, 1H), 2.41 (m, 1H), 1.22-2.23 (m, 15H), 1.13 (s, 3H), 1.02 (s, 3H). ES-MS m/z 449 ([M−1+60]$^-$).

Example 36

Synthesis of (1S,3aS,4R,5S,7aS)-5-((1R,2S,4S)-4-hydroxy-2-(hydroxymethyl)-1-methylcyclohexyl)-4-(hydroxymethyl)-7a-methyl-1-(pyridin-2-yl)octahydro-1H-inden-1-ol (Compound No. 175)

To a solution of (1S,3S,4R)-4-((1S,3aS,4R,5S,7aS)-1-hydroxy-4-(hydroxymethyl)-7a-methyl-1-(pyridin-2-yl)octahydro-1H-inden-5-yl)-3-(hydroxymethyl)-4-methylcyclohexyl acetate (Compound No. 91, 67 mg) in MeOH (2.8 mL) was added potassium carbonate (39 mg, 0.28 mmol) and heated to 40° C. for 1 h. The mixture was concentrated, and the residue was purified by chromatography on silica gel (10:90 MeOH/$CH_2Cl_2$) to give (1S,3aS,4R,5S,7aS)-5-((1R,2S,4S)-4-hydroxy-2-(hydroxymethyl)-1-methylcyclohexyl)-4-(hydroxymethyl)-7a-methyl-1-(pyridin-2-yl)octahydro-1H-inden-1-ol (Compound No. 175, 53 mg, 93%) as a colourless solid. $^1$H NMR ($CD_3OD$): δ 58.50 (d, J=5.1 Hz, 1H), 7.77 (m, 1H), 7.55 (d, J=8.1 Hz, 1H), 7.26 (m, 1H), 3.89 (m, 1H), 3.64 (m, 1H), 3.45 (m, 2H), 3.01 (m, 1H), 2.42 (m, 1H), 1.15-2.11 (m, 16H), 1.04 (s, 3H), 1.03 (s, 3H), 0.07 (m, 1H). ES-MS m/z 404 ([M+1]$^+$).

Example 37

Synthesis of (1S,2R,4R,5S)-5-((1R,2S,4S)-4-hydroxy-2-(hydroxymethyl)-1-methylcyclohexyl)-4-(hydroxymethyl)-1-methyl-1-phenyl-2,3,4,5,6,7-hexahydro-1H-inden-2-ol (Compound No. 178)

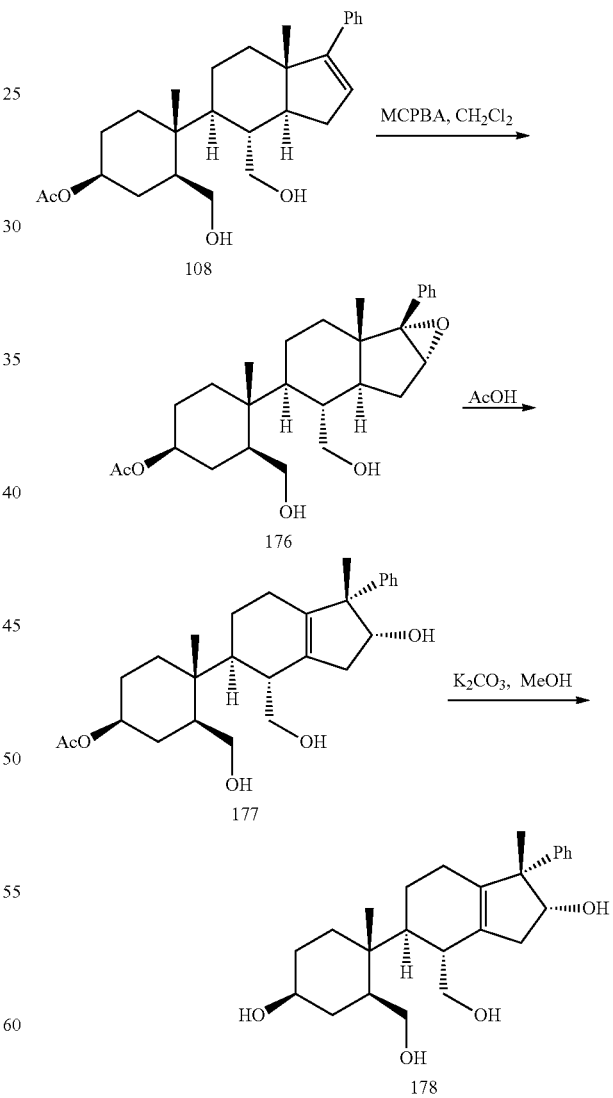

A. MCPBA (77%, 131 mg, 0.585 mmol) was added to a suspension of (1S,3S,4R)-3-(hydroxymethyl)-4-((3aS,6S,7R,7aS)-7-(hydroxymethyl)-3a-methyl-3-phenyl-3a,4,5,6,7, 7a-hexahydro-1H-inden-6-yl)-4-methylcyclohexyl acetate (Compound No. 108, 125 mg, 0.293 mmol) in CH$_2$Cl$_2$ (4.2 mL), and the mixture was stirred at room temperature for 1 h. The mixture was diluted with CH$_2$Cl$_2$ (20 mL) and washed with saturated aqueous Na$_2$SO$_3$ (15 mL) followed by saturated aqueous NaHCO$_3$ (15 mL) and H$_2$O (10 mL). The organic layer was dried (MgSO$_4$) and concentrated to give a colourless film, (1S,3S,4R)-3-(hydroxymethyl)-4-((1aR,1bS,4S,5R,5aS,6aR)-5-(hydroxymethyl)-1b-methyl-1a-phenyloctahydro-1aH-indeno[1,2-b]oxiren-4-yl)-4-methylcyclohexyl acetate (Compound No. 176, 141 mg), that was used in the next step without further purification.

B. A solution of (1S,3S,4R)-3-(hydroxymethyl)-4-((1aR,1bS,4S,5R,5aS,6aR)-5-(hydroxymethyl)-1b-methyl-1a-phenyloctahydro-1aH-indeno[1,2-b]oxiren-4-yl)-4-methylcyclohexyl acetate (Compound No. 176, 141 mg) in AcOH (4 mL) was stirred at room temperature for 17 h then concentrated. Azeotropic removal of remaining AcOH was carried out with PhMe (3×20 mL), and the residue was purified by chromatography on silica gel (EtOAc) to give (1S,3S,4R)-4-((1S,2R,4R,5S)-2-hydroxy-4-(hydroxymethyl)-1-methyl-1-phenyl-2,3,4,5,6,7-hexahydro-1H-inden-5-yl)-3-(hydroxymethyl)-4-methylcyclohexyl acetate (Compound No. 177, 82 mg, 63% over 2 steps) as a colourless foam.

C. To a solution of (1S,3S,4R)-4-((1S,2R,4R,5S)-2-hydroxy-4-(hydroxymethyl)-1-methyl-1-phenyl-2,3,4,5,6,7-hexahydro-1H-inden-5-yl)-3-(hydroxymethyl)-4-methylcyclohexyl acetate (Compound No. 177, 82 mg, 0.19 mmol) in MeOH (3.7 mL) was added potassium carbonate (51 mg, 0.37 mmol) and heated to 40° C. for 1.5 h. The mixture was concentrated, and the residue was purified by chromatography on silica gel (10:90 MeOH/CH$_2$Cl$_2$) to give (1S,2R,4R,5S)-5-((1R,2S,4S)-4-hydroxy-2-(hydroxymethyl)-1-methylcyclohexyl)-4-(hydroxymethyl)-1-methyl-1-phenyl-2,3,4,5,6,7-hexahydro-1H-inden-2-ol (Compound No. 178, 69 mg, 93%) as a colourless solid. $^1$H NMR (CD$_3$OD): δ 7.15-7.31 (m, 5H), 4.05 (m, 1H), 3.73-3.84 (m, 2H), 3.50 (m, 2H), 3.21 (m, 1H), 2.20-2.44 (m, 4H), 1.59-2.03 (m, 7H), 1.21-1.39 (m, 7H), 0.93 (s, 3H). ES-MS m/z 459 ([M−1+60]$^-$).

Example 38

Synthesis of (1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiazol-2-yl)octahydro-1H-inden-1-ol (Compound No. 179)

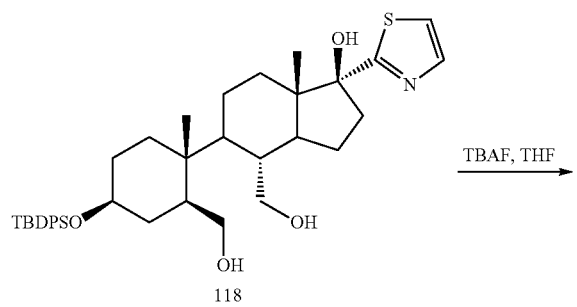

118

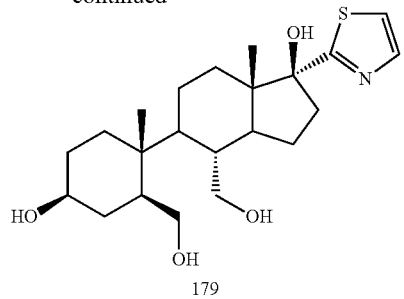

179

TBAF (0.16 mL of 1 M solution in THF, 0.16 mmol) was added to a solution of (1S,3aS,4R,5S,7aS)-5-((1R,2S,4S)-4-((tert-butyldiphenylsilyl)oxy)-2-(hydroxymethyl)-1-methylcyclohexyl)-4-(hydroxymethyl)-7a-methyl-1-(thiazol-2-yl)octahydro-1H-inden-1-ol (Compound No. 118, 51 mg, 0.079 mmol) in THF (3.9 mL) and heated to 50° C. for 3 d. The solution was concentrated, and the residue was purified by chromatography on silica gel (100:7:2 EtOAc/MeOH/NH$_4$OH) to give (1S,3aS,4R,5S,7aS)-5-((1R,2S,4S)-4-hydroxy-2-(hydroxymethyl)-1-methylcyclohexyl)-4-(hydroxymethyl)-7a-methyl-1-(thiazol-2-yl)octahydro-1H-inden-1-ol (Compound No. 179, 24 mg, 39%) as a colourless solid. $^1$H NMR (CD$_3$OD): δ 7.72 (d, J=3.3 Hz, 1H), 7.48 (d, J=3.6 Hz, 1H), 3.87 (m, 1H), 3.66 (m, 1H), 3.54 (m, 1H), 3.41 (m, 1H), 3.05 (m, 1H), 2.43 (m, 1H), 1.94-2.26 (m, 5H), 1.17-1.76 (m, 12H), 1.05 (s, 3H), 1.01 (s, 3H), 0.30 (m, 1H). ES-MS m/z 410 ([M+1]$^+$).

Example 39

His-hSHIP1 Activity of Representative Compounds

Test compounds are dissolved in 95% ethanol to form stock solutions. Before screening, the stock solutions are diluted with Phosphatase Assay Buffer (20 mM Tris-HCL, 10 mM MgCl$_2$, pH 7.5, 0.02% Tween 20) to form working assay solutions that contain 10% ethanol. The assay is carried out on 96-well microtiter plates using a modified procedure of that reported by Ong et al., *Blood* 110, 1942-1949, 2007 and Yang et al., *Org Lett* 7, 1073-1076, 2005, both of which references are incorporated herein by reference in their entirety.

A master mix is prepared that contains 50 µL of His-hSHIP1 enzyme (0.4-1.6 ng/µL final), 25 µL of the substrate, IP4 (25 or 250 µM final), and 50 µL of test compound in 3.3% ethanol (100 µL final). Control blanks are also prepared by replacing His-hSHIP1 enzyme, IP4, or test compounds with Phosphate Assay Buffer. A reference compound that has been shown to activate SHIP1 is also included. Each reaction component is preincubated at 37° C. for 30 min before adding to a 96-well microtiter plate. The master mix is then incubated at 37° C. At time 0, 20, 25 and 30 min, 25 µL of the master mix is removed and transferred to a new 96-well microtiter plate, to which 100 µL of Biomol Green Reagent is added to stop the reaction. After incubating the mixture for 20 min at room temperature for color development, the absorbance is read with SpectraMax Plus 96-well plate reader at a wavelength of 650 nm. Phosphate released is plotted against time to calculate the initial velocities (i.e., slope of the graph) at each IP4 concentration. The initial velocities are baseline corrected and the ratio of initial velocities (IP4$_{25}$/IP4$_{250}$) is calculated and used to rate the test compounds.

According to the above assay, the representative compounds listed in Table 2 below were found to modulate His-hSHIP1 enzyme at concentrations ≤300 μM. The compound numbers in Table 2 correspond to the compound numbers in Table 1 above. Scoring of the compound is expressed as follows:

| Scoring | Initial Velocity Ratio |
| --- | --- |
| +++ | higher than reference or reference - 15% |
| ++ | reference - 16% to reference - 30% |
| + | reference - 31% or lower |
| − | inhibitor |

TABLE 2

| Cpd. No. | Scoring |
| --- | --- |
| 1 | + |
| 2 | + |
| 3 | ++ |
| 4 | + |
| 5 | ++ |
| 6 | ++ |
| 7 | + |
| 8 | + |
| 9 | ++ |
| 10 | ++ |
| 11 | − |
| 12 | +++ |
| 13 | + |
| 14 | ++ |
| 15 | ++ |
| 16 | + |
| 17 | − |
| 19 | ++ |
| 20 | ++ |
| 21 | + |
| 22 | ++ |
| 23 | +++ |
| 24 | ++ |
| 25 | ++ |
| 26 | − |
| 28 | ++ |
| 29 | ++ |
| 30 | + |
| 31 | + |
| 32 | ++ |
| 33 | + |
| 34 | + |
| 36 | ++ |
| 37 | + |

Example 40

Activity of Representative Compounds on Akt Phosphorylation in Lymphocytes

Phosphorylation of AKT has been shown to be modulated by SHIP1 (Helgason et al., *J Exp Med* 191, 781-794, 2000). Jurkat (PTEN−/SHIP1−) or Molt-4 (PTEN−/SHIP1+) cells are starved in serum free RPMI for overnight. In a 15 mL conical tube, 2-3 million serum starved cells (1 million cells per mL) are treated with various concentrations of test compound (0.1, 1, or 10 μM final in 0.1% DMSO) for 30 min at 37° C. followed by stimulation with 100 ng/mL of IGF-1 for 1 h at 37° C. After stimulation, cells are washed once with ice-cold DPBS and lysed with Lysis Buffer (20 mM Tris-HCl, pH 7.5, 140 mM NaCl, 1% NP-40, Complete Mini Protease Inhibitor Cocktail, 10 mM NaF, 1 mM $Na_3VO_4$, 1 mM β-glycerolphosphate) on ice for 30 min with vortexing every 10 min. Samples are then centrifuged at 13,000 rpm for 20 min, and supernatants are collected as total cell lysate samples. Protein concentration is determined using bicinchonic acid assay, and about 15 μg of total protein from each sample is loaded and separated on a 4-12% Tris-Glycine gel. After SDS-PAGE, proteins are transferred from the gel to a nitrocellulose membrane. The membrane is blocked in 5% BSA in PBS containing 0.1% Tween-20 (PBS-T) for 1 h at room temperature before probing with primary antibodies for overnight at 4° C. The following antibodies are used: mouse anti-SHIP1 (1:500 dilution; Santa Cruz, Calif., USA), rabbit anti-phospho-Akt(Ser473) (1:1000 dilution; Cell Signaling Technologies, MA, USA), rabbit anti-Akt (1:1000; Cell Signaling Technologies, MA, USA), and rabbit anti-actin (1:2000; Cell Signaling Technologies, MA, USA). The membrane is then incubated with goat anti-rabbit or anti-mouse secondary antibodies (1:3000) for 1 h at room temperature. Target proteins on the membrane are detected with ECL solution and exposed on a film.

Example 41

Activity of Representative Compounds on Passive Cutaneous Anaphylaxis in Mice

The activity of representative compounds on passive cutaneous anaphylaxis in mice may be evaluated according to the procedures disclosed by Ovary, J Immunol 81, 355-357, 1958 and Halpern et al., *Br J Pharmacol Chemother* 20, 389-398, 1963, both of which are incorporated herein by reference in their entirety.

To induce a passive cutaneous anaphylaxis, mice undergo intradermal ear inoculation on their right ear with 25 ng in 20 μL of anti-DNP-IgE. The left ears are untreated and serve as negative controls. Twenty-four hours after inoculation, all mice are administered test compound by oral gavage (PO). Sixty minutes after oral administration, mice are given a tail vein injection of 2% Evan's Blue (0.2 μm filtered, in 200 μL saline) followed by a second tail IV injection of 100 μg DNP-HSA (in 200 μL). Sixty minutes following the DNP-HAS injection, mice are euthanized using $CO_2$ inhalation. Subsequently, ear biopsies are performed by taking four millimeter punches from both ears, which will then undergo Evan's Blue extraction using formamide incubation in 96 well plates. Eighty μL of eluents are transferred to flat-bottom 96-well plates and absorbance read using SpectraMax M5 spectrophotometer (Molecular Devices, Sunnyvale, Calif., USA) at 620 nm. Background readings from all samples are taken at 740 nm and subtracted from the 620 nm readings. Data are reported as OD.

Example 42

Activity of Representative Compounds on Carrageenan Paw Edema in Mice

The activity of representative compounds on carrageenan paw edema in mice may be evaluated according to the procedures disclosed by Winter et al., *Proc Soc Exp Biol Med* 111, 544-547, 1962 which is incorporated herein by reference in its entirety. To induce edema in the paw, test compounds are administered orally one hour before intraplantar injection of the right hind paw with carrageenan (50 μL of 1% suspension). Hind paw edema, as a measure of inflammation, is recorded using a plethysmometer (Ugo Basile, Italy) 4 hours after λ-carrageenan administration.

All of the U.S. patents, U.S. patent application publications, U.S. patent applications, foreign patents, foreign patent applications and non-patent publications referred to in this specification, including U.S. Provisional Patent Application 61/786,020, filed Mar. 14, 2013, are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (IV):

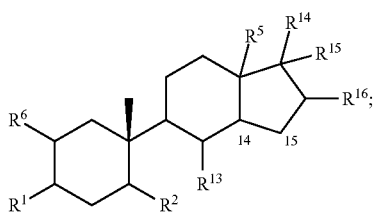

(IV)

wherein:
$R^1$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—$C(O)OR^9$, —$R^8$—$C(O)N(R^9)_2$ or —$N(R^9)C(O)OR^9$;

$R^2$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—$OC(O)R^9$, —$R^8$—$C(O)OR^9$, —$R^8$—$C(O)N(R^9)_2$, —$N(R^9)C(O)OR^9$, —$R^8$—$N(R^9)S(O)_tR^9$ (where t is 1 or 2), —$R^8$—$N(R^9)C(=NR^9)N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl;

$R^5$ is alkyl or $R^5$ is a direct bond to the carbon at C14;
$R^6$ is hydrogen, —$R^8$—$OR^9$ or —$R^8$—$N(R^9)_2$;
$R^{13}$ is —$R^8$—$OR^9$, —$R^8$—$N(R^9)_2$, —$R^8$—O—$R^{10}$—$OR^9$, —$R^8$—O—$R^{10}$—$N(R^9)_2$, —$R^8$—$N(R^9)$—$R^{10}$—$OR^9$, —$R^8$—$N(R^9)$—$R^{10}$—$N(R^9)_2$, —$R^8$—$OC(O)R^9$, —$R^8$—$C(O)OR^9$, —$R^8$—$C(O)N(R^9)_2$, —$N(R^9)C(O)OR^9$, —$R^8$—$N(R^9)S(O)_tR^9$ (where t is 1 or 2), —$R^8$—$N(R^9)C(=NR^9)N(R^9)_2$, alkyl, alkenyl, optionally substituted aralkyl, optionally substituted aralkenyl, optionally substituted heterocyclylalkyl, optionally substituted heteroarylalkyl or optionally substituted heteroarylalkenyl;

$R^{14}$ is alkyl, alkenyl, alkynyl, optionally substituted aryl or optionally substituted heteroaryl;
$R^{15}$ is alkyl, —$R^8$—$OR^9$ or a direct bond to the carbon to which $R^{16}$ is attached, provided that $R^{15}$ is not alkyl when $R^{14}$ is alkyl, alkenyl or alkynyl;
$R^{16}$ is hydrogen, —$R^8$—$OR^9$, —$R^8$—$N(R^9)_2$, or a direct bond to C15, provided that when $R^{16}$ is a direct bond to C15, $R^{15}$ is not a direct bond to the carbon to which $R^{16}$ is attached; and each $R^8$ is independently a direct bond, a straight or branched alkylene chain, a straight or branched alkenylene chain or a straight or branched alkynylene chain;
each $R^9$ is hydrogen, alkyl, optionally substituted aryl and optionally substituted aralkyl; and
each $R^{10}$ is independently a straight or branched alkylene chain, a straight or branched alkenylene chain or a straight or branched alkynylene chain;
or a stereoisomer, enantiomer or tautomer thereof or mixtures thereof, or a pharmaceutically acceptable salt or solvate thereof.

2. The compound of claim 1 wherein:
$R^1$ is —$R^8$—$OR^9$;
$R^2$ is —$R^8$—$OR^9$;
$R^5$ is alkyl or $R^5$ is a direct bond to the carbon at C14;
$R^6$ is hydrogen, —$R^8$—$OR^9$ or —$R^8$—$N(R^9)_2$;
$R^{13}$ is —$R^8$—$OR^9$ or —$R^8$—$N(R^9)_2$;
$R^{14}$ is alkyl, alkenyl, alkynyl, optionally substituted aryl or optionally substituted heteroaryl;
$R^{15}$ is alkyl, —$R^8$—$OR^9$ or a direct bond to the carbon to which $R^{16}$ is attached, provided that $R^{15}$ is not alkyl when $R^{14}$ is alkyl, alkenyl or alkynyl;
$R^{16}$ is hydrogen or —$R^8$—$OR^9$, —$R^8$—$N(R^9)_2$; and
each $R^8$ is independently a direct bond or a straight or branched alkylene chain; and
each $R^9$ is hydrogen, alkyl, optionally substituted aryl and optionally substituted aralkyl.

3. The compound of claim 2 wherein:
$R^1$ is —$R^8$—$OR^9$;
$R^2$ is —$R^8$—$OR^9$;
$R^5$ is alkyl;
$R^6$ is hydrogen;
$R^{13}$ is —$R^8$—$OR^9$ or —$R^8$—$N(R^9)_2$;
$R^{14}$ is alkyl or alkynyl;
$R^{15}$ is —$R^8$—$OR^9$;
$R^{16}$ is hydrogen; and
each $R^8$ is independently a direct bond or a straight or branched alkylene chain; and
each $R^9$ is hydrogen or alkyl.

4. The compound of claim 3 selected from:
(1S,3aS,4R,5S,7aS)-4-(aminomethyl)-5-((1R,2S,4S)-4-hydroxy-2-(hydroxymethyl)-1-methylcyclohexyl)-1,7a-dimethyloctahydro-1H-inden-1-ol;
(1S,3aS,4R,5S,7aS)-5-((1R,2S,4S)-4-hydroxy-2-(hydroxymethyl)-1-methylcyclohexyl)-4-(hydroxymethyl)-1,7a-dimethyloctahydro-1H-inden-1-ol; and
(1R,3aS,4R,5S,7aS)-1-ethynyl-5-((1R,2S,4S)-4-hydroxy-2-(hydroxymethyl)-1-methylcyclohexyl)-4-(hydroxymethyl)-7a-methyloctahydro-1H-inden-1-ol.

5. The compound of claim 2 wherein:
$R^1$ is —$R^8$—$OR^9$;
$R^2$ is —$R^8$—$OR^9$;
$R^5$ is alkyl or $R^5$ is a direct bond to the carbon at C14;
$R^6$ is hydrogen;
$R^{13}$ is —$R^8$—$OR^9$ or —$R^8$—$N(R^9)_2$;
$R^{14}$ is optionally substituted aryl;
$R^{15}$ is alkyl, —$R^8$—$OR^9$ or a direct bond to the carbon to which $R^{16}$ is attached;
$R^{16}$ is hydrogen or —$R^8$—$OR^9$; and
each $R^8$ is independently a direct bond or a straight or branched alkylene chain; and
each $R^9$ is hydrogen or alkyl.

6. The compound of claim 5 selected from:
(1S,3S,4R)-4-((3aS,6S,7R,7aS)-7-(aminomethyl)-3a-methyl-3-phenyl-3a,4,5,6,7,7a-hexahydro-1H-inden-6-yl)-3-(hydroxymethyl)-4-methylcyclohexano;

(1S,3aS,4R,5S,7aS)-4-(aminomethyl)-5-(((1R,2S,4S)-4-hydroxy-2-(hydroxymethyl)-1-methylcyclohexyl)-7a-methyl-1-phenyloctahydro-1H-inden-1-ol;

(1S,2R,4R,5S)-4-(aminomethyl)-5-(((1R,2S,4S)-4-hydroxy-2-(hydroxymethyl)-1-methylcyclohexyl)-1-methyl-1-phenyl-2,3,4,5,6,7-hexahydro-1H-inden-2-ol;

(1S,3S,4R)-3-(hydroxymethyl)-4-(((3aS,6S,7R,7aS)-7-(hydroxymethyl)-3a-methyl-3-phenyl-3a,4,5,6,7,7a-hexahydro-1H-inden-6-yl)-4-methylcyclohexanol;

(1S,3aS,4R,5S,7aS)-5-(((1R,2S,4S)-4-hydroxy-2-(hydroxymethyl)-1-methylcyclohexyl)-4-(hydroxymethyl)-7a-methyl-1-phenyloctahydro-1H-inden-1-ol; and (1S,2R,4R,5S)-5-(((1R,2S,4S)-4-hydroxy-2-(hydroxymethyl)-1-methylcyclohexyl)-4-(hydroxymethyl)-1-methyl-1-phenyl-2,3,4,5,6,7-hexahydro-1H-inden-2-ol.

7. The compound of claim 2 wherein:
$R^1$ is —$R^8$—$OR^9$;
$R^2$ is —$R^8$—$OR^9$;
$R^5$ is alkyl or $R^5$ is a direct bond to the carbon at C14;
$R^6$ is hydrogen;
$R^{13}$ is —$R^8$—$OR^9$ or —$R^8$—$N(R^9)_2$;
$R^{14}$ is optionally substituted heteroaryl;
$R^{15}$ is alkyl, —$R^8$—$OR^9$ or a direct bond to the carbon to which $R^{16}$ is attached;
$R^{16}$ is hydrogen or —$R^8$—$OR^9$, —$R^8$—$N(R^9)_2$; and
each $R^8$ is independently a direct bond or a straight or branched alkylene chain; and
each $R^9$ is hydrogen or alkyl.

8. The compound of claim 7 selected from:
(1S,3aS,4R,5S,7aS)-4-(aminomethyl)-1-(furan-2-yl)-5-((1R,2S,4S)-4-hydroxy-2-(hydroxymethyl)-1-methylcyclohexyl)-7a-methyloctahydro-1H-inden-1-ol;

(1S,3S,4R)-4-((3aS,6S,7R,7aS)-7-(aminomethyl)-3-(furan-2-yl)-3a-methyl-3a,4,5,6,7,7a-hexahydro-1H-inden-6-yl)-3-(hydroxymethyl)-4-methylcyclohexanol;

(1S,3aS,4R,5S,7aS)-4-(aminomethyl)-5-(((1R,2S,4S)-4-hydroxy-2-(hydroxymethyl)-1-methylcyclohexyl)-7a-methyl-1-(thiophen-2-yl)octahydro-1H-inden-1-ol;

(1S,3S,4R)-4-((3aS,6S,7R,7aS)-7-(aminomethyl)-3a-methyl-3-(thiophen-2-yl)-3a,4,5,6,7,7a-hexahydro-1H-inden-6-yl)-3-(hydroxymethyl)-4-methylcyclohexanol;

(1S,3aS,4R,5S,7aS)-4-(aminomethyl)-5-(((1R,2S,4S)-4-hydroxy-2-(hydroxymethyl)-1-methylcyclohexyl)-7a-methyl-1-(pyridin-2-yl)octahydro-1H-inden-1-ol;

(1S,3aS,4R,5S,7aS)-4-(aminomethyl)-5-(((1R,2S,4S)-4-hydroxy-2-(hydroxymethyl)-1-methylcyclohexyl)-7a-methyl-1-(thiazol-2-yl)octahydro-1H-inden-1-ol;

(1S,3S,4R)-4-((3aS,6S,7R,7aS)-3-(furan-2-yl)-7-(hydroxymethyl)-3a-methyl-3a,4,5,6,7,7a-hexahydro-1H-inden-6-yl)-3-(hydroxymethyl)-4-methylcyclohexanol;

(1S,3aS,4R,5S,7aS)-1-(furan-2-yl)-5-(((1R,2S,4S)-4-hydroxy-2-(hydroxymethyl)-1-methylcyclohexyl)-4-(hydroxymethyl)-7a-methyloctahydro-1H-inden-1-ol;

(1S,3aS,4R,5S,7aS)-5-(((1R,2S,4S)-4-hydroxy-2-(hydroxymethyl)-1-methylcyclohexyl)-4-(hydroxymethyl)-7a-methyl-1-(thiophen-2-yl)octahydro-1H-inden-1-ol;

(1S,3S,4R)-3-(hydroxymethyl)-4-((3aS,6S,7R,7aS)-7-(hydroxymethyl)-3a-methyl-3-(thiophen-2-yl)-3a,4,5,6,7,7a-hexahydro-1H-inden-6-yl)-4-methylcyclohexanol;

(1S,3aS,4R,5S,7aS)-5-(((1R,2S,4S)-4-hydroxy-2-(hydroxymethyl)-1-methylcyclohexyl)-4-(hydroxymethyl)-7a-methyl-1-(pyridin-2-yl)octahydro-1H-inden-1-ol; and (1S,3aS,4R,5S,7aS)-5-(((1R,2S,4S)-4-hydroxy-2-(hydroxymethyl)-1-methylcyclohexyl)-4-(hydroxymethyl)-7a-methyl-1-(thiazol-2-yl)octahydro-1H-inden-1-ol.

9. A composition comprising a compound of claim 1, or a stereoisomer, enantiomer or tautomer thereof or mixtures thereof, or a pharmaceutically acceptable salt or solvate thereof, and a pharmaceutically acceptable excipient.

10. A method for modulating SHIP1 comprising administering an effective amount of a compound of claim 1, or a stereoisomer, enantiomer or tautomer thereof or mixtures thereof, or a pharmaceutically acceptable salt or solvate thereof, or a composition of claim 9 to a mammal in need thereof.

11. A method for treating a disease, disorder or condition comprising administering an effective amount of a compound of claim 1, or a stereoisomer, enantiomer or tautomer thereof or mixtures thereof, or a pharmaceutically acceptable salt or solvate thereof, or a composition of claim 9 to a mammal in need thereof, where the disease, disorder or condition is an autoimmune disease, disorder or condition, an inflammatory disease, disorder or condition, or a neoplastic or cell proliferative disease, disorder or condition.

* * * * *